(12) United States Patent
Fukuda et al.

(10) Patent No.: US 6,897,230 B2
(45) Date of Patent: May 24, 2005

(54) BICYCLO[3/1/0] HEXANE CONTAINING OXAZOLIDINONE ANTIBIOTICS AND DERIVATIVES THEREOF

(75) Inventors: Yasumichi Fukuda, Tochigi (JP); Milton L. Hammond, Banchburg, NJ (US)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 111 days.

(21) Appl. No.: 10/123,285

(22) Filed: Apr. 17, 2002

(65) Prior Publication Data

US 2003/0125367 A1 Jul. 3, 2003

Related U.S. Application Data

(60) Provisional application No. 60/363,928, filed on Mar. 14, 2002, and provisional application No. 60/283,956, filed on Apr. 17, 2001.

(51) Int. Cl.$^7$ .................. C07D 265/10; C07D 413/10; A61K 31/421; A61K 31/422; A61P 31/04
(52) U.S. Cl. .................. 514/376; 548/229; 548/231; 548/137; 548/209
(58) Field of Search ............................ 514/376, 326, 514/236.8; 544/137; 546/209; 548/231, 229

(56) References Cited

U.S. PATENT DOCUMENTS

2002/0103186 A1 * 8/2002 Mehta et al. .............. 514/218

FOREIGN PATENT DOCUMENTS

WO      WO 02/06278 A1    7/2001

OTHER PUBLICATIONS

Wolff, Manfred E. "Burger's Medicinal Chemistry, 5ed, Part I", John Wiley & Sons, 1995, pp. 975–977.*
Banker, G.S. et al, "Modern Pharmaceutics, 3ed.", Marcel Dekker, New York, 1996, pp. 451 and 596.*
West, Anthony R., Solid State Chemistry and its Applications, Wiley, New York, 1988, pp. 358 & 365.*

* cited by examiner

*Primary Examiner*—Thomas McKenzie
(74) *Attorney, Agent, or Firm*—McDermott Will & Emery LLP

(57) ABSTRACT

Oxazolidinones having a bicyclic[3.1.0]hexane containing moiety, which are effective against aerobic and anerobic pathogens such as multi-resistant staphylococci, streptococci and enterococci, Bacteroides spp., Clostridia spp. species, as well as acid-fast organisms such as *Mycobacterium tuberculosis* and other mycobacterial species.

The compounds are represented by structural formula I:

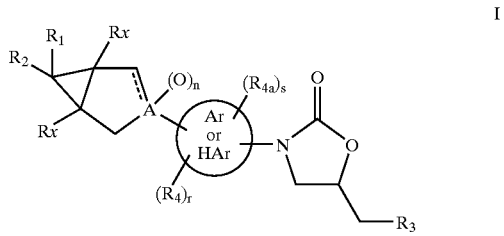

its enantiomer, diastereomer, or pharmaceutically acceptable salt or ester thereof, and wherein the variables $R_1$, $R_2$, $R_3$, $R_4$, $R_{4a}$, A, Ar, HAr, n, r, and s are as defined herein.

40 Claims, No Drawings

1

BICYCLO[3/1/0] HEXANE CONTAINING OXAZOLIDINONE ANTIBIOTICS AND DERIVATIVES THEREOF

CROSS REFERENCE TO RELATED APPLICATIONS

This application claims priority to Provisional Application Ser. No. 60/363,928, filed Mar. 14, 2002, and Provisional Application Ser. No. 60/283,956, filed Apr. 17, 2001.

BACKGROUND OF THE INVENTION

Oxazolidinones represent the first new class of antibacterials to be developed since the quinolones. The oxazolidinones are synthetic antibacterial compounds that are orally or intravenously active against problematic multidrug resistant Gram positive organisms and are not cross-resistant with other antibiotics. See Riedl et al, Recent Developments with Oxazolidinone Antibiotics, *Exp. Opin. Ther. Patents* (1999) 9(5), Ford et al., Oxazolidinones: New Antibacterial Agents, *Trends in Microbiology* 196 Vol.5, No. 5, May 1997 and WO 96/35691.

This invention relates to new oxazolidinones having a bicyclic[3.1.0]hexane containing moiety, which are effective against aerobic and anerobic pathogens such as multi-resistant staphylococci, streptococci and enterococci, Bacteroides spp., Clostridia spp. species, as well as acid-fast organisms such as *Mycobacterium tuberculosis* and other mycobacterial species.

SUMMARY OF THE INVENTION

The present invention relates to compounds of formula I:

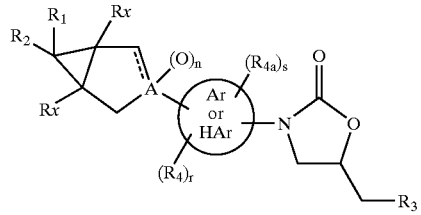

its enantiomer, diastereomer, or pharmaceutically acceptable salt, hydrate or prodrug thereof wherein:

A represents C (when - - - is present), CH, or N (when - - - is not present);

- - - represents a bond;

R represents hydrogen, or $C_{1-6}$ alkyl;

$R_1$ and $R_2$ independently represent i) hydrogen, ii) $NR_5R_6$, iii) $CR_7R_8R_9$, $C(R)_2OR_{14}$, $CH_2NHR_{14}$, iv) $C(=O)R_{13}$, $C(=NOH)H$, $C(=NOR_{13})H$, $C(=NOR_{13})R_{13}$, $C(=NOH)R_{13}$, $C(=O)N(R_{13})_2$, $C(=NOH)N(R_{13})_2$, $NHC(=X_1)N(R_{13})_2$, $(C=NH)R_7$, $N(R_{13})C(=X_1)N(R_{13})_2$, $COOR_{13}$, $SO_2R_{14}$, $N(R_{13})SO_2R_{14}$, $N(R_{13})COR_{14}$, or $(C_{1-6}$ alkyl$)CN$, $CN$, $CH=C$), $OH$, $C(=(O)CHR_{13}$, $C(=NR_{13})R_{13}$, $NHC(=X_1)R_{13}$;

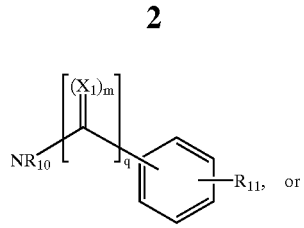

vi) $C_{5-10}$ heterocycle optionally substituted with 1–3 groups of $R_7$, which may be attached through either a carbon or a heteroatom;

represents aryl or heteroaryl, heterocycle, heterocyclyl or heterocyclic, $R_x$ represents hydrogen or $C_{1-6}$ alkyl;

$R_3$ represent i) $NH(C=X_2)R_{12}$, ii) $NHSO_2R_{14}$, iii) $NH(CH_2)_{0-4}$aryl, iv) $NH(CH_2)_{0-4}$heteroaryl, v) $S(CH_2)_{0-4}$aryl, vi) $S(CH_2)_{0-4}$heteroaryl, vii) $O(CH_2)_{0-4}$aryl, or viii) $O(CH_2)_{0-4}$heteroaryl;

$R_4$ and $R_{4a}$ independently represent i) hydrogen, ii) halogen, iii) $C_{1-6}$ alkoxy, or iv) $C_{1-6}$ alkyl r and s independently are 1–3, with the provision that when $(R_{4a})_s$ and $(R_4)_r$ are attached to an Ar or HAr ring the sum of r and s is less than or equal to 4;

$R_5$ and $R_6$ independently represent i) hydrogen, ii) $C_{1-6}$ alkyl optionally substituted with 1–3 groups of halogen, CN, OH, $C_{1-6}$ alkoxy, amino, imino, hydroxyamino, alkoxyamino, $C_{1-6}$ acyloxy, $C_{1-6}$ alkylsulfenyl, $C_{1-6}$ alkylsulfinyl, $C_{1-6}$ alkylsulfonyl, aminosulfonyl, $C_{1-6}$ alkylaminosulfonyl, $C_{1-6}$ dialkylaminosulfonyl, 4-morpholinylsulfonyl, phenyl, pyridine, 5-isoxazolyl, ethylenyloxy, or ethynyl, said phenyl and pyridine optionally substituted with 1–3 halogen, CN, OH, $CF_3$, $C_{1-6}$ alkyl or $C_{1-6}$ alkoxy;

iii) $C_{1-6}$ acyl optionally substituted with 1–3 groups of halogen, OH, SH, $C_{1-6}$ alkoxy, naphthalenoxy, phenoxy, amino, $C_{1-6}$ acylamino, hydroxylamino, alkoxylamino, $C_{1-6}$ acyloxy, aralkyloxy, phenyl, pyridine, $C_{1-6}$ alkylcarbonyl, $C_{1-6}$ alkylamino, $C_{1-6}$ dialkylamino, $C_{1-6}$ hydroxyacyloxy, $C_{1-6}$ alkylsulfenyl, phthalimido, maleimido, succinimido, said phenoxy, phenyl and pyridine optionally substituted with 1–3 groups of halo, OH, CN, $C_{1-6}$ alkoxy, amino, $C_{1-6}$ acylamino, $CF_3$ or $C_{1-6}$ alkyl;

iv) $C_{1-6}$ alkylsulfonyl optionally substituted with 1–3 groups of halogen, OH, $C_{1-6}$ alkoxy, amino, hydroxylamino, alkoxylamino, $C_{1-6}$ acyloxy, or phenyl; said phenyl optionally substituted with 1–3 groups of halo, OH, $C_{1-6}$ alkoxy, amino, $C_{1-6}$ acylamino, $CF_3$ or $C_{1-6}$ alkyl;

v) arylsulfonyl optionally substituted with 1–3 of halogen, $C_{1-6}$ alkoxy, OH or $C_{1-6}$ alkyl;

vi) $C_{1-6}$ alkoxycarbonyl optionally substituted with 1–3 of halogen, OH, $C_{1-6}$ alkoxy, $C_{1-6}$ acyloxy, or phenyl, said phenyl optionally substituted with 1–3 groups of halo, OH, $C_{1-6}$ alkoxy, amino, $C_{1-6}$ acylamino, $CF_3$ or $C_{1-6}$ alkyl;

vii) aminocarbonyl, $C_{1-6}$ alkylaminocarbonyl or $C_{1-6}$ dialkylaminocarbonyl, said alkyl groups optionally substituted with 1–3 groups of halogen, OH, $C_{1-6}$ alkoxy or phenyl viii) five to six membered heterocycles optionally substituted with 1–3 groups of halogen, OH, CN, amino, $C_{1-6}$ acylamino, $C_{1-6}$ alkylsulfonylamino, $C_{1-6}$ alkoxycarbonylamino, $C_{1-6}$ alkoxy, $C_{1-6}$ acyloxy or $C_{1-6}$ alkyl, said alkyl optionally substituted with 1–3 groups of halogen, or $C_{1-6}$ alkoxy;

ix) $C_{3-6}$ cycloalkylcarbonyl optionally substituted with 1–3 groups of halogen, OH, $C_{1-6}$ alkoxy or CN;

x) benzoyl optionally substituted with 1–3 groups of halogen, OH, $C_{1-6}$ alkoxy, $C_{1-6}$ alkyl, $CF_3$, $C_{1-6}$ alkanoyl, amino or $C_{1-6}$ acylamino;

xi) pyrrolylcarbonyl optionally substituted with 1–3 of $C_{1-6}$ alkyl;

xii) $C_{1-2}$ acyloxyacetyl where the acyl is optionally substituted with amino, $C_{1-6}$ alkylamino, $C_{1-6}$ dialkylamino, 4-morpholino, 4-aminophenyl, 4-(dialkylamino)phenyl, 4-(glycylamino)phenyl; or $R_5$ and $R_6$ taken together with any intervening atoms can form a 3 to 7 membered heterocyclic ring containing 1–2 heteroatoms independently chosen from O, S, SO, $SO_2$, N, or $NR_8$;

$R_7$ represent i) hydrogen, halogen, OH, $C_{1-6}$ alkoxy, $C_{1-6}$ alkyl, alkenyl, ii) amino, $C_{1-6}$ alkylamino, $C_{1-6}$ dialkylamino, hydroxylamino or $C_{1-2}$ alkoxyamino all of which can be optionally substituted on the nitrogen with $C_{1-6}$ acyl, $C_{1-6}$ alkylsulfonyl or $C_{1-6}$ alkoxycarbonyl, said acyl and alkylsulfonyl optionally substituted with 1–2 of halogen or OH;

$R_8$ and $R_9$ independently represents i) H, CN, ii) $C_{1-6}$ alkyl optionally substituted with 1–3 halogen, CN, OH, $C_{1-6}$ alkoxy, $C_{1-6}$ acyloxy, or amino, iii) phenyl optionally substituted with 1–3 groups of halogen, OH, $C_{1-6}$ alkoxy; or $R_7$ and $R_8$ taken together can form a 3–7 membered ring optionally interrupted with 1–2 heteroatoms chosen from O, S, SO, $SO_2$, NH, and $NR_8$;

$X_1$ represents I, S, $NR_{13}$, NCN, or $NSO_2R_{14}$ $X_2$ represents O, S, NH or $NSO_2R_{14}$;

$R_{10}$ represents hydrogen, $C_{1-6}$ alkyl or $CO_2R_{15}$;

$R_{11}$ represents hydrogen, $C_{1-6}$ alkyl, $C_{1-6}$ alkanoyl, halogen, amino, $C_{1-6}$ acylamino, $C_{1-6}$ alkoxy, OH or $CF_3$,; $NHC_{1-6}$ alkyl, or $N(C_{1-6}$ alkyl$)_2$, where said alkyl may be substituted with 1–3 groups of halo, OH or $C_{1-6}$ alkoxy;

$R_{12}$ represents hydrogen, $C_{1-6}$ alkyl, $NH_2$, $C_{1-6}$ alkylamino, $C_{1-6}$ alkoxy or $C_{1-6}$ dialkylamino, where said alkyl may be substituted with 1–3 groups of halo, OH or $C_{1-6}$ alkoxy;

Each $R_{13}$ represents independently hydrogen, $C_{1-6}$ alkyl, $NR_5R_6$, $SR_8$, $S(O)R_8$, $S(O)_2R_8$, CN, $C_{1-6}$ alkylS(O)R, $C_{1-6}$ alkoxycarbonyl, hydroxycarbonyl, $C_{1-6}$ acyl, $C_{3-7}$ membered carbon ring optionally interrupted with 1–4 heteroatoms chosen from O, S, SO, $SO_2$, NH and $NR_8$ where said $C_{1-6}$ alkyl or $C_{1-6}$ acyl groups may be independently substituted with 0–3 halogens, hydroxy, $N(R)_2$, $CO_2R$, $C_{6-10}$ aryl, $C_{5-10}$heteroaryl, or $C_{1-6}$ alkoxy groups;

When two $R_{13}$ groups are attached to the same atom or two adjacent atoms they may be taken together to form a 3–7 membered ring optionally interrupted with 1–2 heteroatoms chosen from O, S, SO, $SO_2$, NH, and $NR_8$;

$R_{14}$ represents amino, $C_{1-6}$ alkyl, $C_{1-6}$ haloalkyl, five to six membered heterocycles or phenyl, said phenyl and heterocycles optionally substituted with 1–3 group of halo, $C_{1-6}$ alkoxy, $C_{1-6}$ acylamino, or $C_{1-6}$ alkyl, hydroxy and/or amino, said amino and hydroxy optionally protected with an amino or hydroxy protecting group;

$R_{15}$ is $C_{1-6}$ alkyl or benzyl said benzyl optionally substituted with 1–3 groups of halo, OH, $C_{1-6}$ alkoxy, amino, $C_{1-6}$ acylamino, or $C_{1-6}$ alkyl; and m, n, and q represents 0–1.

Another aspect of the invention is concerned with the use of the novel antibiotic compositions in the treatment of bacterial infections.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 15 carbon atoms unless otherwise defined. It may be straight or branched. Preferred alkyl groups include lower alkyls which have from 1 to 6 carbon atoms such as methyl, ethyl, propyl, isopropyl, butyl and t-butyl. When substituted, alkyl groups may be substituted with up to 3 substituent groups, selected from the groups as herein defined, at any available point of attachment. When the alkyl group is said to be substituted with an alkyl group, this is used interchangeably with "branched alkyl group".

Cycloalkyl is a species of alkyl containing from 3 to 15 carbon atoms, without alternating or resonating double bonds between carbon atoms. It may contain from 1 to 4 rings which are fused. Preferred cycloalkyl groups are cyclopropyl, cyclobutyl, cyclopentyl and cyclohexyl. When substituted, cycloalkyl groups may be substituted with up to 3 substituents which are defined herein by the definition of alkyl.

Alkanoyl refers to a group derived from an aliphatic carboxylic acid of 2 to 4 carbon atoms. Examples are acetyl, propionyl, butyryl and the like.

The term "alkoxy" refers to those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

refers to aryl or heteroaryl, heterocycle, Het, heterocyclyl or heterocyclic as described immediately below.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms. The preferred aryl groups are phenyl, naphthyl and pbenanthrenyl. Aryl groups may likewise be substituted as defined. Preferred substituted aryls include phenyl and naphthyl.

The term heterocycle, heteroaryl, Het, heterocyclyl or heterocyclic, as used herein except where noted, represents a stable 5- to 7-membered mono- or bicyclic or stable 7- to 10-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized (in which case it is properly balanced by a counterion), and including any bicyclic group in which any of the above-defined heterocyclic rings is fused to a benzene ring. The heterocyclic ring may be attached at any heteroatom or carbon atom which results in the creation of a stable structure. The heterocycle, heteroaryl, Het or heterocyclic may be substituted with 1–3 groups of $R_7$. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyrimidonyl, pyridinonyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thiophenyl, imidazopyridinyl, tetrazolyl, triazinyl, thienyl, benzothienyl, thiamorpholinyl sulfoxide, thiamorpholinyl sulfone, and oxadiazolyl. Additional examples of heteroaryls are illustrated by formulas a, b, c and d:

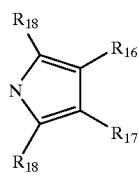

a

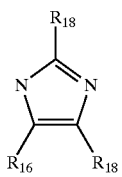

b

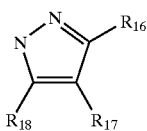

c

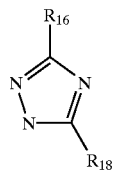

d wherein $R_{16}$ and $R_{17}$ are independently selected from hydrogen, halogen, $C_{1-6}$ alkyl, $C_{2-4}$ alkanoyl, $C_{1-6}$ alkoxy; and $R_{18}$ represents hydrogen, $C_{1-6}$ alkyl, $C_{2-4}$ alkanoyl, $C_{1-6}$ alkoxycarbonyl and carbamoyl.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The terms "quaternary nitrogen" and "positive charge" refer to tetravalent, positively charged nitrogen atoms (balanced as needed by a counterion known in the art) including, e.g., the positively charged nitrogen in a tetraalkylammonium group (e.g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

The term "prodrug" refers to compounds which are drug precursors which, following administration and absorption, release the drug in vivo via some metabolic process. Exemplary prodrugs include acyl amides of the amino compounds of this inventon such as amides of alkanoic($C_{1-6}$)acids, amides of aryl acids (e.g., benzoic acid) and alkane($C_{1-6}$) dioic acids.

Halogen and "halo" refer to bromine, chlorine, fluorine and iodine.

When a group is termed "substituted", unless otherwise indicated, this means that the group contains from 1 to 3 substituents thereon.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

Examples of suitable hydroxyl and amino protecting groups are: trimethylsilyl, triethylsilyl, o-nitrobenzyloxycarbonyl, p-nitrobenzyloxycarbonyl, t-butyldiphenylsilyl, t-butyldimethylsilyl, benzyloxycarbonyl, t-butyloxycarbonyl, 2,2,2-trichloroethyloxycarbonyl, allyloxycarbonyl and the like. Examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butldiphenylsilyl, 2-(trimethylsilyl)ethyl, phenacyl, p-methoxybenzyl, acetonyl, p-methoxyphenyl, 4-pyridylmethyl, t-butyl and the like.

The bicyclo[3.1.0]hexane containing oxazolidinone compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel bicyclic[3.1.0]hexane containing oxazolidinone compounds.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, flmarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The pharmaceutically acceptable esters are such as would be readily apparent to a medicinal chemist, and include those which are hydrolyzed under physiological conditions, such as "biolabile esters", pivaloyloxymethyl, acetoxymethyl, phthalidyl, indanyl and methoxymethyl, and others.

Biolabile esters are biologically hydrolizable, and may be suitable for oral administration, due to good absorption through the stomach or intenstinal mucosa, resistance to gastric acid degrada-tion and other factors. Examples of biolabile esters include compounds.

An embodiment of this invention is realized when A is CH and all other variables are as described herein.

An embodiment of this invention is realized when A is C and - - - is present.

Another embodiment of this invention is realized when A is N and all other variables are as described herein.

Another embodiment of this invention is realized when $R_1$ and $R_2$ independently represent H, $NR_5R_6$, CN, OH, $C(R)_2$ $OR_{14}$, $NHC(=X1)N(R_{13})_2$, $C(=NOH)N(R_{13})_2$, or $CR_7R_8R_9$ and all other variables are as described herein.

Another embodiment of this invention is realized when

is phenyl, pyridine, pyrimidine, or piperidine and all other variables are as described herein.

Another embodiment of this invention is realized when one of $R_1$ and $R_2$ is H and the other is $NR_5R_6$ and all other variables are as described herein.

Another embodiment of this invention is realized when one of $R_1$ and $R_2$ is H and the other is CN and all other variables are as described herein.

Still another embodiment of this invention is realized when $R_5$ and $R_6$ independently are:
i) H,
ii) $C_{1-6}$ alkyl optionally substituted with 1–3 groups of halogen, CN, OH, $C_{1-6}$ alkoxy, amino, hydroxyamino, alkoxyamino, $C_{1-6}$ acyloxy, $C_{1-6}$ alkylsulfenyl, $C_{1-6}$ alkylsulfinyl, $C_{1-6}$ alkylsulfonyl, aminosulfonyl, $C_{1-6}$ alkylaminosulfonyl, $C_{1-6}$ dialkylaminosulfonyl, 4-morpholinylsulfonyl, phenyl, pyridine, 5-isoxazolyl, ethyenyloxy, or ethynyl, said phenyl and pyridine optionally substituted with 1–3 halogen, CN, OH, $CF_3$, $C_{1-6}$ alkyl or $C_{1-6}$ alkoxy;
iii) $C_{1-6}$ acyl optionally substituted with 1–3 groups of halogen, OH, SH, $C_{1-6}$ alkoxy, naphthalenoxy, phenoxy, amino, $C_{1-6}$ acylamino, hydroxylamino, alkoxylamino, $C_{1-6}$ acyloxy, phenyl, pyridine, $C_{1-6}$ alkylcarbonyl, $C_{1-6}$ alkylamino, $C_{1-6}$ dialkylamino, $C_{1-6}$ hydroxyacyloxy, $C_{1-6}$ alkylsulfenyl, phthalimido, maleimido, succinimido, said phenoxy, phenyl and pyridine optionally substituted with 1–3 groups of halo, OH, CN, $C_{1-6}$ alkoxy, amino, $C_{1-6}$ acylamino, $CF_3$ or $C_{1-6}$ alkyl; or
iv) benzoyl optionally substituted with 1–3 groups of halogen, OH, $C_{1-6}$ alkoxy, $C_{1-6}$ alkyl, $CF_3$, $C_{1-6}$ alkanoyl, amino or $C_{1-6}$ acylamino and all other variables are as described herein.

Yet another embodiment of this invention is realized when $X_1$ represents O and all other variables are as described herein.

Another embodiment of this invention is realized when one of $R_1$ or $R_2$ is hydrogen and the other is:

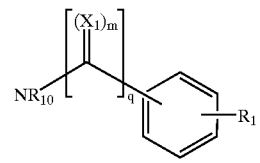

wherein $R_{10}$, $X_1$, m, q, and $R_{11}$ are described herein.

A preferred embodiment of this invention is realized when the structural formula is II:

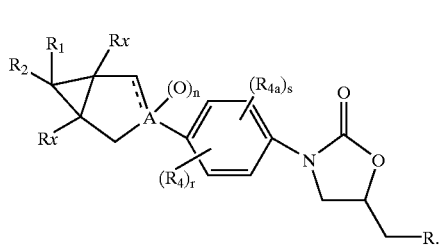

Formula II wherein $R_1$, $R_2$, $R_3$, $R_4$, $R_{4a}$, and Rx are as described herein and A is N.

An embodiment of this invention is realized when A is C and - - - is present.

Another preferred embodiment of this invention is realized when the structural formula is IIIa, or IIIb,:

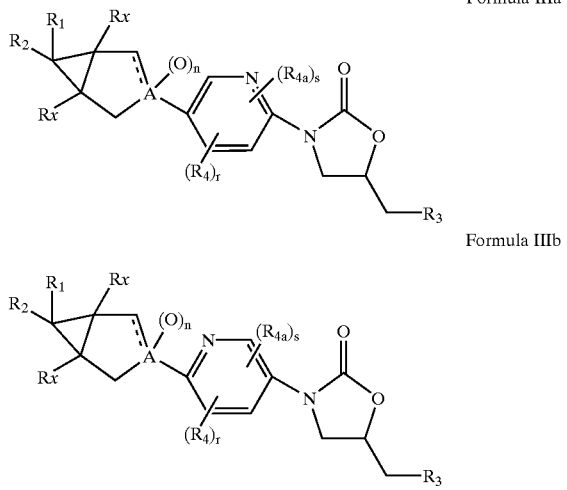

Formula IIIa

Formula IIIb wherein $R_1$, $R_2$, $R_3$, $R_4$, $R_{4a}$, and Rx are as described herein and A is N.

An embodiment of this invention is realized when A is C and - - - is present.

Preferred compounds of this invention are:

N-[5(S)-3-[4-[(1α,5α,6α)-6-(N-Benzyl)amino-3-azabicyclo[3.1.0]hexan-3-yl]-3-fluorophenyl]-2-oxooxazolidin-5-ylmethyl]acetamide, N-[5(S)-3-[4-[(1α,5α,6α)-6-(N-Benzyloxyacetyl)amino-3-azabicyclo[3.1.0]hexan-3-yl]-3-fluorophenyl]-2-oxooxazolidin-5-ylmethyl]acetamide, N-[5(S)-3-[3-Fluoro-4-[(1α,5α,6α)-6-(N-hydroxyacetyl)amino-3-azabicyclo[3.1.0]hexan-3-yl]phenyl]-2-oxooxazolidin-5-ylmethyl]acetamide, N-[5(S)-3-[4-[(1α,5α,6α)-6-(N-Benzyl-N-methyl)amino-3-azabicyclo[3.1.0]hexan-3-yl]-3-fluorophenyl]-2-oxooxazolidin-5-ylmethyl]acetamide, N-[5(S)-3-[3-Fluoro-4-[(1α,5α,6α)-6-(N-methyl)amino-3-azabicyclo[3.1.0]hexan-3-yl]phenyl]-2-oxooxazolidin-5-ylmethyl]acetamide, N-[5(S)-3-[4-[(1α,5α,6α)-6-(N-Benzyloxyacetyl-N-methyl)amino-3-azabicyclo[3.1.0]hexan-3-yl]-3-fluorophenyl]-2-oxooxazolidin-5-ylmethyl]acetamide, N-[5(S)-3-[3-Fluoro-4-[(1α,5α,6α)-6-(N-hydroxyacetyl-N-methyl)amino-3-azabicyclo[3.1.0]hexan-3-yl]phenyl]-2-oxooxazolidin-5-ylmethyl]acetamide, N-[5(S)-3-[4-[(1α,5α,6α)-6-Amino-3-azabicyclo[3.1.0]hexan-3-yl]-3-fluorophenyl]-2-oxooxazolidin-5-ylmethyl]acetamide, N-[5(S)-3-[4-[(1α,5α,6α)-6-(N-Benzyl-N-t-butoxycarbonyl)amino-3-azabicyclo[3.1.0]hexan-3-yl]-3-fluorophenyl]-2-oxooxazolidin-5-ylmethyl]acetamide, N-[5(S)-3-[4-[(1α,5α,6α)-6-(N-Benzyl-N-t-butoxycarbonyl)amino-3-azabicyclo[3.1.0]hexan-3-yl]-3-fluorophenyl]-2-oxooxazolidin-5-ylmethyl]thioacetamide, N-[5(S)-3-[4-[(1α,5α,6α)-6-(N-Benzyl)amino-3-azabicyclo[3.1.0]hexan-3-yl]-3-fluorophenyl]-2-oxooxazolidin-5-ylmethyl]thioacetamide, N-[5(S)-3-[4-[(1α,5α,6α)-6-(N-Benzyl)amino-3-azabicyclo[3.1.0]hexan-3-yl]-3-fluorophenyl]-2-oxooxazolidin-5-ylmethyl]thiourea, N-[5(S)-3-[3-Fluoro-4-[(1α,5α,6α)-6-hydroxymethyl-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-[(2-tetrahydropyranyl)oxy]methyl-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-methoxymethyl-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-(3-isoxazolyl)oxymethyl-3-azabicyclo[3.1.0]hexan-3-yl]phenyl]-2-oxooxazolidin-5-ylmethyl]acetamide, N-[5(S)-3-[4-[(1α,5α,6α)-6-Acetylamino-3-azabicyclo[3.1.0]hexan-3-yl]-3-fluorophenyl]-2-oxooxazolidin-5-ylmethyl]acetamide, N-[5(S)-3-[4-[(1α,5α,6α)-6-Benzoylamino-3-azabicyclo[3.1.0]hexan-3-yl]-3-fluorophenyl]-2-oxooxazolidin-5-ylmethyl]acetamide, N-[5(S)-3-[3-Fluoro-4-[(1α,5α,6α)-6-phenylsulfonylamino-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-methanesulfonylamino-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-carbamoylamino-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-formyl-3-azabicyclo[3.1.0]hexan-3-yl]phenyl]-2-oxooxazolidin-5-ylmethyl]acetamide, N-[5(S)-3-[4-[(1α,5α,6α)-6-Carboxyl-3-azabicyclo[3.1.0]hexan-3-yl]-3-fluorophenyl]-2-oxooxazolidin-5-ylmethyl]acetamide, N-[5(S)-3-[4-[(1α,5α,6α)-6-[(1-Iminoethyl)amino]-3-azabicyclo[3.1.0]hexan-3-yl]-3-fluorophenyl]-2-oxooxazolidin-5-ylmethyl]acetamide, N-[5(S)-3-[4-[(1α,5α,6α)-6-Bromomethyl-3-azabicyclo[3.1.0]hexan-3-yl]-3-fluorophenyl]-2-oxooxazolidin-5-ylmethyl]acetamide, N-[5(S)-3-[4-[(1α,5α,6α)-6-Cyanomethyl-3-azabicyclo[3.1.0]hexan-3-yl]-3-fluorophenyl]-2-oxooxazolidin-5-ylmethyl]acetamide, N-[4-[1-(5(S)-Acetylaminomethyl-2-oxooxazolidin-3-yl)-3-fluoro]phenyl-(1α,5α,6α)-3-azabicyclo[3.1.0]hexan-6-yl]methylpyridinium bromide, N-[5(S)-3-[3-Fluoro-4-[(1α,5α,6α)-6-succinimidoyloxycarbonyl-3-azabicyclo[3.1.0]hexan-3-yl]phenyl]-2-oxooxazolidin-5-ylmethyl]acetamide, N-[5(S)-3-[4-[(1α,5α,6α)-6-Carbamoyl-3-azabicyclo[3.1.0]hexan-3-yl]-3-fluorophenyl]-2-oxooxazolidin-5-ylmethyl]acetamide, N-[5(S)-3-[3-Fluoro-4-[(1α,5α,6α)-6-methoxycarbonyl-3-azabicyclo[3.1.0]hexan-3-yl]phenyl]-2-oxooxazolidin-5-ylmethyl]acetamide, N-[5(S)-3-[4-[(1α,5α,6α)-6-[N',N"-Bis(benzyloxycarbonyl)guanidino]-3-azabicyclo[3.1.0]hexan-3-yl]-3-fluorophenyl]-2-oxooxazolidin-5-ylmethyl]acetamide, N-[5(S)-3-[3-Fluoro-4-[(1α,5α,6α)-6-guanidino-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-methylcarbamoyl-3-azabicyclo[3.1.0]hexan-3-yl]phenyl]-2-oxooxazolidin-5-ylmethyl]acetamide, N-[5(S)-3-[4-[(1α,5α,6α)-6-Dimethylcarbamoyl-3-azabicyclo[3.1.0]hexan-3-yl]-3-fluorophenyl]-2-oxooxazolidin-5-ylmethyl]acetamide, N-[5(S)-3-[3-Fluoro-4-[(1α,5α,6α)-6-[(piperidin-1-yl)carbonyl]-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-[(morpholin-4-yl)carbonyl]-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-[N-(2-hydroxyethyl)carbamoyl]-3-azabicyclo[3.1.0]hexan-3-yl]phenyl]-2-oxooxazolidin-5-ylmethyl]acetamide, N-[5(S)-3-[4-[(1α,5α,6α)-6-(2-Aminoethyl)-3-azabicyclo[3.1.0]hexan-3-yl]-3-fluorophenyl]-2-oxooxazolidin-5-ylmethyl]acetamide, N-[5(S)-3-[3-Fluoro-4-[(1α,5α,6α)-6-(1-hydroxyethyl)-3-azabicyclo[3.1.0]hexan-3-yl]phenyl]-2-oxooxazolidin-5-ylmethyl]acetamide, N-[5(S)-3-[4-[(1α,5α,6α)-6-Acetyl-3-azabicyclo[3.1.0]hexan-3-yl]-3-fluorophenyl]-2-oxooxazolidin-5-ylmethyl]acetamide, (E)-N-[5(S)-3-[3-Fluoro-4-[(1α,5α,6α)-6-[(hydroxyamino)methyl]-3-azabicyclo[0.1.0]hexan-3-yl]phenyl]-2-oxooxazolidin-5-ylmethyl]acetamide, (Z)-N-[5(S)-3-[3-Fluoro-4-[(1α,5α,6α)-6-[(hydroxyamino)methyl]-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-[(methoxyimino)methyl]-3-azabicyclo[3.1.0]hexan-3-yl]phenyl]-2-oxooxazolidin-5-ylmethyl]acetamide, N-[5(S)-3-[4-[(1α,5α,6α)-6-[(t-Butoxycarbonylmethyloxyimino)methyl]-3-azabicyclo[3.1.0]hexan-3-yl]-3-fluorophenyl]-2-oxooxazolidin-5-ylmethyl]acetamide, N-[5(S)-3-[4-[(1α,5α,6α)-6-[(Carboxyolmethyloxyimino)methyl]-3-azabicyclo[3.1.0]hexan-3-yl]-3-fluorophenyl]-2-oxooxazolidin-5-ylmethyl]acetamide, N-[5(S)-3-[4-[(1α,5α,6α)-6-Cyano-3-azabicyclo[3.1.0]hexan-3-yl]-3-fluorophenyl]-2-oxooxazolidin-5-ylmethyl]acetamide, N-[((5S)-3-{4-[(1R,5R,6S)-6-cyanobicyclo[3.1.0.]hex-2-en-3-yl]-3-fluorophenyl}-2-oxo-1,3-oxazolidin-5-yl)methyl]acetamide, N-[5(S)-3-[4-[(1α,5α,6α)-6-Aminobicyclo[3.1.0]hex-2-en-3-yl]-3-fluorophenyl]-2-oxooxazolidin-5-ylmethyl]acetamide hydrochloride, N-[((5S)-3-{4-[(1S,5S,6R)-6-cyanobicyclo[3.1.0]hex-2-en-3-yl]-3-fluorophenyl}-2-oxo-1,3-oxazolidin-5-yl)methyl]acetamide, N-[5(S)-3-[4-[(1R,5R,6S)-6-Cyanobicyclo[3.1.0]hex-2-en-3-yl]-3,5-difluorophenyl]-2-oxooxazolidin-5-ylmethyl]acetamide, N-[5(S)-3-[4-[(1S,5S,6R)-6-Cyanobicyclo[3.1.0]hex-2-en-3-yl]-3,5-difluorophenyl]-2-oxooxazolidin-5-ylmethyl]acetamide, N-[5(S)-3-[4-[(1R,5R,6S)-6-Aminobicyclo[3.1.0]hex-2-en-3-yl]-3-fluorophenyl]-2-oxooxazolidin-5-ylmethyl]acetamide, N-[5(S)-3-[4-[(1S,5S,6R)-6-Aminobicyclo[3.1.0]hex-2-en-3-yl]-3-fluorophenyl]-2-oxooxazolidin-5-ylmethyl]acetamide, N-[5(S)-3-[4-[(1R,5R,6S)-6-Aminobicyclo[3.1.0]hex-2-en-3-yl]-3,5-difluorophenyl]-2-oxooxazolidin-5-ylmethyl]acetamide, N-[5(S)-3-[4-[(1S,5S,6R)-6-Aminobicyclo[3.1.0]hex-2-en-3-yl]-3,5-difluorophenyl]-2-oxooxazolidin-5-ylmethyl]acetamide, N-[5(S)-3-[3-Fluoro-4-[(1R,5R,6S)-6-hydroxymethylbicyclo[3.1.0]hex-2-en-3-yl]phenyl]-2-oxooxazolidin-5-ylmethyl]acetamide, N-[5(S)-3-[3-Fluoro-4-[(1S,5S,6R)-6-hydroxymethylbicyclo[3.1.0]hex-2-en-3-yl]phenyl]-2-oxooxazolidin-5-ylmethyl]acetamide, N-[5(S)-3-[3,5-Difluoro-4-[(1R,5R,6S)-6-hydroxymethylbicyclo[3.1.0]hex-2-en-3-yl]phenyl]-2-oxooxazolidin-5-ylmethyl]acetamide, N-[5(S)-3-[3,5-Difluoro-4-[(1S,5S,6R)-6-hydroxymethylbicyclo[3.1.0]hex-2-en-3-yl]phenyl]-2-oxooxazolidin-5-ylmethyl]acetamide, N-[5(S)-3-[4-[(1α,4α,5α,6α)-6-Aminobicyclo[3.1.0]hexan-3-yl]-3-fluorophenyl]-2-oxooxazolidin-5-ylmethyl]acetamide, N-[5(S)-3-[4-[(1α,4α,5α,6α)-6-Aminobicyclo[3.1.0]hexan-3-yl]-3-fluorophenyl]-2-oxooxazolidin-5-ylmethyl]acetamide, N-[5(S)-3-[4-[(1α,4α,5α,6α)-6-Aminobicyclo[3.1.0]hexan-3-yl]-3,5-difluorophenyl]-2-oxooxazolidin-5-ylmethyl]acetamide, N-[5(S)-3-[4-[(1α,4α,5α,6α)-6-Aminobicyclo[3.1.0]hexan-3-yl]-3,5-difluorophenyl]-2-oxooxazolidin-5-ylmethyl]acetamide, N-[5(S)-3-[4-[(1α,4α,5α,6α)-6-Cyanobicyclo[3.1.0]hexan-3-yl]-3-fluorophenyl]-2-oxooxazolidin-5-ylmethyl]acetamide, N-[5(S)-3-[4-[(1α,4α,5α,6α)-6-Cyanobicyclo[3.1.0]hexan-3-yl]-3-fluorophenyl]-2-oxooxazolidin-5-ylmethyl]acetamide, N-[5(S)-3-[4-[(1α,4α,5α,6α)-6-Cyanobicyclo[3.1.0]hexan-3-yl]-3,5-difluorophenyl]-2-oxooxazolidin-5-ylmethyl]acetamide, N-[5(S)-3-[4-[(1α,4α,5α,6α)-6-Cyanobicyclo[3.1.0]hexan-3-yl]-3,5-difluorophenyl]-2-oxooxazolidin-5-ylmethyl]acetamide, N-[5(S)-3-[3-Fluoro-4-[(1α,4α,5α,6α)-6-hydroxymethylbicyclo[3.1.0]hexan-3-yl]phenyl]-2-oxooxazolidin-5-ylmethyl]acetamide, N-[5(S)-3-[3-Fluoro-4-[(1α,4α,5α,6α)-6-hydroxymethylbicyclo[3.1.0]hexan-3-yl]phenyl]-2-oxooxazolidin-5-ylmethyl]acetamide, N-[5(S)-3-[3,5-Difluoro-4-[(1α,4α,5α,6α)-6-hydroxymethylbicyclo[3.1.0]hexan-3-yl]phenyl]-2-oxooxazolidin-5-ylmethyl]acetamide, N-[5(S)-3-[3,5-Difluoro-4-[(1α,4β,5α,6α)-6-hydroxymethylbicyclo[3.1.0]hexan-3-yl]phenyl]-2-oxooxazolidin-5-ylmethyl]acetamide, (E)-N-[5(S)-3-[3-Fluoro-4-[(1α,5α,6α)-6-[(hydroxyimino)aminomethyl]-3-azabicyclo[3.1.0]hexan-3-yl]phenyl]-2-oxooxazolidin-5-ylmethyl]acetamide, (Z)-N-[5(S)-3-[3-Fluoro-4-[(1α,5α,6α)-6-[(hydroxyimino)aminomethyl]-3-azabicyclo[3.1.0]hexan-3-yl]phenyl]-2-oxooxazolidin-5-ylmethyl]acetamide, (Z)-N-[5(S)-3-[3-Fluoro-4-[(1α,5α,6α)-6-[(hydroxyimino)aminomethyl]-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-[(2-(methoxy)methoxyimino)methyl]-3-azabicyclo[3.1.0]hexan-3-yl]phenyl]-2-oxooxazolidin-5-ylmethyl]acetamide, N-[5(S)-3-[4-[(1α,5α,6α)-6-[(2-(Dimethylamino)ethoxyimino)methyl]-3-azabicyclo[3.1.0]hexan-3-yl]-3-fluorophenyl]-2-oxooxazolidin-5-ylmethyl]acetamide, N-[5(S)-3-[4-[(1α,5α,6α)-6-[(3-(Dimethylamino)
propoxyimino)methyl]-3-azabicyclo[3.1.0]hexan-3-
yl]-3-fluorophenyl]-2-oxooxazolidin-5-ylmethyl]
acetamide, N-[5(S)-3-[3-Fluoro-4-[(1α,5α,6α)-6-[(N-(4-
morpholinyl)imino)methyl]-3-azabicyclo[3.1.0]hexan-
3-yl]phenyl]-2-oxooxazolidin-5-ylmethyl]acetamide, N-[5(S)-3-[4-[(1α,5α,6α)-6-[(1-(1-t-Butoxycarboxyl-1-
methyl)ethoxy)iminomethyl]-3-azabicyclo[3.1.0]
hexan-3-yl]-3-fluorophenyl]-2-oxooxazolidin-5-
ylmethyl]acetamide, N-[5(S)-3-[4-[(1α,5α,6α)-6-[(1-(1-Carboxyl-1-methyl)
ethoxy)iminomethyl]-3-azabicyclo[3.1.0]hexan-3-yl]-
3-fluorophenyl]-2-oxooxazolidin-5-ylmethyl]
acetamide, N-[5(S)-3-[3-Fluoro-4-[(1α,5α,6α)-6-[(2-
hydroxyethoxy)iminomethyl]-3-azabicyclo[3.1.0]
hexan-3-yl]phenyl]-2-oxooxazolidin-5-ylmethyl]
acetamide, N-[5(S)-3-[3-Fluoro-4-[(1α,5α,6α)-6-[(5-
tetrazolylmethoxy)iminomethyl]-3-azabicyclo[3.1.0]
hexan-3-yl]phenyl]-2-oxooxazolidin-5-ylmethyl]
acetamide, N-[5(S)-3-[4-[(1α,5α,6α)-6-Cyano-3-azabicyclo[3.1.0]
hexan-3-yl]-3-fluorophenyl]-2-oxooxazolidin-5-
ylmethyl]acetamide N-Oxide, N-[5(S)-3-[4-[(1α,5α,6α)-6-Ethenyl-3-azabicyclo[3.1.0]
hexan-3-yl]-3-fluorophenyl]-2-oxooxazolidin-5-
ylmethyl]acetamide, N-[5(S)-3-[3-Fluoro-4-[(1α,5α,6α)-6-hydroxy-3-
azabicyclo[3.1.0]hexan-3-yl]phenyl]-2-oxooxazolidin-
5-ylmethyl]acetamide, N-[5(S)-3-[4-[(1α,5α,6α)-6-(t-Butyldimethylsilyl)oxy-3-
azabicyclo[3.1.0]hexan-3-yl]-3-fluorophenyl]-2-
oxooxazolidin-5-ylmethyl]acetamide, N-[5(S)-3-[3-Fluoro-4-[(1α,5α,6α)-6-(2-hydroxyethyl)-
3-azabicyclo[3.1.0]hexan-3-yl]phenyl]-2-
oxooxazolidin-5-ylmethyl]acetamide, N-[5(S)-3-[4-[(1α,5α,6α)-6-(1,2-Dihydroxyethyl)-3-
azabicyclo[3.1.0]hexan-3-yl]-3-fluorophenyl]-2-
oxooxazolidin-5-ylmethyl]acetamide, N-[5(S)-3-[4-[(1α,5α,6α)-6-(2-(t-Butyldimethylsilyl)
oxy-1-hydroxyethyl)-3-azabicyclo[3.1.0]hexan-3-yl]-
3-fluorophenyl]-2-oxooxazolidin-5-ylmethyl]
acetamide, N-[5(S)-3-[4-[(1α,5α,6α)-6-[(2-(t-Butyldimethylsilyl)
oxy)acetyl]-3-azabicyclo[3.1.0]hexan-3-yl]-3-
fluorophenyl]-2-oxooxazolidin-5-ylmethyl]acetamide, N-[5(S)-3-[3-Fluoro-4-[(1α,5α,6α)-6-hydroxyacetyl-3-
azabicyclo[3.1.0]hexan-3-yl]phenyl]-2-oxooxazolidin-
5-ylmethyl]acetamide, N-[5(S)-3-[4-[(1α,5α,6α)-6-[(1-(2,3-Dihydroxy)
propyloxy)iminomethyl]-3-azabicyclo[3.1.0]hexan-3-
yl]-3-fluorophenyl]-2-oxooxazolidin-5-ylmethyl]
acetamide, N-[5(S)-3-[4-[(1α,5α,6α)-6-[(2-(1,3-Dihydroxy)
propyloxy)iminomethyl]-3-azabicyclo[3.1.0]hexan-3-
yl]-3-fluorophenyl]-2-oxooxazolidin-5-ylmethyl]
acetamide, N-[5(S)-3-[3-Fluoro-4-[(1α,5α,6α)-6-[(1-(2-(2-
hydroxyethoxy))ethoxy)iminomethyl]-3-azabicyclo
[3.1.0]hexan-3-yl]phenyl]-2-oxooxazolidin-5-
ylmethyl]acetamide, N-[5(S)-3-[4-[(1α,5α,6α)-6-(Cyanomethyloxy)
iminomethyl]-3-azabicyclo[3.1.0]hexan-3-yl]-3-
fluorophenyl]-2-oxooxazolidin-5-ylmethyl]acetamide, N-[5(S)-3-[3-Fluoro-4-[(1α,5α,6α)-6-[(1-(2-methylthio)
ethoxy)iminomethyl]-3-azabicyclo[3.1.0]hexan-3-yl]
phenyl]-2-oxooxazolidin-5-ylmethyl]acetamide, N-[5(S)-3-[3-Fluoro-4-[(1α,5α,6α)-6-[(1-(2-
methylsulfinyl)ethoxy)iminomethyl]-3-azabicyclo
[3.1.0]hexan-3-yl]phenyl]-2-oxooxazolidin-5-
ylmethyl]acetamide, N-[5(S)-3-[3-Fluoro-4-[(1α,5α,6α)-6-[(1-(2-
methylsulfonyl)ethoxy)iminomethyl]-3-azabicyclo
[3.1.0]hexan-3-yl]phenyl]-2-oxooxazolidin-5-
ylmethyl]acetamide, N-[5(S)-3-[4-[(1α,5α,6α)-6-Aminomethyl-3-azabicyclo
[3.1.0]hexan-3-yl]-3-fluorophenyl]-2-oxooxazolidin-
5-ylmethyl]acetamide, N-[5(S)-3-[3-Fluoro-4-[(1α,5α,6α)-6-(hydroxyethyl)
amino-3-azabicyclo[3.1.0]hexan-3-yl]phenyl]-2-
oxooxazolidin-5-ylmethyl]acetamide, N-[5(S)-3-[4-[(1α,5α,6α)-6-(2-Aminoethyl)amino-3-
azabicyclo[3.1.0]hexan-3-yl]-3-fluorophenyl]-2-
oxooxazolidin-5-ylmethyl]acetamide, N-[5(S)-3-[3-Fluoro-4-[(1α,5α,6α)-6-(pyridin-2-yl)
amino-3-azabicyclo[3.1.0]hexan-3-yl]phenyl]-2-
oxooxazolidin-5-ylmethyl]acetamide, N-[5(S)-3-[4-[(1α,5α,6α)-6-(3-Cyanopyridin-2-yl)
amino-3-azabicyclo[3.1.0]hexan-3-yl ]-3-
fluorophenyl]-2-oxooxazolidin-5-ylmethyl]acetamide, N-[5(S)-3-[4-[(1α,5α,6α)-6-(5-Cyanopyridin-2-yl)
amino-3-azabicyclo[3.1.0]hexan-3-yl]-3-
fluorophenyl]-2-oxooxazolidin-5-ylmethyl]acetamide, N-[5(S)-3-[4-[(1α,5α,6α)-6-(3-Cyanopyrazin-2-yl)
amino-3-azabicyclo[3.1.0]hexan-3-yl]-3-
fluorophenyl]-2-oxooxazolidin-5-ylmethyl]acetamide, N-[5(S)-3-[3-Fluoro-4-[(1α,5α,6α)$_6$-(pyrimidin-2-yl)
amino-3-azabicyclo[3.1.0]hexan-3-yl]phenyl]-2-
oxooxazolidin-5-ylmethyl]acetamide, N-[5(S)-3-[4-[(1α,5α,6α)-6-(4-Aminopyrimidin-2-yl)
amino-3-azabicyclo[3.1.0]hexan-3-yl]-3-
fluorophenyl]-2-oxooxazolidin-5-ylmethyl]acetamide, N-[5(S)-3-[4-[(1α,5α,6α)-6-Amino-3-azabicyclo[3.1.0]
hexan-3-yl]-3,5-difluorophenyl]-2-oxooxazolidin-5-
ylmethyl]acetamide, N-[5(S)-3-[3,5-Difluoro-4-[(1α,5α,6α)-6-
hydroxymethyl-3-azabicyclo[3.1.0]hexan-3-yl]
phenyl]-2-oxooxazolidin-5-ylmethyl]acetamide, N-[5(S)-3-[3,5-Difluoro-4-[(1α,5α,6α)-6-formyl-3-
azabicyclo[3.1.0]hexan-3-yl]phenyl]-2-oxooxazolidin-
5-ylmethyl]acetamide, N-[5(S)-3-[4-[(1α,5α,6α)-6-Cyanomethyl-3-azabicyclo
[3.1.0]hexan-3-yl]-3,5-difluorophenyl]-2-
oxooxazolidin-5-ylmethyl]acetamide, N-[5(S)-3-[3,5-Difluoro-4-[(1α,5α,6α)-6-
[(hydroxyimino)methyl]-3-azabicyclo[3.1.0]hexan-3-
yl]phenyl]-2-oxooxazolidin-5-ylmethyl]acetamide, N-[5(S)-3-[4-[(1α,5α,6α)-6-Cyano-3-azabicyclo[3.1.0]
hexan-3-yl]-3,5-difluorophenyl]-2-oxooxazolidin-5-
ylmethyl]acetamide, N-[5(S)-3-[3,5-Difluoro-4-[(1α,5α,6α)-6-[(1-(2,3-
dihydroxy)propyloxy)iminomethyl]-3-azabicyclo
[3.1.0]hexan-3-yl]phenyl]-2-oxooxazolidin-5-
ylmethyl]acetamide, N-[5(S)-3-[3,5-Difluoro-4-[(1α,5α,6α)-6-[(2-(1,3-
dihydroxy)propyloxy)iminomethyl]-3-azabicyclo
[3.1.0]hexan-3-yl]phenyl]-2-oxooxazolidin-5-
ylmethyl]acetamide, N-[5(S)-3-[3,5-Difluoro-4-[(1α,5α,6α)-6-[(1-(2-(2-
hydroxyethoxy)ethoxy)iminomethyl]-3-azabicyclo
[3.1.0]hexan-3-yl]phenyl]-2-oxooxazolidin-5-
ylmethyl]acetamide, N-[5(S)-3-[3,5-Difluoro-4-[(1α,5α,6α)-6-[(2-
hydroxyethoxy)iminomethyl]-3-azabicyclo[3.1.0]
hexan-3-yl]phenyl]-2-oxooxazolidin-5-ylmethyl]
acetamide, N-[5(S)-3-[4-[(1α,5α,6α)-6-Amino-3-azabicyclo[3.1.0]
hexan-3-yl]-3-fluorophenyl]-2-oxooxazolidin-5-
ylmethyl]difluoroacetamide, 5(S)-3-[4-[(1α,5α,6α)-6-Amino-3-azabicyclo[3.1.0]
hexan-3-yl]-3-fluorophenyl]-5-(methoxythiocarbonyl)
aminomethyloxazolidin-2-one, 5(R)-3-[4-[(1α,5α,6α)-6-Amino-3-azabicyclo[3.1.0]
hexan-3-yl]-3-fluorophenyl]-5-(isoxazol-3-yl)
oxymethyloxazolidin-2-one, 5(S)-3-[4-[(1α,5α,6α)-6-Amino-3-azabicyclo[3.1.0]
hexan-3-yl]-3-fluorophenyl]-5-(isoxazol-3-yl)
aminomethyloxazolidin-2-one, 5(S)-3-[4-[(1α,5α,6α)-6-Cyano-3-azabicyclo[3.1.0]
hexan-3-yl]-3-fluorophenyl]-5-(isoxazol-3-yl)
aminomethyloxazolidin-2-one, 5(S)-3-[4-[(1α,5α,6α)-6-Amino-3-azabicyclo[3.1.0]
hexan-3-yl]-3-fluorophenyl]-5-(1,2,4-oxadiazol-3-yl)
aminomethyloxazolidin-2-one, 5(S)-3-[4-[(1α,5α,6α)-6-Cyano-3-azabicyclo[3.1.0]
hexan-3-yl]-3-fluorophenyl]-5-(1,2,4-oxadiazol-3-yl)
aminomethyloxazolidin-2-one, and 5(S)-3-[4-[(1α,5α,6α)-6-Amino-3-azabicyclo[3.1.0]
hexan-3-yl]-3-fluorophenyl]-5-(pyridin-2-yl)
aminomethyloxazolidin-2-one.

Alternatively, compounds of the claimed invention are represented as

| Example Number | Structure |
|---|---|
| 1 | 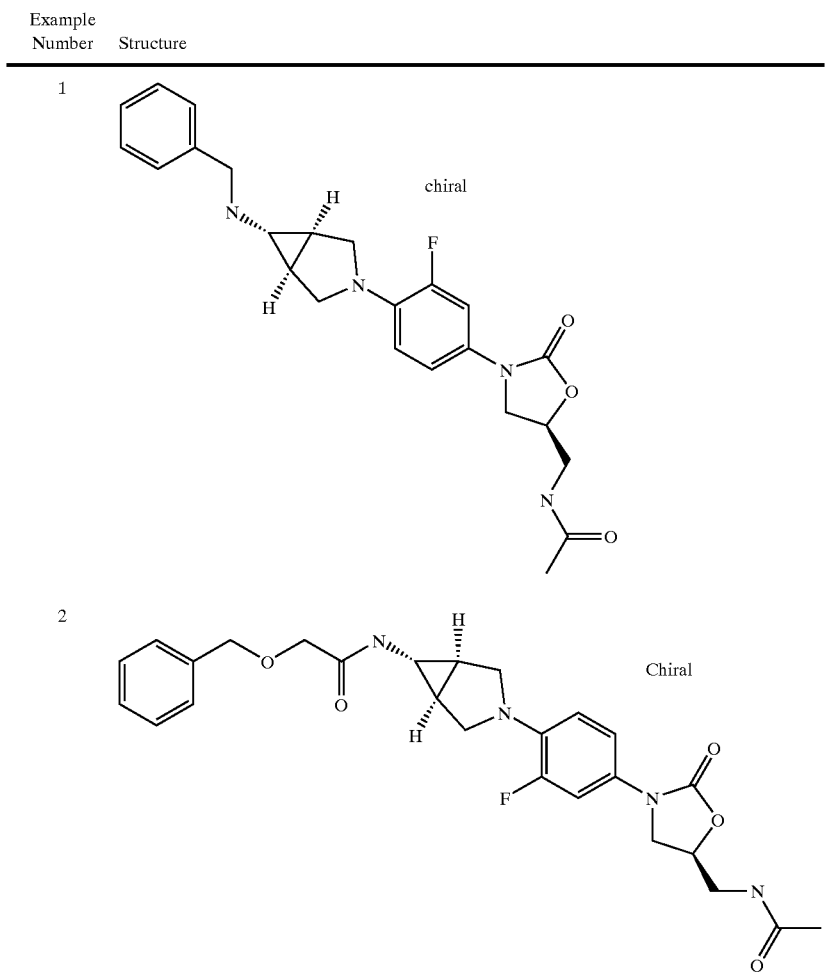 |
| 2 | 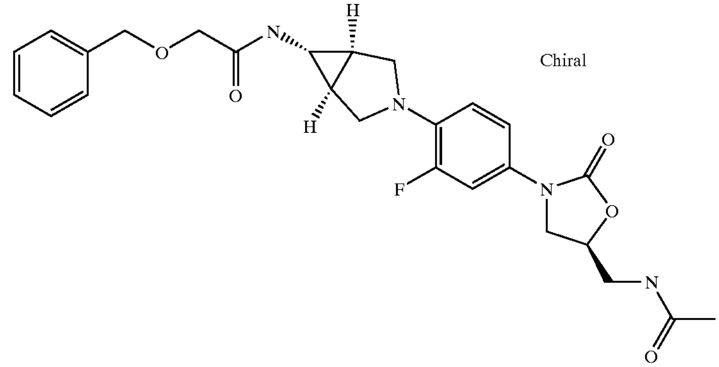 |

-continued
| Example Number | Structure |
|---|---|
| 3 | 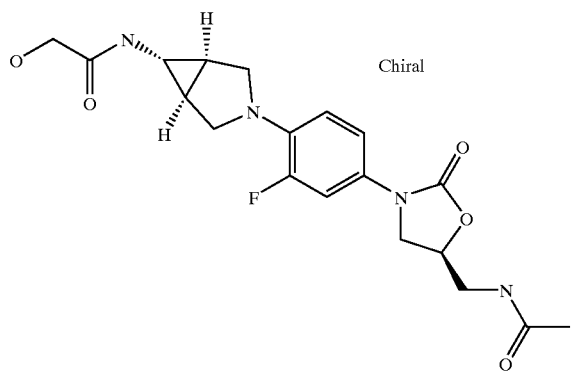 |
| 4 | 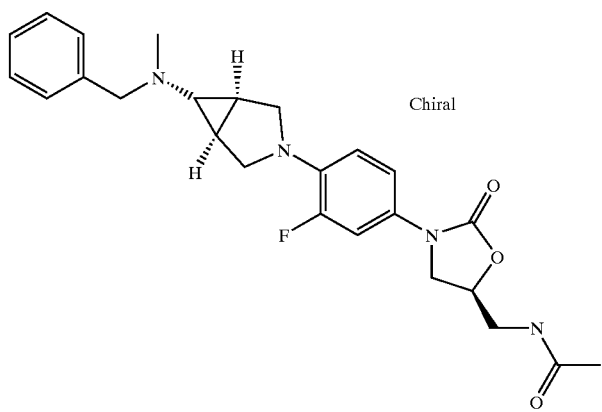 |
| 5 | 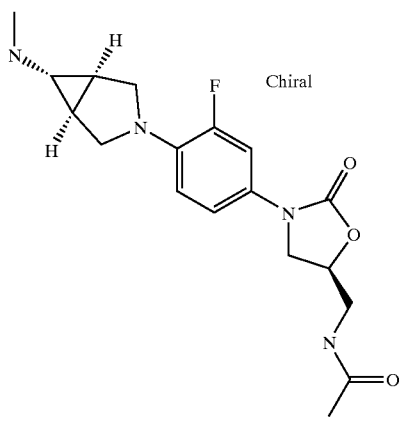 |

-continued
| Example Number | Structure |
|---|---|
| 6 | 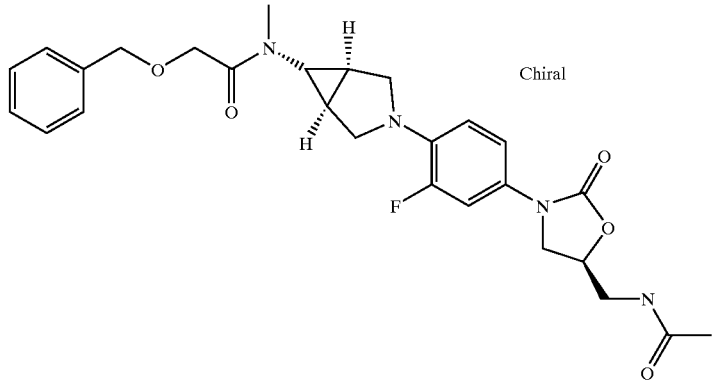 |
| 7 | 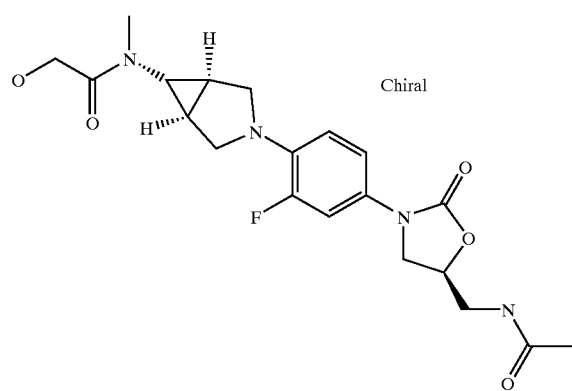 |
| 8 | 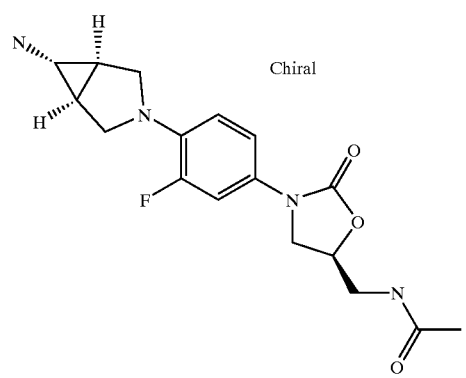 |
| 11 | 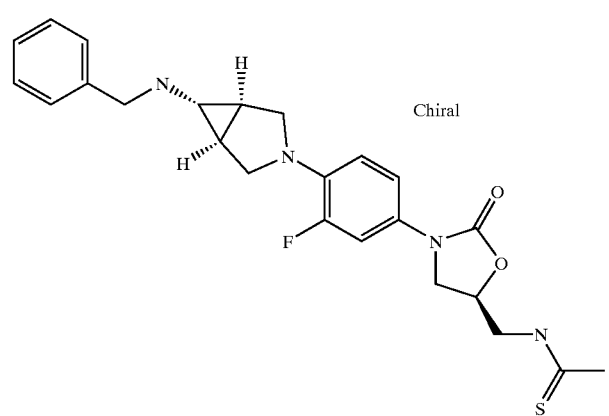 |

-continued
| Example Number | Structure |
|---|---|
| 12 | 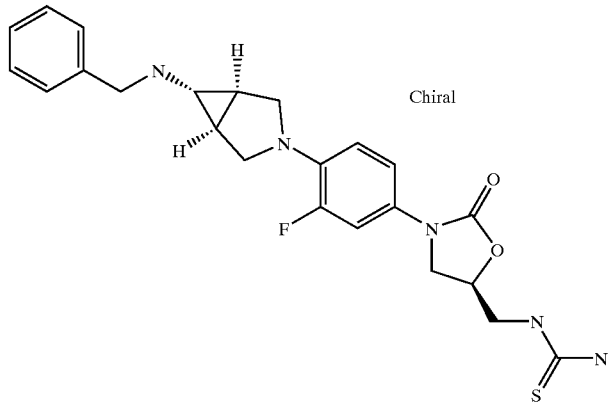 |
| 13 | 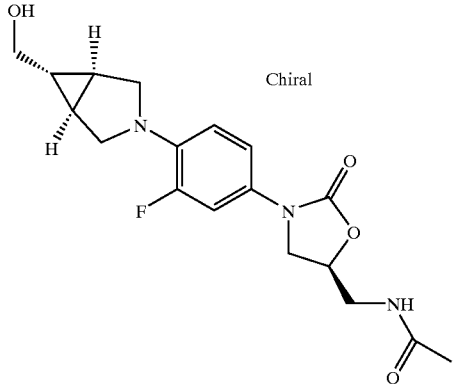 |
| 15 | 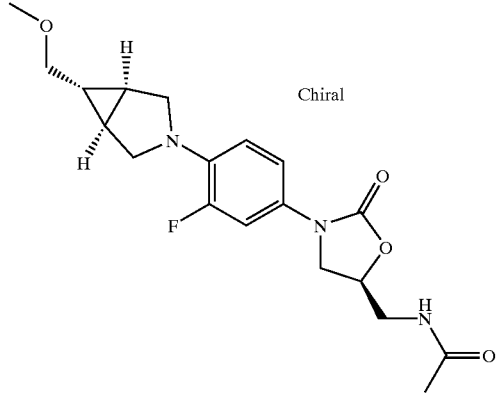 |

-continued
| Example Number | Structure |
|---|---|
| 16 | 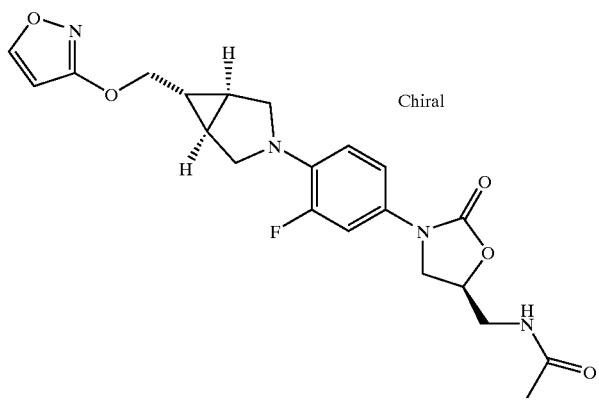 |
| 17 | 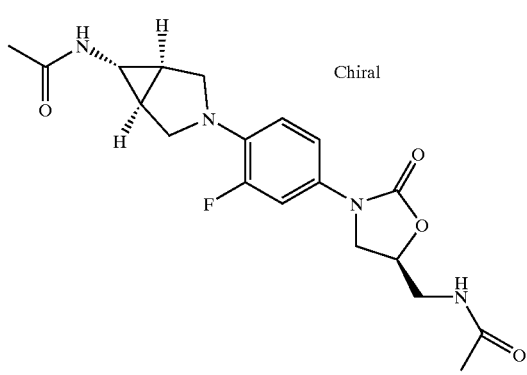 |
| 18 | 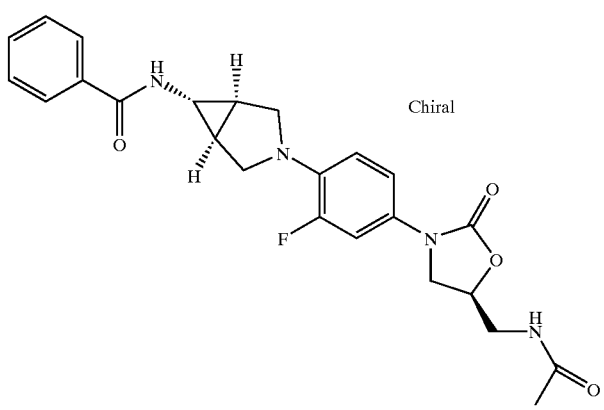 |
| 19 | 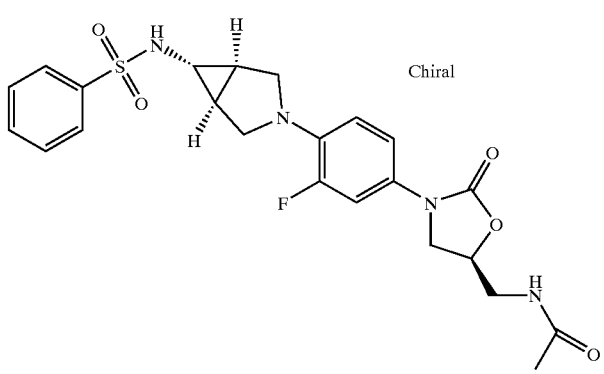 |

-continued

| Example Number | Structure |
|---|---|
| 20 | (chiral structure) |
| 21 | (chiral structure) |
| 22 | (chiral structure) |
| 23 | (chiral structure) |

-continued
| Example Number | Structure |
|---|---|
| 24 | 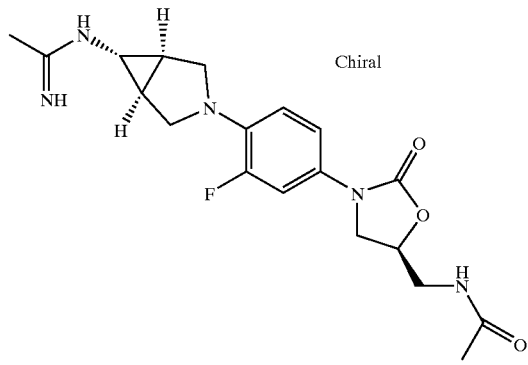 |
| 26 | 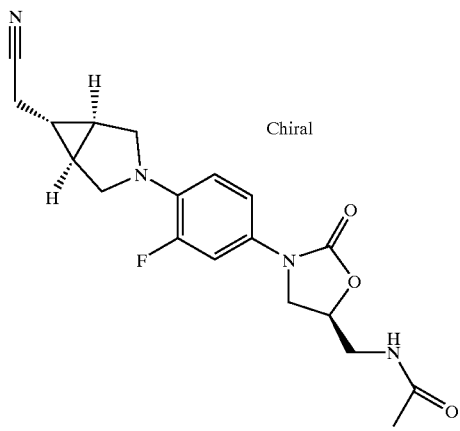 |
| 27 | 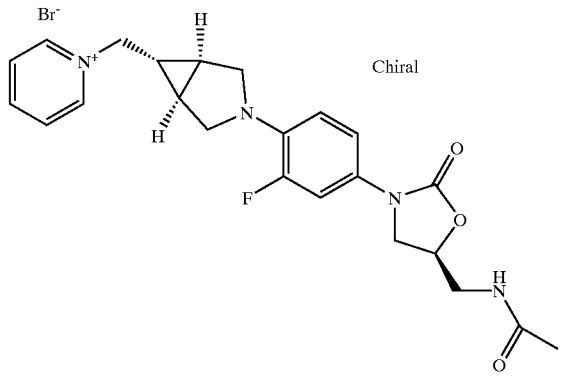 |

-continued
| Example Number | Structure |
|---|---|
| 29 | 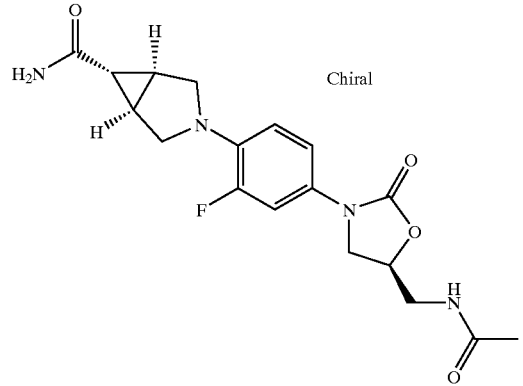 |
| 30 | 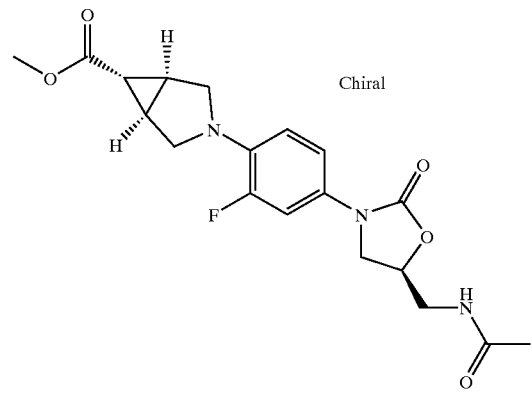 |
| 33 | 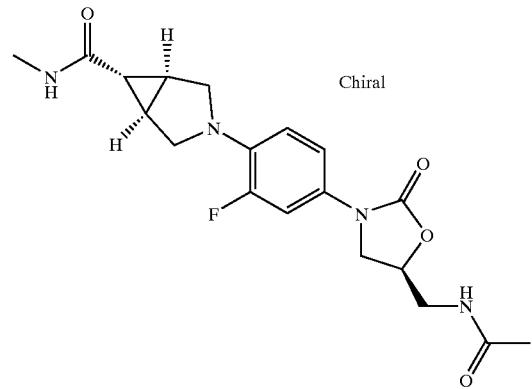 |

| Example Number | Structure |
|---|---|
| 34 | 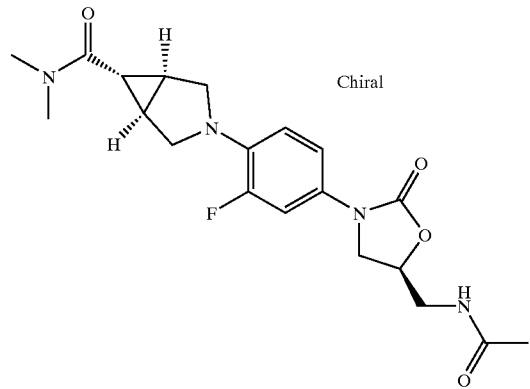 |
| 35 | 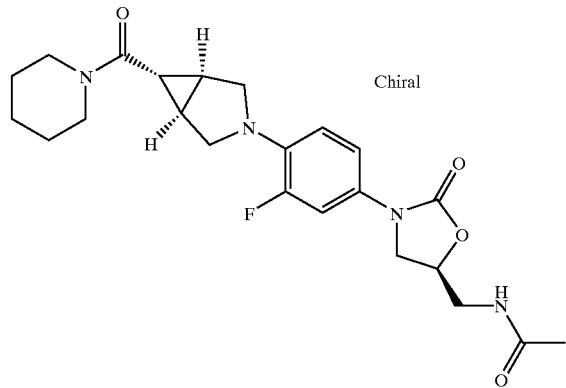 |
| 36 | 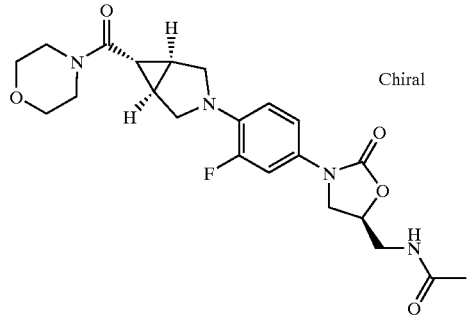 |
| 37 | 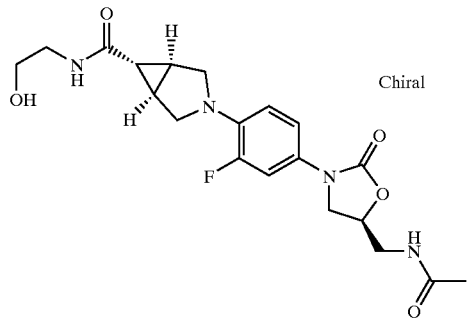 |

-continued
| Example Number | Structure |
|---|---|
| 38 | 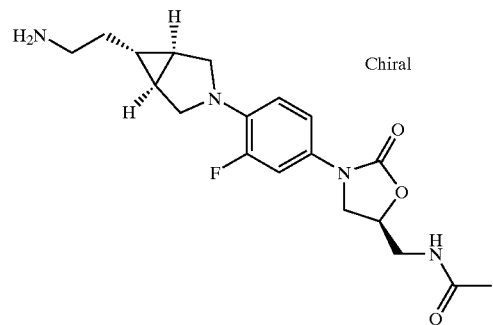 Chiral |
| 40 | 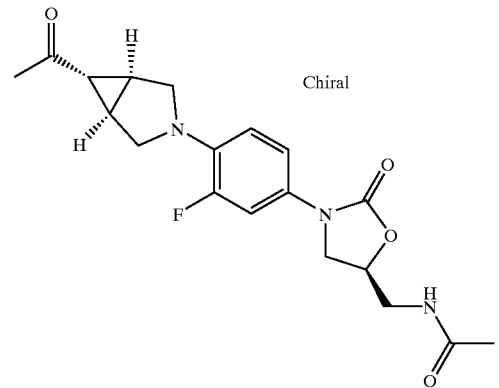 Chiral |
| 41 | 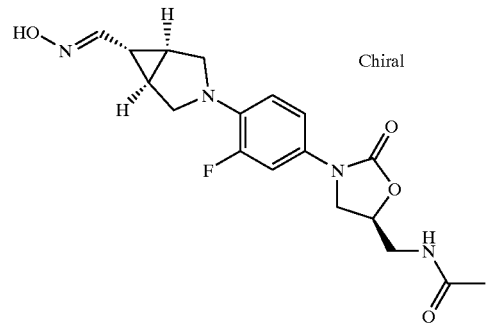 Chiral |
| 42 | 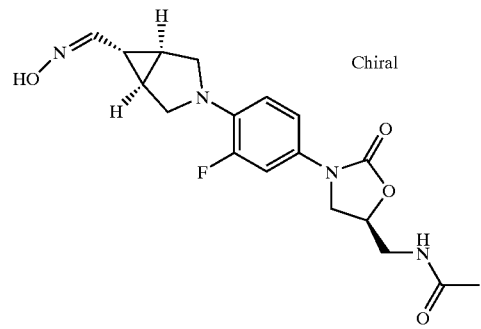 Chiral |

-continued
| Example Number | Structure |
|---|---|
| 43 | 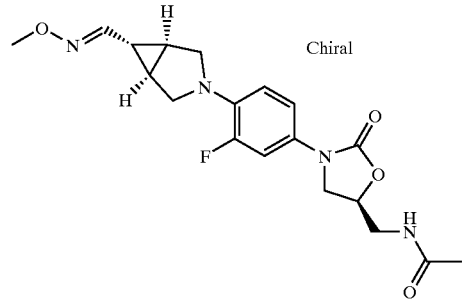 |
| 44 | 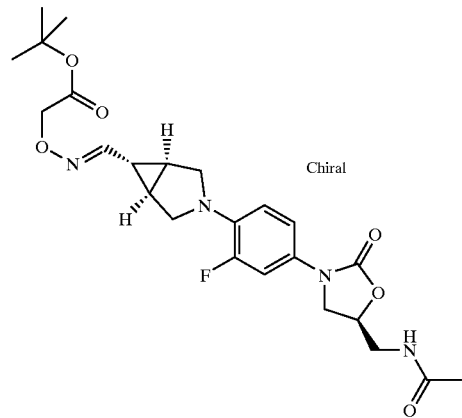 |
| 45 | 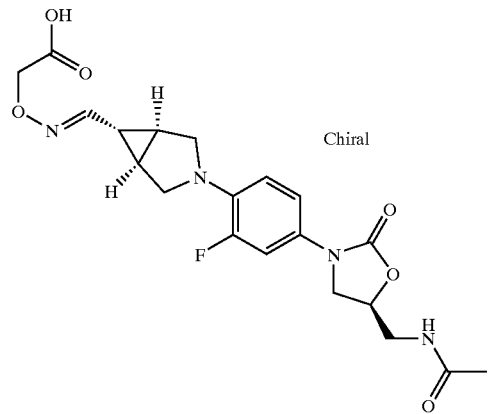 |
| 46 | 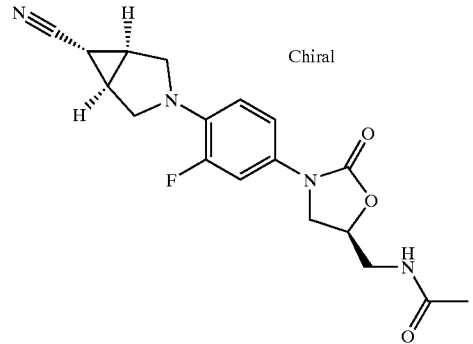 |

-continued
| Example Number | Structure |
|---|---|
| 47 | 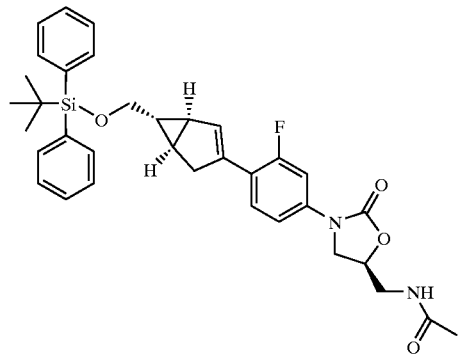 |
| 48 | 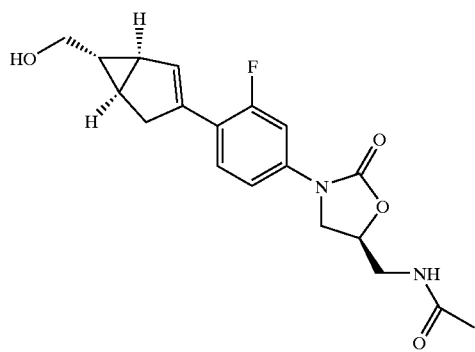 |
| 49 | 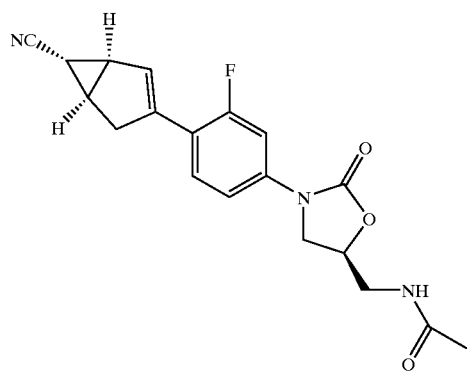 |
| 50 | 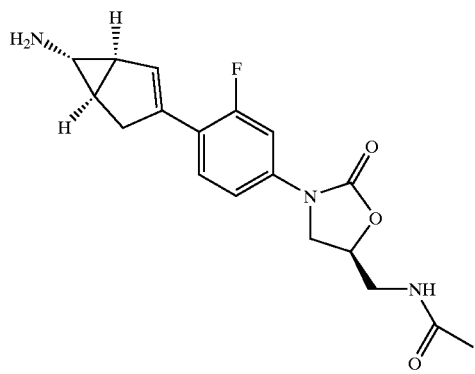 |

The following are also preferred compounds of the invention: 5(S)-3-[4-[(1α,5α,6α)-6-Amino-3-azabicyclo[3.1.0]hexan-3-yl]-3,5-difluorophenyl]-5-[(1,2,4-oxadiazolyl-3-yl)amino]methyloxazolidin-2-one, 5(S)-3-[4-[(1α,5α,6α)-6-Amino-3-azabicyclo[3.1.0]hexan-3-yl]-3,5-difluorophenyl]-5-[(isoxazolyl-3-yl)amino]methyloxazolidin-2-one, 5(S)-3-[4-[(1α,5α,6α)-6-Amino-3-azabicyclo[3.1.0]hexan-3-yl]phenyl]-5-[(isoxazolyl-3-yl)amino]methyloxazolidin-2-one, 5(S)-3-[4-[(1α,5α,6α)-6-Cyanobicyclo[3.1.0]hex-2-en-3-yl]phenyl]-5-[N-(1,2,4-oxadiazolyl-3-yl)]aminomethyloxazolidin-2-one, 5(S)-3-[4-[(1α,5α,6α)-6-Cyanobicyclo[3.1.0]hex-2-en-3-yl]phenyl]-5-[(isoxazolyl-3-yl)amino]methyloxazolidin-2-one, 5(R)-3-[4-[(1α,5α,6α)-6-Cyanobicyclo[3.1.0]hex-2-en-3-yl]phenyl]-5-[(isoxazolyl-3-yl)oxy]methyloxazolidin-2-one, N-[5(S)-3-[4-[(α,5α,6α)-6-[(N-Cyano-1-iminoethyl)amino]-3-azabicyclo[3.1.0]hexan-3-yl]-3,5-difluorophenyl]-2-oxooxazolidin-5-ylmethyl]acetamide, N-[5(S)-3-[4-[(1α,5α,6α)-6-(5-Amino-4-cyano-1,3-Amino-4-cyano-1,3-oxazol-2-yl)-3-azabicyclo[3.1.0]hexan-3-yl]-3-fluorophenyl]-2-oxooxazolidin-5-ylmethyl]acetamide, N-[5(S)-3-[4-[(1α,5α,6α)-6-(5-Amino-4-cyano-1,3-oxazol-2-yl)bicyclo[3.1.0]hex-2-en-3-yl]-3-fluorophenyl]-2-oxooxazolidin-5-ylmethyl]acetamide, N-[5(S)-3-[4-[(1α,5α,6α)-6-Amino-3-azabicyclo[3.1.0]hexan-3-yl]phenyl]-2-oxooxazolidin-5-ylmethyl]acetamide, N-[5(S)-3-[4-[(1α,5α,6α)-6-Hydroxymethylbicyclo[3.1.0]hex-2-en-2-yl]phenyl]-2-oxooxazolidin-5-ylmethyl]acetamide, N-[5(S)-3-[4-[(1α,5α,6α)-6-[(Hydroxyimino)methyl]bicyclo[3.1.0]hex-2-en-2-yl]phenyl]-2-oxooxazolidin-5-ylmethyl]acetamide, N-[5(S)-3-[4-[(1α,5α,6α)-6-Cyanobicyclo[3.1.0]hex-2-en-2-yl]phenyl]-2-oxooxazolidin-5-ylmethyl]acetamide, N-[5(S)-3-[3-Fluoro-4-[(1α,5α,6β)-6-hydroxymethylbicyclo[3.1.0]hex-2-en-3-yl]phenyl]-2-oxooxazolidin-5-ylmethyl]acetamide, N-[5(S)-3-[4-[(1α,5α,6α)-6-Cyanobicyclo[3.1.0]hex-2-en-3-yl]-3-fluorophenyl]-2-oxooxazolidin-5-ylmethyl]acetamide, N-[5(S)-3-[4-[(1α,5α,6β)-6-Hydroxymethylbicyclo[3.1.0]hex-2-en-3-yl]phenyl]-2-oxooxazolidin-5-ylmethyl]acetamide, N-[5(S)-3-[4-[(1α,5α,6β)-6-Cyanobicyclo[3.1.0]hex-2-en-3-yl]phenyl]-2-oxooxazolidin-5-ylmethyl]acetamide, N-[5(S)-3-[4-[(1α,5α,6α)-6-Hydroxymethylbicyclo[3.1.0]hex-2-en-3-yl]phenyl]-2-oxooxazolidin-5-ylmethyl]acetamide (diastereomer A), N-[5(S)-3-[4-[(1α,5α,6α)-6-Cyanobicyclo[3.1.0]hex-2-en-3-yl]phenyl]-2-oxooxazolidin-5-ylmethyl]acetamide (diastereomer A), N-[5(S)-3-[4-[(1α,5α,6α)-6-Hydroxymethylbicyclo[3.1.0]hex-2-en-3-yl]phenyl]-2-oxooxazolidin-5-ylmethyl]acetamide (diastereomer B), N-[5(S)-3-[4-[(1α,5α,6α)-6-Cyanobicyclo[3.1.0]hex-2-en-3-yl]phenyl]-2-oxooxazolidin-5-ylmethyl]acetamide (diastereomer B), N-[5(S)-3-[4-[(1α,5α,6α)-6-[(1-Cyano-2-dimethylamino)ethen-1-yl]-3-azabicyclo[3.1.0]hexan-3-yl]-3-fluorophenyl]-2-oxooxazolidin-5-ylmethyl]acetamide, N-[5(S)-3-[4-[(1α,5α,6α)-6-(3-Amino-1H-pyrazol-4-yl)-3-azabicyclo[3.1.0]hexan-3-yl]-3-fluorophenyl]-2-oxooxazolidin-5-ylmethyl]acetamide.

(E)-N-[5(S)-3-[4-[(1α,5α,6α)-6-[Amino(hydroxyimino)methyl]-3-azabicyclo[3.1.0]hexan-3-yl]-3-fluorophenyl]-2-oxooxazolidin-5-ylmethyl]acetamide, (Z)-N-[5(S)-3-[4-[(1α,5α,6α)-6-[Amino(hydroxyimino)methyl]-3-azabicyclo[3.1.0]hexan-3-yl]-3-fluorophenyl]-2-oxooxazolidin-5-ylmethyl]acetamide, N-[5(S)-3-[4-[(1α,5α,6α)-6-[1-(2-t-Butyldiphenylsilyloxy-1-hydroxy)ethyl]-3-azabicyclo[3.1.0]hexan-3-yl]-3-fluorophenyl]-2-oxooxazolidin-5-ylmethyl]acetamide, N-[5(S)-3-[4-[(1α,5α,6α)-6-[(2-(t-Butyldiphenylsilyl)oxy)acetyl]-3-azabicyclo[3.1.0]hexan-3-yl]-3-fluorophenyl]-2-oxooxazolidin-5-ylmethyl]acetamide, N-[5(S)-3-[5-[(1α,5α,6α)-6-Hydroxymethylbicyclo[3.1.0]hex-2-en-3-yl]pyridin-2-yl]-2-oxooxazolidin-5-ylmethyl]acetamide, N-[5(S)-3-[5-[(1α,5α,6α)-6-[(t-Butyldiphenylsilyl)oxy]methylbicyclo[3.1.0]hex-2-en-3-yl]pyridin-2-yl]-2-oxooxazolidin-5-ylmethyl]acetamide, N-[5(S)-3-[5-[(1α,5α,6α)-6-Cyanobicyclo[3.1.0]hex-2-en-3-yl]pyridin-2-yl]-2-oxooxazolidin-5-ylmethyl]acetamide, N-[5(S)-3-[3,5-Difluoro-4-[(1α,5α,6α)-6-[(hydroxyimino)methyl]bicyclo[3.1.0]hex-2-en-3-yl]phenyl]-2-oxooxazolidin-5-ylmethyl]acetamide, N-[5(S)-3-[3,5-Difluoro-4-[(1α,5α,6α)-6-formylbicyclo[3.1.0]hex-2-en-3-yl]phenyl]-2-oxooxazolidin-5-ylmethyl]acetamide, N-[5(S)-3-[4-[(1R,5R,6S)-6-cyanobicyclo[3.1.0]hex-2-en-3-yl]phenyl]-2-oxooxazolidin-5-ylmethyl]acetamide, N-[5(S)-3-[4-[(1S,5S,6R)-6-cyanobicyclo[3.1.0]hex-2-en-3-yl]phenyl]-2-oxooxazolidin-5-ylmethyl]acetamide, N-[5(S)-3-[4-[(1α,5α,6α)-6-(1-Cyanoethyl)-3-azabicyclo[3.1.0]hexan-3-yl]-3-fluorophenyl]-2-oxooxazolidin-5-ylmethyl]acetamide, N-[5(S)-3-[4-[(1α,5α,6α)-6-(1-Cyano-1-methylethyl)-3-azabicyclo[3.1.0]hexan-3-yl]-3-fluorophenyl]-2-oxooxazolidin-5-ylmethyl]acetamide, 5(S)-3-[4-[(1R,5R,6S)-6-Cyanobicyclo[3.1.0]hex-2-en-3-yl]-3-fluorophenyl]-5-[(1,2,4-oxadiazolyl-3-yl)amino]methyloxazolidin-2-one, 5(S)-3-[4-[(1S,5S,6R)-6-Cyanobicyclo[3.1.0]hex-2-en-3-yl]-3-fluorophenyl]-5-[(1,2,4-oxadiazolyl-3-yl)amino]methyloxazolidin-2-one, N-[5(S)-3-[6-[(1α,5α,6α)-6-Hydroxymethylbicyclo[3.1.0]hex-2-en-3-yl]pyridin-3-yl]-2-oxooxazolidin-5-ylmethyl]acetamide, N-[5(S)-3-[6-[(1α,5α,6α)-6-(Hydroxyimino)methylbicyclo[3.1.0]hex-2-en-3-yl]pyridin-3-yl]-2-oxooxazolidin-5-ylmethyl]acetamide, N-[5(S)-3-[6-[(1α,5α,6α)-6-Cyanobicyclo[3.1.0]hex-2-en-3-yl]pyridin-3-yl]-2-oxooxazolidin-5-ylmethyl]acetamide, N-[5(S)-3-[4-[(1α,5α,6α)-6-Cyano-3-azabicyclo[3.1.0]hexan-3-yl]-3-fluorophenyl]-2-oxooxazolidin-5-ylmethyl]thioacetamide, N-[5(S)-3-[6-[(1α,5α,6α)-6-Cyanobicyclo[3.1.0]hex-2-en-3-yl]pyridin-3-yl]-2-oxooxazolidin-5-ylmethyl]thioacetamide, N-[5(S)-3-[4-[(1α,5α,6α)-6-Cyanobicyclo[3.1.0]hex-2-en-3-yl]phenyl]-2-oxooxazolidin-5-ylmethyl]thioacetamide, N-[5(S)-3-[4-[(1α,5α,6α)-6-(N-Benzyl-N-t-butoxycarbonyl)amino-3-azabicyclo[3.1.0]hexan-3-yl]-3,5-difluorophenyl]-2-oxooxazolidin-5-ylmethyl]acetamide, N-[5(S)-3-[4-[(1α,3α,5α,6α)-6-Cyanobicyclo[3.1.0]hexan-3-yl]-3-fluorophenyl]-2-oxooxazolidin-5-ylmethyl]thioacetamide, N-[5(S)-3-[3-Fluoro-4-[(1α,3α,5α,6α)-6-thiocarbamoylbicyclo[3.1.0]hexan-3-yl]phenyl]-2-oxooxazolidin-5-ylmethyl]acetamide, 5(R)-3-[3-Fluoro-4-[(1α,5α,6α)-6-[(2-tetrahydropyranyl)oxy]methyl-3-azabicyclo[3.1.0]hexan-3-yl]phenyl]-5-[(isoxazolyl-3-yl)oxy]methyloxazolidin, 5(R)-3-[3-Fluoro-4-[(1α,5α,6α)-6-hydroxymethyl-3-azabicyclo[3.1.0]hexan-3-yl]phenyl]-5-[(isoxazolyl-3-yl)oxy]methyloxazolidin-2-one, 5(R)-3-[3-Fluoro-4-[(1α,5α,6α)-6-[(isoxazolyl-3-yl)oxy]methyl-3-azabicyclo[3.1.0]hexan-3-yl]phenyl]-5-[(isoxazolyl-3-yl)oxy]methyloxazolidin-2-one, 5(R)-3-[3-Fluoro-4-[(1α,5α,6α)-6-methoxymethyl-3-azabicyclo[3.1.0]hexan-3-yl]phenyl]-5-[(isoxazolyl-3-yl)oxy]methyloxazolidin-2-one, 5(R)-3-[4-[(1α,5α,6α)-6-(t-Butoxycarbonyl)amino-3-azabicyclo[3.1.0]hexan-3-yl]-3-fluorophenyl]-5-[(isoxazolyl-3-yl)oxy]methyloxazolidin-2-one, 5(S)-3-[4-[(1R,5R,6S)-6-Cyanobicyclo[3.1.0]hex-2-en-3-yl]-3-fluorophenyl]-5-[N-(t-butoxycarbonyl)-N-(1,2,4-oxadiazolyl-3-yl)]aminomethyloxazolidin-2-one, 5(S)-3-[4-[(1S,5S,6R)-6-Cyanobicyclo[3.1.0]hex-2-en-3-yl]-3-fluorophenyl]-5-[N-(t-butoxycarbonyl)-N-(1,2,4-oxadiazolyl-3-yl)]aminomethyloxazolidin-2-one.

Suitable subjects for the administration of the formulation of the present invention include mammals, primates, man, and other animals. In vitro antibacterial activity is predictive of in vivo activity when the compositions are administered to a mammal infected with a susceptible bacterial organism.

Using standard susceptibility tests, the compositions of the invention are determined to be active against MRSA and enterococcal infections.

The compounds of the invention are formulated in pharmaceutical compositions by combining the compounds with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophilized or non-lyophilized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The novel antibiotic compositions of this invention for human delivery per unit dosage, whether liquid or solid, comprise from about 0.01% to as high as about 99% of the bicyclo[3.1.0]hexane discussed herein, the preferred range being from about 10–60% and from about 1% to about 99.99% of one or more of other antibiotics such as those discussed herein, preferably from about 40% to about 90%. The composition will generally contain from about 125 mg to about 3.0 g of the bicyclo[3.1.0]hexane discussed herein; however, in general, it is preferable to employ dosage amounts in the range of from about 250 mg to 1000 mg and from about 200 mg to about 5 g of the other antibiotics discussed herein; preferably from about 250 mg to about 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal the claimed composition in an amount effective to treat said infection.

The preferred methods of administration of the claimed compositions include oral and parenteral, e.g., i.v. infusion, i.v. bolus and i.m. injection formulated so that a unit dosage comprises a therapeutically effective amount of each active component or some submultiple thereof.

For adults, about 5–50 mg/kg of body weight, preferably about 250 mg to about 1000 mg per person of the bicyclo[3.1.0]hexane antibacterial compound and about 250 mg, to about 1000 mg per person of the other antibiotic(s) given one to four times daily is preferred. More specifically, for mild infections a dose of about 250 mg two or three times daily of the bicyclo[3.1.0]hexane antibacterial compound and about 250 mg two or three times daily of the other antibiotic is recommended. For moderate infections against highly susceptible gram positive organisms a dose of about 500 mg each of the bicyclo[3.1.0]hexane and the other antibiotics, three or four times daily is recommended. For severe, life-threatening infections against organisms at the upper limits of sensitivity to the antibiotic, a dose of about 500–2000 mg each of the bicyclo[3.1.0]hexane and the other antibiotics, three to four times daily may be recommended.

For children, a dose of about 5–25 mg/kg of body weight given 2, 3, or 4 times per day is preferred; a dose of 10 mg/kg is typically recommended.

The compounds of the present invention can be prepared according to the procedures of the following schemes and examples, using appropriate materials, and are further exemplified by the following specific examples. The compounds illustrated in the examples are not, however, to be construed as forming the only genus that is considered as the invention. The following examples further illustrate details for the preparation of compounds of the present invention. Those skilled in the art will readily understand that known variations of the conditions and processes of the following preparative procedures can be used to prepare the compounds of the present invention. All temperatures are in degrees Celsius unless otherwise noted.

The compounds of the present invention are prepared according to the Schemes I–VI. In the Schemes that follow X is used to denote an appropriate leaving group and as such may vary in nature depending on the exact reaction conditions employed. Some typical leaving groups may be fluoro, chloro, bromo, iodo, tosyl, mesyl, trifluoromethanesulfonate etc. but these should not be construed as limiting as many leaving groups are well known to those skilled in the art. Scheme I describes the preparation of compounds of the invention in which A is a nitrogen atom and the 3-azabicyclo [3.1.0]hexane has a 6 amino substituent. In step 1 of scheme I a 6-amino-3-azabicyclo[3.1.0]hexane in which the 6-amino substituent is appropriately protected with the protecting groups P and P' is allowed to react with an aryl or appropriate heteroaryl compound bearing a nitro group and a leaving group in the presence or absence of a solvent. Appropriate protecting groups are well known to those skilled in the art and may include but are not limited to such groups as t-butoxycarbonyl, benzyloxycarbonyl or easily removed alkyl substituents such as the benzyl substituent. Examples of appropriate aryl and heteroaryl reaction partners may include, but are not limited to, 3,4-difluoronitrobenzene, 4-fluoronitrobenzene, or 2-nitro-5-fluoropyridine. Examples of appropriate solvents that may be employed are acetonitrile, tetrahydrofuran, methylene chloride, dichloroethane, toluene, dichlorobenzene, or other such solvents well known to those skilled in the art. The reaction is allowed to proceed at an appropriate temperature, which, depending on the solvent may be between 0° C. and 150° C. until such time that the reaction is determined to be complete. The product is then isolated and may or may not be further purified at the pleasure of the investigator and carried on to step 2.

The nitroaryl or heteroaryl compound obtained in step 1 is reduced to the corresponding amino compound in step 2. This transformation may be accomplished by a variety of reducing agents familiar to those skilled in the art such as hydrogenation over an appropriate catalyst such as palladium, platinum, or ruthenium on activated carbon or by chemical methods such reaction $FeCl_3$, $SnCl_2$, or $ZnCl_2$. The resulting amine is then protected with an appropriate protecting group, P", such as benzyloxycarbonyl or t-butoxycarbonyl. The resulting protected aryl or heteroaryl amines are then isolated and carried on to step 3.

In step 3 the protected aryl or heteroaryl amine obtained as the product of step 2 is further reacted with a strong base such as n-butyl lithium or t-butyl lithium to form an anionic species which is then condensed with a glycidyl ester to form the 5-hydroxymethyloxazolidinone which is the product of step 3. It should be realized that reaction with a racemic glycidyl ester will result in the preparation of a racemic 5-hydroxymethyloxazolidinone while reaction with a chiral glycidyl ester will result in a chiral oxazolidinone. If an R-glycidylester is employed, the product will be an R-5-hydroxymethyloxazolidinone and likewise if an S-glycidylester is employed the product will be an S-5-hydroxymethyloxazolidinone. Step 3 is conducted in a suitable solvent such as ether or tetrahydrofuran and is generally conducted at a temperature between −100° C. and 50° C. for a time necessary for complete reaction to occur. In a preferred embodiment of this reaction a solution of n-butyl lithium is added to a solution of the aryl or heteroaryl amine at −78° C., then the glycidyl ester is added and the resulting mixture allowed to warm to room temperature until the Scheme I

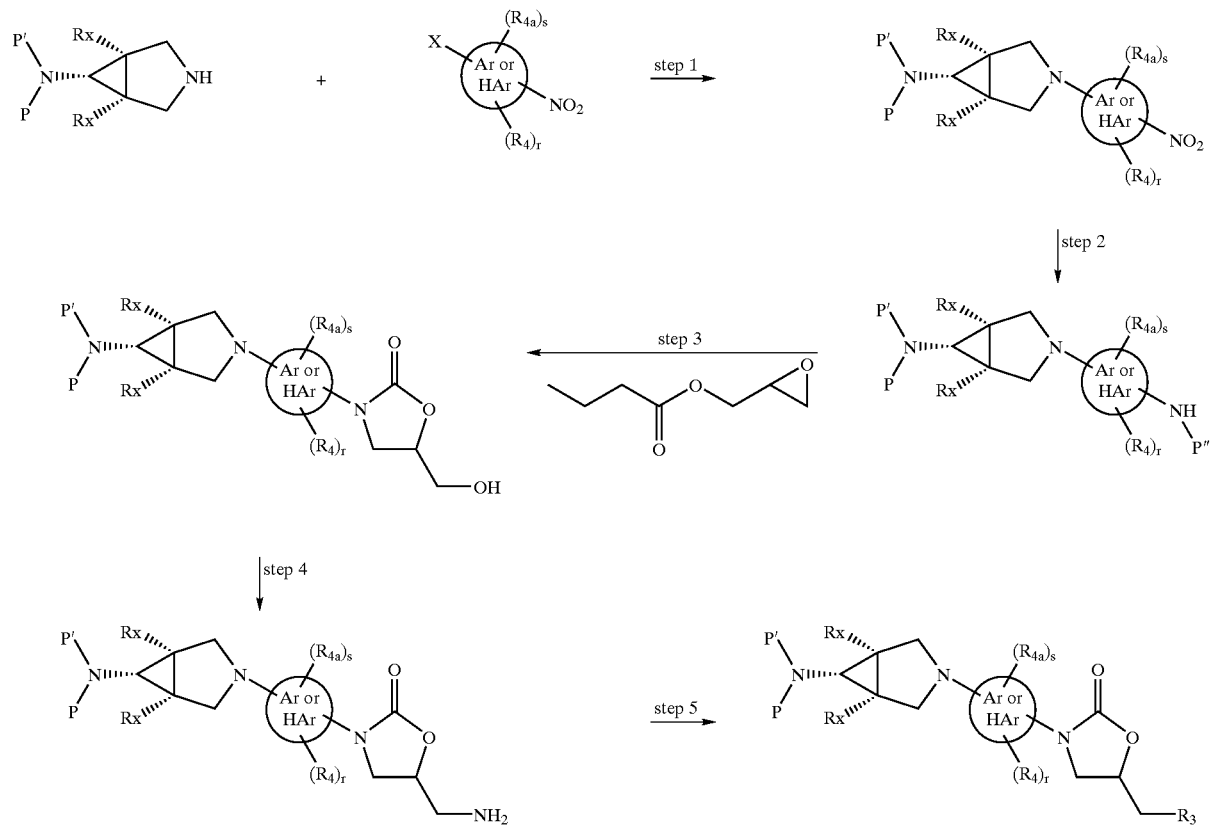

reaction is judged to be complete. The product is then isolated from the reaction mixture by standard techniques and, if necessary, the product may be purified.

In step 4 of Scheme I, the 5-hydroxymethyloxazolidinone is converted to a 5-aminomethyloxazolidinone in a three step process. First the hydroxy group is activated by conversion to a leaving group, X. This is generally accomplished by acylation with acylating agents such as methanesulfonyl chloride, p-toluenesulfonyl chloride or the like, generally with the addition of a hindered base such as triethylamine, diisoproroylethyl amine or the like to scavenge the acid produced in the reaction. Alternatively, if the nature of X is chosen to be a halide such as a bromide or iodide then reagents such as phosphorous tribromide, triphenylphosphonium dibromide or triphenylphosphonium diuodide may be chosen. Suitable solvents include but are not limited to ether, acetonitrile, tetrahydroflran, chlorinated hydrocarbons such as methylene chloride or dichloroethane, pyridine, collidine, or dioxane. In a second step the leaving group is displaced with sodium azide in a suitable solvent such as dimethylformamide, dimethylsulfoxide, or tetramethylurea, tetrahydrofaran and the like at a temperature between 0° C. and 100° C. When the reaction is judged to be complete the product is isolated and the resulting 5-azidooxazolidinone is reduced to the amine. A number of methods for the reduction of azides to amines may be used including hydrogenation over an appropriate catalyst such as palladium or platinum, particularly deactivated catalysts such as Lindlar's catalyst (palladium on $CaCO_3$ deactivated with PbO), or other reducing agents may be employed such as triphenylphosphine or $SnCl_2$. The particular method chosen for this reduction is readily made by one of ordinary skill in the art and is dependent upon the structure of the entirety of the molecule.

In step 5 the 5-aminooxazolidinone is acylated and converted to $R_3$. It is recognized that the exact nature of the reagents used for this conversion is dependent is dependent on the exact nature of the $R_3$ desired. For example if $R_3$ is desired to be an acetylamine group a suitable reagents for performing the acylation would be acetic anhydride, acetyl chloride or the like. However if $R_3$ is desired to be a thioacetylamine group ethyldithioacetate may be an appropriate acylating agent, while 1,1'-thiocarbonyldi-2(1H)-pyridone followed by treatment of the resulting intermediate with aqueous ammonia might be an appropriate procedure if thioureido group was desired for $R_3$. The appropriate conditions and reagents for any particular $R_3$ group will be readily identified by those of ordinary skill in the art.

Further elaboration of the compounds of the present invention prepared in Scheme I may be carried out by the methods shown in Scheme II. In this case in step 1–4 the amino protecting groups, P and P' may be removed together or sequentially by procedures which will be familiar to those skilled in the art for the particular P and P' to be removed. In certain cases a protecting group P may also be present in the compound of the present invention. For example in the case where P is benzyl and P' is t-butoxycarbonyl simple removal of P' by treatment with an appropriate acid such as trifluoroacetic acid or hydrochloric acid in a suitable solvent such as methanol of methylene chloride will result in a compound in which P' is removed and P is retained. As shown in step 5, in some cases the compound in which P is retained may be further modified by means of reductive alkylation, alkylation, or acylation to form compounds, which are also of the present invention and incorporate an $R_5$ as described in the specification. Those skilled in the art will recognize that there are a variety of reagents and reaction conditions available for performing this chemical transformation which include, but are not limited to, the treatment of the product of step 2 with aldehydes, such as formaldehyde, and a reducing agent such as sodium cyanoborohydride, treatment with acylating agents such as anhydrides, acid chlorides, isocyanates, iminoethers, isothiouronium salts, sulfonyl halides, or treatment with alkylating agents such as alkyl iodides, bromides, triflates, or mesylates. Some specific examples of detailed reagents and reaction conditions for carrying out step 5 are detailed in the examples but these should not be construed as limiting for the preparation of compounds of current invention.

Scheme II

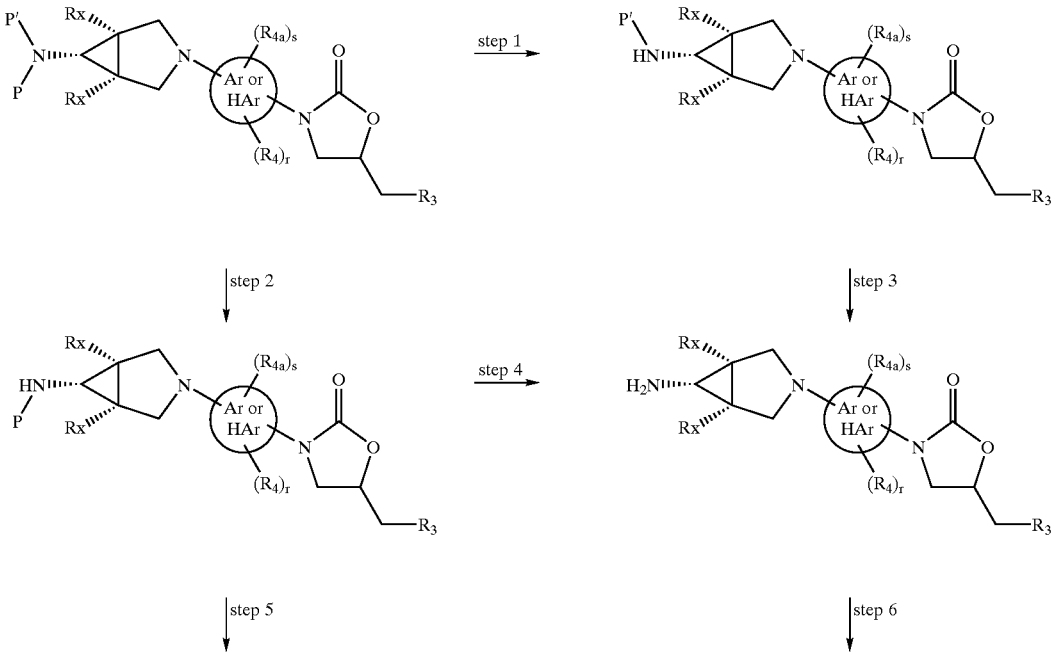

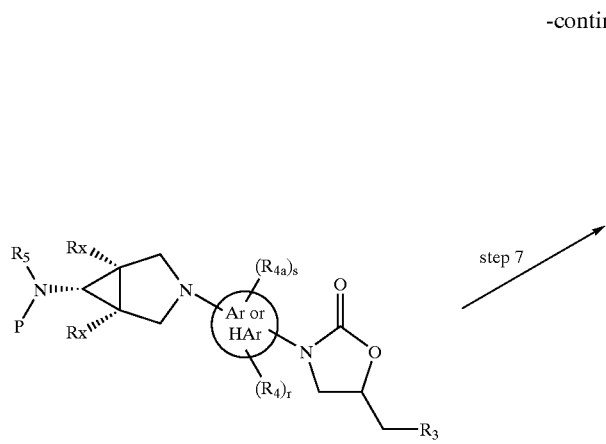

step 7

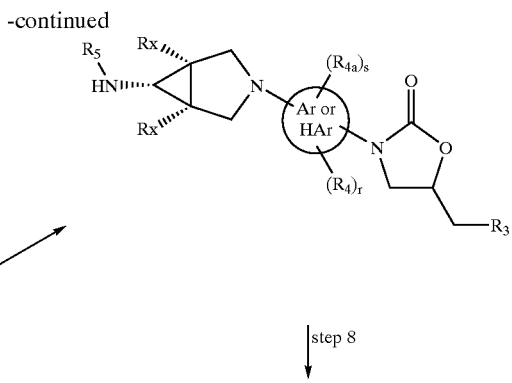

step 8

In a similar manner step 6 exemplifies the further modification compounds in which both of the protecting group, P and P', have been removed. Those skilled in the art will recognize that there are a variety of reagents and reaction conditions available for performing this chemical transformation which include, but are not limited to, the treatment of the completely deprotected product of step 3 or 4 with aldehydes, such as formaldehyde, and a reducing agent such as sodium cyanoborohydride, treatment with acylating agents such as anhydrides, acid chlorides, isocyanates, iminoethers, isothiouronium salts, sulfonyl halides, or treatment with alkylating agents such as alkyl iodides, bromides, triflates, or mesylates. Some specific examples of detailed reagents and reaction conditions for carrying out step 6 are detailed in the examples but these should not be construed as limiting for the preparation of compounds of current invention.

As can be seen for step 7, the product of step 5 may be further modified by removal of the protecting group P to afford the same products as those obtained by step 6. It is recognized that the exact conditions for the removal of P will depend on the exact nature of P but these procedures are well known and can be easily determined by those of ordinary skill in the art.

Step 8 exemplifies the procedures employed for the incorporation of $R_6$, which is structurally independent from that of $R_5$. As shown in step 8, the product of step 6 or 7 may be further modified by alkylation or acylation. Those skilled in the art will recognize that there are a variety of reagents and reaction conditions available for performing this chemical transformation which include, but are not limited to, the treatment of the product of step 6 or 7 with aldehydes, such as formaldehyde, and a reducing agent such as sodium cyanoborohydride, treatment with acylating agents such as anhydrides, acid chlorides, isocyanates, iminoethers, isothiouronium salts, sulfonyl halides, or treatment with alkylating agents such as alkyl iodides, bromides, triflates, or mesylates. Some specific examples of detailed reagents and reaction conditions for carrying out step 8 are detailed in the examples but these should not be construed as limiting for the preparation of compounds of current invention.

Scheme III describes the preparation of compounds of the invention in which A is a nitrogen atom and the 3-azabicyclo[3.1.0]hexane has a 6 carbon substituent. The synthetic sequence is similar to that described in Scheme I except that P''' is a protecting group suitable for the protection of an hydroxyl group or is an alkyl group. Examples of appropriate P''' include, but are not limited to alkyl groups, such as methyl, aralkyl groups such as benzyl or p-methoxybenzyl, silyl groups such as t-butyldiphenylsilyl, t-butyldimethylsilyl and the like, or ether groups such as tetrahydropyranyl or methoxymethyl. In step 1 of scheme III a 3-azabicyclo[3.1.0]hexane in which the 6-alkyl substituent is appropriately protected with the protecting groups P''' is allowed to react with an aryl or appropriate heteroaryl compound bearing a nitro group and a leaving group in the presence or absence of a solvent. Examples of appropriate aryl and heteroaryl reaction partners may include, but are not limited to, 3,4-difluoro-nitrobenzene, 4-fluoronitrobenzene, or 2-nitro-5-fluoropyridine. Examples of appropriate solvents that may be employed are acetonitrile, tetrahydrofuran, methylene chloride, dichloroethane, toluene, dichlorobenzene, or other such solvents well known to those skilled in the art. The reaction is allowed to proceed at an appropriate temperature, which, depending on the solvent may be between 0° C. and 150° C. until such time that the reaction is determined to be complete. The product is then isolated and may or may not be further purified at the pleasure of the investigator and carried on to step 2.

Scheme III

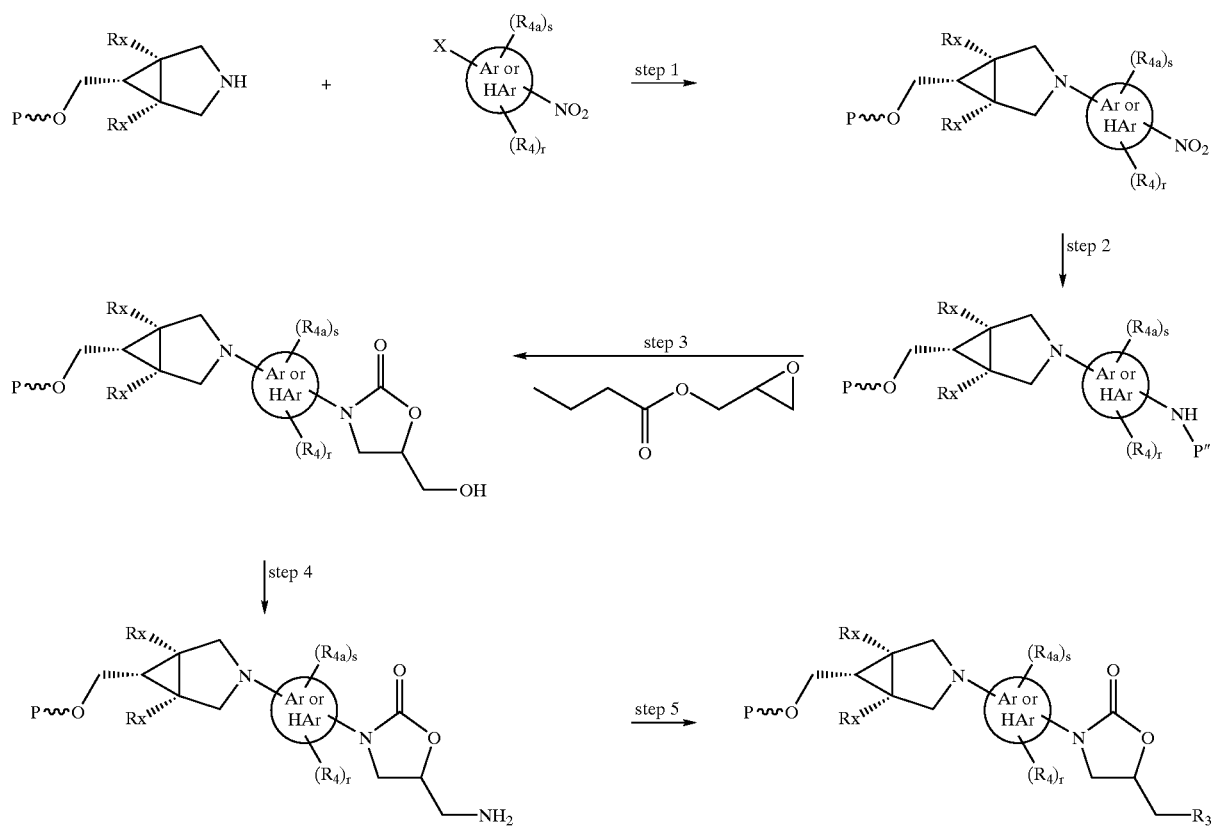

The nitroaryl or heteroaryl compound obtained in step 1 is reduced to the corresponding amino compound in step 2. This transformation may be accomplished by a variety of reducing agents familiar to those skilled in the art such as hydrogenation over an appropriate catalyst such as palladium, platinum, or ruthenium on activated carbon or by chemical methods such reaction $FeCl_3$, $SnCl_2$, or $ZnCl_2$. The resulting amine is then protected with an appropriate protecting group, P″, such as benzyloxycarbonyl or t-butoxycarbonyl. The resulting protected aryl or heteroaryl amines are then isolated and carried on to step 3.

In step 3 the protected aryl or heteroaryl amine obtained as the product of step 2 is further reacted with a strong base such as n-butyl lithium or t-butyl lithium to form an anionic species which is then condensed with a glycidyl ester to form the 5-hydroxymethyloxazolidinone which is the product of step 3. It should be realized that reaction with a racemic glycidyl ester will result in the preparation of a racemic 5-hydroxymethyloxazolidinone while reaction with a chiral glycidyl ester will result in a chiral oxazolidinone. If an R-glycidylester is employed, the product will be an S-5-hydroxymethyloxazolidinone and likewise if an S-glycidylester is employed the product will be an R-5-hydroxymethyloxazolidinone. Step 3 is conducted in a suitable solvent such as ether or tetrahydrofuran and is generally conducted at a temperature between −100° C. and 50° C. for a time necessary for complete reaction to occur. In a preferred embodiment of this reaction a solution of n-butyl lithium is added to a solution of the aryl or heteroaryl amine at −78° C., then the glycidyl ester is added and the resulting mixture allowed to warm to room temperature until the reaction is judged to be complete. The product is then isolated from the reaction mixture by standard techniques and, if necessary, the product may be purified.

In step 4 of Scheme I, the 5-hydroxymethyloxazolidinone is converted to a 5-aminomethyloxazolidinone in a three step process. First the hydroxy group is activated by conversion to a leaving group, X. This is generally accomplished by acylation with acylating agents such as methanesulfonyl chloride, p-toluenesulfonyl chloride or the like, generally with the addition of a hindered base such as triethylamine, diisoproproylethyl amine or the like to scavenge the acid produced in the reaction. Suitable solvents include but are not limited to ether, tetrahydrofuran, chlorinated hydrocarbons such as methylene chloride or dichloroethane, pyridine, collidine, or dioxane. In a second step the leaving group is displaced with sodium azide in a suitable solvent such as dimethylformamide, dimethylsulfoxide, tetramethylurea, or tetrahydrofuran and the like at a temperature between 0° C. and 100° C. When the reaction is judged to be complete the product is isolated and the resulting 5-azidooxazolidinone is reduced to the amine. A number of methods for the reduction of azides to amines may be used including hydrogenation over an appropriate catalyst such as palladium or platinum, particularly deactivated catalysts such as Lindlar's catalyst (palladium on $CaCO_3$ deactivated with PbO), or other reducing agents may be employed such as triphenylphosphine or $SnCl_2$. The particular method chosen for this reduction is readily made by one of ordinary skill in the art as is dependent upon the structure of the entirety of the molecule.

In step 5 the 5-aminooxazolidinone is acylated and converted to $R_3$. It is recognized that the exact nature of the reagents used for this conversion is dependent is dependent on the exact nature of the $R_3$ desired. For example if $R_3$ is desired to be an acetylamine group a suitable reagents for performing the acylation would be acetic anhydride, acetyl chloride or the like. However if $R_3$ is desired to be a thioacetylamine group ethyldithioacetate may be an appropriate acylating agent, while 1,1'-thiocarbonyldi-2(1H)-pyridone followed by treatment of the resulting intermediate with aqueous ammonia might be an appropriate procedure if thioureido group was desired for $R_3$. The appropriate conditions and reagents for any particular $R_3$ group will be readily identified by those of ordinary skill in the art.

be true when P''' is an alkyl or aralkyl group. However, in other cases further chemical modification of the product of step 5 from Scheme III may be desirable. A general method for these chemical modifications is exemplified in Scheme IV. In step 1 the protecting group P''' is removed to reveal the free hydroxymethyl group for further manipulation. It is recognized that the precise reaction conditions for step 1 will be dependent on the structure of the molecule in its entirety in general and on the particular structural nature of the precise P''' to be removed. Such reaction conditions are readily determined by those of ordinary skill in the art. Step Scheme IV

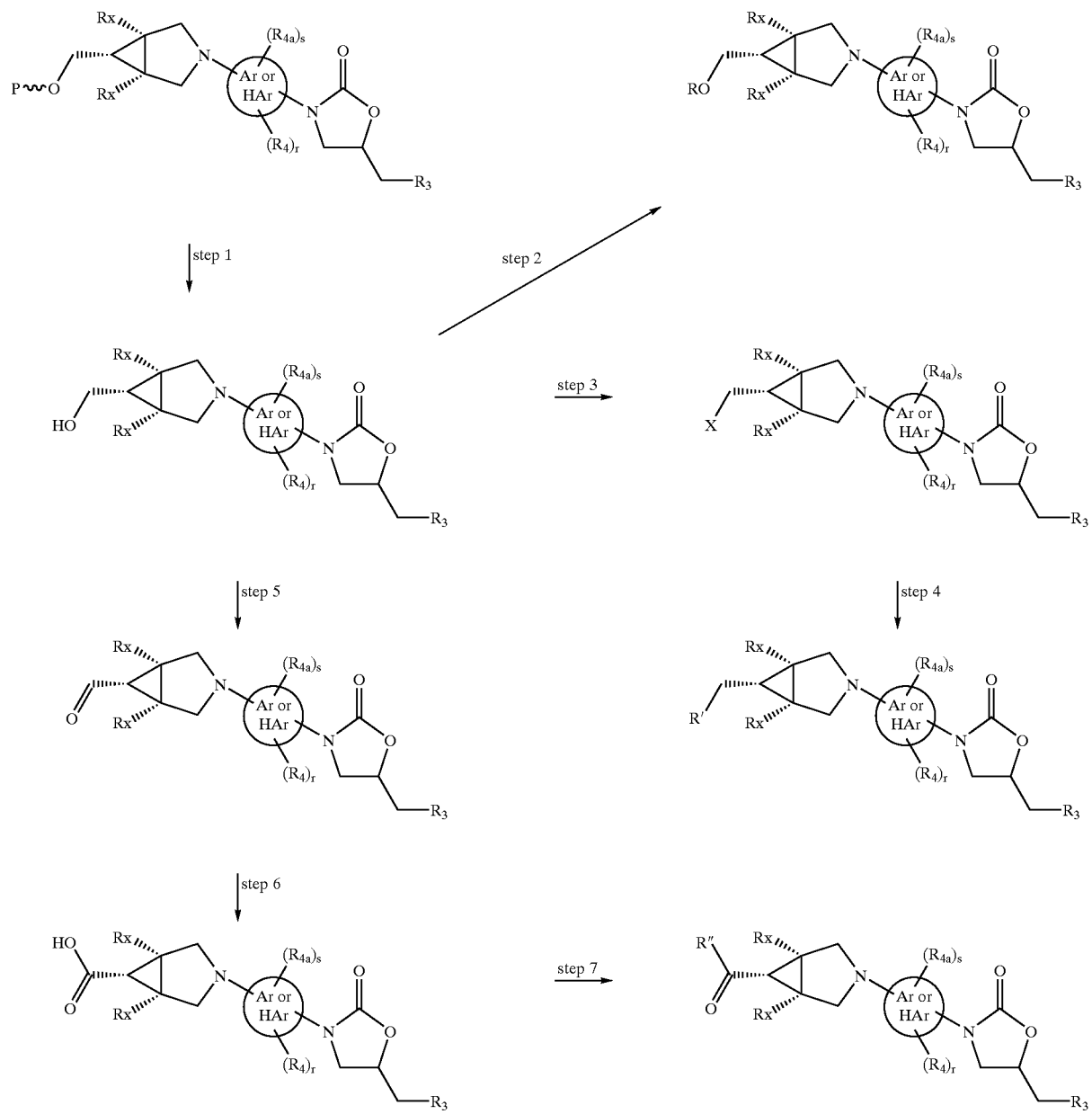

Scheme IV describes the further modification of compound prepared in Scheme III. It is recognized that in many cases the product of step 5 from Scheme III is in and of itself a compound of the current invention. This may particularly 2 exemplifies the direct activation and displacement of the hydroxy group by substituents with a hydroxy group. This transformation is typically performed by the in situ activation of the hydroxy towards displacement with an azodicarboxylate ester such as diethyl azodicrboxylate or diisopropylazodicarboxylate, in the presence of a phosphine such as triphenylphosphine in an aprotic solvent such as tetrahydrofuran. However a more general way of activating the hydroxyl towards displacement with a wide variety of potential nucleophiles is exemplified in step 3 and involves the modification of the hydroxy group to a leaving group, X. It will be recognized by those skilled in the art that the particular conditions and reagents employed will be dependent on the particular group X. This is generally accomplished by acylation with acylating agents such as methanesulfonyl chloride, p-toluenesulfonyl chloride or the like, generally with the addition of a hindered base such as triethylamine, diisoproylethyl amine or the like to scavenge the acid produced in the reaction. Alternatively, if a the nature of X is chosen to be a halide such as a bromide or iodide then reagents such as phosphorous tribromide, triphenylphosphonium dibromide, carbon tetrabromide and triphenyl phoshine, or triphenylphosphonium diiodide may be chosen. Suitable solvents include but are not limited to ether, acetonitrile, tetrahydrofuran, chlorinated hydrocarbons such as methylene chloride or dichloroethane, pyridine, collidine, or dioxane.

Step 4 exemplifies the procedure for the conversion of the product of step 3 to compounds of the instant invention containing an $R_7$ substituent. It is to be recognized that the leaving groups as defined by X above form a subset of the substructures represented in $R_7$ and as such are incorporated into the current invention. It is the further modification of these intermediates that is described in step 4. The reaction conditions required for the introduction of $R_7$ will vary depending on the exact nature of the $R_7$ employed as will be readily recognized by one of ordinary skill in the art but generally involve the reaction of a nucleophile in the appropriate solvent with the product of step 3 containing a leaving group X at a temperature between −78° C. and 150° C. sufficient for the reaction to proceed at the desired rate. When the reaction is judged to be complete the product of step 4 is isolated using conditions well known to those skilled in the art. Some representative nucleophiles that may be used to further exemplify, but not limit, step 4 include carbon nucleophiles, such as cyanide, enolate anions, or organometallic anions, nitrogen nucleophiles, such amines, imide anions, and nitrogen containing heteroaryl compounds, oxygen nuclophiles, such as alkoxides or hydroperoxides, or sulfur nucleophiles such as thiolates.

In step 5 of Scheme 4, the hydroxymethyl compound is oxidized to the corresponding aldehyde. A plethora of reagents is available to those skilled in the art for performing this transformation. Among these are chromium based reagents such as chromium trioxide and complexes of chromium trioxide with pyridine in solvents such as pyridine of methylene chloride, cerium ammonium nitrate, N-chlorosucchininmide, dimethylsulfoxide and activating agents such as oxalyl chloride or dicyclohexylcarbodiimide, and 1-hydroxy-1,2-benziodoxol-2 (1H)-one 1-oxide in dimethylsulfoxide.

In step 6 the aldehyde prepared in step 5 is further oxidized to the acid under conditions well known to those skilled in the art. A preferred reagent for performing this transformation is silver oxide although a variety oxidizing agents such as peracids, including m-chloroperbenzoic acid, peracetic acid and trifluoroperacetic acid, chromic acid, or bromine may be considered as non-limiting alternatives.

In step 7 the carboxylic acid produced as the product of step 6 can be further modified. Typically this is may be done by converting the hydroxyl of the carboxylic acid to a leaving group. Although it is readily recognized that many potential leaving groups can be considered and are well known to those of only ordinary skill in the art, some preferred methods include conversion of the carboxylic acid to the acid chloride by treatment with thionyl chloride or oxalyl chloride, formation of a mixed anhydride by treatment with a dehydrating agent such dicyclohexylcarbodiimide followed by a 2,2-dimethylpropionic acid, or formation of an active ester by treatment with a dehydrating agent such as dicyclohexylcarbodiimide and N-hydroxysuccinimide or pentfluorophenol. The resulting activated carboxylic acid may then be treated with a nucleophile, either in situ or after intermediate isolation of the activated carboxylic acid, to produce the molecules of the instant invention. Typical solvents for this transformation are well known and include methylene chloride, chloroform, carbon tetrachloride, ethers such as tetrahydrofuran, dioxane, and diethyl ether, ethyl acetate and other esters. Typical nucleophiles include alcohols to form esters, primary or secondary amines or ammonia to form amides, and carbon nucleophiles such as organometallic species to afford ketones and tertiary carbinol derivatives.

The preparation of the compounds of the present invention where A contains a carbon atom is shown in Schemes V–VI. In step 1 of Scheme V an appropriately protected 3-trifluoromethansulfonyl-6-amino-bicyclo[3.1.0]hexene is reacted with a suitably substituted 2-oxo-3-(4-trimethylstannylphenyl)-5-substituted oxazolidinone in the presence of an appropriate solvent and a palladium catalyst to afford the cross-coupled product. A preferred amino protecting group is bis (t-butoxycarbonyl). Preferred palladium catalysts include but are not limited to tris (dibenzylideneacetone)palladium, and mixtures of palladium on carbon, copper(I)iodide and triphenylarsenate and the like. A preferred solvent is N-methylpyrollidinone. Upon isolation the product of step 2 may be further modified in a fashion directly analogous to those described in Scheme II. Alternatively in step 2 of Scheme V the double bond may be reduced by hydrogenation in the presence of a catalyst to afford the corresponding bicyclo[3.1.0]hexane. It is recognized that the particular conditions employed for this hydrogenation may differ depending on the exact compound desired but generally hydrogen pressures between 1–100 atmospheres will be applied at a temperature between 0° C. and 10° C. An appropriate catalyst will be readily chosen by those skilled in the art, but may include palladium, ruthenium, or platinum on carbon. In turn the bicyclo[3.1.0] hexane obtained may be further modified by methods analogous to those described in Scheme II.

Scheme V

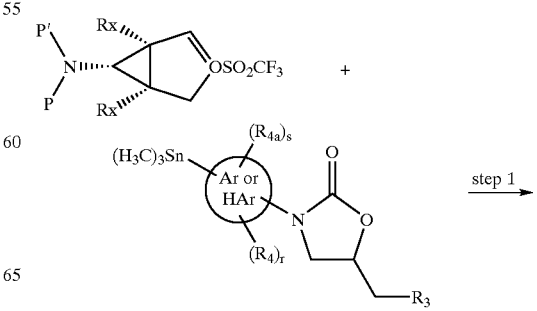

step 1

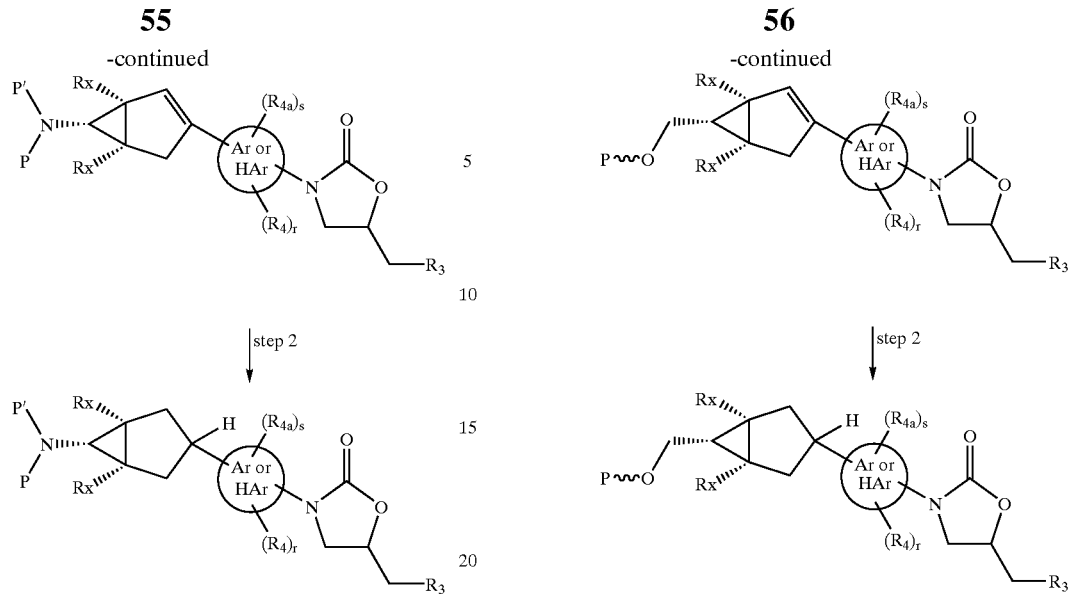

Scheme VI describes the preparation of further compounds of the present invention in which A contains a carbon atom. In step 1 of Scheme VI an appropriately protected 3-trifluoromethansulfonyl-6-hydroxymethyl-bicyclo[3.1.0] hexene is reacted with a suitably substituted 2-oxo-3-(4-trimethylstannylphenyl)-5-substituted oxazolidinone in the presence of an appropriate solvent and a palladium catalyst to afford the cross-coupled product. A preferred hydroxy protecting group is the t-butyldiphenylsilyl group. Preferred palladium catalysts include but are not limited to tris (dibenzylideneacetone)palladium, and mixtures of palladium on carbon, copper(I)iodide and triphenylarsenate and the like. A preferred solvent is N-methylpyrollidinone. Upon isolation the product of step my be further modified in a fashion directly analogous to those described in Scheme IV. Alternatively in step 2 of Scheme VI the double bond may be reduced by hydrogenation in the presence of a catalyst to afford the corresponding bicyclo[3.1.0]hexane. It is recognized that the particular conditions employed for this hydrogenation may differ depending on the exact compound desired but generally hydrogen pressures between 1–100 atmospheres will be applied at a temperature between 0° C. and 100° C. An appropriate catalyst will be readily chosen by those skilled in the art, but may include palladium, ruthenium, or platinum on carbon. In turn the bicyclo[3.1.0] hexane obtained may be further modified by methods analogous to those described in Scheme IV.

Scheme VI

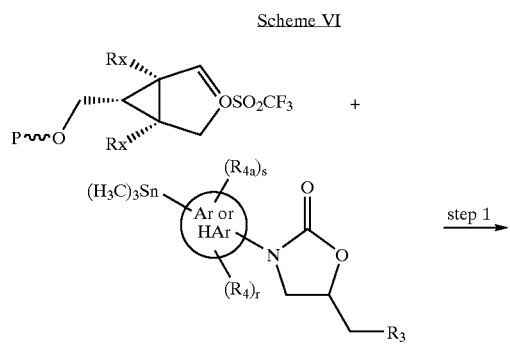

Antibacterial Activity

The pharmaceutically-acceptable compounds of the present invention are useful antibacterial agents having a good spectrum of activity in vitro against standard bacterial strains, which are used to screen for activity against pathogenic bacteria. Notably, the pharmaceutically-acceptable compounds of the present invention show activity against vancomycin-resistant enterococci, streptococci including penicillin-resistant *S. pneumoniae*, methicillin-resistant *S. aureus*, *M. catarrhalis*, and *C. pneumoniae*. The antibacterial spectrum and potency of a particular compound may be determined in a standard test system.

The following in vitro results were obtained based on an agar dilution method except for *C. pneumoniae*. The activity is presented as the minimum inhibitory concentration (MIC).

*S. aureus* and *M. catarrhalis* were tested on Mueller-Hinton agar, using an approximate inoculum of $1 \times 10^4$ cfu/spot an incubation temperature of 35 C. for 24 hours. The MIC was defined as the lowest concentration at which no visible bacterial growth was observed.

Streptococci and enterococci were tested on Mueller-Hinton agar supplemented with 5% defibrinated horse blood, using an approximate inoculum of $1 \times 10^4$ cfu/spot an incubation temperature of 35° C. in an atmosphere of 5% $CO_2$ for 24 hours. The MIC was defined as the lowest concentration at which no visible bacterial growth was observed.

*C. pneumoniae* was tested using minimum essential medium supplemented with 10% heat-inactivated fetal bovine serum, 2 mM L-glutamine, 1 mg/ml cycloheximide and non essential amino acid. HeLa 229 cells were inoculated with $10^4$ inclusion-forming units of *C. pneumoniae* strain per mL. Infected cells were incubated with test compounds in complete medium at 35C in an atmosphere of 5% $CO_2$ for 72 hours. Cells monolayers were fixed in methanol, stained for chlamydial inclusions with an fluorescein-conjugated anti-Chlamydia monoclonal antibody, and were observed with fluorescence microscope. The MIC was defined as the lowest concentration at which no inclusion was observed.

|  | MIC (μg/ml) | | | | |
| --- | --- | --- | --- | --- | --- |
| Strains | Example 8 | Example 22 | Example 41 | Example 46 | Linezolid |
| *Staphylococcus aureus* | | | | | |
| Smith | 0.5 | 0.06 | 0.06 | 0.25 | 1 |
| CR | 4 | 0.5 | 0.5 | 1 | 16 |
| MR | 1 | 0.016 | 0.06 | 0.25 | 1 |
| *Streptococcus pneumoniae* | | | | | |
| IID553 | 1 | 0.5 | 0.5 | 0.5 | 2 |
| PRQR | 1 | 0.5 | 0.5 | 0.25 | 1 |
| *Streptococcus pyogenes* | | | | | |
| IID692 | 0.5 | 0.5 | 0.5 | 0.25 | 1 |
| *Enterococcus faecium* | | | | | |
| VRQR | 2 | 0.5 | 0.5 | 0.5 | 2 |
| *Moraxella catarrhalis* | | | | | |
| ATCC25238 | NT | 2 | 4 | 2 | 4 |
| *Chlamydia pneumoniae* | | | | | |
| ATCC VR-1360 | 0.5 | NT | NT | NT | 8 |

CR = chloramphenicol resistant
MR = methicillin resistant
PRQR = penicillin resistant, quinolone resistant
VRQR = vancomycin resistant, quinolone resistant
NT = not tested The invention described herein is exemplified by the following non-limiting examples. The compound data is designated in accordance to *General Guidelines for Manuscript Preparation*, J. Org. Chem. Vol. 66, pg. 19A, Issue 1, 2001.

EXAMPLE 1

N-[5(S)-3-[4-[(1α,5α,6α)-6-(N-Benzyl)amino-3-azabicyclo[3.1.0]hexan-3-yl]-3-fluorophenyl]-2-oxooxazolidin-5-ylmethyl]acetamide.

To a solution of N-[5(S)-3-[4-[(1α,5α,6α)-6-(N-benzyl-N-t-butoxy carbonyl)amino-3-azabicyclo[3.1.0]hexan-3-yl]-3-fluorophenyl]-2-oxooxazolidin-5-ylmethyl]acetamide (3.02 g) in methanol (9 mL) was added a solution of hydrogen chloride in methanol (6 mL) at 0° C., and the mixture was stirred at room temperature for 3 hours. After diluting the mixture by the addition of dichloromethane, the solution was made to alkaline by the addition of saturated sodium hydrogencarbonate solution. The resulting mixture was extracted with dichloromethane. The organic extracts were dried over anhydrous sodium sulfate, filtered, and then concentrated in vacuo. Flash chromatography (silica, dichloromethane:methanol=–8:1) of the residue gave N-[5(S)-3-[4-[(1α,5α,6α)-6-(N-benzyl)amino-3-azabicyclo[3.1.0]hexan-3-yl]-3-fluorophenyl]-2-oxooxazolidin-5-ylmethyl]acetamide (2.32 g).

$^1$H NMR (CDCl$_3$) δ 1.66 (s, 2H), 2.02 (s, 3H), 2.23 (t, J=2.0 Hz, 1H), 3.25 (d, J=8.8 Hz, 2H), 3.50–3.80 (m, 5H), 3.84 (s, 2H), 3.98 (t, J=8.8 Hz, 1H), 4.70–4.80 (m, 1H), 6.56 (t, J=9.3 Hz, 1H), 6.97 (dd, J=9.3, 2.0 Hz, 1H), 7.20–7.40 (m, 6H).

MS (EI$^+$) m/z: 438 (M$^+$).

HRMS (EI$^+$) for C$_{24}$H$_{27}$FN$_4$O$_3$ (M$^+$): calcd, 438.2067; found, 438.2066.

EXAMPLE 2

N-[5(S)-3-[4-[(1α,5α,6α)-6-(N-Benzyloxyacetyl)amino-3-azabicyclo[3.1.0]hexan-3-yl]-3-fluorophenyl]-2-oxooxazolidin-5-ylmethyl]acetamide.

To a suspension of N-[5(S)-3-[4-[(1α,5α,6α)-6-amino-3-azabicyclo[3.1.0]hexan-3-yl]-3-fluorophenyl]-2-oxooxazolidin-5-ylmethyl]acetamide (716 mg) and triethylamine (861 μL) in dichloromethane (4 mL) was added benzyloxyacetyl chloride (512 μL) at 0° C., and the mixture was stirred at the same temperature for 30 min. After quenching the reaction by the addition of 1N hydrochloric acid, the mixture was extracted with dichloromethane. The dichloromethane solution was washed with water, aqueous hydrogencarbonate solution and brine. The organic extracts were dried over anhydrous sodium sulfate, filtered, and then concentrated in vacuo. Flash chromatography (silica, ethyl acetate:methanol=10:1) of the residue gave N-[5(S)-3-[4-(1α,5α,6α)-6-(N-benzyloxyacetyl)amino-3-azabicyclo[3.1.0]hexan-3-yl]-3-fluorophenyl]-2-oxooxazolidin-5-ylmethyl]acetamide (673 mg).

$^1$H NMR (CDCl$_3$) δ 1.78 (s, 2H), 2.02 (s, 3H), 2.76 (d, J=2.4 Hz, 1H), 3.27 (d, J=8.8 Hz, 2H), 3.50–3.80 (m, 5H), 3.90–4.10 (m, 1H), 3.97 (s, 2H), 4.56 (s, 2H), 4.70–4.80 (m, 1H), 6.59 (t, J=9.3 Hz, 1H), 6.98 (dd, J=9.3, 2.4 Hz, 1H), 7.20–7.40 (m, 6H).

MS (EI$^+$) m/z: 496 (M$^+$).

HRMS (EI$^+$) for C$_{26}$H$_{29}$FN$_4$O$_5$ (M$^+$): calcd, 496.2122; found, 496.2152.

EXAMPLE 3

N-[5(S)-3-[3-Fluoro-4-[(1α,5α,6α)-6-(N-hydroxyacetyl)amino-3-azabicyclo[3.1.0]hexan-3-yl]phenyl]-2-oxooxazolidin-5-ylmethyl]acetamide.

To a suspension of N-[5(S)-3-[4-[(1α,5α,6α)-6-(N-benzyloxyacetyl)amino-3-azabicyclo[3.1.0]hexan-3-yl]-3-fluorophenyl]-2-oxooxazolidin-5-ylmethyl]acetamide (476 mg) and palladium catalyst (7.5% on charcoal, 476 mg) in methanol (24 mL) was added ammonium formate (445 mg), and the mixture was heated at reflux for 5 hours. After filtration of the catalyst, the filtrate was concentrated in vacuo to give N-[5(S)-3-[3-fluoro-4-[(1α,5α,6α)-6-(N-hydroxyacetyl)amino-3-azabicyclo[3.1.0]hexan -3-yl] phenyl]-2-oxooxazolidin-5-ylmethyl]acetamide (82.5 mg).

$^1$H NMR (DMSO-d$_6$) δ 1.82 (s, 3H), 1.87 (s, 2H), 2.60–2.70 (m, 1H), 3.19 (d, J=8.8 Hz, 2H), 3.6–3.39 (m, 2H), 3.60–3.70 (m, 3H), 3.78 (d, J=5.4 Hz, 2H), 4.03 (t, J=9.0 Hz, 1H), 4.60–4.70 (m, 1H), 6.77 (t, J=9.3 Hz, 1H), 7.08 (dd, J=9.3, 2.4 Hz, 1H), 7.38 (dd, J=16.1, 2.4 Hz, 1 μl).

MS (FAB$^+$) m/z: 407 (MH$^+$).

HRMS (FAB$^+$) for C$_{19}$H$_{24}$FN$_4$O$_5$ (MH$^+$): calcd, 407.1731; found, 407.1728.

EXAMPLE 4

N-[5(S)-3-[4-[(1α,5α,6α)-6-(N-Benzgl-N-methyl amino-3-azabicyclo[3.1.0]hexan-3-yl]-3-fluorophenyl]-2-oxooxazolidin-5-ylmethyl]acetamide.

To a solution of N-[5(S)-3-[4-[(1α,5α,6α)-6-(N-benzyl) amino-3-azabicyclo[3.1.0]hexan-3-yl]-3-fluorophenyl]-2-oxooxazolidin-5-ylmethyl]acetamide (954 mg) in tetrahydrofuran (14 mL) were added formalin (37%, 1.72 mL), sodium tris(acetoxy)borohydride (971 mg), and acetic acid (250 μL), and the mixture was stirred at room temperature for 2 hours. After quenching the reaction by the addition of aqueous sodium hydrogencarbonate solution, the resulting precipitates were collected by filtration, and then dissolved with dichloromethane. The dichloromethane solution was dried over anhydrous sodium sulfate, filtered, and then concentrated in vacuo. Flash chromatography (silica, dichloromethane:methanol=10:1) of the residue gave N-[5 (S)-3-[4-[(1α,5α,6α)-6-(N-benzyl-N-methyl)amino-3-azabicyclo[3.1.0]hexan-3-yl]-3-fluorophenyl]-2-oxooxazolidin-5-ylmethyl]acetamide (1.11 g).

$^1$H-NMR (CDCl$_3$) δ 1.64 (s, 2H), 1.79 (s, 1H), 2.02 (s, 3H), 2.30 (s, 3H), 3.23 (d, J=9.3 Hz, 2H), 3.50–3.80 (m, 7H), 3.99 (t, J=8.8 Hz, 1H), 4.70–4.80 (m, 1H), 6.57 (t, J=9.3 Hz, 1H), 6.98 (dd, J=9.3, 2.4 Hz, 1H), 7.20–7.40 (m, 6H).

MS (EI$^+$) m/z: 452 (M$^+$).

HRMS (EI$^+$) for C$_{25}$H$_{29}$FN$_4$O$_3$ (M$^+$): calcd, 452.2224; found, 452.2226.

EXAMPLE 5

N-[5(S)-3-[3-Fluoro-4-[(1α,5α,6α)-6-(N-methyl)amino-3-azabicyclo[3.1.0]hexan-3-yl]phenyl]-2-oxooxazolidin-5-ylethyl]acetamide.

A suspension of N-[5(S)-3-[4-[(1α,5α,6α)-6-(N-benzyl-N-methyl)amino-3-azabicyclo[3.1.0]hexan-3-yl]-3-fluorophenyl]-2-oxooxazolidin-5-ylmethyl]acetamide (794 mg) and palladium catalyst (7.5% on charcoal, 714 mg) in methanol (32 mL) was hydrogenated at 1 atm for 5.5 hours at room temperature. After filtration of the catalyst, the filtrate was concentrated in vacuo. Treatment of the residue with methanol gave N-[5(S)-3-[3-fluoro-4-[(1α,5α,6α)-6-(N-methyl)amino-3-azabicyclo[3.1.0]hexan-3-yl]phenyl]-2-oxooxazolidin-5-ylmethyl]acetamide (182 mg).

$^1$H NMR (DMSO-d$_6$) δ 1.66 (s, 2H), 1.76 (s, 1H), 1.82 (s, 3H), 2.27 (s, 3H), 3.19 (d, J=7.8 Hz, 2H), 3.30–3.40 (m, 2H), 3.55 (d, 2H), 3.64 (dd, J=8.8, 6.4 Hz, 1), 4.02 (t, J=8.8 Hz, 1H), 4.60–4.70 (m, 1H), 6.70 (t, J=9.3 Hz, 1H), 7.05 (dd, J=9.3, 2.4 Hz, 1H), 7.35 (dd, J=16.1, 2.4 Hz, 1H).

MS (FAB$^+$) m/z: 363 (MH$^+$).

HRMS (FAB$^+$) for C$_{18}$H$_{24}$FN$_4$O$_3$ (M$^+$): calcd, 363.1832; found, 363.1833.

EXAMPLE 6

N-[5(S)-3-[4-[(1α,5α,6α)-6-(N-Benzaloxyacetyl-N-methyl)amino-3-azabicyclo[3.1.0]hexan-3-yl]-3-fluorophenyl]-2-oxooxazolidin-5-ylmethyl]acetamide.

The title compound N-[5(S)-3-[4-[(1α,5α,6α)-6-(N-benzyloxyacetyl-N-methyl)amino-3-azabicyclo[3.1.0] hexan-3-yl]-3-fluorophenyl]-2-oxooxazolidin-5-ylmethyl] acetamide (363 mg) was prepared from N-[5(S)-3-[3-fluoro-4-[(1α,5α,6α)-6-(N-methyl)amino-3-azabicyclo[3.1.0] hexan-3-yl]phenyl]-2-oxooxazolidin-5-ylmethyl]acetamide (526 mg) in the same manner as described for EXAMPLE 2.

$^1$H NMR (CDCl$_3$) δ 1.91 (s, 2H), 2.02 (s, 3H), 2.72 (s, 1H), 2.96 (s, 3H), 3.26 (d, J=9.3 Hz, 2H), 3.50–3.80 (m, 5H), 3.99 (t, J=9.3 Hz, 1H), 4.32 (s, 2H), 4.70–4.80 (m, 1H), 6.58 (t, J=9.3 Hz, 1H), 6.90–7.10 (m, 1H), 7.20–7.40 (m, 6H).

MS (FAB$^+$) m/z: 511 (MH$^+$).

HRMS (FAB$^+$) for C$_{27}$H$_{32}$FN$_4$O$_5$ (MH$^+$): calcd, 511.2357; found, 511.2342.

EXAMPLE 7

N-[5(S)-3-[3-Fluoro-4-[(1α,5α,6α)-6-(-hydroxyacetyl-N-methyl)amino-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-(N-hydroxyacetyl-N-methyl)amino-3-azabicyclo[3.1.0] hexan-3-yl]phenyl]-2-oxooxazolidin-5-ylmethyl]acetamide (191 mg) was prepared from N-[5(S)-3-[4-[(1α,5α,6α)-6-(N-benzyloxyacetyl-N-methyl)amino-3-azabicyclo[3.1.0] hexan-3-yl]-3-fluorophenyl]-2-oxooxazolidin-5-ylmethyl] acetamide (312 mg) in the same manner as described for EXAMPLE 3

$^1$H NMR (DMSO-d$_6$) δ 1.82 (s, 3H), 2.09 (s, 2H), 2.65 (s, 1H), 2.84 (s, 3H), 3.24 (d, J=8.8 Hz, 2H), 3.36–3.39 (m, 2H), 3.60–3.70 (m, 3H), 4.03 (t, J=9.0 Hz, 1H), 4.24 (s, 2H), 4.60–4.70 (m, 1H), 6.76 (t, J=9.8 Hz, 1H), 7.08 (dd, J=9.8, 2.4 Hz, 1H), 7.38 (dd, J=16.1, 2.4 Hz, 1H).

MS (FAB$^+$) m/z: 421 (MH$^+$).

HRMS (FAB$^+$) for C$_{20}$H$_{26}$FN$_4$O$_5$ (MH$^+$): calcd, 421.1887; found, 421.1862.

EXAMPLE 8

N-[5(S)-3-[4-[(1α,5α,6α)-6-Amino-3-azabicyclo[3.1.0] hexan-3-yl]-3-fluorophenyl]-2-oxooxazolidin-5-ylmethyl] acetamide.

A suspension of 4-[(1α,5α,6α)-6-(N-benzyl)amino-3-azabicyclo[3.1.0]hexan-3-yl]-3-fluorophenyl]-2-oxooxazolidin-5-ylmethyl]acetamide (954 mg) and palladium catalyst (7.5% on charcoal, 668 mg) in methanol (38 mL) was hydrogenated at 1 atm for 7 hours at room temperature. After filtration of the catalyst, the filtrate was concentrated in vacuo to give N-[5(S)-3-[4-[(1α,5α,6α)-6-amino-3-azabicyclo[3.1.0]hexan-3-yl]-3-fluorophenyl]-2-oxooxazolidin-5-ylmethyl]acetamide (716 mg).

$^1$H NMR (DMSO-d$_6$) δ 1.47 (s, 2H), 1.82 (s, 3H), 2.15 (s, 1H), 3.17 (d, J-8.8 Hz, 2H), 3.30–3.40 (m, 2H), 3.52 (dd, J=8.8, 2.4 Hz, 2H), 3.64 (dd, J=9.3, 6.4 Hz, 1H), 4.02 (t, J=9.3 Hz, 1H), 4.60–4.70 (m, 1H), 6.67–6.72 (m, 1H), 7.05 (dd, J=8.8, 2.4 Hz, 1H), 7.35 (dd, J=16.1, 2.4 Hz, 1H).

MS (EI$^+$) m/z: 348 (M$^+$).

HRMS (EI$^+$) for C$_{17}$H$_{21}$FN$_4$O$_3$ (M$^+$): calcd, 348.1598; found, 348.1635.

EXAMPLE 9

N-[5(S)-3-[4-[(1α,5α,6α)-6-(Benzyl-N-t-butoxycarbonyl)amino-3-azabicyclo[3.1.0]hexan-3-yl]-3-fluorophenyl]-2-oxooxazolidin-5-ylmethyl]acetamide.

Step 1

5(R)-3-[4-[(1α,5α,6α)-6-(N-Benzyl-N-t-butoxycarbonyl)amino-3-azabicyclo[3.1.0]hexan-3-yl]-3-fluorophenyl]-5-hydroxymethyloxazolidin-2-one.

To a solution of 4-[(1α,5α,6α)-6-(N-benzyl-N-t-butoxycarbonyl)amino-3-azabicyclo[3.1.0]hexan-3-yl]-1-benzyloxycarbonylamino-3-fluorobenzene (6.46 g) in dry tetrahydrofuran (65 mL) was added a solution of n-butyllithium in hexane (1.6 M, 8.51 mL) at −78° C., and the mixture was stirred at the same temperature for 30 min. (R)-Glycidyl butylate (2.11 mL) was added to the mixture at −78° C. and the mixture was allowed to stand at room temperature for 4 hours. After quenching the reaction with the addition of aqueous ammonium chloride solution and dilution with ethyl acetate, the resulting mixture was washed with brine, dried over anhydrous sodium sulfate, filtered, and then concentrated in vacuo. Flash chromatography (silica, hexane:ethyl acetate=1:5) of the residue gave 5(R)-3-[4-[(1α,5α,6α)-6-(N-benzyl-N-t-butoxycarbonyl)amino-3-azabicyclo[3.1.0]hexan-3-yl]-3-fluorophenyl]-5-hydroxymethyloxazolidin-2-one (3.95 g).

$^1$HNMR (CDCl$_3$) δ 1.49 (s, 9H), 1.90 (s, 2H), 2.47 (s, 1H), 3.27 (d, J=8.8 Hz, 2H), 3.50–4.00 (m, 4H), 3.88 (dd, J=8.8, 6.8 Hz, 1H), 3.95 (t, J=8.8 Hz, 1H), 4.45 (s, 2H), 4.60–4.80 (m, 1H), 6.55 (t, J=9.3 Hz, 1H), 7.02 (dd, J=8.8, 2.4 Hz, 1H), 7.20–7.40 (m, 6H).

MS (EI$^+$) m/z: 497 (M$^+$).

Step 2

5(R)-Azidomethyl-3-[4-[(1α,5α,6α)-6-(N-benzyl-N-t-butoxycarbonyl)amino-3-azabicyclo[3.1.0]hexan-3-yl]-3-fluorophenyl]oxazolidin-2-one.

To a solution of 5(R)-3-[4-[(1α,5α,6α)-6-(N-benzyl-N-t-butoxy carbonyl)amino-3-azabicyclo[3.1.0]hexan-3-yl]-3-fluorophenyl]-5-hydroxymethyl oxazolidin-2-one (3.95 g) in dichloromethane (119 mL) were successively added triethylamine (2.22 mL) and methanesulfonyl chloride (922 μL) at 0° C., and the mixture was stirred at the same temperature for 5 min. The mixture was washed with 1N hydrochloric acid, water, aqueous sodium hydrogencarbonate solution, and brine. The organic extracts were dried over anhydrous sodium sulfate, filtered, and then concentrated in vacuo to give 5(R)-3-[4-[(1α,5α,6α)-6-(N-benzyl-N-t-butoxycarbonyl)amino-3-azabicyclo[3.1.0]hexan-3-yl]-3-fluorophenyl]-5-methane sulfonyloxymethyloxazolidin-2-one. This was used in the next step without further purification. The mixture of crude 5R)-3-[4-[(1α,5α,6α)-6-N-benzyl-N-t-butoxycarbonyl)amino-3-azabicyclo[3.1.0]hexan-3-yl]-3-fluorophenyl]-5-methane sulfonyloxymethyloxazolidin-2-one thus obtained and sodium azide (1.78 g) in N,N-dimethylformamide (90 mL) was heated at 70° C. for 15 hours, and then concentrated in vacuo. The residue was diluted with ethyl acetate and washed with water and brine. The organic extracts were dried over anhydrous sodium sulfate, filtered, and then concentrated in vacuo. Flash chromatography (silica, hexane:ethyl acetate=10:9) of the residue gave 5(R)-azidomethyl-3-[4-[(1α,5α,6α)-6-(N-benzyl-N-t-butoxycarbonyl)amino-3-azabicyclo[3.1.0]hexan-3-yl]-3-fluorophenyl]oxazolidin-2-one (3.40 g).

$^1$H NMR (CDCl$_3$) δ 1.49 (s, 9H), 1.90 (s, 2H), 2.46 (s, 1H), 3.28 (d, J=8.8 Hz, 2H), 3.50–3.80 (m, 4H), 3.76 (dd, J=8.8, 6.1 Hz, 1H), 4.00 (t, J=8.8 Hz, 1H), 4.45 (s, 2H), 4.70–4.80 (m, 1H), 6.55 (t, J=9.3 Hz, 1H), 6.90–7.10 (m, 1H), 7.20–7.40 (m, 6H).

MS (EI$^+$) m/z: 522 (M$^+$).

Step 3

5(R)-Aminomethyl-3-[4-[(1α,5α,6α)-6-(N-benzyl-N-t-butoxycarbonyl)amino-3-azabicyclo[3.1.0]hexan-3-yl]-3-fluorophenyl]oxazolidin-2-one.

A suspension of 5(R)-azidomethyl-3-[4-[(1α,5α,6α)-6-(N-benzyl-N-t-butoxycarbonyl)amino-3-azabicyclo[3.1.0]hexan-3-yl]-3-fluorophenyl]oxazolidin-2-one (3.40 g) and Lindlar catalyst (5% palladium on CaCO$_3$ partially poisoned with lead, 1.70 g) in dichloromethane (20 mL) and methanol (102 mL) was hydrogenated at 1 atm for 2.5 hours at room temperature. After filtration of the catalyst, the filtrate was concentrated in vacuo to give 5(R)-aminomethyl-3-[4-[(1α,5α,6α)-6-(N-benzyl-N-t-butoxycarbonyl)amino-3-azabicyclo[3.1.0]hexan-3-yl]-3-fluorophenyl]oxazolidin-2-one (3.27 g).

Step 4

N-[5(S)-3-[4-[(1α,5α,6α)-6-(N-Benzyl-N-t-butoxycarbonyl)amino-3-azabicyclo[3.1.0]hexan-3-yl]-3-fluorophenyl]-2-oxooxazolidin-5-ylmethyl]acetamide.

To a solution of 5(R)-aminomethyl-3-[4-[(1α,5α,6α)-6-(N-benzyl-N-t-butoxycarbonyl)amino-3-azabicyclo[3.1.0]hexan-3-yl]-3-fluorophenyl]oxazolidin-2-one (3.27 g) in dichloromethane (65 m) was added triethylamine (1.09 mL) and acetic anhydride (696 μL) at 0 C., and the mixture was stirred at the same temperature for 30 min. After quenching the reaction by the addition of water, the mixture was extracted with dichloromethane. The organic extracts were dried over anhydrous sodium sulfate, filtered, and then concentrated in vacuo. Flash chromatography (silica, ethyl acetate:methanol=20:1) of the residue gave N-[5(S)-3-[4-[(1α,5α,6α)-6-(N-benzyl-N-t-butoxycarbonyl)amino-3-azabicyclo[3.1.0]hexan-3-yl]-3-fluorophenyl]-2-oxooxazolidin-5-ylmethyl]acetamide (3.19 g).

$^1$H NMR (CDCl$_3$) δ 1.49 (s, 9H) 1.90 (s, 2H) 2.01 (s, 3H) 2.46 (s, 1H) 3.27 (d, J=8.3 Hz, 2H) 3.50–3.80 (m, 5H) 3.97 (t, J=9.0 Hz, 1H) 4.45 (s, 2H) 4.70–4.80 (m, 1H) 6.54 (t, J=9.3 Hz, 1H) 6.96 (dd, J=9.3, 2.4 Hz, 1H) 7.20–7.40 (m, 6H).

MS (EI$^+$) m/z: 538 (M$^+$).

EXAMPLE 10

N-[5(S)-3-[4-[(1α,5α,6α)-6-(N-Benzyl-N-t-butoxycarbonyl)amino-3-azabicyclo[3.1.0]hexan-3-yl]-3-fluorophenyl]-2-oxooxazolidin-5-ylmethyl]thioacetamide.

To a solution of 5(R)-aminomethyl-3-[4-[(1α,5α,6α)-6-(N-benzyl-N-t-butoxycarbonyl)amino-3-azabicyclo[3.1.0]hexan-3-yl]-3-fluorophenyl]oxazolidin-2-one (323 mg) in tetrahydrofuran (2 mL) was added triethylamine (200 μL) and ethyl dithioacetate (84 μL), and the mixture was stirred at room temperature for 11 days, and then concentrated in vacuo. Flash chromatography (silica, hexane:ethyl acetate=4:5) of the residue gave N-[5(S)-3-[4-[(1α,5α,6α)-6-(N-benzyl-N-t-butoxycarbonyl)amino-3-azabicyclo[3.1.0]hexan-3-yl]-3-fluorophenyl]-2-oxooxazolidin-5-ylmethyl]thioacetamide (241 mg).

$^1$H NMR (CDCl$_3$) δ 1.58 (s, 9H), 1.80–2.00 (m, 2H), 2.40–2.50 (m, 1H), 2.59 (s, 3H), 3.28 (d, J=8.8 Hz, 2H), 3.60–3.70 (m, 2H), 3.75 (d, J=9.3, 6.8 Hz, 1H), 3.90–4.10 (m, 2H), 4.20–4.30 (m, 1H), 4.45 (s, 2H), 4.90–5.00 (m, 1H), 6.54 (t, J=9.3 Hz, 1H), 6.95 (dd, J=9.3, 2.4 Hz, 1H), 7.20–7.40 (m, 6H).

MS (FAB$^+$) m/z: 555 (MH$^+$).

EXAMPLE 11

N-[5(S)-3-[4-[(1α,5α,6α)-6-(N-Benzyl)amino-3-azabicyclo[3.1.0]hexan-3-yl]-3-fluorophenyl]-2-oxooxazolidin-5-ylmethyl]thioacetamide.

To a solution of N-[5(S)-3-[4-[(1α,5α,6α)-6-(N-benzyl-N-t-butoxycarbonyl)amino-3-azabicyclo[3.1.0]hexan-3-yl]-3-fluorophenyl]-2-oxooxazolidin-5-ylmethyl]thioacetamide (238 mg) in methanol (2 mL) was added a solution of hydrogen chloride in methanol (4.4 mL) at 0° C., and the mixture was stirred at room temperature for 1 hour. After quenching the reaction by the addition of aqueous sodium hydrogencarbonate solution, the resulting mixture was extracted with dichloromethane. The organic extracts were dried over anhydrous sodium sulfate, filtered, and then concentrated in vacuo. Flash chromatography (silica, ethyl acetate:methanol=15:1) of the residue gave N-[5(S)-3-[4-[(1α,5α,6α)-6-(N-benzyl)amino-3-azabicyclo[3.1.0]hexan-3-yl]-3-fluorophenyl]-2-oxooxazolidin-5-ylmethyl]thioacetamide (114 mg).

$^1$H NMR (DMSO-d$_6$) δ 1.58 (s, 2H), 1.99 (s, 1H), 2.42 (s, 3H), 3.16 (d, J=9.3 Hz, 2H), 3.49 (dd, J=9.3, 2.9 Hz, 2H), 3.70 (s, 2H), 3.70–3.80 (m, 1H), 3.80–3.90 (m, 1H), 4.06 (t, J=9.0 Hz, 1H), 4.80–4.90 (m, 1H), 6.68 (t, J=8.8 Hz, 1H), 7.05 (dd, J=8.8, 2.4 Hz, 1H), 7.20–7.40 (m, 6H).

MS (FAB$^+$) m/z: 455 (MH$^+$).

HRMS (FAB$^+$) for C$_{24}$H$_{27}$FN$_4$O$_2$S (MH$^+$): calcd, 454.1839; found, 455.1936.

EXAMPLE 12

N-[5(S)-3-[4-[(1α,5α,6α)-6-(N-Benzyl)amino-3-azabicyclo[3.1.0]hexan-3-yl]-3-fluorophenyl]-2-oxooxazolidin-5-ylmethyl]thiourea.

Step 1

N-[5(S)-3-[4-[(1α,5α,6α)-6-(N-Benzyl-N-t-butoxycarbonyl)amino-3-azabicyclo[3.1.0]hexan-3-yl]-3-fluorophenyl]-2-oxooxazolidin-5-ylmethyl]isothiocyanate.

To a solution of 5(R)-aminomethyl-3-[4-[(1α,5α,6α)-6-(N-benzyl-N-t-butoxycarbonyl)amino-3-azabicyclo[3.1.0]hexan-3-yl]-3-fluorophenyl]oxazolidin-2-one (149 mg) in dichloromethane (3 mL) was added a solution of 1,1'-thiocarbonyldi-2 (1H)-pyridone (86.2 mg) in dichloromethane (5 mL) at 0° C., and the mixture was stirred at room temperature for 3 hours. The mixture was washed with water and brine, dried over anhydrous sodium sulfate, filtered, and then concentrated in vacuo. Flash chromatography (silica, hexane:ethyl acetate=3:5) of the residue gave N-[5(S)-3-[4-[(1α,5α,6α)-6-(N-benzyl-N-t-butoxycarbonyl) amino-3-azabicyclo[3.1.0]hexan-3-yl]-3-fluorophenyl]-2-oxooxazolidin-5-ylmethyl]isothiocyanate (135 mg).

$^1$H NMR (CDCl$_3$) δ 1.49 (s, 9H), 1.90 (s, 2H), 2.45 (s, 1H), 3.29 (d, J=8.3 Hz, 2H), 3.50–3.80 (m, 2H), 3.70–4.00 (m, 3H), 4.10 (t, J=9.0 Hz, 1H), 4.45 (s, 2H), 4.70–4.80 (m, 1H), 6.56 (t, J=9.3 Hz, 1H), 7.01 (dd, J=9.3, 2.9 Hz, 1H), 7.20–7.30 (m, 6H).

MS (EI$^+$) m/z: 538 (M$^+$).

Step 2

N-[5(S)-3-[4-[(1α,5α,6α)-6-(N-Benzyl)amino-3-azabicyclo[3.1.0]hexan-3-yl]-3-fluorophenyl]-2-oxooxazolidin-5-ylmethyl]thiourea.

To a suspension of N-[5(S)-3-[4-[(1α,5α,6α)-6-(N-benzyl-N-t-butoxycarbonyl)amino-3-azabicyclo[3.1.0]hexan-3-yl]-3-fluorophenyl]-2-oxooxazolidin-5-ylmethyl]isothiocyanate (135 mg) in methanol (0.5 mL) was added a solution of ammonia in methanol (7N solution, 3.57 mL), and the mixture was stirred at room temperature for 1 hour, and then concentrated in vacuo to give N-[5(S)-3-[4-[(1α,5α,6α)-6-(N-benzyl-N-t-butoxycarbonyl)amino-3-azabicyclo[3.1.0]hexan-3-yl]-3-fluorophenyl]-2-oxooxazolidin-5-ylmethyl]thiourea. This compound was used without further purification. N-[5(S)-3-[4-[(1α,5α,6α)-6-(N-benzyl)amino-3-azabicyclo[3.1.0]hexan-3-yl]-3-fluorophenyl]-2-oxooxazolidin-5-ylmethyl]thiourea (84.3 mg) was prepared from the crude N-[5(S)-3-[4-[(1α,5α,6α)-6-(N-benzyl-N-t-butoxycarbonyl)amino-3-azabicyclo[3.1.0]hexan-3-yl]-3-fluorophenyl]-2-oxooxazolidin-5-ylmethyl]thiourea in the same manner as described for EXAMPLE 11.

$^1$H NMR (DMSO-d$_6$) δ 1.61 (s, 2H), 2.04 (s, 1H), 3.16 (d, J=9.3 Hz, 2H), 3.49 (dd, J=9.3, 2.0 Hz, 2H), 3.60–3.90 (m, 3H), 3.74 (s, 2H), 4.03 (t, J=9.0 Hz, 1H), 4.78 (brs, 1H), 6.69 (t, J=8.8 Hz, 1H), 7.05 (dd, J=8.8, 2.4 Hz, 1H), 7.10–7.40 (m, 6H).

MS (FAB$^+$) m/z: 456 (MH$^+$).

HRMS (FAB$^+$) for C$_{23}$H$_{27}$FN$_5$O$_2$S (MH$^+$): calcd, 456.1870; found, 456.1850.

EXAMPLE 13

N-[5(S)-3-[3-Fluoro-4-[(1α,5α,6α)-6-hydroxymethyl-3-azabicyclo[3.1.0]hexan-3-yl]phenyl]-2-oxooxazolidin-5-ylmethyl]acetamide.

To a solution of N-[5(S)-3-[3-fluoro-4-[(1α,5α,6α)-6-[(2-tetrahydropyranyl)oxy]methyl-3-azabicyclo[3.1.0]hexan-3-yl]phenyl]-2-oxooxazolidin-5-ylmethyl]acetamide (583 mg) in methanol (10 mL) was added a solution of hydrogen chloride in methanol (saturated, 1.5 mL), and the mixture was stirred at room temperature for 1 hour, and then concentrated in vacuo. The residue was dissolved in water (5 mL), made to alkaline by the addition of saturated sodium hydrogencarbonate solution. The resulting precipitates were collected by filtration, washed with water, and then dried in vacuo to give N-[5(S)-3-[3-fluoro-4-[(1α,5α,6α)-6-hydroxymethyl-3-azabicyclo[3.1.0]hexan-3-yl]phenyl]-2-oxooxazolidin-5-ylmethyl]acetamide (377 mg).

$^1$H NMR (DMSO-d$_6$) δ 0.99–1.04 (m, 1H), 1.48–1.53 (m, 2H), 1.82 (s, 3H), 3.16 (d, J=8.9 Hz, 2H), 3.28–3.32 (m, 2H), 3.38 (t, J=5.4 Hz, 2H), 3.56 (dd, J=9.3, 2.0 Hz, 2H), 3.65 (dd, J=9.2, 6.4 Hz, 1H), 4.03 (t, J=9.3 Hz, 1H), 4.49 (t, J=5.4 Hz, 1H), 4.63–4.70 (m, 1H), 6.74 (t, J=9.3 Hz, 1H), 7.06 (dd, J=8.8, 2.4 Hz, 1H), 7.36 (dd, J=16.1, 2.4 Hz, 1H), 8.22 (t, J=5.4 Hz, 1H).

MS (EI$^+$) m/z: 363 (M$^+$).

EXAMPLE 14

N-[5(S)-3-[3-Fluoro-4-[(1α,5α,6α)-6-[(2-tetrahydropyranyl)oxy]methyl-3-azabicyclo[3.1.0]hexan-3-yl]phenyl]-2-oxooxazolidin-5-ylmethyl]acetamide.

Step 1

5(R)-3-[3-Fluoro-4-[(1α,5α,6α)-6-[(2-tetrahydropyranyl)oxy]methyl-3-azabicyclo[3.1.0]hexan-3-yl]phenyl]-5-hydroxymethyloxazolidin-2-one.

The title compound 5(R)-3-[3-fluoro-4-[(1α,5α,6α)-6-[(2-tetrahydropyranyl)oxy]methyl-3-azabicyclo[3.1.0]hexan-3-yl]phenyl]-5-hydroxymethyloxazolidin-2-one (702 mg) was prepared from 1-benzyloxycarbonyl amino-3-fluoro-4-[(1α,5α,6α)-6-[(2-tetrahydropyranyl)oxy]methyl-3-azabicyclo[3.1.0]hexan-3-yl]benzene (1.19 g) in the same manner as described for EXAMPLE 9.

MS (EI$^+$) m/z: 406 (M$^+$).

HRMS (EI$^+$) for C$_{21}$H$_{27}$FN$_2$O$_5$ (M$^+$): calcd, 406.1904; found, 406.1930.

Step 2

5(R)-Azidomethyl-3-[3-fluoro-4-[(1α,5α,6α)-6-[(2-tetrahydropyranyl)oxy]methyl-3-azabicyclo[3.1.0]hexan-3-yl]phenyl]oxazolidin-2-one.

The title compound 5(R)-azidomethyl-3-[3-fluoro-4-[(1α,5α,6α)-6-[(2-tetrahydropyranyl)oxy]methyl-3-azabicyclo[3.1.0]hexan-3-yl]phenyl]oxazolidin-2-one (659 mg) was prepared from 5(R)-3-[3-fluoro-4-[(1α,5α,6α)-6-[(2-tetrahydropyranyl)oxy]methyl-3-azabicyclo[3.1.0]hexan-3-yl]phenyl]-5-hydroxymethyloxazolidin-2-one (698 mg) in the same manner as described for EXAMPLE 9.

MS (EI$^+$) m/z: 431 (M$^+$).

HRMS (EI$^+$) for $C_{21}H_{26}FN_5O_4$ (M$^+$): calcd, 431.1969; found, 431.1960.

Step 3

N-[5(S)-3-[3-Fluoro-4-[(1α,5α,6α)-6-[(2-tetrahydropyranyl)oxy]methyl-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-[(2-tetrahydropyranyl)oxy]methyl-3-azabicyclo[3.1.0]hexan-3-yl]phenyl]-2-oxooxazolidin-5-ylmethyl]acetamide (588 mg) was prepared from 5(R)-azidomethyl-3-[3-fluoro-4-[(1α,5α,6α)-6-[(2-tetrahydropyranyl)oxy]methyl-3-azabicyclo[3.1.0]hexan-3-yl]phenyl]oxazolidin-2-one (655 mg) in the same manner as described for EXAMPLE 9.

EXAMPLE 15

N-[5(S)-3-[3-Fluoro-4-[(1α,5α,6α)-6-methoxymethyl-3-azabicyclo[3.1.0]hexan-3-yl]phenyl]-2-oxooxazolidin-5-ylmethyl]acetamide.

Step 1

5(R)-3-[3-Fluoro-4-[(1α,5α,6α)-6-methoxymethyl-3-azabicyclo[3.1.0]hexan-3-yl]phenyl]-5-hydroxymethyloxazolidin-2-one.

The title compound 5(R)-3-[3-fluoro-4-[(1α,5α,6α)-6-methoxymethyl-3-azabicyclo[3.1.0]hexan-3-yl]phenyl]-5-hydroxymethyloxazolidin-2-one (345 mg) was prepared from 1-benzyloxycarbonylamino-3-fluoro-4-[(1α,5α,6α)-6-methoxymethyl-3-azabicyclo[3.1.0]hexan-3-yl]benzene (450 mg) in the same manner as described for EXAMPLE 9.

MS (EI$^+$) m/z: 336 (M$^+$).

HRMS (EI$^+$) for $C_{17}H_{21}FN_2O_4$(M$^+$): calcd, 336.1485; found, 336.1477.

Step 2

5(R)-Azidomethyl-3-[3-fluoro-4-[(1α,5α,6α)-6-methoxymethyl-3-azabicyclo[3.1.0]hexan-3-yl]phenyl]oxazolidin-2-one.

The title compound 5(R)-azidomethyl-3-[3-fluoro-4-[(1α,5α,6α)-6-methoxymethyl-3-azabicyclo[3.1.0]hexan-3-yl]phenyl]oxazolidin-2-one (332 mg) was prepared from 5(R)-3-[3-fluoro-4-[(1α,5α,6α)-6-methoxymethyl-3-azabicyclo[3.1.0]hexan-3-yl]phenyl]-5-hydroxymethyloxazolidin-2-one (290 mg) in the same manner as described for EXAMPLE 9.

Step 3

N-[5(S)-3-[3-Fluoro-4-[(1α,5α,6α)-6-methoxymethyl-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-methoxymethyl-3-azabicyclo[3.1.0]hexan-3-yl]phenyl]-2-oxooxazolidin-5-ylmethyl]acetamide (286 mg) was prepared from 5(R)-azidomethyl-3-[3-fluoro-4-[(1α,5α,6α)-6-methoxymethyl-3-azabicyclo[3.1.0]hexan-3-yl]phenyl]oxazolidin-2-one (332 mg) in the same manner as described for EXAMPLE 9.

MS (EI$^+$) m/z: 377 (M$^+$).

EXAMPLE 16

N-[5(S)-3-[3-Fluoro-4-[(1α,5α,6α)-6-(3-isoxazolyl)oxymethyl-3-azabicyclo[3.1.0]hexan-3-yl]phenyl]-2-oxooxazolidin-5-ylmethyl]acetamide.

To a suspension of N-[5(S)-3-[3-fluoro-4-[(1α,5α,6α)-6-hydroxymethyl-3-azabicyclo[3.1.0]hexan-3-yl]phenyl]-2-oxooxazolidin-5-ylmethyl]acetamide (500 mg), 3-hydroxyisoxazole (152 mg), and triphenylphosphine (541 mg) in tetrahydrofuran (6 mL) was added diisopropyl azodicarboxylate (362 mg), and the mixture was stirred at room temperature for 1 hour, and then concentrated in vacuo. Flash chromatography (silica, ethyl acetate:methanol=9:1) of the residue gave N-[5(S)-3-[3-fluoro-4-[(1α,5α,6α)-6-(3-isoxazolyl)oxymethyl-3-azabicyclo[3.1.0]hexan-3-yl]phenyl]-2-oxooxazolidin-5-ylmethyl]acetamide (398 mg).

MS (EI$^+$) m/z: 430 (M$^+$).

HRMS (EI$^+$) for $C_{21}H_{23}FN_4O_5$ (M$^+$): calcd, 430.1652; found, 430.1698.

EXAMPLE 17

N-[5(S)-3-[4-[(1α,5α,6α)-6-Acetylamino-3-azabicyclo[3.1.0]hexan-3-yl]-3-fluorophenyl]-2-oxooxazolidin-5-ylmethyl]acetamide.

To a solution of N-[5(S)-3-[4-[(1α,5α,6α)-6-amino-3-azabicyclo[3.1.0]hexan-3-yl]-3-fluorophenyl]-2-oxooxazolidin-5-ylmethyl]acetamide (105 mg) in pyridine (3 mL) was added acetic anhydride (57 μL), and the mixture was stirred at 50° C. for 2 hours, and then concentrated in vacuo. Flash chromatography (silica, dichloromethane:methanol=10:1) of the residue gave N-[5(S)-3-[4-[(1α,5α,6α)-6-acetylamino-3-azabicyclo[3.1.0]hexan-3-yl]-3-fluorophenyl]-2-oxooxazolidin-5-ylmethyl]acetamide (88.6 mg).

MS (EI$^+$) m/z: 390 (M$^+$).

HRMS (EI$^+$) for $C_{19}H_{23}FN_4O_4$(M$^+$): calcd, 390.1703; found, 390.1694.

EXAMPLE 18

N-[5(S)-3-[4-[(1α,5α,6α)-6-Benzoylamino-3-azabicyclo[3.1.0]hexan-3-yl]-3-fluorophenyl]-2-oxooxazolidin-5-ylmethyl]acetamide.

To a solution of N-[5(S)-3-[4-[(1α,5α,6α)-6-amino-3-azabicyclo[3.1.0]hexan-3-yl]-3-fluorophenyl]-2-oxooxazolidin-5-ylmethyl]acetamide (105 mg) in pyridine (1 mL) and dichloromethane (4 mL) was added benzoyl chloride (70 μL), and the mixture was stirred at 0° C. for 30 min, and then concentrated in vacuo. Flash chromatography (silica, dichloromethane:methanol=9:1) of the residue gave N-[5(S)-3-[4-[(1α,5α,6α)-6-benzoylamino-3-azabicyclo[3.1.0]hexan-3-yl]-3-fluorophenyl]-2-oxooxazolidin-5-ylmethyl]acetamide (96.2 mg).

MS (EI$^+$) m/z: 452 (M$^+$).

HRMS (EI$^+$) for $C_{24}H_{25}FN_4O_4$ (M$^+$): calcd, 452.1860; found, 452.1874.

EXAMPLE 19

N-[5(S)-3-[3-Fluoro-4-[(1α,5α,6α)-6-phenylsulfonylamino-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-phenylsulfonyl amino-3-azabicyclo[3.1.0]hexan-3-yl]phenyl]-2-oxooxazolidin-5-ylmethyl]acetamide (97.7 mg) was prepared from N-[5(S)-3-[4-[(1α,5α,6α)-6-amino-3- azabicyclo[3.1.0]hexan-3-yl]-3-fluorophenyl]-2-oxooxazolidin-5-ylmethyl]acetamide (105 mg) and benzenesulfonyl chloride (77 µL) in the same manner as described for EXAMPLE 18.

MS (EI$^+$) m/z: 488 (M$^+$).

HRMS (EI$^+$) for $C_{23}H_{25}FN_4O_5S$ (M$^+$): calcd, 488.1530; found, 488.1547.

EXAMPLE 20

N-[5(S)-3-[3-Fluoro-4-[(1α,5α,6α)-6-methanesulfonylamino-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-mathanesulfonylamino-3-azabicyclo[3.1.0]hexan-3-yl]phenyl]-2-oxooxazolidin-5-ylmethyl]acetamide (118 mg) was prepared from N-[5(S)-3-[4-[(1α,5α,6α)-6-amino-3-azabicyclo[3.1.0]hexan-3-yl]-3-fluorophenyl]-2-oxooxazolidin-5-ylmethyl]acetamide (105 mg) and methanesulfonyl chloride (46 µL) in the same manner as described for EXAMPLE 18.

MS (EI$^+$) m/z: 426 (M$^+$).

HRMS (EI$^+$) for $C_{18}H_{23}FN_4O_5S$ (M$^+$): calcd, 426.1373; found, 426.1376.

EXAMPLE 21

N-[5(S)-3-[3-Fluoro-4-[(1α,5α,6α)-6-carbamoylamino-3-azabicyclo[3.1.0]hexan-3-yl]phenyl]-2-oxooxazolidin-5-ylmethyl]acetamide.

To a solution of N-[5(S)-3-[4-[(1α,5α,6α)-6-amino-3-azabicyclo[3.1.0]hexan-3-yl]-3-fluorophenyl]-2-oxooxazolidin-5-ylmethyl]acetamide (139 mg) in dimethylformamide (5 mL) was added trimethylsilyl isocyanate (0.27 mL), and the mixture was stirred at room temperature for 4 hours, and then concentrated in vacuo. Flash chromatography (silica, dichloromethane:methanol:NH$_4$OH=50:8:0.5) of the residue gave N-[5(S)-3-[3-fluoro-4-[(1α,5α,6α)-6-carbamoylamino-3-azabicyclo[3.1.0]hexan-3-yl]phenyl]-2-oxooxazolidin-5-ylmethyl]acetamide (112 mg).

MS (EI$^+$) m/z: 392 (M$^+$).

HRMS (EI$^+$) for $C_{18}H_{23}FN_5O_4$ (M$^+$): calcd, 392.1734; found, 392.1731.

EXAMPLE 22

N-[5(S)-3-[3-Fluoro-4-[(1α,5α,6α)-6-formyl-3-azabicyclo[3.1.0]hexan-3-yl]phenyl]-2-oxooxazolidin-5-ylmethyl]acetamide.

To a solution of N-[5(S)-3-[3-fluoro-4-[(1α,5α,6α)-6-hydroxymethyl-3-azabicyclo[3.1.0]hexan-3-yl]phenyl]-2-oxooxazolidin-5-ylmethyl]acetamide (1.00 g) in dimethyl sulfoxide (10 mL) was added 1-hydroxy-1,2-benziodoxol-3(1H)-one 1-oxide (1.16 g), and the mixture was stirred at room temperature for 2 hours. After dilution with water, the mixture was extracted with ethyl acetate. The organic extracts were washed with brine, dried over anhydrous magnesium sulfate, and then concentrated in vacuo. Flash chromatography (silica, ethyl acetate:methanol=19:1) of the residue gave N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (766 mg).

MS (EI$^+$) m/z: 361 (M$^+$).

HRMS (EI$^+$) for $C_{18}H_{20}FN_3O_4$(M$^+$): calcd, 361.1438; found, 361.1469.

EXAMPLE 23

N-[5(S)-3-[4-[(1α,5α,6α)-6-Carboxyl-3-azabicyclo[3.1.0]hexan-3-yl]-3-fluorophenl]-2-oxooxazolidin-5-ylmethyl]acetamide.

To a solution of N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (321 mg) in methanol (17 mL) were added 1N sodium hydroxide solution (1.78 mL) and silver(I) oxide (309 mg), and the mixture was stirred at room temperature for 6 hours. After insoluble materials were filtered off, the filtrate was concentrated in vacuo, and then the residue was added chloroform. The resulting precipitates were collected by filtration, washed with 1N hydrochloric acid and water, and then dried to give N-[5(S)-3-[4-[(1α,5α,6α)-6-carboxyl-3-azabicyclo[3.1.0]hexan-3-yl]-3-fluorophenyl]-2-oxooxazolidin-5-ylmethyl]acetamide (297 mg).

MS (EI$^+$) m/z: 377 (M$^+$).

HRMS (EI$^+$) for $C_{18}H_{20}FN_3O_5$ (M): calcd, 377.1387; found, 377.1367.

EXAMPLE 24

N-[5(S)-3-[4-[(1α,5α,6α)-6-[(1-Iminoethyl)amino]-3-azabicyclo[3.1.0]hexan-3-yl]-3-fluorophenyl]-2-oxooxazolidin-5-ylmethyl]acetamide.

To a solution of N-[5(S)-3-[4-[(1α,5α,6α)-6-amino-3-azabicyclo[3.1.0]hexan-3-yl]-3-fluorophenyl]-2-oxooxazolidin-5-ylmethyl]acetamide (139 mg) in methanol (5 mL) was added potassium carbonate (112 mg) and ethanimidic acid ethyl ester hydrochloride (98.8 mg), and the mixture was stirred at room temperature for 12 hours. After insoluble materials were filtered off, the filtrate was concentrated in vacuo. Flash chromatography (silica, dichloromethane:methanol:NH$_4$OH=20:10:1) of the residue gave N-[5(S)-3-[4-[(1α,5α,6α)-6-[(1-iminoethyl)amino]-3-azabicyclo[3.1.0]hexan-3-yl]-3-fluorophenyl]-2-oxooxazolidin-5-ylmethyl]acetamide (76.9 mg).

MS (FAB$^+$) m/z: 390 (MH$^+$).

HRMS (FAB$^+$) for $C_{19}H_{25}FN_5O_3$ (MH$^+$): calcd, 390.1941; found, 390.1966.

EXAMPLE 25

N-[5(S)-3-[4-[(1α,5α,6α)-6-Bromomethyl-3-azabicyclo[3.1.0]hexan-3-yl]-3-fluorophenyl]-2-oxooxazolidin-5-ylmethyl]acetamide.

To a solution of N-[5(S)-3-[3-fluoro-4-[(1α,5α,6α)-6-hydroxymethyl-3-azabicyclo[3.1.0]hexan-3-yl]phenyl]-2-oxooxazolidin-5-ylmethyl]acetamide (36.3 mg) and tetrabromomethane (49.7 mg) in dichloromethane (1 mL) was added triphenylphosphine (39.3 mg), and the mixture was stirred at room temperature for 2 hours, and then concentrated in vacuo. Flash chromatography (silica, ethyl acetate:methanol=19:1) of the residue gave N-[5(S)-3-[4-[(1α,5α,6α)-6-bromomethyl-3-azabicyclo[3.1.0]hexan-3-yl]-3-fluorophenyl]-2-oxooxazolidin-5-ylmethyl]acetamide (30.1 mg).

MS (EI$^+$) m/z: 425 (M$^+$).

HRMS (EI$^+$) for $C_{18}H_{21}BrFN_3O_3$ (M): calcd, 425.0750; found, 425.0739.

EXAMPLE 26

N-[5(S)-3-[4-[(1α,5α,6α)-6-Cyanomethyl-3-azabicyclo[3.1.0]hexan-3-yl]-3-fluorophenyl]-2-oxooxazolidin-5-ylmethyl]acetamide.

A solution of N-[5(S)-3-[4-[(1α,5α,6α)-6-bromomethyl-3-azabicyclo[3.1.0]hexan-3-yl]-3-fluorophenyl]-2-oxooxazolidin-5-ylmethyl]acetamide (300 mg) and sodium cyanide (52.0 mg) in dimethylformamide (1.4 mL) was stirred at room temperature for 1 day, and then concentrated in vacuo. The residue was dissolved in dichloromethane, the solution was washed with water, dried over anhydrous magnesium sulfate, filtered, and then concentrated in vacuo. Flash chromatography (silica, ethyl acetate:methanol=19:1) of the residue gave N-[5(S)-3-[4-[(1α,5α,6α)-6-cyanomethyl-3-azabicyclo[3.1.0]hexan-3-yl]-3-fluorophenyl]-2-oxooxazolidin-5-ylmethyl]acetamide (259 mg).

MS (EI$^+$) m/z: 372 (M$^+$).

HRMS (EI$^+$) for $C_{19}H_{21}FN_4O_3$ (M$^+$): calcd, 372.1598; found, 372.1596.

EXAMPLE 27

N-[4-[1-(5(S)-Acetylaminomethyl-2-oxooxazolidin-3-yl)-3-fluoro]phenyl-(1α,5α,6α)-3-azabicyclo[3.1.0]hexan-6-yl]methylpyridinium bromide.

A solution of N-[5(S)-3-[4-[(1a,5ac,6a)-6-bromomethyl-3-azabicyclo[3.1.0]hexan-3-yl]-3-fluorophenyl]-2-oxooxazolidin-5-ylmethyl]acetamide (115 mg) in pyridine (5 mL) was stirred at room temperature for 3 days, and then concentrated in vacuo. The methanol solution of the residue was treated with charcoal, filtered, and then concentrated in vacuo. The aqueous solution of the residue was lyophilized to give N-[4-[1-(5(S)-acetylaminomethyl-2-oxooxazolidin-3-yl)-3-fluoro]phenyl-(1α,5α,6α)-3-azabicyclo[3.1.0]hexan-6-yl]methylpyridinium bromide (128 mg).

MS (FAB$^+$) m/z: 425 [(M–Br)$^+$].

HRMS (FAB$^+$) for $C_{23}H_{26}FN_4O_3$ [(M–Br)$^+$]: calcd, 425.1989; found, 425.1950.

EXAMPLE 28

N-[5(S)-3-[3-Fluoro-4-[(1α,5α,6α)-6-succinimidoyloxycarbonyl-3-azabicyclo[3.1.0]hexan-3-yl]phenyl]-2-oxooxazolidin-5-ylmethyl]acetamide.

To a solution of N-[5(S)-3-[4-[(1α,5α,6α)-6-carboxyl-3-azabicyclo[3.1.0]hexan-3-yl]-3-fluorophenyl]-2-oxooxazolidin-5-ylmethyl]acetamide (280 mg) in dimethylformamide (5 mL) were added N-hydroxysuccinimide (124 mg) and 1,3-dicyclohexylcarbodiimide (230 mg), and the mixture as stirred at room temperature for 2 days. After insoluble materials were filtered off and washed with ethyl acetate. The filtrate was washed with saturated sodium hydrogencarbonate solution and brine, dried over anhydrous magnesium sulfate, filtered, and then concentrated in vacuo. Flash chromatography (silica, ethyl acetate:methanol=19:1) of the residue gave N-[5(S)-3-[3-fluoro-4-[(1α,5α,6α)-6-succinimidoyloxycarbonyl-3-azabicyclo[3.1.0]hexan-3-yl]phenyl]-2-oxooxazolidin-5-ylmethyl]acetamide (349 mg).

MS (FAB$^+$) m/z: 475 (MH$^+$).

HRMS (FAB$^+$) for $C_{22}H_{24}FN_4O_7$ (MH$^+$): calcd, 475.1629; found, 475.1618.

EXAMPLE 29

N-[5(S)-3-[4-[(1α,5α,6α)-6-Carbamoyl-3-azabicyclo[3.1.0]hexan-3-yl]-3-fluorophenyl]-2-oxooxazolidin-5-ylmethyl]acetamide.

To a solution of N-[5(S)-3-[3-fluoro-4-[(1 c,5o,6a)-6-succinimidoyl oxycarbonyl-3-azabicyclo[3.1.0]hexan-3-yl]phenyl]-2-oxooxazolidin-5-ylmethyl]acetamide (160 mg) in tetrahydrofuran (5 mL) was added aqueous ammonium hydroxide solution (28%, 1 mL), and the mixture was stirred at room temperature for 1 hour, and then concentrated in vacuo. The residue was treated with water, the resulting precipitates were collected by filtration and washed with water and tetrahydrofuran to give N-[5(S)-3-[4-[(1α,5α,6α)-6-carbamoyl-3-azabicyclo[3.1.0]hexan-3-yl]-3-fluorophenyl]-2-oxooxazolidin-5-ylmethyl]acetamide (115 mg).

MS (EI$^+$) m/z: 376 (M$^+$).

HRMS (EI$^+$) for $C_{18}H_{21}FN_4O_4$ (M): calcd, 376.1547; found, 376.1552.

EXAMPLE 30

N-[5(S)-3-[3-Fluoro-4-[(1α,5α,6α)-6-methoxycarbonyl-3-azabicyclo[3.1.0]hexan-3-yl]phenyl]-2-oxooxazolidin-5-ylmethyl]acetamide.

To a solution of N-[5(S)-3-[4-[(1α,5α,6α)-6-carboxyl-3-azabicyclo[3.1.0]hexan-3-yl]-3-fluorophenyl]-2-oxooxazolidin-5-ylmethyl]acetamide (100 mg) in dimethylformamide (2 mL) was added methanol (17.0 mg) and 1,3-dicyclohexylcarbodiimide (109 mg), and the mixture was stirred at room temperature for 6 hours, and then concentrated in vacuo. Flash chromatography (silica, ethyl acetate:methanol=19:1) of the residue gave N-[5(S)-3-[3-fluoro-4-[(1α,5α,6α)-6-methoxycarbonyl-3-azabicyclo[3.1.0]hexan-3-yl]phenyl]-2-oxooxazolidin-5-ylmethyl]acetamide (101 mg).

MS (EI$^+$) m/z: 391 (M$^+$).

HRMS (EI$^+$) for $C_{19}H_{22}FN_3O_5$ (M$^+$): calcd, 391.1543; found, 391.1515.

EXAMPLE 31

N-[5(S)-3-[4-[(1α,5α,6α)-6-[N',N"-Bis(benzyloxycarbonyl)guanidino]-3-azabicyclo[3.1.0]hexan-3-yl]-3-fluorophenyl]-2-oxooxazolidin-5-ylmethyl]acetamide.

To a solution of N-[5(S)-3-[4-[(1α,5α,6α)-6-amino-3-azabicyclo[3.1.0]hexan-3-yl]-3-fluorophenyl]-2-oxooxazolidin-5-ylmethyl]acetamide (157 mg) and 1,3-bis(benzyloxycarbonyl)-2-methyl-2-thiopseudourea (161 mg) in N,N-dimethylformamide (3 mL) was added triethylamine (125 EL), and the mixture was stirred at room temperature for 1 day. After dilution with dichloromethane, the mixture was washed with water and brine, dried over dried over anhydrous sodium sulfate, and then concentrated in vacuo. Flash chromatography (silica, hexane:ethyl acetate=5:2) of the residue gave N-[5(S)-3-[4-[(1α,5α,6α)-6-[N',N'-bis(benzyloxycarbonyl)guanigino]-3-azabicyclo[3.1.0]hexan-3-yl]-3-fluorophenyl]-2-oxooxazolidin-5-ylmethyl]acetamide (288 mg).

MS (FAB$^+$) m/z: 659 (MH$^+$).

EXAMPLE 32

N-[5(S)-3-[3-Fluoro-4-[(1α,5α,6α)-6-guanidino-3-azabicyclo[3.1.0]hexan-3-yl]phenyl]-2-oxooxazolidin-5-ylmethyl]acetamide.

A suspension of N-[5(S)-3-[4-[(1α,5α,6α)-6-[N',N''-bis(benzyloxycarbonyl)guanidino]-3-azabicyclo[3.1.0]hexan-3-yl]-3-fluorophenyl]-2-oxooxazolidin-5-ylmethyl]acetamide (224 mg) and palladium catalyst (10% on charcoal, 67.2 mg) in methanol (5 mL) and dichloromethane (5 mL) was hydrogenated at 1 atm for 7 hours at room temperature. After filtration of the catalyst, the filtrate was concentrated in vacuo to give N-[5(S)-3-[3-fluoro-4-[(1α,5α,6α)-6-guanidino-3-azabicyclo[3.1.0]hexan-3-yl]phenyl]-2-oxooxazolidin-5-ylmethyl]acetamide (127 mg).

MS (FAB$^+$) m/z: 390 (MH$^+$).

HRMS (FAB$^+$) for $C_{18}H_{24}FN_6O_3$ (MH$^+$): calcd, 391.1894; found, 390.1888.

EXAMPLE 33

N-[5(S)-3-[3-Fluoro-4-[(1α,5α,6α)-6-methylcarbamoyl-3-azabicyclo[3.1.0]hexan-3-yl]phenyl]-2-oxooxazolidin-5-ylmethyl]acetamide.

To a solution of N-[5(S)-3-[3-fluoro-4-[(1α,5α,6α)-6-succinimidoyl oxycarbonyl-3-azabicyclo[3.1.0]hexan-3-yl]phenyl]-2-oxooxazolidin-5-ylmethyl]acetamide (180 mg) in tetrahydrofuran (10 mL) was added methylamine (30% ethanol solution, 0.40 mL) at room temperature, and the mixture was stirred for 30 min. The resulting precipitates were collected by filtration, washed with water and tetrahydrofuran to give N-[5(S)-3-[3-fluoro-4-[(1α,5α,6α)-6-methylcarbamoyl-3-azabicyclo[3.1.0]hexan-3-yl]phenyl]-2-oxooxazolidin-5-ylmethyl]acetamide (141 mg).

MS (EI$^+$) m/z: 390 (M$^+$).

HRMS (EI$^+$) for $C_{19}H_{23}FN_4O_4$ (M$^+$): calcd, 390.1703; found, 390.1710.

EXAMPLE 34

N-[5(S)-3-[4-[(1α,5α,6α)-6-Dimethylcarbamoyl-3-azabicyclo[3.1.0]hexan-3-yl]-3-fluorophenyl]-2-oxooxazolidin-5-ylmethyl]acetamide.

To a solution of N-[5(S)-3-[3-fluoro-4-[(1α,5α,6α)-6-succinimidoyl oxycarbonyl-3-azabicyclo[3.1.0]hexan-3-yl]phenyl]-2-oxooxazolidin-5-ylmethyl]acetamide (180 mg) in tetrahydrofuran (4 mL) was added a solution of dimethylamine hydrochloride (309 mg) and sodium hydrogencarbonate (637 mg) in water (1 mL), and the mixture was stirred at room temperature for 1 hour, and then concentrated in vacuo. The residue was treated with water, the resulting precipitates were collected by filtration and washed with water and tetrahydrofuran to give N-[5(S)-3-[4-[(1α,5α,6α)-6-dimethylcarbamoyl-3-azabicyclo[3.1.0]hexan-3-yl]-3-fluorophenyl]-2-oxooxazolidin-5-ylmethyl]acetamide (138 mg).

MS (EI$^+$) m/z: 404 (M$^+$).

HRMS (EI$^+$) for $C_{20}H_{25}FN_4O_4$ (M$^+$): calcd, 404.1860; found, 404.1864.

EXAMPLE 35

N-[5(S)-3-[3-Fluoro-4-[(1α,5α,6α)-6-[(piperidin-1-yl)carbonyl]-3-azabicyclo[3.1.0]hexan-3-yl]phenyl]-2-oxooxazolidin-5-ylmethyl]acetamide.

To a solution of N-[5(S)-3-[3-fluoro-4-[(1α,5α,6α)-6-succinimidoyl oxycarbonyl-3-azabicyclo[3.1.0]hexan-3-yl]phenyl]-2-oxooxazolidin-5-ylmethyl]acetamide (150 mg) in tetrahydrofuran (5 mL) was added piperidine (135 mg), and the mixture was stirred at room temperature for 2 hours, and then concentrated in vacuo. The residue was treated with water, the resulting precipitates were collected by filtration and washed with water to give N-[5(S)-3-[3-fluoro-4-[(1α,5α,6α)-6-(piperidin-1-yl)carbonyl-3-azabicyclo[3.1.0]hexan-3-yl]phenyl]-2-oxooxazolidin-5-ylmethyl]acetamide (128 mg).

MS (EI$^+$) m/z: 444 (M$^+$).

HRMS (EI$^+$) for $C_{23}H_{29}FN_4O_4$ (M$^+$): calcd, 444.2173; found, 444.2152.

EXAMPLE 36

N-[5(S)-3-[3-Fluoro-4-[(1α,5α,6α)-6-[(morpholin-4-yl)carbonyl]-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-(morpholin-4-yl)carbonyl-3-azabicyclo[3.1.0]hexan-3-yl]phenyl]-2-oxooxazolidin-5-ylmethyl]acetamide (128 mg) was prepared from N-[5(S)-3-[3-fluoro-4-[(1α,5α,6α)-6-succinimidoyloxycarbonyl-3-azabicyclo[3.1.0]hexan-3-yl]phenyl]-2-oxooxazolidin-5-ylmethyl]acetamide (150 mg) and morpholine (138 mg) in the same manner as described for EXAMPLE 35.

MS (EI$^+$) m/z: 446 (M$^+$).

HRMS (EI$^+$) for $C_{22}H_{27}FN_4O_5$ (M$^+$): calcd, 446.1965; found, 446.1984.

EXAMPLE 37

N-[5(S)-3-[3-Fluoro-4-[(1α,5α,6α)-6-[N-(2-hydroxyethyl)carbamoyl]-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-[N-(2-hydroxyethyl)]carbamoyl-3-azabicyclo[3.1.0]hexan-3-yl]phenyl]-2-oxooxazolidin-5-ylmethyl]acetamide (130 mg) was prepared from N-[5(S)-3-[3-fluoro-4-[(1α,5α,6α)-6-succinimidoyloxycarbonyl-3-azabicyclo[3.1.0]hexan-3-yl]phenyl]-2-oxooxazolidin-5-ylmethyl]acetamide (180 mg) and ethanolamine (116 mg) in the same manner as described for EXAMPLE 35.

MS (FAB$^+$) m/z: 420 (M$^+$).

HRMS (FAB$^+$) for $C_{20}H_{25}FN_4O_5$ (M$^+$): calcd, 420.1809; found, 420.1779.

EXAMPLE 38

N-[5(S)-3-[4-[(1α,5α,6α)-6-(2-Aminoethyl)-3-azabicyclo[3.1.0]hexan-3-yl]-3-fluorophenyl]-2-oxooxazolidin-5-ylmethyl]acetamide.

To a solution of N-[5(S)-3-[4-[(1α,5α,6α)-6-cyanomethyl-3-azabicyclo[3.1.0]hexan-3-yl]-3-fluorophenyl]-2-oxooxazolidin-5-ylmethyl]acetamide (262 mg) in methanol (7 mL) was added cobalt(II) chloride hexahydrate (335 mg) and sodium borohydride (266 mg) at 0° C., and the mixture was stirred for 1 hour. After quenching the reaction by the addition of 1N hydrochloric acid (7 mL), and the mixture was stirred at room temperature for 30 min, and then concentrated in vacuo. The residue was made to alkaline by the addition of ammonium hydroxide solution, and then concentrated in vacuo. Flash chromatography (silica NH type, ethyl acetate:methanol=9:1) of the residue gave N-[5(S)-3-[4-[(1α,5α,6α)-6-(2-aminoethyl)-3-azabicyclo[3.1.0]hexan-3-yl]-3-fluorophenyl]-2-oxooxazolidin-5-ylmethyl]acetamide (139 mg).

MS (FAB$^+$) m/z: 376 (M$^+$).

HRMS (FAB$^+$) for $C_{19}H_{25}FN_4O_3$ (M$^+$): calcd, 376.1911; found, 376.1899.

EXAMPLE 39

N-[5(S)-3-[3-Fluoro-4-[(1α,5α,6α)-6-(1-hydroxyethyl)-3-azabicyclo[3.1.0]hexan-3-yl]phenyl]-2-oxooxazolidin-5-ylmethyl]acetamide.

To a solution of N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (340 mg) in dioxane (20 mL) was added methylmagnesium iodide (3.0M solution in diethyl ether 1.25 mL) at 0° C., and the mixture was stirred at room temperature for 14 hours. After quenching the reaction by the addition of saturated ammonium chloride solution, the mixture was extracted with ethyl acetate. The organic extracts were washed with brine, dried over anhydrous magnesium sulfate, and then concentrated in vacuo. Flash chromatography (silica, ethyl acetate:methanol=50:1) of the residue gave N-[5(S)-3-[3-fluoro-4-[(1α,5α,6α)-6-(1-hydroxyethyl)-3-azabicyclo[3.1.0]hexan-3-yl]phenyl]-2-oxooxazolidin-5-ylmethyl]acetamide (163 mg).

MS (EI$^+$) m/z: 377 (M$^+$).

HRMS (EI$^+$) for $C_{19}H_{24}FN_3O_4$ (M$^+$): calcd, 377.1751; found, 377.1740.

EXAMPLE 40

N-[5(S)-3-[4-[(1α,5α,6α)-6-Acetyl-3-azabicyclo[3.1.0]hexan-3-yl]-3-fluorophenyl]-2-oxooxazolidin-5-ylmethyl]acetamide.

To a solution of N-[5(S)-3-[3-fluoro-4-[(1α,5α,6α)-6-(1-hydroxyethyl)-3-azabicyclo[3.1.0]hexan-3-yl]phenyl]-2-oxooxazolidin-5-ylmethyl]acetamide (160 mg) in dimethyl sulfoxide (4 mL) was added 1-hydroxy-1,2-benziodoxol-3(1H)-one 1-oxide (178 mg), and the mixture was stirred at room temperature for 6 hours. After dilution the mixture with saturated sodium hydrogencarbonate solution, the mixture was extracted with ethyl acetate. The organic extracts were washed with brine, dried over anhydrous magnesium sulfate, and then concentrated in vacuo. Flash chromatography (silica, ethyl acetate:methanol=20:1) of the residue gave N-[5(S)-3-[4-[(1α,5α,6α)-6-acetyl-3-azabicyclo[3.1.0]hexan-3-yl]-3-fluorophenyl]-2-oxooxazolidin-5-ylmethyl]acetamide (119 mg).

MS (EI$^+$) m/z: 375 (M$^+$).

HRMS (EI$^+$) for $C_{19}H_{22}FN_3O_4$(M$^+$): calcd, 375.1594; found, 375.1556.

EXAMPLE 41

(E)-N-[5(S)-3-[3-Fluoro-4-[(1α,5α,6α)-6-[(hydroxyimino)methyl]-3-azabicyclo[3.1.0]hexan-3-yl]phenyl]-2-oxooxazolidin-5-ylmethyl]acetamide.

To a solution of N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (130 mg) and sodium acetate (177 mg) in methanol (5 mL) was added hydroxylamine hydrochloride (75.0 mg), and the mixture was stirred at room temperature for 2 hours, and then concentrated in vacuo. The residue was treated with water, and the resulting precipitates were collected by the filtration, washed with water to give (E)-N-[5(S)-3-[3-fluoro-4-[(1α,5α,6α)-6-[(hydroxyimino)methyl]-3-azabicyclo[3.1.0]hexan-3-yl]phenyl]-2-oxooxazolidin-5-ylmethyl]acetamide (132 mg).

MS (EI$^+$) m/z: 376 (M$^+$).

HRMS (EI$^+$) for $C_{18}H_{21}FN_4O_4$(M$^+$): calcd, 376.1547; found, 376.1558.

EXAMPLE 42

(Z)-N-[5(S)-3-[3-Fluoro-4-[(1α,5α,6α)-6-[(hydroxyimino)methyl]-3-azabicyclo[3.1.0]hexan-3-yl]phenyl]-2-oxooxazolidin-5-ylmethyl]acetamide.

To a solution of N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (100 mg) and sodium acetate (90.8 mg) in methanol (5 mL) was added hydroxylamine hydrochloride (38.5 mg), and the mixture was stirred at room temperature for 20 min, and then concentrated in vacuo. The residue was treated with water, and the resulting precipitates were collected by the filtration, washed with water. The methanol solution of the filtrate was concentrated in vacuo. Preparative thin layer chromatography (silica, ethyl acetate:methanol=20:1) of the residue gave (Z)-N-[5(S)-3-[3-fluoro-4-[(1α,5α,6α)-6-[(hydroxyimino)methyl]-3-azabicyclo[3.1.0]hexan-3-yl]phenyl]-2-oxooxazolidin-5-ylmethyl]acetamide (34.0 mg).

MS (EI$^+$) m/z: 376 (M$^+$).

HRMS (EI$^+$) for $C_{18}H_{21}FN_4O_4$ (M$^+$): calcd, 376.1547; found, 376.1582.

EXAMPLE 43

N-[5(S)-3-[3-Fluoro-4-[(1α,5α,6α)-6-[(methoxyimino)methyl]-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-[(methoxyimino)methyl]-3-azabicyclo[3.1.0]hexan-3-yl]phenyl]-2-oxooxazolidin-5-ylmethyl]acetamide (152 mg) was prepared from N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (150 mg) and O-methylhydroxylamine hydrochloride (104 mg) in the same manner as described for EXAMPLE 41.

MS (EI$^+$) m/z: 390 (M$^+$).

HRMS (EI$^+$) for $C_{19}H_{23}FN_4O_4$ (M$^+$): calcd, 390.1703; found, 390.1717.

EXAMPLE 44

N-[5(S)-3-[4-[(1α,5α,6α)-6-[(t-Butoxycarbonylmethyloxyimino)methyl]-3-azabicyclo[3.1.0]hexan-3-yl]-3-fluorophenyl]-2-oxooxazolidin-5-ylmethyl]acetamide.

To a solution of O-(t-butoxycarbonylmethyl)hydroxylamine (157 mg) in methanol (7 mL) was added N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (350 mg), and the mixture was stirred at room temperature for 1 hour, and then concentrated in vacuo. Flash chromatography (silica, ethyl acetate:methanol=20:1) of the residue gave N-[5(S)-3-[4-[(1α,5α,6α)-6-[(t-butoxycarbonylmethyloxyimino)methyl]-3-azabicyclo[3.1.0]hexan-3-yl]-3-fluorophenyl]-2-oxooxazolidin-5-ylmethyl]acetamide (473 mg).

MS (EI$^+$) m/z: 490 (M$^+$).

HRMS (EI$^+$) for $C_{24}H_3{}_1FN_4O_6$ (M$^+$): calcd, 490.2228; found, 490.2273.

EXAMPLE 45

N-[5(S)-3-[4-[(1α,5α,6α)-6-[(Carboxylmethyloxyimino)methyl]-3-azabicyclo[3.1.0]hexan-3-yl]-3-fluorophenyl]-2-oxooxazolidin-5-ylmethyl]acetamide.

To a solution of N-[5(S)-3-[4-[(1α,5α,6α)-6-[(t-butoxycarbonylmethyloxyimino)methyl]-3-azabicyclo[3.1.0]hexan-3-yl]-3-fluorophenyl]-2-oxooxazolidin-5-ylmethyl]acetamide (220 mg) in dichloromethane (5 mL) was added trifluoroacetic acid (1 mL) at 0° C., and the mixture was stirred at room temperature for 12 hours, and then concentrated in vacuo. The residue was treated with water and acetonitrile, and the resulting precipitates were collected by filtration to give N-[5(S)-3-[4-[(1α,5α,6α)-6-[(carboxylmethyloxyimino)methyl]-3-azabicyclo[3.1.0]hexan-3-yl]-3-fluorophenyl]-2-oxooxazolidin-5-ylmethyl]acetamide (120 mg).

MS (FAB$^+$) m/z: 433 [(M−H)$^+$].

HRMS (FAB$^+$) for $C_{20}H_{22}FN_4O_6$ [(M−H)$^+$]: calcd, 433.1523; found, 433.1501.

EXAMPLE 46

N-[5(S)-3-[4-[(1α,5α,6α)-6-Cyano-3-azabicyclo[3.1.0]hexan-3-yl]-3-fluorophenyl]-2-oxooxazolidin-5-ylmethyl]acetamide.

To a solution of N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (164 mg) in tetrahydrofuran (3 mL) was added diisopropyl azodicarboxylate (151 mg) and triphenylphosphine (392 mg), and the mixture was stirred at room temperature for 10 min. Flash chromatography (silica, ethyl acetate:methanol=9:1) of the mixture gave N-[5(S)-3-[4-[(1α,5α,6α)-6-cyano-3-azabicyclo[3.1.0]hexan-3-yl]-3-fluorophenyl]-2-oxooxazolidin-5-ylmethyl]acetamide (150 mg).

MS (EI$^+$) m/z: 358 (M$^+$).

HRMS (EI$^+$) for $C_{18}H_{19}FN_4O_3$ (M$^+$): calcd, 358.1441; found, 358.1477.

EXAMPLE 47

N-[5(S)-3-[4-[(1α,5α,6α)-6-[(t-Butyldiphenylsilyl)oxy]methylbicyclo[3.1.0]hex-2-en-3-yl]-3-fluorophenyl]-2-oxooxazolidin-5-ylmethyl]acetamide.

A suspension of lithium chloride (25 mg), tris(dibenzylideneacetone)dipalladium(0)-chloroform adduct (10 mg), and (1α,5α,6α)-6-[(t-butyldiphenylsilyl)oxy]methyl-3-[(trifluoromethanesulfonyl)oxy]bicyclo[3.1.0]hex-2-ene (99 mg) in N-methylpyrrolidone (0.4 mL) was stirred at room temperature for 5 min under Ar atmosphere. The resulting mixture was added a solution of N-[5(S)-3-[3-fluoro-4-(trimethylstannyl)phenyl]-2-oxooxazolidin-5-ylmethyl]acetamide (100 mg) in N-methylpyrrolidone (0.4 mL), and the mixture was stirred at room temperature for 16 hours. After addition of ethyl acetate and water, insoluble materials were filtered off. The organic extracts were washed with 10% ammonium hydroxide solution, water, and brine, dried over anhydrous sodium sulfate, and then concentrated in vacuo. Flash chromatography (silica, ethyl acetate:methanol=30:1) of the residue gave N-[5(S)-3-[4-[(1α,5α,6α)-6-[(t-butyldiphenylsilyl)oxy]methylbicyclo[3.1.0]hex-2-en-3-yl]-3-fluorophenyl]-2-oxooxazolidin-5-ylmethyl]acetamide (79 mg).

$^1$H NMR (CDCl$_3$) δ 0.73–0.75 (m, 1H), 1.05 (s, 9H), 1.50–1.60 (m, 1H), 1.80–1.90 (m, 1H), 2.02 (s, 3H), 2.60–2.70 (m, 1H), 2.90–3.00 (m, 1H), 3.50–3.80 (m, 5H), 4.04 (t, J=8.8 Hz, 1H), 4.76–4.78 (m, 1H), 6.47 (m, 1H), 7.10–7.70 (m, 13H).

MS (FAB$^+$) m/z: 599 (MH$^+$).

EXAMPLE 48

N-[5(S)-3-[3-Fluoro-4-[(1α,5α,6α)-6-hydroxymethylbicyclo[3.1.0]hex-2-en-3-yl]phenyl]-2-oxooxazolidin-5-ylmethyl]acetamide.

To a solution of N-[5(S)-3-[4-[(1α,5α,6α)-6-[(t-butyldiphenylsilyl)oxy]methylbicyclo[3.1.0]hex-2-en-3-yl]-3-fluorophenyl]-2-oxooxazolidin-5-ylmethyl]acetamide (383 mg) in tetrahydrofuran (2 ml) was added a solution of tetrabutylammonium fluoride in tetrahydrofuran (1M, 1.28 mL) at 0° C., and the mixture was stirred at room temperature for 2.5 hours. After dilution the mixture with water, the resulting mixture was extracted with ethyl acetate. The organic extracts were washed with brine, dried over anhydrous sodium sulfate, and then concentrated in vacuo. Flash chromatography (silica, ethyl acetate:methanol=10:1) of the residue gave N-[5(S)-3-[3-fluoro-4-[(1α,5α,6α)-6-hydroxymethylbicyclo[3.1.0]hex-2-en-3-yl]phenyl]-2-oxooxazolidin-5-ylmethyl]acetamide (111 mg).

$^1$H NMR (DMSO-d$_6$) δ 0.50–0.60 (m, 1H), 1.56–1.60 (m, 1H), 1.81 (s, 3H), 1.87–1.90 (m, 1H), 2.70 (d, J=17.1 Hz, 1H), 2.95 (dd, J=17.1, 7.3 Hz, 1H), 3.20–3.40 (m, 2H), 3.40 (t, J=5.4 Hz, 2H), 3.71 (dd, J=8.8, 6.4 Hz, 1H), 4.10 (t, J=8.8 Hz, 1H), 4.68–4.75 (m, 1H), 6.43 (m, 1H), 7.21–7.24 (m, 1H), 7.33 (t, J=8.8 Hz, 1H), 7.40–7.50 (m, 1H).

MS (FAB$^+$) m/z: 361 (MH$^+$).

HRMS (FAB$^+$) for $C_{19}H_{22}FN_2O_4$ (MH$^+$): calcd, 361.1564; found, 361.1555.

EXAMPLE 49

N-[5(S)-3-[4-[(1α,5α,6α)-6-Cyanobicyclo[3.1.0]hex-2-en-3-yl]-3-fluorophenyl]-2-oxooxazolidin-5-ylmethyl]acetamide.

To a suspension of N-[5(S)-3-[3-fluoro-4-[(1α,5α,6α)-6-hydroxymethylbicyclo[3.1.0]hex-2-en-3-yl]phenyl]-2-oxooxazolidin-5-ylmethyl]acetamide (270 mg) in dichloromethane (8 mL) were added N-methylmorpholine N-oxide (136 mg), molecular sieves 4A (powdered, 188 mg), and tetrapropylammonium perruthenate (27 mg) at room temperature, the resulting mixture was stirred for 1 hour. After insoluble materials were filtered off, the filtrate was concentrated in vacuo to give N-[5(S)-3-[3-fluoro-4-[(1α,5α,6α)-6-formylbicyclo[3.1.0]hex-2-en-3-yl]phenyl]-2-oxooxazolidin-5-ylmethyl]acetamide. This was used in the next step without further purification. Sodium acetate (375 mg) was added a solution of hydroxylamine hydrochloride (165 mg) in methanol (8 mL), the mixture was stirred at room temperature for 1 hour. The resulting mixture was added crude N-[5(S)-3-[3-fluoro-4-[(1α,5α,6α)-6-formylbicyclo[3.1.0]hex-2-en-3-yl]phenyl]-2-oxooxazolidin-5-ylmethyl]acetamide and methanol (5 mL), and the whole was sonicated for 10 minutes and stirred at room temperature for 1 hour, and then concentrated in vacuo. The residue was diluted with water, the resulting precipitates were collected by filtration, and then dried in vacuo to give N-[5(S)-3-[3-fluoro-4-[(1α,5α,6α)-6-[(hydroxyimino)methyl]bicyclo[3.1.0]hex-2-en-3-yl]phenyl]-2-oxooxazolidin-5-ylmethyl]acetamide. This was used in the next step without further purification. To a suspension of crude N-[5(S)-3-[3-fluoro-4-[(1α,5α,6α)-6-[(hydroxyimino)methyl]bicyclo[3.1.0]hex-2-en-3-yl]phenyl]-2-oxooxazolidin-5-ylmethyl]acetamide in tetrahydrofaran (8 mL) were added diisopropyl azodicarboxylate (228 mg) and triphenylphosphine (608 mg), and the mixture was stirred at room temperature for 2 hours, allowed to stand overnight, and then concentrated in vacuo. Flash chromatography (silica, ethyl acetate:methanol=10:1) of the residue gave N-[5(S)-3-[4-[(1α,5α,6α)-6-cyanobicyclo[3.1.0]hex-2-en-3-yl]-3-fluorophenyl]-2-oxooxazolidin-5-ylmethyl] acetamide (173 mg).

$^1$H NMR (CDCl$_3$) δ 0.90–1.00 (m, 1H), 2.02 (s, 3H), 2.30–2.40 (m, 1H), 2.68–2.72 (m, 1H), 2.90 (d, J=17.6 Hz, 1H), 3.18 (dd, J=17.6, 6.4 Hz, 1H), 3.60–3.80 (m, 2H), 3.77 (dd, J=8.8, 6.4 Hz, 1H), 4.04 (t, J=8.8 Hz, 1H), 4.76–4.82 (m, 1H), 6.45 (m, 1H), 7.14 (dt, J=8.3, 2.0 Hz, 1H), 7.20 (t, J=8.3 Hz, 1H), 7.43 (dt, J=14.2, 2.0 Hz, 1H).

MS (EI$^+$) m/z: 355 (M$^+$).

HRMS (EI$^+$) for C$_{19}$H$_{18}$FN$_3$O$_3$ (M$^+$): calcd, 355.1332; found, 355.1354.

EXAMPLE 50

N-[5(S)-3-[4-[(1α,5α,6α)-6-Aminobicyclo[3.1.0]hex-2-en-3-yl]-3-fluorophenyl]-2-oxooxazolidin-5-ylmethyl] acetamide Hydrochloride.

A suspension of lithium chloride (286 mg), tris(dibenzylideneacetone)dipalladium(0)-chloroform adduct (233 mg), and (1α,5α,6α)-6-[bis(t-butoxycarbonyl)amino]-3-[(trifluoromethanesulfonyl)oxy]-bicyclo[3.1.0]hex-2-ene (997 mg) in N-methylpyrrolidone (6 mL) was stirred at room temperature for 5 min under Ar atmosphere. The resulting mixture was added a solution of N-[5(S)-3-[3-fluoro-4-(trimethylstannyl)phenyl]-2-oxooxazolidin-5-ylmethyl]acetamide (1.12 g) in N-methylpyrrolidone (6 mL), and the mixture was stirred at 40° C. for 24 hours. After dilution the mixture with ethyl acetate and water, insoluble materials were filtered off. The organic extracts were washed with 10% ammonium hydroxide solution, water, and brine, dried over anhydrous sodium sulfate, and then concentrated in vacuo. Flash chromatography (silica, ethyl acetate acetone=5:1) of the residue gave N-[5(S)-3-[4-[(1α,5α,6α)-6-[bis(t-butoxycarbonyl)amino]bicyclo[3.1.0]hex-2-en-3-yl]-3-fluorophenyl]-2-oxooxazolidin-5-ylmethyl]acetamide (503 mg). To a solution of N-[5(S)-3-[4-[(1α,5α,6α)-6-[bis(t-butoxycarbonyl)amino]bicyclo[3.1.0]hex-2-en-3-yl]-3-fluorophenyl]-2-oxooxazolidin-5-ylmethyl]acetamide (503 mg) in tetrahydrofaran (1 mL) was added a solution of hydrogen chloride in ethanol (1 mL), and the mixture was stirred at room temperature for 1 hour. After dilution the mixture with diethyl ether, the resulting precipitates were collected by filtration to give N-[5(S)-3-[4-[(1α,5α,6α)-6-aminobicyclo[3.1.0]hex-2-en-3-yl]-3-fluorophenyl]-2-oxooxazolidin-5-ylmethyl]acetamidehydrochloride (161 mg).

mp: 215–220° C.

$^1$H NMR (DMSO-d$_6$) δ 1.81 (s, 3H), 2.00–2.03 (m, 1H), 2.03–2.10 (m, 1H), 2.40–2.42 (m, 1H), 2.81 (d, J=17.1 Hz, 1H), 3.06 (dd, J=17.1, 7.3 Hz, 1H), 3.30–3.70 (m, 2H), 3.72 (dd, J=8.8, 6.4 Hz, 1H), 4.10 (t, J=8.8 Hz, 1H), 4.70–4.80 (m, 1H), 6.34 (s, 1H), 7.20–7.30 (dt, 1H), 7.37 (t, J=8.8 Hz, 1H), 7.46–7.50 (dt, 1H).

MS (FAB$^+$) m/z: 346 (MH$^+$) (free base).

HRMS (FAB$^+$) for C$_{18}$H$_{21}$FN$_3$O$_3$ (MH$^+$): calcd, 346.1567; found, 346.1571 (free base).

EXAMPLE 51

N-[5(S)-3-[4-[(1α,5α,6α)-6-Azidomethyl-3-azabicyclo[3.1.0]hexan-3-yl]-3-fluorophenyl]-2-oxooxazolidin-5-ylmethyl]acetamide.

A suspension of N-[5(S)-3-[4-[(1α,5α,6α)-6-bromomethyl-3-azabicyclo[3.1.0]hexan-3-yl]-3-fluorophenyl]-2-oxooxazolidin-5-ylmethyl]acetamide (213 mg) and sodium azide (114 mg) in DMF (3 mL) was heated at 70° C. for 48 hours. After diluting the mixture with ethyl acetate, the solution was washed water and brine. The organic extracts were dried over anhydrous sodium sulfate, filtered, and then concentrated in vacuo. Flash chromatography (silica, ethyl acetate:methanol=15:1) of the residue gave N-[5(S)-3-[4-[(1α,5α,6α)-6-azidomethyl-3-azabicyclo[3.1.0]hexan-3-yl]-3-fluorophenyl]-2-oxooxazolidin-5-ylmethyl]acetamide (160 mg).

MS (EI$^+$) m/z: 388 (M$^+$).

HRMS (EI$^+$) for C$_{18}$H$_{21}$FN$_6$O$_3$ (M$^+$): calcd, 388.1659; found, 388.1697.

EXAMPLE 52

N-[5(S)-3-[4-[(1α,5α,6α)-6-Aminomethyl-3-azabicyclo[3.1.0]hexan-3-yl]-3-fluorophenyl]-2-oxooxazolidin-5-ylmethyl]acetamide.

A suspension of N-[5(S)-3-[4-[(1α,5α,6α)-6-azidomethyl-3-azabicyclo[3.1.0]hexan-3-yl]-3-fluorophenyl]-2-oxooxazolidin-5-ylmethyl]acetamide (153 mg) and palladium catalyst (10% on charcoal, 31 mg) in methanol (5 mL) and dichloromethane (1 mL) was hydrogenated at 1 atm for 4.5 hours at room temperature. After filtration of the catalyst, the filtrate was concentrated in vacuo. Treatment of the residue with ethanol-diisopropyl ether gave N-[5(S)-3-[4-[(1α,5α,6α)-6-aminomethyl-3-azabicyclo[3.1.0]hexan-3-yl]-3-fluorophenyl]-2-oxooxazolidin-5-ylmethyl]acetamide (132 mg).

MS (EI$^+$) m/z: 362 (M$^+$).

HRMS (EI$^+$) for C$_{18}$H$_{23}$FN$_4$O$_3$ (M$^+$): calcd, 362.1754; found, 362.1782.

EXAMPLE 53

N-[5(S)-3-[3-Fluoro-4-[(1α,5α,6α)-6-(pyridin-2-yl)amino-3-azabicyclo[3.1.0]hexan-3-yl]phenyl]-2-oxooxazolidin-5-ylmethyl]acetamide.

The mixture of N-[5(S)-3-[4-[(1α,5α,6α)-6-amino-3-azabicyclo[3.1.0]hexan-3-yl]-3-fluorophenyl]-2-oxooxazolidin-5-ylmethyl]acetamide (348 mg), 2-pyridyl triflate (295 mg) and triethylamine (209 μL) in DMSO (2 mL) was heated at 100° C. for 36 hours. After diluting the mixture with dichloromethane-methanol (10:1), the mixture was washed with water, dried over anhydrous sodium sulfate, filtered, and then concentrated in vacuo. Flash chromatography (silica, ethyl acetate:methanol=12:1) of the residue gave N-[5(S)-3-[3-fluoro-4-[(1α,5α,6α)-6-(pyridin-2-yl)amino-3-azabicyclo[3.1.0]hexan-3-yl]phenyl]-2-oxooxazolidin-5-ylmethyl]acetamide (76.5 mg).

$^1$H NMR (DMSO-d$_6$) δ 1.76 (s, 2H), 1.82 (s, 3H), 3.27–3.40 (m, 5H), 3.64–3.74 (m, 3H), 4.04 (t, J=9.0 Hz, 1H), 4.67 (m, 1H), 6.53–6.57 (m, 2H), 6.74–6.80 (m, 2H), 7.09 (dd, J=8.8, 2.4 Hz, 1H), 7.37–7.47 (m, 2H), 7.99 (d, J=3.7 Hz, 1H), 8.27 (t, J=5.9 Hz, 1H).

MS (EI$^+$) m/z: 425 (M$^+$).

EXAMPLE 54

(E)-N-[5(S)-3-[4-[(1α,5α,6α)-6-[N-Benzyl-(N-benzyloxycarbonylmethyl]amino-3-azabicyclo[3.1.0]hexan-3-yl]-3-fluorophenyl]-2-oxooxazolidin-5-ylmethyl] acetamide.

To a suspension of N-[5(S)-3-[4-[(1α,5α,6α)-6-(N-benzyl)amino-3-azabicyclo[3.1.0]hexan-3-yl]-3-fluorophenyl]-2-oxooxazolidin-5-ylmethyl]acetamide (592 mg) and potassium carbonate (224 mg) in DMF (4.5 mL) was added benzyl bromoacetate (235 μL) at 0° C., and the mixture was stirred at room temperature for 2.5 hours. After diluting the mixture with ethyl acetate, the solution was washed water and brine. The organic extracts were dried over anhydrous sodium sulfate, filtered, and then concentrated in vacuo. Flash chromatography (silica, ethyl acetate:methanol=25:1) of the residue gave N-[5(S)-3-[4-[(1α,5α,6α)-6-[N-benzyl-(N-benzyloxycarbonyl)methyl]amino-3-azabicyclo[3.1.0]hexan-3-yl]-3-fluorophenyl]-2-oxooxazolidin-5-ylmethyl]acetamide (756 mg).

MS (EI$^+$) m/z: 587 (M$^+$).

HRMS (EI$^+$) for $C_{33}H_{36}FN_4O_5$ (M$^+$): calcd, 587.2670; found, 587.2669.

EXAMPLE 55

N-[5(S)-3-[3-Fluoro-4-[(1α,5α,6α)-6-[-(2-hydroxyethyl)]amino-3-azabicyclo[3.1.0]hexan-3-yl]phenyl]-2-oxooxazolidin-5-ylmethyl]acetamide.

Step 1

N-[5(S)-3-[3-Fluoro-4-[(1α,5α,6α)-6-[N-benzyl-N-(2-hydroxyethyl)]amino-3-azabicyclo[3.1.0]hexan-3-yl]phenyl]-2-oxooxazolidin-5-ylmethyl]acetamide.

A suspension of N-[5(S)-3-[4-[(1α,5α,6α)-6-[N-benzyl-(N-benzyloxycarbonyl)methyl]amino-3-azabicyclo[3.1.0]hexan-3-yl]-3-fluorophenyl]-2-oxooxazolidin-5-ylmethyl]acetamide (751 mg), lithium chloride (271 mg) and sodium borohydride (242 mg) in tetrahydrofuran (5 mL) and ethanol (5 mL) was stirred at room temperature for 12 hours. After diluting the mixture with water, the solution was extracted with ethyl acetate. The organic extracts were washed with brine, dried over anhydrous sodium sulfate, filtered, and then concentrated in vacuo. Flash chromatography (silica, dichloromethane:methanol:acetone=15:1:0.5) of the residue gave N-[5(S)-3-[3-fluoro-4-[(1α,5α,6α)-6-[N-benzyl-N-(2-hydroxyethyl)]amino-3-azabicyclo[3.1.0]hexan-3-yl]phenyl]-2-oxooxazolidin-5-ylmethyl]acetamide (601 mg).

Step 2

N-[5(S)-3-[3-Fluoro-4-[(1α,5α,6α)-6-[N-(2-hydroxyethyl)]amino-3-azabicyclo[3.1.0]hexan-3-yl]phenyl]-2-oxooxazolidin-5-ylmethyl]acetamide.

A suspension of N-[5(S)-3-[3-fluoro-4-[(1α,5α,6α)-6-[N-benzyl-N-(2-hydroxyethyl)]amino-3-azabicyclo[3.1.0]hexan-3-yl]phenyl]-2-oxooxazolidin-5-ylmethyl]acetamide (594 mg) and palladium catalyst (10% on charcoal, 297 mg) in methanol (5 mL) was hydrogenated at 1 atm for 8 hours at room temperature. After filtration of the catalyst, the filtrate was concentrated in vacuo to give N-[5(S)-3-[3-fluoro-4-[(1α,5α,6α)-6-[N-(2-hydroxyethyl)]amino-3-azabicyclo[3.1.0]hexan-3-yl]phenyl]-2-oxooxazolidin-5-ylmethyl]acetamide (482 mg).

MS (FAB$^+$) m/z: 393 (MH$^+$).

HRMS (FAB$^+$) for $C_{19}H_{26}FN_4O_4$ (IF): calcd, 393.1938; found, 393.1949.

EXAMPLE 56

N-[5(S)-3-[4-[(1α,5α,6α)-6-[N-Benzyloxycarbonyl-N-(2-hydroxyethyl)]amino-3-azabicyclo[3.1.0]hexan-3-yl]-3-fluorophenyl]-2-oxooxazolidin-5-ylmethyl]acetamide.

To the mixture of N-[5(S)-3-[3-fluoro-4-[(1α,5α,6α)-6-[N-(2-hydroxyethyl)]amino-3-azabicyclo[3.1.0]hexan-3-yl]phenyl]-2-oxooxazolidin-5-ylmethyl]acetamide (287 mg) and sodium hydrogencarbonate (61.3 mg) in dioxane (4 mL) and water (1.6 mL) was added benzyl chloroformate (104 μL) at 0° C., and the mixture was stirred at the same temperature for 20 min. After diluting the mixture with ethyl acetate, the solution was washed water and brine. The organic extracts were dried over anhydrous sodium sulfate, filtered, and then concentrated in vacuo to give N-[5(S)-3-[4-[(1α,5α,6α)-6-[N-benzyloxycarbonyl-N-(2-hydroxyethyl)]amino-3-azabicyclo[3.1.0]hexan-3-yl]-3-fluorophenyl]-2-oxooxazolidin-5-ylmethyl]acetamide (228 mg).

MS (FAB$^+$) m/z: 526 (M–H$^+$).

HRMS (FAB$^+$) for $C_{27}H_{31}FN_4O_6$ (MH$^+$): calcd, 526.2228; found, 526.2203.

EXAMPLE 57

N-[5(S)-3-[4-[(1α,5α,6α)-6-[N-(2-Azidoethyl)-N-benzyloxycarbonyl]amino-3-azabicyclo[3.1.0]hexan-3-yl]-3-fluorophenyl]-2-oxooxazolidin-5-ylmethyl]acetamide.

Step 1

N-[5(S)-3-[4-[(1α,5α,6aα)-6-[N-Benzyloxycarbonyl-N-(2-methanesulfonyloxyethyl)]amino-3-azabicyclo[3.1.0]hexan-3-yl]-3-fluorophenyl]-2-oxooxazolidin-5-ylmethyl]acetamide.

To a solution of N-[5(S)-3-[4-[(1α,5α,6α)-6-[N-benzyloxycarbonyl-N-(2-hydroxyethyl)]amino-3-azabicyclo[3.1.0]hexan-3-yl]-3-fluorophenyl]-2-oxooxazolidin-5-ylmethyl]acetamide (211 mg) in dichloromethane (4 mL) was added triethylamine (279 μL) and methanesulfonyl chloride (155 mL) at 0° C., and the mixture was stirred at the same temperature for 20 min. The mixture was washed with water, dried over anhydrous sodium sulfate, filtered, and then concentrated in vacuo to give N-[5(S)-3-[4-[(1α,5α,6α)-6-[N-benzyloxycarbonyl-N-(2-methanesulfonyloxyethyl)]amino-3-azabicyclo[3.1.0]hexan-3-yl]-3-fluorophenyl]-2-oxooxazolidin-5-ylmethyl]acetamide (276 mg).

Step 2

N-[5(S)-3-[4-[(1α,5α,6α)-6-[N-(2-Azidoethyl)-N-benzyloxycarbonyl]amino-3-azabicyclo[3.1.0]hexan-3-yl]-3-fluorophenyl]-2-oxooxazolidin-5-ylmethyl]acetamide. The mixture of N-[5(S)-3-[4-[(1α,5α,6α)-6-[N-benzyloxycarbonyl-N-(2-methanesulfonyloxyethyl)]amino-3-azabicyclo[3.1.0]hexan-3-yl]-3-fluorophenyl]-2-oxooxazolidin-5-ylmethyl]acetamide (276 mg) and sodium azide (91.0 mg) in DMF (3 mL) was heated at 70° C. for 12 hours. After diluting the mixture with ethyl acetate, the solution was washed water. The organic extracts were dried over anhydrous sodium sulfate, filtered, and then concentrated in vacuo. Flash chromatography (silica, ethyl acetate:methanol=20:1) of the residue gave N-[5(S)-3-[4-[(1α,5α,6α)-6-[N-(2-azidoethyl)-N-benzyloxycarbonyl]amino-3-azabicyclo[3.1.0]hexan-3-yl]-3-fluorophenyl]-2-oxooxazolidin-5-ylmethyl]acetamide (158 mg).

MS (FAB$^+$) m/z: 551 (M–H$^+$).

HRMS (FAB$^+$) for $C_{27}H_{30}FN_7O_5$ (M–H$^+$): calcd, 551.2292; found, 551.2282.

EXAMPLE 58

N-[5(S)-3-[4-[(α1α,5α,6α)-6-(2-Aminoethyl)amino-3-azabicyclo[3.1.0]hexan-3-yl]-3-fluorophenyl]-2-oxooxazolidin-5-ylmethyl]acetamide.

A suspension of N-[5(S)-3-[4-[(1α,5α,6α)-6-[N-(2-azidoethyl)-N-benzyloxycarbonyl]amino-3-azabicyclo[3.1.0]hexan-3-yl]-3-fluorophenyl]-2-oxooxazolidin-5-ylmethyl]acetamide (155 mg) and palladium catalyst (10% on charcoal, 77.5 mg) in tetrahydrofuran (4 mL) and ethanol (2 mL) was hydrogenated at 1 atm for 7 hours at room temperature. After filtration of the catalyst, the filtrate was concentrated in vacuo. Flash chromatography (NH-silica, dichloromethane:methanol=97:3) of the residue gave N-[5(S)-3-[4-[(1α,5α,6α)-6-(2-aminoethyl)amino-3-azabicyclo[3.1.0]hexan-3-yl]-3-fluorophenyl]-2-oxooxazolidin-5-ylmethyl]acetamide (65.3 mg).

MS (FAB$^+$) m/z: 392 (MH$^+$).

HRMS (FAB$^+$) for $C_{19}H_{27}FN_5O_3$ (MH$^+$): calcd, 392.2098; found, 392.2107.

EXAMPLE 59

N-[5(S)-3-[4-[(1α,5α,6α)-6-(3-Cyanopyrazin-2-yl)amino-3-azabicyclo[3.1.0]hexan-3-yl]-3-fluorophenyl]-2-oxooxazolidin-5-ylmethyl]acetamide.

The mixture of N-[5(S)-3-[4-[(1α,5α,6α)-6-amino-3-azabicyclo[3.1.0]hexan-3-yl]-3-fluorophenyl]-2-oxooxazolidin-5-ylmethyl]acetamide (105 mg), 3-chloro-2-cyanopyrazine (46.0 mg), and triethylamine (63 μL) was heated at 100° C. for 6 hours. Flash chromatography (silica, ethyl acetate:methanol=7:3) of the mixture gave N-[5(S)-3-[4-[(1α,5α,6α)-6-(3-cyanopyrazin-2-yl)amino-3-azabicyclo[3.1.0]hexan-3-yl]-3-fluorophenyl]-2-oxooxazolidin-5-ylmethyl]acetamide (75.3 mg).

MS (EI$^+$) m/z: 451 (M$^+$).

HRMS (EI$^+$) for $C_{19}H_{27}FN_5O_3$ (M$^+$): calcd, 451.1768; found, 451.1742.

EXAMPLE 60

N-[5(S)-3-[4-[(1α,5α,6α)-6-(3-Cyanopyridin-2-yl)amino-3-azabicyclo[3.1.0]hexan-3-yl]-3-fluorophenyl]-2-oxooxazolidin-5-ylmethyl]acetamide.

The title compound N-[5(S)-3-[4-[(1α,5α,6α)-6-(3-cyanopyridin-2-yl)amino-3-azabicyclo[3.1.0]hexan-3-yl]-3-fluorophenyl]-2-oxooxazolidin-5-ylmethyl]acetamide (100 mg) was prepared from N-[5(S)-3-[4-[(1α,5α,6α)-6-amino-3-azabicyclo[3.1.0]hexan-3-yl]-3-fluorophenyl]-2-oxooxazolidin-5-ylmethyl]acetamide (105 mg), 2-chloro-3-cyanopyridine (46 mg) in the same manner as described for EXAMPLE 59.

MS (EI$^+$) m/z: 450 (M$^+$).

HRMS (EI$^+$) for $C_{23}H_{23}FN_6O_3$ (M$^+$): calcd, 450.1816; found, 450.1838.

EXAMPLE 61

N-[5(S)-3-[4-[(1α,5α,6α)-6-(5-Cyanopyridin-2-yl)amino-3-azabicyclo[3.1.0]hexan-3-yl]-3-fluorophenyl]-2-oxooxazolidin-5-ylmethyl]acetamide.

The title compound N-[5(S)-3-[4-[(1α,5α,6α)-6-(5-cyanopyridin-2-yl)amino-3-azabicyclo[3.1.0]hexan-3-yl]-3-fluorophenyl]-2-oxooxazolidin-5-ylmethyl]acetamide (135 mg) was prepared from N-[5(S)-3-[4-[(1α,5α,6α)-6-amino-3-azabicyclo[3.1.0]hexan-3-yl]-3-fluorophenyl]-2-oxooxazolidin-5-ylmethyl]acetamide (139 mg), 2-chloro-5-cyanopyridine (67 mg) in the same manner as described for EXAMPLE 59.

MS (EI$^+$) m/z: 450 (M$^+$).

HRMS (EI$^+$) for $C_{23}H_{23}FN_6O_3$ (M): calcd, 450.1816; found, 450.1799.

EXAMPLE 62

N-[5(S)-3-[3-Fluoro-4-[(1α,5α,6α)-6-(pyrimidin-2-yl)amino-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-(pyrimidin-2-yl)amino-3-azabicyclo[3.1.0]hexan-3-yl]phenyl]-2-oxooxazolidin-5-ylmethyl]acetamide (109 mg) was prepared from N-[5(S)-3-[4-[(1α,5α,6α)-6-amino-3-azabicyclo[3.1.0]hexan-3-yl]-3-fluorophenyl]-2-oxooxazolidin-5-ylmethyl]acetamide (105 mg), 2-fluoropyrimidine (44 mg) in the same manner as described for EXAMPLE 59.

MS (EI$^+$) m/z: 426 (M$^+$).

HRMS (EI$^+$) for $C_{21}H_{23}FN_6O_3$ (M$^+$): calcd, 426.1816; found, 426.1825.

EXAMPLE 63

N-[5(S)-3-[4-[(1α,5α,6α)-6-(t-Butoxycarbonyl)amino-3-azabicyclo[3.1.0]hexan-3-yl]-3-fluorophenyl]-2-oxooxazolidin-5-ylmethyl]difluoroacetamide.

To a solution of N-[5(S)-3-[4-[(1α,5α,6α)-6-(t-butoxycarbonyl)amino-3-azabicyclo[3.1.0]hexan-3-yl]-3-fluorophenyl]-2-oxooxazolidin-5-ylmethyl]amine (126 mg) in pyridine (2 mL) was added difluoroacetic anhydride (81 mg) at 0° C., and the mixture was stirred at room temperature for 1 hour. After dilution of the mixture with ethyl acetate, the solution was washed with 1 N hydrochloric acid, brine and saturated sodium hydrogencarbonate solution. The organic extracts were dried over anhydrous sodium sulfate, filtered, and then concentrated in vacuo. Flash chromatography (silica, dichloromethane:acetone=5:1) of the residue gave N-[5(S)-3-[4-[(1a,5a,6a)-6-(t-butoxycarbonyl)amino-3-azabicyclo[3.1.0]hexan-3-yl]-3-fluorophenyl]-2-oxooxazolidin-5-ylmethyl]difluoroacetamide (108 mg).

MS (EI$^+$) m/z: 484 (M$^+$).

HRMS (EI$^+$) for $C_{22}H_{27}F_3N_4O_5$ (M$^+$): calcd, 484.1934; found, 484.1889.

EXAMPLE 64

N-[5(S)-3-[4-[(1α,5α,6α)-6-Amino-3-azabicyclo[3.1.0]hexan-3-yl]-3-fluorophenyl]-2-oxooxazolidin-5-ylmethyl]difluoroacetamide.

To a suspension of N-[5(S)-3-[4-[(1α,5α,6α)-6-(t-butoxycarbonyl)amino-3-azabicyclo[3.1.0]hexan-3-yl]-3-fluorophenyl]-2-oxooxazolidin-5-ylmethyl]difluoroacetamide (169 mg) in dichloromethane (2 mL) was added trifluoroacetic acid (2 mL), the mixture was stirred at room temperature for 1 hour, and then concentrated in vacuo. After dilution the residue with dichloromethane and methanol, the mixture was added saturated sodium hydrogencarbonate solution, and then concentrated in vacuo. Flash chromatography (silica, dichloromethane:acetone=5:1) of the residue gave N-[5(S)-3-[4-[(1α,5α,6α)-6-amino-3-azabicyclo[3.1.0]hexan-3yl]-3-fluorophenyl]-2-oxooxazolidin-5-ylmethyl]difluoroacetamide (95.3 mg).

MS (EI$^+$) m/z: 384 (M$^+$).

HRMS (EI$^+$) for $C_{17}H_{19}F_3N_4O_3$ (M$^+$): calcd, 384.1409; found, 406.1389.

EXAMPLE 65

(E)-N-[5(S)-3-[4-[(1α,5α,6α)-6-[Amino(hydroxyimino)methyl]-3-azabicyclo[3.1.0]hexan-3-yl]-3-fluorophenyl]-2-oxooxazolidin-5-ylmethyl]acetamide and (Z)-N-[5(S)-3-[4-[(1α,5α,6α)-6-[amino(hydroxyimino)methyl]-3-azabicyclo[3.1.0]hexan-3-yl]-3-fluorophenyl]-2-oxooxazolidin-5-ylmethyl]acetamide.

To a suspension of N-[5(S)-3-[4-[(1α,5α,6α)-6-cyano-3-azabicyclo[3.1.0]hexan-3-yl]-3-fluorophenyl]-2-oxooxazolidin-5-ylmethyl]acetamide (180 mg) in ethanol was added hydroxylamine hydrochloride (210 mg) and sodium acetate (494 mg) was heated at reflux for 30 hours, and then concentrated in vacuo. After addition of water to the residue, the resulting precipitates were collected by filtration and dried in air. Flash chromatography (silica, dichloromethane:methanol=4:1) of the precipitates gave (E)-N-[5(S)-3-[4-[(1α,5α,6α)-6-[amino(hydroxyimino)methyl]-3-azabicyclo[3.1.0]hexan-3-yl]-3-fluorophenyl]-2-oxo oxazolidin-5-ylmethyl]acetamide (78 mg) and (Z)-N-[5(S)-3-[4-[(1α,5α,6α)-6-amino[(hydroxyimino)methyl]-3-azabicyclo[3.1.0]hexan-3-yl]-3-fluorophenyl]-2-oxooxazolidin-5-ylmethyl]acetamide (35 mg).

(E)-form: MS (FAB$^+$) m/z: 392 (MH$^+$).

HRMS (FAB$^+$) for $C_{19}H_{23}FN_5O_4$(MH$^+$): calcd, 392.1734; found, 392.1750.

EXAMPLE 66

N-[5(S)-3-[3-Fluoro-4-[(1α,5α,6α)-6-[(2-(methoxy)ethoxyimino)methyl]-3-azabicyclo[3.1.0]hexan-3-yl]phenyl]-2-oxooxazolidin-5-ylmethyl]acetamide.

The mixture of N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (150 mg) and crude O-(2-methoxyethyl)hydroxylamine (prepared from N-(2-methoxyethoxy)phthalimide (442 mg)) in ethanol (5 mL) and dichloromethane (1 mL) was stirred at room temperature for 3 hours, and then concentrated in vacuo. Flash chromatography (silica, ethyl acetate:methanol=19:1) of the residue gave N-[5(S)-3-[3-fluoro-4-[(1α,5α,6α)-6-[(2-(methoxy)ethoxyimino)methyl]-3-azabicyclo[3.1.0]hexan-3-yl]phenyl]-2-oxooxazolidin-5-ylmethyl]acetamide (172 mg).

MS (EI$^+$) m/z: 434 (M$^+$).

HRMS (EI$^+$) for $C_{21}H_{27}FN_4O_5$ (M$^+$): calcd, 434.1965; found, 434.1923.

EXAMPLE 67

N-[5(S)-3-[4-[(1α,5α,6α)-6-[(2-(Dimethylamino)ethoxyimino)methyl]-3-azabicyclo[3.1.0]hexan-3-yl]-3-fluorophenyl]-2-oxooxazolidin-5-ylmethyl]acetamide.

The title compound N-[5(S)-3-[4-[(1α,5α,6α)-6-[(2-(dimethylamino)ethoxyimino)methyl]-3-azabicyclo[3.1.0]hexan-3-yl]-3-fluorophenyl]-2-oxooxazolidin-5-ylmethyl]acetamide (152 mg) was prepared from N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (150 mg), crude O-(dimethylaminoethyl)hydroxylamine hydrochloride (prepared from N-(2-dimethylaminoethoxy)phthalimide (469 mg)), and sodium acetate (328 mg) in the same manner as described for EXAMPLE 66.

MS (EI$^+$) m/z: 447 (M$^+$).

HRMS (EI$^+$) for $C_{22}H_{30}FN_5O_4$ (M$^+$): calcd, 447.2282; found, 447.2275.

EXAMPLE 68

N-[5(S)-3-[4-[(1α,5α,6α)-6-[(2-(Dimethylamino)propoxyimino)methyl]-3-azabicyclo[3.1.0]hexan-3-yl]-3-fluorophenyl]-2-oxooxazolidin-5-ylmethyl]acetamide.

The title compound N-[5(S)-3-[4-[(1α,5α,6α)-6-[(2-(dimethylamino)propoxyimino)methyl]-3-azabicyclo[3.1.0]hexan-3-yl]-3-fluorophenyl]-2-oxooxazolidin-5-ylmethyl]acetamide (176 mg) was prepared from N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (150 mg), crude O-(dimethylaminopropyl)hydroxylamine hydrochloride (prepared from N-(2-dimethylaminopropoxy)phthalimide (497 mg)), and sodium acetate (328 mg) in the same manner as described for EXAMPLE 66.

MS (EI$^+$) m/z: 461 (M$^+$).

HRMS (EI$^+$) for $C_{23}H_{32}FN_5O_4$(M$^+$): calcd, 461.2438; found, 461.2414.

EXAMPLE 69

N-[5(S)-3-[3-Fluoro-4-[(1α,5α,6α)-6-[(2-hydroxyethoxy)iminomethyl]-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-[(2-hydroxyethoxy)iminomethyl]-3-azabicyclo[3.1.0]hexan-3-yl]phenyl]-2-oxooxazolidin-5-ylmethyl]acetamide (149 mg) was prepared from N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (150 mg) and crude O-(2-hydroxyethyl)hydroxylamine (prepared from N-(2-hydroxyethoxy)phthalimide (414 mg)) in the same manner as described for EXAMPLE 66.

MS (EI$^+$) m/z: 420 (M$^+$).

HRMS (EI$^+$) for $C_{20}H_{25}FN_4O_5$ (M$^+$): calcd, 420.1809; found, 420.1778.

EXAMPLE 70

N-[5(S)-3-[4-[(1α,5α,6α)-6-[(1-(1-t-Butoxycarboxl-1-methyl)ethoxy)iminomethyl]-3-azabicyclo[3.1.0]hexan-3-yl]-3-fluorophenyl]-2-oxooxazolidin-5-ylmethyl]acetamide.

The title compound N-[5(S)-3-[4-[(1α,5α,6α)-6-[(1-(1-t-butoxycarboxyl-1-methyl)ethoxy)iminomethyl]-3-azabicyclo[3.1.0]hexan-3-yl]-3-fluorophenyl]-2-oxooxazolidin-5-ylmethyl]acetamide (280 mg) was prepared from N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (200 mg) and crude O-[1-(1-t-butylcarbonyl-1-methyl)ethyl]hydroxylamine (prepared from N-[1-(1-t-butoxycarboxyl-1-methyl)ethoxy]phthalimide (611 mg)) in the same manner as described for EXAMPLE 66.

MS (EI$^+$) m/z: 518 (M$^+$).

HRMS (EI$^+$) for $C_{26}H_{35}FN_4O_6$ (M$^+$): calcd, 518.2541; found, 518.2549.

EXAMPLE 71

N-[5(S)-3-[4-[(1α,5α,6α)-6-[(1-(1-Carboxyl-1-methyl)ethoxy)iminomethyl]-3-azabicyclo[3.1.0]hexan-3-yl]-3-fluorophenyl]-2-oxooxazolidin-5-ylmethyl]acetamide.

To a solution of N-[5(S)-3-[4-[(1x,5a,6a)-6-[(1-(1-t-butoxycarboxyl-1-methyl)ethoxy)iminomethyl]-3-azabicyclo[3.1.0]hexan-3-yl]-3-fluorophenyl]-2-oxooxazolidin-5-ylmethyl]acetamide (230 mg) in dichloromethane (8 mL) was added trifluoroacetic acid (2 mL), and the mixture was stirred at room temperature for 18 hours, and then concentrated in vacuo. After addition of water to the residue, the resulting precipitates were collected by filtration, washed with water and ethyl acetate and, dried to give N-[5(S)-3-[4-[(1α,5α,6α)-6-[(1-(1-carboxyl-1-methyl)ethoxy)iminomethyl]-3-azabicyclo[3.1.0]hexan-3-yl]-3-fluorophenyl]-2-oxooxazolidin-5-ylmethyl]acetamide (149 mg).

MS (FAB$^+$) m/z: 461 (M–H$^+$).

HRMS (FAB$^+$) for $C_{22}H_{26}FN_4O_6$ (M–H$^+$): calcd, 461.1836; found, 461.1849.

EXAMPLE 72

N-[5(S)-3-[3-Fluoro-4-[(1α,5α,6α)-6-[(5-tetrazolylmethoxy)iminomethyl]-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-[(5-tetrazolylmethoxy)iminomethyl]-3-azabicyclo[3.1.0]hexan-3-yl]phenyl]-2-oxooxazolidin-5-ylmethyl]acetamide (125 mg) was prepared from N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (120 mg), crude O-[(5-tetrazolyl)methyl]hydroxylamine hydrochloride (prepared from N-[(5-tetrazolyl)methoxy]phthalimide (220 mg)), and sodium acetate (221 mg) in the same manner as described for EXAMPLE 66.

MS (FAB$^+$) m/z: 459 (MH$^+$).

HRMS (FAB$^+$) for $C_{20}H_{24}FN_8O_4$ (MH$^+$): calcd, 459.1905; found, 459.1916.

EXAMPLE 73

N-[5(S)-3-[3-Fluoro-4-[(1α,5α,6α)-6-[(N-(4-morpholinyl)imino)methyl]-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-[(N-(4-morpholinyl)imino)methyl]-3-azabicyclo[3.1.0]hexan-3-yl]phenyl]-2-oxooxazolidin-5-ylmethyl]acetamide (175 mg) was prepared from N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (150 mg) and 4-aminomorpholine (55 mg) in the same manner as described for EXAMPLE 66.

MS (EI$^+$) m/z: 445 (M$^+$).

HRMS (EI$^+$) for $C_{22}H_{28}FN_5O_4$ (M$^+$): calcd, 445.2125; found, 445.2111.

EXAMPLE 74

N-[5(S)-3-[4-[(1α,5α,6α)-6-[(1-(2,3-Dihydroxy)propyloxy)iminomethyl]-3-azabicyclo[3.1.0]hexan-3-yl]-3-fluorophenyl]-2-oxooxazolidin-5-ylmethyl]acetamide.

The title compound N-[5(S)-3-[4-[(1α,5α,6α)-6-[(1-(2,3-dihydroxy)propyloxy)iminomethyl]-3-azabicyclo[3.1.0]hexan-3-yl]-3-fluorophenyl]-2-oxooxazolidin-5-ylmethyl]acetamide (186 mg) was prepared from N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (150 mg), O-[1-(2,3-dihydroxy)propyl]hydroxylamine hydrochloride (119 mg), and sodium acetate (136 mg) in the same manner as described for EXAMPLE 66.

MS (FAB$^+$) m/z: 451 (MH$^+$).

HRMS (FAB$^+$) for $C_{21}H_{28}FN_4O_6$(MH$^+$): calcd, 451.1993; found, 451.2013.

EXAMPLE 75

N-[5(S)-3-[4-[(1α,5α,6α)-6-[(2-(1,3-Dihydroxy)propyloxy)iminomethyl]-3-azabicyclo[3.1.0]hexan-3-yl]-3-fluorophenyl]-2-oxooxazolidin-5-ylmethyl]acetamide.

The title compound N-[5(S)-3-[4-[(1α,5α,6α)-6-[(2-(1,3-dihydroxy)propyloxy)iminomethyl]-3-azabicyclo[3.1.0]hexan-3-yl]-3-fluorophenyl]-2-oxooxazolidin-5-ylmethyl]acetamide (178 mg) was prepared from N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (150 mg), O-[2-(1,3-dihydroxy)propyl]hydroxylamine hydrochloride (119 mg), and sodium acetate (136 mg) in the same manner as described for EXAMPLE 66.

MS (FAB$^+$) m/z: 451 (MH$^+$).

HRMS (FAB$^+$) for $C_{21}H_{28}FN_4O_6$ (MH$^+$): calcd, 451.1993; found, 451.1978.

EXAMPLE 76

N-[5(S)-3-[3-Fluoro-4-[(1α,5α,6α)-6-[(1-(2-(2-hydroxyethoxy))ethoxy) iminomethyl]-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-[(1-(2-(2-hydroxyethoxy))ethoxy)iminomethyl]-3-azabicyclo[3.1.0]hexan-3-yl]phenyl]-2-oxooxazolidin-5-ylmethyl]acetamide (184 mg) was prepared from N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (150 mg), O-[2-(2-hydroxyethoxy)ethyl]hydroxylamine hydrochloride (131 mg), and sodium acetate (136 mg) in the same manner as described for EXAMPLE 66.

MS (EI$^+$) m/z: 465 (M$^+$).

HRMS (EI$^+$) for $C_{22}H_{30}FN_4O_6$ (M$^+$): calcd, 465.2149; found, 465.2168.

EXAMPLE 77

N-[5(S)-3-[4-[(1α,5α,6α)-6-(Cyanomethyloxy)iminomethyl]-3-azabicyclo[3.1.0]hexan-3-yl]-3-fluorophenyl]-2-oxooxazolidin-5-ylmethyl]acetamide.

The title compound N-[5(S)-3-[4-[(1α,5α,6α)-6-(cyanomethyloxy)iminomethyl]-3-azabicyclo[3.1.0]hexan-3-yl]-3-fluorophenyl]-2-oxooxazolidin-5-ylmethyl]acetamide (168 mg) was prepared from N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (150 mg) and crude O-(cyanomethyl)hydroxylamine (prepared from N-(cyanomethoxy)phthalimide (202 mg)) in the same manner as described for EXAMPLE 66.

MS (EI$^+$) m/z: 415 (M$^+$).

HRMS (EI$^+$) for $C_{20}H_{22}FN_5O_4$ (M$^+$): calcd, 415.1656; found, 415.1637.

EXAMPLE 78

N-[5(S)-3-[4-[(1α,5α,6α)-6-Cyano-3-azabicyclo[3.1.0]hexan-3-yl]-3-fluorophenyl]-2-oxooxazolidin-5-ylmethyl]acetamide N-Oxide.

To a solution of N-[5(S)-3-[4-[(1α,5α,6α)-6-cyano-3-azabicyclo[3.1.0]hexan-3-yl]-3-fluorophenyl]-2-oxooxazolidin-5-ylmethyl]acetamide (85.0 mg) in dichloromethane (3 mL) was added m-chloroperbenzoic acid (81.9 mg) at 0° C., and the mixture was stirred at room temperature for 30 min. After addition of piperidine (120 mg, polymer bounded, 3.5 mmol/g resin), the mixture was stirred at room temperature for 30 min, and then added powdered sodium hydrogencarbonate (40 mg). Flash chromatography (silica, dichloromethane:methanol=4:1) of the mixture gave N-[5(S)-3-[4-[(1α,5α,6α)-6-cyano-3-azabicyclo[3.1.0]hexan-3-yl]-3-fluorophenyl]-2-oxooxazolidin-5-ylmethyl]acetamide N-Oxide (79 mg).

MS (FAB$^+$) m/z: 375 (MH$^+$).

HRMS (FAB$^+$) for $C_{18}H_{20}FN_4O_4$ (MH$^+$): calcd, 375.1469; found, 375.1450.

EXAMPLE 79

N-[5(S)-3-[4-[(1α,5α,6α)-6-Ethenyl-3-azabicyclo[3.1.0]hexan-3-yl]-3-fluorophenyl]-2-oxooxazolidin-5-ylmethyl]acetamide.

To a solution of dimsyl sodium in dimethyl sulfoxide (prepared from sodium hydride (60 mg) and dimethyl sulfoxide (1.5 mL)) was added a solution of methyltriphenylphosphonium bromide (536 mg) in dimethyl sulfoxide (1 mL) at room temperature, and the mixture was stirred at the same temperature for 1 hour. To the resulting mixture was added a solution of N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (361 mg) in dimethyl sulfoxide (1 mL) at room temperature, and the mixture was stirred at the same temperature for 1 hour. After quenching the reaction by the addition of water, the mixture was extracted with ethyl acetate. The organic extracts were washed with brine, dried over anhydrous magnesium sulfate, and then concentrated in vacuo. Flash chromatography (silica, ethyl acetate:methanol=20:1) of the residue gave N-[5(S)-3-[4-[(1α,5α,6α)-6-ethenyl-3-azabicyclo[3.1.0]hexan-3-yl]-3-fluorophenyl]-2-oxooxazolidin-5-ylmethyl]acetamide (310 mg).

MS (EI$^+$) m/z: 359 (M$^+$).

HRMS (EI$^+$) for $C_{19}H_{22}FN_3O_3$ (M$^+$): calcd, 359.1645; found, 359.1671.

EXAMPLE 80

N-[5(S)-3-[3-Fluoro-4-[(1α,5α,6α)-6-(2-hydroxyethyl)-3-azabicyclo[3.1.0]hexan-3-yl]phenyl]-2-oxooxazolidin-5-ylmethyl]acetamide.

To a solution of N-[5(S)-3-[4-[(1α,5α,6α)-6-ethenyl-3-azabicyclo[3.1.0]hexan-3-yl]-3-fluorophenyl]-2-oxooxazolidin-5-ylmethyl]acetamide (120 mg) in tetrahydrofuran (3 mL) was added 9-BBN (0.5 M solution in tetrahydrofuran, 0.8 mL) at 0° C., and the mixture was stirred at room temperature for 6 hours. Further amount of 9-BBN (0.5 M solution in tetrahydrofuran, 0.8 mL) was added to the mixture at 0° C., and the mixture was stirred at room temperature for 12 hours. Hydrogen peroxide (30%, 0.1 mL) and 2 N sodium hydroxide solution (0.5 mL) were added to the mixture at 0° C., and the mixture was stirred at room temperature for 30 min. After addition of 5% sodium thiosulfate solution, the mixture was exrtacted with ethyl acetate. The organic extracts were washed with brine, dried over anhydrous magnesium sulfate, and then concentrated in vacuo. Flash chromatography (silica, ethyl acetate:methanol=10:1) of the residue gave N-[5(S)-3-[3-fluoro-4-[(1α,5α,6α)-6-(2-hydroxyethyl)-3-azabicyclo[3.1.0]hexan-3-yl]phenyl]-2-oxooxazolidin-5-ylmethyl]acetamide (44 mg).

MS (EI$^+$) m/z: 377 (M$^+$).

HRMS (EI$^+$) for $C_{19}H_{24}FN_3O_4$ (M$^+$): calcd, 377.1751; found, 377.1747.

EXAMPLE 81

N-[5(S)-3-[4-[(1α,5α,6α)-6-[1-(2-t-Butyldiphenylsilyloxy-1-hydroxy)ethyl]-3-azabicyclo[3.1.0]hexan-3-yl]-3-fluorophenyl]-2-oxooxazolidin-5-ylmethyl]acetamide.

Step 1

N-[5(S)-3-[4-[(1α,5α,6α)-6-(1,2-Dihydroxyethyl)-3-azabicyclo[3.1.0]hexan-3-yl]-3-fluorophenyl]-2-oxooxazolidin-5-ylmethyl]acetamide.

To a solution of N-[5(S)-3-[4-[(1α,5α,6α)-6-ethenyl-3-azabicyclo[3.1.0]hexan-3-yl]-3-fluorophenyl]-2-oxooxazolidin-5-ylmethyl]acetamide (280 mg) in acetonitrile (3 mL), acetone (3 mL), and water (3 mL) was added N-methylmorpholine N-oxide (NMO, 137 mg) and osmium oxide (capsuled, 10% w/w, 792 mg), and the mixture was stirred at room temperature for 3 weeks. After insoluble materials were filtered off, the filtrate was concentrated in vacuo. Flash chromatography (silica, ethyl acetate:methanol=5:1) of the residue gave N-[5(S)-3-[4-[(1α,5α,6α)-6-(1,2-dihydroxyethyl)-3-azabicyclo[3.1.0]hexan-3-yl]-3-fluorophenyl]-2-oxooxazolidin-5-ylmethyl]acetamide (147 mg).

Step 2

N-[5(S)-3-[4-[(1α,5α,6α)-6-[1-(2-t-Butyldiphenylsilyloxy-1-hydroxy)ethyl]-3-azabicyclo[3.1.0]hexan-3-yl]-3-fluorophenyl]-2-oxooxazolidin-5-ylmethyl]acetamide.

To a solution of N-[5(S)-3-[4-[(1α,5α,6α)-6-(1,2-dihydroxyethyl)-3-azabicyclo[3.1.0]hexan-3-yl]-3-fluorophenyl]-2-oxooxazolidin-5-ylmethyl]acetamide (100 mg) in DMF (2 mL) and dichloromethane (2 mL) was added (4-dimethylamino)pyridine (93 mg) and t-butyldiphenylsilylchloride (139 mg) at room temperature, and the mixture was stirred at the same temperature for 30 min. After quenching the reaction by the addition of saturated sodium hydrogencarbonate solution, the mixture was extracted with ethyl acetate. The organic extracts were dried over anhydrous magnesium sulfate, and then concentrated in vacuo. Flash chromatography (silica, ethyl acetate:methanol=15:1) of the residue gave N-[5(S)-3-[4-[(1α,5α,6α)-6-[1-(2-t-butyldiphenylsilyloxy-1-hydroxy)ethyl]-3-azabicyclo[3.1.0]hexan-3-yl]-3-fluorophenyl]-2-oxooxazolidin-5-ylmethyl]acetamide (144 mg).

MS (EI$^+$) m/z: 631 (M$^+$).

HRMS (EI$^+$) for $C_{35}H_{42}FN_3O_5Si$ (M$^+$): calcd, 631.2878; found, 631.2816.

EXAMPLE 82

N-[5(S)-3-[4-[(1α,5α,6α)-6-[(2-(t-Butyldiphenylsilyl)oxy)acetyl]-3-azabicyclo[3.1.0]hexan-3-yl-3-fluorophenyl-2-oxooxazolidin-5-ylmethyl]acetamide.

The title compound N-[5(S)-3-[4-[(1α,5α,6α)-6-[(2-(t-butyldiphenylsilyl)oxy)acetyl]-3-azabicyclo[3.1.0]hexan-3-yl]-3-fluorophenyl]-2-oxooxazolidin-5-ylmethyl]acetamide (129 mg) was prepared from N-[5(S)-3-[4-[(1α,5α,6α)-6-[1-(2-t-butyldiphenylsilyloxy-1-hydroxy)ethyl]-3-azabicyclo[3.1.0]hexan-3-yl]-3-fluorophenyl]-2-oxooxazolidin-5-ylmethyl]acetamide (142 mg) in the same manner as described for EXAMPLE 22.

MS (EI$^+$) m/z: 629 (M$^+$).

HRMS (EI$^+$) for $C_{35}H_{40}FN_3O_5Si$ (M$^+$): calcd, 629.2721; found, 629.2689.

EXAMPLE 83

N-[5(S)-3-[3-Fluoro-4-[(1α,5α,6α)-6-hydroxyacetyl-3-azabicyclo[3.1.0]hexan-3-yl]phenyl]-2-oxooxazolidin-5-ylmethyl]acetamide.

To a solution of N-[5(S)-3-[4-[(1α,5α,6α)-6-[1-(2-t-butyldiphenylsilyloxy-1-hydroxy)ethyl]-3-azabicyclo[3.1.0]hexan-3-yl]-3-fluorophenyl]-2-oxooxazolidin-5-ylmethyl]acetamide (129 mg) in tetrahydrofuran (3 mL) was added acetic acid (36.9 mg) and tetrabutylammonium fluoride (TBAF, 1 M solution in tetrahydrofuran, 410 μL) at room temperature, and the mixture was stirred for 1 hour. After quenching the reaction by the addition of saturated ammonium chloride solution and brine, the mixture was extracted with ethyl acetate. The organic extracts were dried over anhydrous magnesium sulfate, and then concentrated in vacuo. Flash chromatography (silica, ethyl acetate:methanol=9:1) of the residue gave N-[5(S)-3-[3-fluoro-4-[(1α,5α,6α)-6-hydroxyacetyl-3-azabicyclo[3.1.0]hexan-3-yl]phenyl]-2-oxooxazolidin-5-ylmethyl]acetamide (67 mg).

MS (EI$^+$) m/z: 391 (M$^+$).
HRMS (EI$^+$) for $C_{19}H_{22}FN_3O_5$ (M$^+$): calcd, 391.1543; found, 391.1500.

EXAMPLE 84

N-[5(S)-3-[3-Fluoro-4-[(1α,5α,6α)-6-hydroxy-3-azabicyclo[3.1.0]hexan-3-yl]phenyl]-2-oxooxazolidin-5-ylmethyl]acetamide.

Step 1

5(R)-3-[4-[(1α,5α,6α)-6-t-Butyldimethylsilyloxy-3-azabicyclo[3.1.0]hexan-3-yl]-3-fluorophenyl]-5-hydroxymethyloxazolidin-2-one.

The title compound 5(R)-3-[4-[(1α,5α,6α)-6-t-butyldimethylsilyloxy-3-azabicyclo[3.1.0]hexan-3-yl]-3-fluorophenyl]-5-hydroxymethyloxazolidin-2-one (200 mg) was prepared from 1-benzyloxycarbonylamino-4-[(1α,5α,6α)-6-t-butyldimethylsilyloxy-3-azabicyclo[3.1.0]hexan-3-yl]-3-fluorobenzene (320 mg) and (R)-glycidylbutyrate (101 mg) in the same manner as described for EXAMPLE 9.

MS (EI$^+$) m/z: 422 (M$^+$).
HRMS (EI$^+$) for $C_{21}H_{31}FN_2O_4Si$ (M$^+$): calcd, 422.2037; found, 422.2059.

Step 2

5(R)-Azidomethyl-3-[4-[(1α,5α,6α)-6-t-butyldimethylsilyloxy-3-azabicyclo[3.1.0]hexan-3-yl]-3-fluorophenyl]oxazolidin-2-one.

The title compound 5(R)-azidomethyl-3-[4-[(1α,5α,6α)-6-t-butyldimethylsilyloxy-3-azabicyclo[3.1.0]hexan-3-yl]-3-fluorophenyl]oxazolidin-2-one (202 mg) was prepared from (R)-3-[4-[(1α,5α,6α)-6-t-butyldimethylsilyloxy-3-azabicyclo[3.1.0]hexan-3-yl]-3-fluorophenyl]-5-hydroxymethyloxazolidin-2-one (190 mg) in the same manner as described for EXAMPLE 9.

MS (EI$^+$) m/z: 447 (M$^+$).
HRMS (EI$^+$) for $C_{21}H_{30}FN_5O_3Si$ (M$^+$): calcd, 447.2102; found, 447.2119.

Step 3

N-[5(S)-3-[4-[(1α,5α,6α)-6-t-Butyldimethylsilyloxy-3-azabicyclo[3.1.0]hexan-3-yl]-3-fluorophenyl]-2-oxooxazolidin-5-ylmethyl]acetamide.

The title compound N-[5(S)-3-[4-[(1α,5α,6α)-6-t-butyldimethylsilyloxy-3-azabicyclo[3.1.0]hexan-3-yl]-3-fluorophenyl]-2-oxooxazolidin-5-ylmethyl]acetamide was prepared from the above crude 5(R)-azidomethyl-3-[4-[(1α,5α,6α)-6-t-butyldimethylsilyloxy-3-azabicyclo[3.1.0]hexan-3-yl]-3-fluorophenyl]oxazolidin-2-one in the same manner as described for EXAMPLE 9.

Step 4

N-[5(S)-3-[3-Fluoro-4-[(1α,5α,6α)-6-hydroxy-3-azabicyclo[3.1.0]hexan-3-yl]phenyl]-2-oxooxazolidin-5-ylmethyl]acetamide.

To a solution of the above crude N-[5(S)-3-[4-[(1α,5α,6α)-6-t-butyldimethylsilyloxy-3-azabicyclo[3.1.0]hexan-3-yl]-3-fluorophenyl]-2-oxooxazolidin-5-ylmethyl]acetamide in tetrahydrofuran (5 mL) was added tetrabutylammonium fluoride (TBAF, 1 M solution in tetrahydrofuran, 500 μL) at room temperature, and the mixture was stirred for 30 min. After quenching the reaction by the addition of saturated ammonium chloride solution, the mixture was extracted with ethyl acetate. The organic extracts were washed with brine, dried over anhydrous magnesium sulfate, and then concentrated in vacuo. Flash chromatography (silica, ethyl acetate:methanol=9:1) of the residue gave N-[5(S)-3-[3-fluoro-4-[(1α,5α,6α)-6-hydroxy-3-azabicyclo[3.1.0]hexan-3-yl]phenyl]-2-oxooxazolidin-5-ylmethyl]acetamide (94.0 mg).

MS (EI$^+$) m/z: 349 (M$^+$).
HRMS (EI$^+$) for $C_{17}H_{20}FN_3O_4$ (M$^+$): calcd, 349.1438; found, 349.1455.

EXAMPLE 85

N-[5(S)-3-[3-Fluoro-4-[(1α,5α,6α)-6-[(1-(2-methylthio)ethoxy)iminomethyl]-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-[(1-(2-methylthio) ethoxy)iminomethyl]-3-azabicyclo[3.1.0]hexan-3-yl]phenyl]-2-oxooxazolidin-5-ylmethyl]acetamide (172 mg) was prepared from N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (150 mg) and crude O-(2-methylthio)ethylhydroxylamine (prepared from N-(2-methylthioethoxy) phthalimide (197 mg)) in the same manner as described for EXAMPLE 66.

MS (EI$^+$) m/z: 450 (M$^+$).
HRMS (EI$^+$) for $C_{21}H_{27}FN_4O_4S$ (M$^+$): calcd, 450.1737; found, 450.1736.

EXAMPLE 86

N-[5(S)-3-[3-Fluoro-4-[(1α,5α,6α)-6-[(1-(2-methylsulfinyl)ethoxy)iminomethyl]-3-azabicyclo[3.1.0]hexan-3-yl]phenyl]-2-oxooxazolidin-5-ylmethyl]acetamide.

The title compound N-[5(S)-3-[3-fluoro-4-[(1α,5α,6α)-6-[(1-(2-methylsulfinyl) ethoxy)iminomethyl]-3-azabicyclo[3.1.0]hexan-3-yl]phenyl]-2-oxooxazolidin-5-ylmethyl]acetamide (188 mg) was prepared from N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (150 mg) and crude O-(2-methylsulfinyl)ethylhydroxylamine (prepared from N-(2-methyl sulfinylethoxy) phthalimide (210 mg)) in the same manner as described for EXAMPLE 66.

MS (FAB$^+$) m/z: 467 (MH$^+$).
HRMS (FAB$^+$) for $C_{21}H_{28}FN_4O_5S$ (MH$^+$): calcd, 467.1764; found, 467.1760.

EXAMPLE 87

N-[5(S)-3-[3-Fluoro-4-[(1α,5α,6α)-6-[(1-(2-methylsulfonyl)ethoxy)iminomethyl]--3-azabicyclo[3.1.0]hexan-3-yl]phenyl]-2-oxooxazolidin-5-ylmethyl]acetamide The title compound N-[5(S)-3-[3-fluoro-4-[(1α,5α,6α)-6-[(1-(2-methylsulfonyl)ethoxy)iminomethyl]-3-azabicyclo[3.1.0]hexan-3-yl]phenyl]-2-oxooxazolidin-5-ylmethyl]

acetamide (194 mg) was prepared from N-[5(S)-3-[3-fluoro-4-[(1α,5α,6α)-6-formyl-3-azabicyclo[3.1.0]hexan-3-yl]phenyl]-2-oxooxazolidin-5-ylmethyl]acetamide (150 mg) and crude O-(2-methylsulfonyl)ethylhydroxylamine (prepared from N-(2-methyl sulfinylethoxy)phthalimide (224 mg)) in the same manner as described for EXAMPLE 66.

MS (FAB$^+$) m/z: 482 (M$^+$).

HRMS (FAB$^+$) for $C_{21}H_{27}FN_4O_6S$ (M$^+$): calcd, 482.1635; found, 482.1656.

EXAMPLE 88

N-[5(S)-3-[5-[(1α,5α,6α)-6-Hydroxymethylbicyclo[3.1.0]hex-2-en-3-yl]pyridin-2-yl]-2-oxooxazolidin-5-ylmethyl]acetamide.

Step 1

N-[5(S)-3-[5-[(1α,5α,6α)-6-[(t-Butyldiphenylsilyl)oxy]methylbicyclo[3.1.0]hex-2-en-3-yl]pyridin-2-yl]-2-oxooxazolidin-5-ylmethyl]acetamide.

The mixture of N-[5(S)-3-(5-bromopyridin-2-yl)-2-oxooxazolidin-5-ylmethyl]acetamide (170 mg), (1α,5α,6α)-6-[(t-butyldiphenylsilyl)oxy]methyl-3-(4,4,5,5-tetramethyl-1,3,2-dioxaborolyl)bicyclo[3.1.0]hex-2-ene (334 mg), tetrakis(triphenylphosphine)palladium(0) (31.3 mg), and tri-potassium phosphate (n-hydrate, 345 mg) in dioxane (10 mL) and water (2 mL) was heated at 80° C. for 1 hour, and then concentrated in vacuo. Flash chromatography (silica, ethyl acetate:methanol=19:1) of the residue gave N-[5(S)-3-[5-[(1α,5α,6α)-6-[(t-butyldiphenylsilyl)oxy]methylbicyclo[3.1.0]hex-2-en-3-yl]pyridin-2-yl]-2-oxooxazolidin-5-ylmethyl]acetamide (291 mg).

Step 2

N-[5(S)-3-[5-[(1α,5α,6α)-6-Hydroxymethylbicyclo[3.1.0]hex-2-en-3-yl]pyridin-2-yl]-2-oxooxazolidin-5-ylmethyl]acetamide.

The title compound N-[5(S)-3-[5-[(1α,5α,6α)-6-hydroxymethylbicyclo[3.1.0]hex-2-en-3-yl]pyridin-2-yl]-2-oxooxazolidin-5-ylmethyl]acetamide (103 mg) was prepared from N-[5(S)-3-[5-[(1α,5α,6α)-6-[(t-butyldiphenylsilyl)oxy]methylbicyclo[3.1.0]hex-2-en-3-yl]pyridin-2-yl]-2-oxooxazolidin-5-ylmethyl]acetamide (278 mg) in the same manner as described for EXAMPLE 83.

MS (EI$^+$) m/z: 343 (M$^+$).

HRMS (EI$^+$) for $C_{18}H_{21}N_3O_4$ (M$^+$): calcd, 343.1532; found, 343.1522.

EXAMPLE 89

N-[5(S)-3-[5-[(1α,5α,6α)-6-Cyanobicyclo[3.1.0]hex-2-en-3-yl]pyridin-2-yl]-2-oxooxazolidin-5-ylmethyl]acetamide.

The title compound N-[5(S)-3-[5-[(1α,5α,6α)-6-cyanobicyclo[3.1.0]hex-2-en-3-yl]pyridin-2-yl]-2-oxooxazolidin-5-ylmethyl]acetamide (74 mg) was prepared from N-[5(S)-3-[5-[(1α,5α,6α)-6-hydroxymethylbicyclo[3.1.0]hex-2-en-3-yl]pyridin-2-yl]-2-oxooxazolidin-5-ylmethyl]acetamide (90 mg) in the same manner as described for Example 49.

MS (EI$^+$) m/z: 338 (M$^+$).

HRMS (EI$^+$) for $C_{18}H_{18}N_4O_3$ (M$^+$): calcd, 338.1379; found, 338.1387.

EXAMPLE 90

N-[5(S)-3-[3,5-Difluoro-4-[(1α,5α,6α)-6-hydroxymethylbicyclo[3.1.0]hex-2-en-3-yl]phenyl]-2-oxooxazolidin-5-ylmethyl]acetamide.

The mixture of N-[5(S)-3-[3,5-difluoro-4-[(trifluoromethanesulfonyl)oxy]phenyl]-2-oxooxazolidin-5-ylmethyl]acetamide (601 mg), (1α,5α,6α)-6-[(t-butyldiphenylsilyl)oxy]methyl-3-(4,4,5,5-tetramethyl-1,3,2-dioxaborolyl)bicyclo[3.1.0]hex-2-ene (682 mg), tetrakis(triphenylphosphine)palladium(0) (166 mg), and 2 M sodium carbonate solution (2.88 mL) in dioxane (28 mL) was heated at 100° C. for 2 hours, and then concentrated in vacuo. Flash chromatography (silica, ethyl acetate:methanol=19:1) of the residue gave N-[5(S)-3-[3,5-difluoro-4-[(1α,5α,6α)-6-[(t-butyldiphenylsilyl)oxy]methylbicyclo[3.1.0]hex-2-en-3-yl]phenyl]-2-oxooxazolidin-5-ylmethyl]acetamide.

The title compound N-[5(S)-3-[3,5-difluoro-4-[(1α,5α,6α)-6-hydroxymethylbicyclo[3.1.0]hex-2-en-3-yl]phenyl]-2-oxooxazolidin-5-ylmethyl]acetamide (467 mg) was prepared from the above N-[5(S)-3-[3,5-difluoro-4-[(1α,5α,6α)-6-[(t-butyldiphenylsilyl)oxy]methylbicyclo[3.1.0]hex-2-en-3-yl]phenyl]-2-oxooxazolidin-5-ylmethyl]acetamide in the same manner as described for Example 83.

MS (EI$^+$) m/z: 378 (M$^+$).

HRMS (EI$^+$) for $C_{19}H_2OF_2N_2O_4$ (M$^+$): calcd, 378.1391; found, 378.1381.

EXAMPLE 91

N-[5(S)-3-[3,5-Difluoro-4-[(1α,5α,6α)-6-cyanobicyclo[3.1.0]hex-2-en-3-yl]phenyl]-2-oxooxazolidin-5-ylmethyl]acetamide.

The title compound N-[5(S)-3-[3,5-difluoro-4-[(1α,5α,6α)-6-cyanobicyclo[3.1.0]hex-2-en-3-yl]phenyl]-2-oxooxazolidin-5-ylmethyl]acetamide (45 mg) was prepared from N-[5(S)-3-[3,5-difluoro-4-[(1α,5α,6α)-6-hydroxymethylbicyclo[3.1.0]hex-2-en-3-yl]phenyl]-2-oxooxazolidin-5-ylmethyl]acetamide (378 mg) in the same manner as described for Example 49.

MS (EI$^+$) m/z: 373 (M$^+$).

HRMS (EI$^+$) for $C_{19}H_{17}F_2N_3O_3$ (M$^+$): calcd, 373.1238; found, 373.1268.

EXAMPLE 92

N-[5(S)-3-[4-[(1α,5α,6α)-6-(1-Cyanoethyl)-3-azabicyclo[3.1.0]hexan-3-yl]-3-fluorophenyl]-2-oxooxazolidin-5-ylmethyl]acetamide.

Step 1

5(R)-3-[3-Fluoro-4-[(1α,5α,6α)-6-hydroxymethyl-3-azabicyclo[3.1.0]hexan-3-yl]phenyl]-5-[(triisopropylsilyl)oxy]methyloxazolidin-2-one.

To a solution of 5(R)-3-[3-fluoro-4-[(1α,5α,6α)-6-[(2-tetrahydropyranyl)oxy]methyl-3-azabicyclo[3.1.0]hexan-3-yl]phenyl]-5-hydroxymethyloxazolidin-2-one (4.80 g) in dichloromethane (80 mL) was added imidazole (1.21 g), (4-dimethylamino)pyridine (721 mg), and triisopropylsilyl-chloride (2.73 g) at 0° C., and the mixture was stirred at room temperature for 12 hours. The mixture was washed with water, 5% hydrochloric acid, and brine. The organic extracts were dried over anhydrous magnesium sulfate, filtered, and then concentrated in vacuo to give 5(R)-3-[3-fluoro-4-[(1α,5α,6α)-6-[(2-tetrahydro pyranyl)oxy]methyl-3-azabicyclo[3.1.0]hexan-3-yl]phenyl]-5-[(triisopropylsilyl)oxy]methyloxazolidin-2-one.

To a solution of the crude 5(R)-3-[3-fluoro-4-[(1α,5α, 6α)-6-[(2-tetrahydropyranyl)oxy]methyl-3-azabicyclo [3.1.0]hexan-3-yl]phenyl]-5-[(triisopropylsilyl)oxy] methyloxazolidin-2-one in methanol (67 mL) was added p-toluenesulfonic acid hydrate (674 mg), and the mixture was stirred at room temperature for 8 hours. After quenching the reaction by the addition of saturated sodium hydrogencarbonate solution and brine, the mixture was extracted with ethyl acetate. The organic extracts were dried over anhydrous magnesium sulfate, filtered, and then concentrated in vacuo. Flash chromatography (silica, hexane ethyl acetate= 2:3) of the residue gave 5(R)-3-[3-fluoro-4-[(1α,5α,6α)-6-hydroxymethyl-3-azabicyclo[3.1.0]hexan-3-yl]phenyl]-5-[(triisopropylsilyl)oxy]methyloxazolidin-2-one (5.31 g).

MS (EI$^+$) m/z: 478 (M$^+$).

HRMS (EI$^+$) for $C_{25}H_{39}FN_2O_4Si$ (M$^+$): calcd, 478.2663; found, 478.2667.

Step 2

5(R)-3-[4-[(1α,5α,6α)-6-Bromomethyl-3-azabicyclo[3.1.0]hexan-3-yl]-3-fluorophenyl]-5-[(triisopropylsilyl)oxy]methyloxazolidin-2-one.

The title compound 5(R)-3-[4-[(1α,5α,6α)-6-bromomethyl-3-azabicyclo[3.1.0]hexan-3-yl]-3-fluorophenyl]-5-[(triisopropylsilyl)oxy]methyloxazolidin-2-one (3.70 g) was prepared from 5(R)-3-[3-fluoro-4-[(1α, 5α,6α)-6-hydroxymethyl-3-azabicyclo[3.1.0]hexan-3-yl] phenyl]-5-[(triisopropylsilyl)oxy]methyloxazolidin-2-one (3.40 g) in the same manner as described for EXAMPLE 25.

MS (EI$^+$) m/z: 540 (M$^+$).

HRMS (EI$^+$) for $C_{25}H_{38}BrFN_2O_3Si$ (M$^+$): calcd, 540.1819; found, 540.1848.

Step 3

5(R)-3-[4-[(1α,5α,6α)-6-Cyanomethyl-3-azabicyclo[3.1.0]hexan-3-yl]-3-fluorophenyl]-5-[(triisopropylsilyl)oxy]methyloxazolidin-2-one.

The title compound 5(R)-3-[4-[(1α,5α,6α)-6-cyanomethyl-3-azabicyclo[3.1.0]hexan-3-yl]-3-fluorophenyl]-5-[(triisopropylsilyl)oxy]methyloxazolidin-2-one (3.25 g) was prepared from 5(R)-3-[4-[(1α,5α,6α)-6-bromomethyl-3-azabicyclo[3.1.0]hexan-3-yl]-3-fluorophenyl]-5-[(triisopropylsilyl)oxy]methyloxazolidin-2-one (3.70 g) in the same manner as described for EXAMPLE 26.

MS (EI$^+$) m/z: 487 (M$^+$).

HRMS (EI$^+$) for $C_{26}H_{38}FN_3O_3Si$ (M$^+$): calcd, 487.2666; found, 487.2674.

Step 4

5(R)-3-[4-[(1α,5α,6α)-6-(1-Cyanoethyl)-3-azabicyclo[3.1.0]hexan-3-yl]-3-fluorophenyl]-5-[(triisopropylsilyl)oxy]methyloxazolidin-2-one and 5(R)-3-[4-[(1α,5α,6α)-6-(1-cyano-1-methylethyl)-3-azabicyclo[3.1.0]hexan-3-yl]-3-fluorophenyl]-5-[(triisopropylsilyl)oxy]methyloxazolidin-2-one.

To a solution of 5(R)-3-[4-[(1α,5α,6α)-6-cyanomethyl-3-azabicyclo[3.1.0]hexan-3-yl]-3-fluorophenyl]-5-[(triisopropylsilyl)oxy]methyloxazolidin-2-one (1.10 g) and methyliodide (309 µL) in tetrahydrofuran (25 mL) was added potassium bis(trimethylsilyl)amide (0.5 M in toluene, 9.92 mL) at 0° C. for 15 min, and the mixture was stirred at the same temperature for 1 hour. After quenching the reaction by the addition of saturated ammonium chloride solution, the mixture was extracted with ethyl acetate. The organic extracts were washed with brine, dried over anhydrous magnesium sulfate, filtered, and then concentrated in vacuo. Flash chromatography (silica, hexane ethyl acetate= 7:3) of the residue gave 5(R)-3-[4-[(1α,5α,6α)-6-(1-cyanoethyl)-3-azabicyclo[3.1.0]hexan-3-yl]-3-fluorophenyl]-5-[(triisopropylsilyl)oxy]methyloxazolidin-2-one (326 mg) and 5(R)-3-[4-[(1α,5α,6α)-6-(1-cyano-1-methylethyl)-3-azabicyclo[3.1.0]hexan-3-yl]-3-fluorophenyl]-5-[(triisopropylsilyl)oxy]methyloxazolidin-2-one (758 mg).

5(R)-3-[4-[(1α,5α,6α)-6-(1-cyanoethyl)-3-azabicyclo[3.1.0]hexan-3-yl]-3-fluorophenyl]-5-[(triisopropylsilyl)oxy]methyloxazolidin-2-one: MS (EI$^+$) m/z: 501 (M$^+$).

HRMS (EI$^+$) for $C_{27}H_{40}FN_3O_3Si$ (M$^+$): calcd, 501.2823; found, 501.2785.

5(R)-3-[4-[(1α,5α,6α)-6-(1-cyano-1-methylethyl)-3-azabicyclo[3.1.0]hexan-3-yl]-3-fluorophenyl]-5-[(triisopropylsilyl)oxy]methyloxazolidin-2-one: MS (EI$^+$) m/z: 515 (M$^+$).

HRMS (EI$^+$) for $C_{28}H_{42}FN_3O_3Si$ (M$^+$): calcd, 515.2979; found, 515.2999.

Step 5

5(R)-3-[4-[(1α,5α,6α)-6-(1-Cyanoethyl)-3-azabicyclo[3.1.0]hexan-3-yl]-3-fluorophenyl]-5-hydroxymethyloxazolidin-2-one.

The title compound 5(R)-3-[4-[(1α,5α,6α)-6-(1-cyanoethyl)-3-azabicyclo[3.1.0]hexan-3-yl]-3-fluorophenyl]-5-hydroxymethyloxazolidin-2-one (430 mg) was prepared from 5(R)-3-[4-[(1α,5α,6α)-6-(1-cyanoethyl)-3-azabicyclo[3.1.0]hexan-3-yl]-3-fluorophenyl]-5-[(triisopropylsilyl)oxy]methyloxazolidin-2-one (720 mg) in the same manner as described for EXAMPLE 83.

MS (EI$^+$) m/z: 345 (M$^+$).

HRMS (EI$^+$) for $C_{18}H_{20}FN_3O_3$ (M$^+$): calcd, 345.1489; found, 345.1528.

Step 6

5(R)-Azidomethyl-3-[4-[(1α,5α,6α)-6-(1-cyanoethyl)-3-azabicyclo[3.1.0]hexan-3-yl]-3-fluorophenyl]oxazolidin-2-one.

The title compound 5(R)-azidomethyl-3-[4-[(1α,5α,6α)-6-(1-cyanoethyl)-3-azabicyclo[3.1.0]hexan-3-yl]-3-fluorophenyl]oxazolidin-2-one (204 mg) was prepared from 5(R)-3-[4-[(1α,5α,6α)-6-(1-cyanoethyl)-3-azabicyclo[3.1.0]hexan-3-yl]-3-fluoro-phenyl]-5-hydroxymethyloxazolidin-2-one (218 mg) in the same manner as described for Example 9.

MS (EI$^+$) m/z: 370 (M$^+$).

HRMS (EI$^+$) for $C_{18}H_{19}FN_6O_2$ (M$^+$): calcd, 370.1554; found, 370.1560.

Step 7

N-[5(S)-3-[4-[(1α,5α,6α)-6-(1-Cyanoethyl)-3-azabicyclo[3.1.0]hexan-3-yl]-3-fluorophenyl]-2-oxooxazolidin-5-ylmethyl]acetamide.

The title compound N-[5(S)-3-[4-[(1α,5α,6α)-6-(1-cyanoethyl)-3-azabicyclo[3.1.0]hexan-3-yl]-3-fluorophenyl]-2-oxooxazolidin-5-ylmethyl]acetamide (195 mg) was prepared from 5(R)-azidomethyl-3-[4-[(1α,5α, 6α)-6-(1-cyanoethyl)-3-azabicyclo[3.1.0]hexan-3-yl]-3-fluorophenyl]oxazolidin-2-one (197 mg) in the same manner as described for Example 9.

MS (EI$^+$) m/z: 386 (M$^+$).

HRMS (EI$^+$) for $C_{20}H_{23}FN_4O_3$ (M$^+$): calcd, 386.1754; found, 386.1738.

EXAMPLE 93

N-[5(S)-3-[4-[(1α,5α,6α)-6-(1-Cyano-1-methylethyl)-3-azabicyclo[3.1.0]hexan-3-yl]-3-fluorophenyl]-2-oxooxazolidin-5-ylmethyl]acetamide.

Step 1.

5(R)-3-[4-[(1α,5α,6α)-6-(1-Cyano-1-methylethyl)-3-azabicyclo[3.1.0]hexan-3-yl]-3-fluorophenyl]-5-hydroxymethyloxazolidin-2-one.

The title compound 5(R)-3-[4-[(1α,5α,6α)-6-(1-cyano-1-methylethyl)-3-azabicyclo[3.1.0]hexan-3-yl]-3-fluorophenyl]-5-hydroxymethyloxazolidin-2-one (175 mg) was prepared from 5(R)-3-[4-[(1α,5α,6α)-6-(1-cyano-1-methylethyl)-3-azabicyclo[3.1.0]hexan-3-yl]-3-fluorophenyl]-5-[(triisopropylsilyl)oxy]methyloxazolidin-2-one (277 mg) in the same manner as described for EXAMPLE 83.

MS (EI$^+$) m/z: 359 (M$^+$).

HRMS (EI$^+$) for $C_{19}H_{22}FN_3O_3$ (M$^+$): calcd, 359.1645; found, 359.1629.

Step 2

5(R)-Azidomethyl-3-[4-[(1α,5α,6α)-6-(1-cyano-1-methylethyl)-3-azabicyclo[3.1.0]hexan-3-yl]-3-fluorophenyl]oxazolidin-2-one.

The title compound 5(R)-azidomethyl-3-[4-[(1α,5α,6α)-6-(1-cyano-1-methylethyl)-3-azabicyclo[3.1.0]hexan-3-yl]-3-fluorophenyl]oxazolidin-2-one (159 mg) was prepared from 5(R)-3-[4-[(1α,5α,6α)-6-(1-cyano-1-methylethyl)-3-azabicyclo [3.1.0]hexan-3-yl]-3-fluorophenyl]-5-hydroxymethyloxazolidin-2-one (166 mg) in the same manner as described for Example 9.

MS (EI$^+$) m/z: 384 (M$^+$).

HRMS (EI$^+$) for $C_{19}H_{21}FN_6O_2$ (M$^+$): calcd, 384.1710; found, 384.1721.

Step 3

[5(S)-3-[4-[(1α,5α,6α)-6-(1-Cyano-1-methylethyl)-3-azabicyclo[3.1.0]hexan-3-yl]-3-fluorophenyl]-2-oxooxazolidin-5-ylmethyl]acetamide.

The title compound N-[5(S)-3-[4-[(1α,5α,6α)-6-(1-cyano-1-methylethyl)-3-azabicyclo[3.1.0]hexan-3-yl]-3-fluorophenyl]-2-oxooxazolidin-5-ylmethyl]acetamide (150 mg) was prepared from 5(R)-azidomethyl-3-[4-[(1α,5α,6α)-6-(1-cyano-1-methylethyl)-3-azabicyclo[3.1.0]hexan-3-yl]-3-fluorophenyl]oxazolidin-2-one (152 mg) in the same manner as described for Example 9.

MS (EI$^+$) m/z: 400 (M$^+$).

HRMS (EI$^+$) for $C_{21}H_{25}FN_4O_3$ (M$^+$): calcd, 400.1911; found, 400.1925.

EXAMPLE 94

N-[5(S)-3-[6-[(1α,5α,6α)-6-Hydroxymethylbicyclo[3.1.0]hex-2-en-3-yl]pyridin-3-yl]-2-oxooxazolidin-5-ylmethyl]acetamide.

Step 1

N-[5(S)-3-[6-[(1α,5α,6α)-6-[(t-Butyldiphenylsilyloxy]methylbicyclo[3.1.0]hex-2-en-3-yl]pyridin-3-yl]-2-oxooxazolidin-5-ylmethyl]acetamide.

The title compound N-[5(S)-3-[6-[(1α,5α,6α)-6-[(t-butyldiphenylsilyl)xy]methylbicyclo[3.1.0]hex-2-en-3-yl]pyridin-3-yl]-2-oxooxazolidin-5-ylmethyl]acetamide (1.30 g) was prepared from N-[5(S)-3-(6-bromopyridin-3-yl)-2-oxooxazolidin-5-ylmethyl]acetamide (717 mg) and (1α,5α,6α)-6-[(t-butyldiphenylsilyl)oxy]methyl-3-(4,4,5,5-tetramethyl-1,3,2-dioxaborolyl)bicyclo[3.1.0]hex-2-ene (1.30 g) in the same manner as described for Example 88.

MS (FAB$^+$) m/z: 582 (MH$^+$).

HRMS (FAB$^+$) for $C_{34}H_{40}N_3O_4Si$ (MH$^+$): calcd, 582.2788; found, 582.2783.

Step 2

N-[5(S)-3-[6-[(1α,5α,6α)-6-Hydroxymethylbicyclo[3.1.0]hex-2-en-3-yl]pyridin-3-yl]-2-oxooxazolidin-5-ylmethyl]acetamide.

The title compound N-[5(S)-3-[6-[(1α,5α,6α)-6-hydroxymethylbicyclo[3.1.0]hex-2-en-3-yl]pyridin-3-yl]-2-oxooxazolidin-5-ylmethyl]acetamide (658 mg) was prepared from N-[5(S)-3-[6-[(1α,5α,6α)-6-[(t-butyldiphenylsilyl)oxy]methylbicyclo[3.1.0]hex-2-en-3-yl]pyridin-3-yl]-2-oxooxazolidin-5-ylmethyl]acetamide (1.30 g) in the same manner as described for EXAMPLE 83.

MS (EI$^+$) m/z: 343 (M$^+$).

HRMS (EI$^+$) for $C_{18}H_{21}N_3O_4$ (M$^+$): calcd, 343.1532; found, 343.1547.

EXAMPLE 95

N-[5(S)-3-[6-[(1α,5α,6α)-6-(Hydroxyimino)methylbicyclo[3.1.0]hex-2-en-3-yl]pyridin-3-yl]-2-oxooxazolidin-5-ylmethyl]acetamide.

The title compound N-[5(S)-3-[6-[(1α,5α,6α)-6-(hydroxyimino)methylbicyclo[3.1.0]hex-2-en-3-yl]pyridin-3-yl]-2-oxooxazolidin-5-ylmethyl]acetamide (343 mg) was prepared from N-[5(S)-3-[6-[(1α,5α,6α)-6-hydroxymethylbicyclo[3.1.0]hex-2-en-3-yl]pyridin-3-yl]-2-oxooxazolidin-5-ylmethyl]acetamide (400 mg) in the same manner as described for Example 22 and 66.

MS (FAB$^+$) m/z: 357 (MH$^+$).

HRMS (FAB$^+$) for $C_{18}H_{21}N_4O_4$ (MH$^+$): calcd, 357.1563; found, 357.1577.

EXAMPLE 96

N-[5(S)-3-[6-[(1α,5α,6α)-6-Cyanobicyclo[3.1.0]hex-2-en-3-yl]pyridin-3-yl]2-oxooxazolidin-5-ylmethyl]acetamide.

The title compound N-[5(S)-3-[6-[(1α,5α,6α)-6-cyanobicyclo[3.1.0]hex-2-en-3-yl]pyridin-3-yl]-2-oxooxazolidin-5-ylmethyl]acetamide (210 mg) was prepared from N-[5(S)-3-[6-[(1α,5α,6α)-6-(hydroxyimino)methylbicyclo[3.1.0]hex-2-en-3-yl]pyridin-3-yl]-2-oxooxazolidin-5-ylmethyl]acetamide (243 mg) in the same manner as described for Example 49.

MS (EI$^+$) m/z: 338 (M$^+$).

HRMS (EI$^+$) for $C_{18}H_{18}N_4O_3$ (M$^+$): calcd, 338.1379; found, 338.1403.

EXAMPLE 97

N-[5(S)-3-[4-[(1α,5α,6α)-6-Cyano-3-azabicyclo[3.1.0]hexan-3-yl]-3-fluorophenyl]-2-oxooxazolidin-5-ylmethyl]thioacetamide.

To a solution of N-[5(S)-3-[4-[(1α,5α,6×)-6-cyano-3-azabicyclo[3.1.0]hexan-3-yl]-3-fluorophenyl]-2-oxooxazolidin-5-ylmethyl]acetamide (380 mg) in dioxane (2 mL) and toluene (2 mL) was added Lawesson's reagent (300 mg), and the mixture was heated at 80° C. for 1 hour. Flash chromatography (silica, hexane:ethyl acetate=2:3) of the mixture gave N-[5(S)-3-[4-[(1α,5α,6α)-6-cyano-3-azabicyclo[3.1.0]hexan-3-yl]-3-fluorophenyl]-2-oxooxazolidin-5-ylmethyl]thioacetamide (280 mg).

MS (FAB$^+$) m/z: 375 (MH$^+$).

HRMS (FAB$^+$) for $C_{18}H_{20}FN_4O_2S$ (MH$^+$): calcd, 375.1291; found, 375.1292.

EXAMPLE 98

N-[5(S)-3-[6-[(1α,5α,6α)-6-Cyanobicyclo[3.1.0]hex-2-en-3-yl]pyridin-3-yl]-2-oxooxazolidin-5-ylmethyl]thioacetamide.

The title compound N-[5(S)-3-[6-[(1α,5α,6α)-6-cyanobicyclo[3.1.0]hex-2-en-3-yl]pyridin-3-yl]-2-oxooxazolidin-5-ylmethyl]thioacetamide (58.5 mg) was prepared from N-[5(S)-3-[6-[(1α,5α,6α)-6-cyanobicyclo[3.1.0]hex-2-en-3-yl]pyridin-3-yl]-2-oxooxazolidin-5-ylmethyl]acetamide (165 mg) in the same manner as described for Example 97.

MS (FAB$^+$) m/z: 355 (MH$^+$).

HRMS (FAB$^+$) for $C_{18}H_{19}N_4O_2S$ (MH$^+$): calcd, 355.1229; found, 355.1268.

EXAMPLE 99

N-[5(S)-3-[4-[(1α,5α,6α)-6-Cyanobicyclo[3.1.0]hex-2-en-3-yl]phenyl]-2-oxooxazolidin-5-ylmethyl]thioacetamide.

The title compound N-[5(S)-3-[4-[(1α,5α,6α)-6-cyanobicyclo[3.1.0]hex-2-en-3-yl]phenyl]-2-oxooxazolidin-5-ylmethyl]thioacetamide (112 mg) was prepared from N-[5(S)-3-[4-[(1α,5α,6α)-6-cyanobicyclo[3.1.0]hex-2-en-3-yl]phenyl]-2-oxooxazolidin-5-ylmethyl]acetamide (170 mg) in the same manner as described for Example 97.

MS (FAB$^+$) m/z: 354 (MH$^+$).

HRMS (FAB$^+$) for $C_{19}H_{20}N_3O_2S$ (MH$^+$): calcd, 354.1276; found, 354.1272.

EXAMPLE 100

N-[5(S)-3-[4-[(1α,5α,6α)-6-(N-Benzyl-N-t-butoxycarbonyl)amino-3-azabicyclo[3.1.0]hexan-3-yl]-3,5-difluorophenyl]-2-oxooxazolidin-5-ylmethyl]acetamide.

Step 1

5(R)-3-[4-[(1α,5α,6α)-6-(N-Benzyl-N-t-butoxycarbonyl)amino-3-azabicyclo[3.1.0]hexan-3-yl]-3,5-difluorophenyl]-5-hydroxymethyloxazolidin-2-one.

The title compound 5(R)-3-[4-[(1α,5α,6α)-6-(N-benzyl-N-t-butoxycarbonyl)amino-3-azabicyclo[3.1.0]hexan-3-yl]-3,5-difluorophenyl]-5-hydroxymethyloxazolidin-2-one (3.15 g) was prepared from 4-[(1α,5α,6α)-6-(N-benzyl-N-t-butoxycarbonyl)amino-3-azabicyclo[3.1.0]hexan-3-yl]-1-benzyloxycarbonylamino-3,5-difluorobenzene (4.60 g) in the same manner as described for Example 9.

MS (FAB$^+$) m/z: 516 (MH$^+$).

HRMS (FAB$^+$) for $C_{27}H_{32}F_2N_3O_5$): calcd, 516.2310; found, 516.2332.

Step 2

N-[5(S)-3-[4-[(1α,5α,6α)-6-(N-Benzyl-N-t-butoxycarbonyl)amino-3-azabicyclo[3.1.0]hexan-3-yl]-3,5-difluorophenyl]-2-oxooxazolidin-5-ylmethyl]acetamide.

The title compound N-[5(S)-3-[4-[(1α,5α,6α)-6-(N-benzyl-N-t-butoxycarbonyl)amino-3-azabicyclo[3.1.0]hexan-3-yl]-3,5-difluorophenyl]-2-oxooxazolidin-5-ylmethyl]acetamide (849 mg) was prepared from 5(R)-3-[4-[(1α,5α,6α)-6-(N-benzyl-N-t-butoxycarbonyl)amino-3-azabicyclo[3.1.0]hexan-3-yl]-3,5-difluorophenyl]-5-hydroxymethyloxazolidin-2-one (1.00 g) in the same manner as described for Example 9.

MS (FAB$^+$) m/z: 557 (MH$^+$).

HRMS (FAB$^+$) for $C_{29}H_{35}F_2N_4O_5$ (MH$^+$): calcd, 557.2576; found, 557.2586.

EXAMPLE 101

N-[5(S)-3-[4-[(1α,5α,6α)-6-Amino-3-azabicyclo[3.1.0]hexan-3-yl]-3,5-difluorophenyl]-2-oxooxazolidin-5-ylmethyl]acetamide.

The title compound N-[5(S)-3-[4-[(1α,5α,6α)-6-amino-3-azabicyclo[3.1.0]hexan-3-yl]-3,5-difluorophenyl]-2-oxooxazolidin-5-ylmethyl]acetamide (220 mg) was prepared from N-[5(S)-3-[4-[(1α,5α,6α)-6-(N-benzyl-N-t-butoxycarbonyl)amino-3-azabicyclo[3.1.0]hexan-3-yl]-3,5-difluorophenyl]-2-oxooxazolidin-5-ylmethyl]acetamide (590 mg) in the same manner as described for Example 1 and 8.

MS (EI$^+$) m/z: 366 (M$^+$).

HRMS (EI$^+$) for $C_{17}H_{20}F_2N_4O_3$ (M$^+$): calcd, 366.1503; found, 366.1543.

EXAMPLE 102

N-[5(S)-3-[3,5-Difluoro-4-[(1α,5α,6α)-6-hydroxymethyl-3-azabicyclo[3.1.0]hexan-3-yl]phenyl]-2-oxooxazolidin-5-ylmethyl]acetamide.

Step 1

5(R)-3-[3,5-Difluoro-4-[(1α,5α,6α)-6-[(2-tetrahydropyranyl)oxy]methyl-3-azabicyclo[3.1.0]hexan-3-yl]phenyl]-5-hydroxymethyloxazolidin-2-one.

The title compound 5(R)-3-[3,5-difluoro-4-[(1α,5α,6α)-6-[(2-tetrahydropyranyl)oxy]methyl-3-azabicyclo[3.1.0]hexan-3-yl]phenyl]-5-hydroxymethyloxazolidin-2-one (5.47 g) was prepared from 1-benzyloxycarbonylamino-3,5-difluoro-4-[(1α,5α,6α)-6-[(2-tetrahydropyranyl)oxy]methyl-3-azabicyclo[3.1.0]hexan-3-yl]benzene (7.50 g) in the same manner as described for EXAMPLE 9.

Step 2

N-[5(S)-3-[3,5-Difluoro-4-[(1α,5α,6α)-6-[(2-tetrahydropyranyl)oxy]methyl-3-azabicyclo[3.1.0]hexan-3-yl]phenyl]-2-oxooxazolidin-5-ylmethyl]acetamide.

The title compound N-[5(S)-3-[3,5-Difluoro-4-[(1α,5α,6α)-6-[(2-tetrahydropyranyl)oxy]methyl-3-azabicyclo[3.1.0]hexan-3-yl]phenyl]-2-oxooxazolidin-5-ylmethyl]acetamide (4.65 g) was prepared from 5(R)-3-[3,5-difluoro-4-[(1α,5α,6α)-6-[(2-tetrahydropyranyl)oxy]methyl-3-azabicyclo[3.1.0]hexan-3-yl]phenyl]-5-hydroxymethyloxazolidin-2-one (5.36 g) in the same manner as described for EXAMPLE 9.

$^+$H NMR (CDCl$_3$) δ 1.19–1.87 (m, 9H), 2.02 (s, 3H), 3.41–4.77 (m, 14H), 6.17 (t, J=5.9 Hz, 1H), 7.01 (d, J=11.7 Hz, 1H).

Step 3

N-[5(S)-3-[3,5-Difluoro-4-[(1α,5α,6α)-6-hydroxymethyl-3-azabicyclo[3.1.0]hexan-3-yl]phenyl]-2-oxooxazolidin-5-ylmethyl]acetamide.

The title compound N-[5(S)-3-[3,5-difluoro-4-[(1α,5α,6α)-6α)-6-hydroxymethyl-3-azabicyclo[3.1.0]hexan-3-yl]phenyl]-2-oxooxazolidin-5-ylmethyl]acetamide (3.00 g) was prepared from N-[5(S)-3-[3,5-difluoro-4-[(1α,5α,6α)-6-[(2-tetrahydropyranyl)oxy]methyl-3-azabicyclo[3.1.0]hexan-3-yl]phenyl]-2-oxooxazolidin-5-ylmethyl]acetamide (4.65 g) in the same manner as described for EXAMPLE 13.

MS (FAB$^+$) m/z: 381 (M$^+$).

HRMS (FAB$^+$) for $C_{18}H_{21}F_2N_3O_4$ (MH$^+$): calcd, 381.1500; found, 381.1518.

EXAMPLE 103

N-[5(S)-3-[3,5-Difluoro-4-[(1α,5α,6α)-6-formyl-3-azabicyclo[3.1.0]hexan-3-yl]phenyl]-2-oxooxazolidin-5-ylmethyl]acetamide.

The title compound N-[5(S)-3-[3,5-difluoro-4-[(1α,5α,6α)-6-formyl-3-azabicyclo[3.1.0]hexan-3-yl]phenyl]-2-oxooxazolidin-5-ylmethyl]acetamide (281 mg) was prepared from N-[5(S)-3-[3,5-difluoro-4-[(1α,5α,6α)-6-hydroxymethylbicyclo[3.1.0]hex-2-en-3-yl]phenyl]-2-oxooxazolidin-5-ylmethyl]acetamide (300 mg) in the same manner as described for EXAMPLE 22.

MS (EI$^+$) m/z: 379 (M$^+$).

HRMS (EI$^+$) for $C_{18}H_{20}FN_3O_4$ (M$^+$): calcd, 379.1344; found, 379.1311.

EXAMPLE 104

N-[5(S)-3-[3,5-Difluoro-4-[(1α,5α,6α)-6-[(hydroxyimino)methyl]-3-azabicyclo[3.1.0]hexan-3-yl]phenyl]-2-oxooxazolidin-5-ylmethyl]acetamide.

The title compound N-[5(S)-3-[3,5-difluoro-4-[(1α,5α,6α)-6-[(hydroxyimino)methyl]-3-azabicyclo[3.1.0]hexan- 3-yl]phenyl]-2-oxooxazolidin-5-ylmethyl]acetamide (261 mg) was prepared from N-[5(S)-3-[3,5-difluoro-4-[(1α,5α,6α)-6-formyl-3-azabicyclo[3.1.0]hexan-3-yl]phenyl]-2-oxooxazolidin-5-ylmethyl]acetamide (274 mg) in the same manner as described for EXAMPLE 41.

MS (FAB$^+$) m/z: 395 (MH$^+$).

HRMS (FAB$^+$) for $C_{18}H_{21}F_2N_4O_4$ (MH+): calcd, 395.1531; found, 395.1538.

EXAMPLE 105

N-[5(S)-3-[4-[(1α,5α,6α)-6-Cyano-3-azabicyclo[3.1.0]hexan-3-yl]-3,5-difluorophenyl]-2-oxooxazolidin-5-ylmethyl]acetamide.

The title compound N-[5(S)-3-[4-[(1α,5α,6α)-6-cyano-3-azabicyclo[3.1.0]hexan-3-yl]-3,5-difluorophenyl]-2-oxooxazolidin-5-ylmethyl]acetamide (147 mg) was prepared from N-[5(S)-3-[3,5-difluoro-4-[(1α,5α,6α)-6-[(hydroxyimino)methyl]-3-azabicyclo [3.1.0]hexan-3-yl]phenyl]-2-oxooxazolidin-5-ylmethyl]acetamide (155 mg) in the same manner as described for EXAMPLE 46.

MS (EI$^+$) m/z: 376 (M$^+$).

HRMS (EI$^+$) for $C_{18}H_{18}F_2N_4O_3$ (M$^+$): calcd, 376.1347; found, 376.1328.

EXAMPLE 106

N-[5(S)-3-[4-[(1α,5α,6α)-6-Cyanomethyl1–3-azabicyclo[3.1.0]hexan-3-yl]-3,5-difluorophenyl]-2-oxooxazolidin-5-ylmethyl]acetamide.

The title compound N-[5(S)-3-[4-[(1α,5α,6α)-6-cyanomethyl-3-azabicyclo[3.1.0]hexan-3-yl]-3,5-difluorophenyl]-2-oxooxazolidin-5-ylmethyl]acetamide (69 mg) was prepared from N-[5(S)-3-[3,5-difluoro-4-[(1α,5α,6α)-6-hydroxymethylbicyclo[3.1.0]hex-2-en-3-yl]phenyl]-2-oxooxazolidin-5-ylmethyl]acetamide (110 mg) in the same manner as described for EXAMPLE 25 and 26.

MS (EI$^+$) m/z: 390 (M$^+$).

HRMS (EI$^+$) for $C_{19}H_{20}F_2N_4O_3$ (M$^+$): calcd, 390.1503; found, 390.1532.

EXAMPLE 107

N-[5(S)-3-[3,5-Difluoro-4-[(1α,5α,6α)-6-[(1-(2.3-Dihydroxy)propyloxy)iminomethyl]-3-azabicyclo[3.1.0]hexan-3-yl]phenyl]-2-oxooxazolidin-5-ylmethyl]acetamide.

The title compound N-[5(S)-3-[3,5-difluoro-4-[(1α,5α,6α)-6-[(1-(2,3-dihydroxy)propyloxy)iminomethyl]-3-azabicyclo[3.1.0]hexan-3-yl]phenyl]-2-oxooxazolidin-5-ylmethyl]acetamide (163 mg) was prepared from N-[5(S)-3-[3,5-difluoro-4-[(1α,5α,6α)-6-formyl-3-azabicyclo[3.1.0]hexan-3-yl]phenyl]-2-oxooxazolidin-5-ylmethyl]acetamide (200 mg), O-[1-(2,3-dihydroxy)propyl]hydroxylamine hydrochloride (314 mg), and sodium acetate (260 mg) in the same manner as described for EXAMPLE 66.

MS (FAB$^+$) m/z: 469 (MH$^+$).

HRMS (FAB$^+$) for $C_{21}H_{27}F_2N_4O_6$ (MH$^+$): calcd, 469.1899; found, 469.1885.

EXAMPLE 108

N-[5(S)-3-[3,5-Difluoro-4-[(1α,5α,6α)-6-[(2-hydroxyethoxy)iminomethyl]-3-azabicyclo[3.1.0]hexan-3-yl]phenyl]-2-oxooxazolidin-5-ylmethyl]acetamide.

The title compound N-[5(S)-3-[3,5-difluoro-4-[(1α,5α,6α)-6α)-6-[(2-hydroxyethoxy)iminomethyl]-3-azabicyclo[3.1.0]hexan-3-yl]phenyl]-2-oxooxazolidin-5-ylmethyl]acetamide (210 mg) was prepared from N-[5(S)-3-[3,5-difluoro-4-[(1α,5α,6α)-6-formyl-3-azabicyclo[3.1.0]hexan-3-yl]phenyl]-2-oxooxazolidin-5-ylmethyl]acetamide (202 mg) and crude O-(2-hydroxyethyl)hydroxylamine (prepared from N-(2-hydroxyethoxy)phthalimide (507 mg)) in the same manner as described for EXAMPLE 66.

MS (EI$^+$) m/z: 438 (M$^+$).

HRMS (EI$^+$) for $C_{20}H_{24}F_2N_4O_5$ (M$^+$): calcd, 438.1715; found, 438.1735.

EXAMPLE 109

N-[5(S)-3-[3,5-Difluoro-4-[(1α,5α,6α)-6-[(1-(2-(2-hydroxyethoxy))ethoiminomethyl]-3-azabicyclo[3.1.0]hexan-3-yl]phenyl]-2-oxooxazolidin-5-ylmethyl]acetamide.

The title compound N-[5(S)-3-[3,5-difluoro-4-[(1α,5α,6α)-6-[(1-(2-(2-hydroxyethoxy))ethoxy)iminomethyl]-3-azabicyclo[3.1.0]hexan-3-yl]phenyl]-2-oxooxazolidin-5-ylmethyl]acetamide (345 mg) was prepared from N-[5(S)-3-[3,5-difluoro-4-[(1α,5α,6α)-6-formyl-3-azabicyclo[3.1.0]hexan-3-yl]phenyl]-2-oxooxazolidin-5-ylmethyl]acetamide (300 mg), crude O-[2-(2-hydroxyethoxy) ethyl]hydroxylamine hydrochloride (prepared from N-[2-(2-hydroxyethoxy)ethoxy]phthalimide (766 mg)), and sodium acetate (500 mg) in the same manner as described for EXAMPLE 66.

MS (EI$^+$) m/z: 482 (M$^+$).

HRMS (EI$^+$) for $C_{22}H_{30}FN_4O_6$ (M$^+$): calcd, 482.1977; found, 482.1986.

EXAMPLE 110

N-[5(S)-3-[3,5-Difluoro-4-[(1α,5α,6α)-6-[(2-(1,3-dihydroxy)propyloxy)iminomethyl]-3-azabicyclo[3.1.0]hexan-3-1]phenyl]-2-oxooxazolidin-5-ylmethyl]acetamide.

The title compound N-[5(S)-3-[3,5-difluoro-4-[(1α,5α,6α)-6-[(2-(1,3-dihydroxy)propyloxy)iminomethyl]-3-azabicyclo[3.1.0]hexan-3-yl]phenyl]-2-oxooxazolidin-5-ylmethyl]acetamide (220 mg) was prepared from N-[5(S)-3-[3,5-difluoro-4-[(1α,5α,6α)-6-formyl-3-azabicyclo[3.1.0]hexan-3-yl]phenyl]-2-oxooxazolidin-5-ylmethyl]acetamide (198 mg), O-[2-(1,3-dihydroxy)propyl]hydroxylamine hydrochloride (173 mg), and sodium acetate (195 mg) in the same manner as described for EXAMPLE 66.

MS (EI$^+$) m/z: 468 (M$^+$).

HRMS (EI$^+$) for $C_{21}H_{26}F_2N_4O_6$ (M$^+$): calcd, 468.1820; found, 468.1823.

EXAMPLE 111

N-[5(S)-3-[4-[(1α,5α,6α)-6-[(t-Butyldiphenylsilyl)oxy]methylbicyclo[3.1.0]hex-2-en-3-yl]phenyl]-2-oxooxazolidin-5-ylmethyl]acetamide.

The title compound N-[5(S)-3-[4-[(1α,5α,6α)-6-[(t-butyldiphenylsilyl)oxy]methylbicyclo[3.1.0]hex-2-en-3-yl]phenyl]-2-oxooxazolidin-5-ylmethyl]acetamide (370 mg) was prepared from N-[5(S)-3-[4-(trimethylstannyl)phenyl]-2-oxooxazolidin-5-ylmethyl]acetamide (619 mg) and (1α,5α,6α)-6-[(t-butyldiphenylsilyl)oxy]methyl-3-[(trifluoromethanesulfonyl)oxy]bicyclo[3.1.0]hex-2-ene (646 mg) in the same manner as described for EXAMPLE 47.

MS (FAB$^+$) m/z: 581 (MH$^+$).

$^+$H NMR (CDCl$_3$) δ 1.05 (s, 9H), 1.58 (s, 1H), 1.82 (m, 1H), 2.02 (s, 3H), 2.67 (d, J=17.1 Hz, 1H), 2.93 (dd, J=17.1, 7.8 Hz, 1H), 3.52–4.07 (m, 7H), 4.77 (m, 1H), 6.04 (m, 1H), 6.27 (d, J=2.0 Hz, 1H), 7.28–7.70 (m, 14H).

EXAMPLE 112

N-[5(S)-3-[4-[(1α,5α,6α)-6-Hydroxymethylbicyclo[3.1.0]hex-2-en-3-yl]phenyl]-2-oxooxazolidin-5-ylmethyl]acetamide.

The title compound N-[5(S)-3-[4-[(1α,5α,6α)-6-hydroxymethylbicyclo[3.1.0]hex-2-en-3-yl]phenyl]-2-oxooxazolidin-5-ylmethyl]acetamide (174 mg) was prepared from N-[5(S)-3-[4-[(1α,5α,6α)-6-[(t-butyldiphenylsilyl)oxy]methylbicyclo[3.1.0]hex-2-en-3-yl]phenyl]-2-oxooxazolidin-5-ylmethyl]acetamide (370 mg) in the same manner as described for EXAMPLE 48.

MS (EI⁺) m/z: 342 (M⁺).

$^1$H NMR (DMSO-d$_6$) δ 0.63 (m, 1H), 1.66 (m, 1H), 1.89 (s, 3H), 1.91 (m, 1H), 2.72 (d, J=16.6 Hz, 1H), 2.96 (dd, J=16.6, 7.8 Hz, 1H), 3.25–3.48 (m, 4H), 3.79 (dd, J=8.8 Hz, 6.8 Hz, 1H), 4.16 (t, J=8.8 Hz, 1H), 4.58 (t, J=5.9 Hz, 1H), 4.77 (m, 1H), 6.48 (d, J=2.0 Hz, 1H), 7.45 (d, J=9.3 Hz, 2H), 7.52 (d, J=9.3 Hz, 2H), 8.31 (t, J=5.9 Hz, 1H).

EXAMPLE 113

N-[5(S)-3-[4-[(1α,5α,6α)-6-Cyanobicyclo[3.1.0]hex-2-en-3-yl]phenyl]-2-oxooxazolidin-5-ylmethyl]acetamide.

The title compound N-[5(S)-3-[4-[()-6-cyanobicyclo[3.1.0]hex-2-en-3-yl]phenyl]-2-oxooxazolidin-5-ylmethyl]acetamide (104 mg) was prepared from N-[5(S)-3-[4-[(1α,5α,6α)-6-hydroxymethylbicyclo[3.1.0]hex-2-en-3-yl]phenyl]-2-oxooxazolidin-5-ylmethyl]acetamide (168 mg) in the same manner as described for EXAMPLE 49.

MS (EI⁺) m/z: 337 (M⁺).

HRMS (EI⁺) for C$_{19}$H$_{19}$N$_3$O$_3$ (M⁺): calcd, 337.1426; found, 337.1461.

EXAMPLE 114

N-[5(S)-3-[4-[(1α,5α,6α)-6-Cyanobicyclo[3.1.0]hexan-3-yl]-3-fluorophenyl]-2-oxooxazolidin-5-ylmethyl]acetamide.

The title compound N-[5(S)-3-[4-[(1α,5α,6α)-6-cyanobicyclo[3.1.0]hexan-3-yl]-3-fluorophenyl]-2-oxooxazolidin-5-ylmethyl]acetamide (111 mg) was prepared from N-[5(S)-3-[4-[(1α,5α,6α)-6-cyanobicyclo[3.1.0]hex-2-en-3-yl]-3-fluorophenyl]-2-oxooxazolidin-5-ylmethyl]acetamide (123 mg) in the same manner as described for EXAMPLE 8

MS (FAB⁺) m/z: 358 (MH⁺).

HRMS (FAB⁺) for C$_{19}$H$_{21}$FN$_3$O$_3$ (MH⁺): calcd, 358.1567; found, 358.1560.

EXAMPLE 115

N-[5(S)-3-[4-[(1α,5α,6α)-6-Cyanobicyclo[3.1.0]hexan-3-yl]-3-fluorophenyl]-2-oxooxazolidin-5-ylmethyl]thioacetamide (114A) and N-[5(S)-3-[3-Fluoro-4-[(1α,5α,6α)-6-thiocarbamoylbicyclo[3.1.0]hexan-3-yl]phenyl]-2-oxooxazolidin-5-ylmethyl]acetamide (114B).

The title compounds N-[5(S)-3-[4-[(1α,5α,6α)-6-cyanobicyclo[3.1.0]hexan-3-yl]-3-fluorophenyl]-2-oxooxazolidin-5-ylmethyl]thioacetamide (22 mg) and N-[5(S)-3-[3-Fluoro-4-[(1α,5α,6α)-6-thiocarbamoylbicyclo[3.1.0]hexan-3-yl]phenyl]-2-oxooxazolidin-5-ylmethyl]acetamide (47 mg) were prepared from N-[5(S)-3-[4-[(1α,5α,6α)-6-cyanobicyclo[3.1.0]hexan-3-yl]-3-fluorophenyl]-2-oxooxazolidin-5-ylmethyl]acetamide (99 mg) in the same manner as described for EXAMPLE 97.

114A: MS (FAB⁺) m/z: 374 (MH⁺).

HRMS (FAB⁺) for C$_{19}$H$_{21}$FN$_3$O$_2$S (MH⁺): calcd, 374.1339; found, 374.1342.

114B: MS (FAB⁺) m/z: 408.

HRMS (FAB⁺) for C$_{19}$H$_{23}$FN$_3$O$_2$S$_2$ (MH⁺): calcd, 408.1216; found, 408.1224.

EXAMPLE 116

5(R)-3-[3-Fluoro-4-[(1α,5α,6α)-6-[(2-tetrahydropyranyl)oxy]methyl-3-azabicyclo[3.1.0]hexan-3-yl]phenyl]-5-[(isoxazolyl-3-yl)oxy]methyloxazolidin-2-one.

The title compound 5(R)-3-[3-fluoro-4-[(1α,5α,6α)-6-[(2-tetrahydropyranyl)oxy]methyl-3-azabicyclo[3.1.0]hexan-3-yl]phenyl]-5-[(isoxazolyl-3-yl)oxy]methyloxazolidin-2-one (889 mg) was prepared from 5(R)-3-[3-fluoro-4-[(1α,5α,6α)-6-[(2-tetrahydropyranyl)oxy]methyl-3-azabicyclo[3.1.0]hexan-3-yl]phenyl]-5-hydroxymethyloxazolidin-2-one (702 mg) in the same manner as described for EXAMPLE 16.

MS (EI⁺) m/z: 473 (M⁺).

HRMS (EI⁺) for C$_{24}$H$_{28}$FN$_3$O$_6$ (M⁺): calcd, 473.1962; found, 473.1975.

EXAMPLE 117

5(R)-3-[3-Fluoro-4-[(1α,5α,6α)-6-hydroxymethyl-3-azabicyclo[3.1.0]hexan-3-yl]phenyl]-5-[(isoxazolyl-3-yl)oxy]methyloxazolidin-2-one.

The title compound 5(R)-3-[3-fluoro-4-[(1α,5α,6α)-6-hydroxymethyl-3-azabicyclo[3.1.0]hexan-3-yl]phenyl]-5-[(isoxazolyl-3-yl)oxy]methyloxazolidin-2-one (645 mg) was prepared from 5(R)-3-[3-fluoro-4-[(1α,5α,6α)-6-[(2-tetrahydropyranyl)oxy]methyl-3-azabicyclo[3.1.0]hexan-3-yl]phenyl]-5-[(isoxazolyl-3-yl)oxy]methyloxazolidin-2-one (810 mg) in the same manner as described for EXAMPLE 13.

MS (EI⁺) m/z: 389 (M⁺).

HRMS (EI⁺) for C$_{19}$H$_{20}$FN$_3$O$_5$ (M⁺): calcd, 389.1387; found, 389.1397.

EXAMPLE 118

5(R)-3-[3-Fluoro-4-[(1α,5α,6α)-6-[(isoxazolyl-3-yl)oxy]methyl-3-azabicyclo[3.1.0]hexan-3-yl]phenyl]-5-[(isoxazolyl-3-yl)oxy]methyloxazolidin-2-one.

The title compound 5(R)-3-[3-fluoro-4-[(1α,5α,6α)-6-[(isoxazolyl-3-yl)oxy]methyl-3-azabicyclo[3.1.0]hexan-3-yl]phenyl]-5-[(isoxazolyl-3-yl)oxy]methyloxazolidin-2-one (200 mg) was prepared from 5(R)-3-[3-fluoro-4-[(1α,5α,6α)-6-hydroxymethyl-3-azabicyclo[3.1.0]hexan-3-yl]phenyl]-5-[(isoxazolyl-3-yl)oxy]methyloxazolidin-2-one (260 mg) in the same manner as described for EXAMPLE 16.

MS (EI⁺) m/z: 456 (M⁺).

HRMS (EI⁺) for C$_{22}$H$_{21}$FN$_4$O$_6$ (M⁺): calcd, 456.1445; found, 456.1446.

EXAMPLE 119

5(R)-3-[3-Fluoro-4-[(1α,5α,6α)-6-methoxymethyl-3-azabicyclo[3.1.0]hexan-3-yl]phenyl]-5-[(isoxazolyl-3-yl)oxy]methyloxazolidin-2-one.

The title compound 5(R)-3-[3-fluoro-4-[(1α,5α,6α)-6-methoxymethyl-3-azabicyclo[3.1.0]hexan-3-yl]phenyl]-5-

[(isoxazolyl-3-yl)oxy]methyloxazolidin-2-one (110 mg) was prepared from 5(R)-3-[3-fluoro-4-[(1α,5α,6α)-6-hydroxymethyl-3-azabicyclo[3.1.0]hexan-3-yl]phenyl]-5-[(isoxazolyl-3-yl)oxy]methyloxazolidin-2-one (200 mg) in the same manner as described for PREPARATIVE EXAMPLE 5.

MS (EI$^+$) m/z: 403 (M$^+$).

HRMS (EI$^+$) for $C_{20}H_{22}FN_3O_5$ (M$^+$): calcd, 403.1543; found, 403.1536.

EXAMPLE 120

5(R)-3-[4-([1α,5α,6α)-6-(t-Butoxycarbonyl)amino-3-azabicyclo[3.1.0]hexan-3-yl]-3-fluorophenyl]-5-[(isoxazolyl-3-yl)oxy]methyloxazolidin-2-one.

The title compound 5(R)-3-[4-[(1α,5α,6α)-6-(t-butoxycarbonyl)amino-3-azabicyclo[3.1.0]hexan-3-yl]-3-fluorophenyl]-5-[(isoxazolyl-3-yl)oxy]methyloxazolidin-2-one (322 mg) was prepared from 5(R)-3-[4-[(1α,5α,6α)-6-(t-butoxycarbonyl)amino-3-azabicyclo[3.1.0]hexan-3-yl]-3-fluorophenyl]-5-hydroxymethyloxazolidin-2-one (306 mg) in the same manner as described for EXAMPLE 16.

MS (EI$^+$) m/z: 474 (M$^+$).

HRMS (EI$^+$) for $C_{23}H_{27}FN_4O_6$ (M$^+$): calcd, 474.1915; found, 474.1919.

EXAMPLE 121

5(R)-3-[4-[(1α,5α,6α)-6-Amino-3-azabicyclo[3.1.0]hexan-3-yl]-3-fluorophenyl]-5-[(isoxazolyl-3-yl)oxy]methyloxazolidin-2-one.

The title compound 5(R)-3-[4-[(1α,5α,6α)-6-amino-3-azabicyclo[3.1.0]hexan-3-yl]-3-fluorophenyl]-5-[(isoxazolyl-3-yl)oxy]methyloxazolidin-2-one (98 mg) was prepared from 5(R)-3-[4-[(1α,5α,6α)-6-(t-butoxycarbonyl)amino-3-azabicyclo[3.1.0]hexan-3-yl]-3-fluorophenyl]-5-[(isoxazolyl-3-yl)oxy]methyloxazolidin-2-one (166 mg) in the same manner as described for EXAMPLE 64.

MS (EI$^+$) m/z: 374 (M$^+$).

HRMS (EI$^+$) for $C_{18}H_{19}FN_4O_4$ (M$^+$): calcd, 374.1390; found, 374.1400.

EXAMPLE 122

5(S)-3-[4-[(1α,5α,6α)-6-Cyanobicyclo[3.1.0]hex-2-en-3-yl]-3-fluorophenyl]-5-[N-(t-butoxycarbonyl)-N-(1,2,4-oxadiazolyl-3-yl)]aminomethyloxazolidin-2-one.

The a suspension of 5(R)-3-[4-[(1α,5α,6α)-6-cyanobicyclo[3.1.0]hex-2-en-3-yl]-3-fluorophenyl]-5-hydroxymethyloxazolidin-2-one (178 mg), 3-N-(t-butoxycarbonyl)amino-1,2,4-oxadiazole (157 mg), and tetramethylazodicarboxamide (195 mg) in benzene (36 mL) was added tributylphosphine (229 mg), and the mixture was heated at 60° C. for 49 hours. After insoluble materials were filtered off, the filtrate was concentrated in vacuo. Flash chromatography (silica, hexane:ethyl acetate=4:5) of the residue gave 5(S)-3-[4-[(1α,5α,6α)-6-cyanobicyclo[3.1.0]hex-2-en-3-yl]-3-fluorophenyl]-5-[N-(t-butoxycarbonyl)-N-(1,2,4-oxadiazolyl-3-yl)]aminomethyloxazolidin-2-one (207 mg).

MS (EI$^+$) m/z: 481 (M$^+$).

$^1$H NMR (CDCl$_3$) δ 0.95 (t, J=2.4 Hz, 1H), 1.54 (s, 9H), 2.37 (m, 1H), 2.70 (m, 1H), 2.91 (d, J=17.6 Hz, 1H), 3.19 (dd, J=17.6, 6.4 Hz, 1H), 3.85 (dd, J=9.3, 5.9 Hz, 1H), 4.07–4.15 (m, 2H), 4.32 (dd, J=14.7, 6.8 Hz, 1H), 4.99 (m, 1H), 6.45 (s, 1H), 7.17–7.43 (m, 3H), 8.59 (s, 1H).

EXAMPLE 123

5(S)-3-[4-[(1α,5α,6α)-6-Cyanobicyclo[3.1.0]hex-2-en-3-yl]-3-fluorophenyl]-5-[(1.2.4-oxadiazolyl-3-yl)amino]methyloxazolidin-2-one.

The title compound 5(S)-3-[4-[(1α,5α,6α)-6-cyanobicyclo[3.1.0]hex-2-en-3-yl]-3-fluorophenyl]-5-[(1,2,4-oxadiazolyl-3-yl)amino]methyloxazolidin-2-one (118 mg) was prepared from 5(S)-3-[4-[(1α,5α,6α)-6-cyanobicyclo[3.1.0]hex-2-en-3-yl]-3-fluorophenyl]-5-[N-(t-butoxycarbonyl)-N-(1,2,4-oxadiazolyl-3-yl)]aminomethyloxazolidin-2-one (185 mg) in the same manner as described for EXAMPLE 64.

MS (EI$^+$) m/z: 381 (M$^+$).

HRMS (EI$^+$) for $C_{19}H_{16}FN_5O_3$ (M$^+$): calcd, 381.1237; found, 381.1241.

EXAMPLE 124

5(S)-3-[4-[(1α,5α,6α)-6-Amino-3-azabicyclo[3.1.0]hexan-3-yl]-3-fluorophenyl]-5-[(isoxazolyl-3-yl)amino]methyloxazolidin-2-one.
Step 1
5(S)-3-[4-[(1α,5α,6α)-6-(t-Butoxycarbonyl)amino-3-azabicyclo[3.1.0]hexan-3-yl]-3-fluorophenyl]-5-[N-(t-butoxycarbonyl)-N-(isoxazolyl-3-yl)]aminomethyloxazolidin-2-one.

The title compound 5(S)-3-[4-[(1α,5α,6α)-6-(t-butoxycarbonyl)amino-3-azabicyclo[3.1.0]hexan-3-yl]-3-fluorophenyl]-5-[N-(t-butoxycarbonyl)-N-(isoxazolyl-3-yl)]aminomethyloxazolidin-2-one (276 mg) was prepared from 5(R)-3-[4-[(1α,5α,6α)-6-(t-butoxycarbonyl)amino-3-azabicyclo[3.1.0]hexan-3-yl]-3-fluorophenyl]-5-hydroxymethyloxazolidin-2-one (256 mg) and 3-N-(t-butoxycarbonyl)aminoisoxazole (174 mg) in the same manner as described for EXAMPLE 122.

MS (FAB$^+$) m/z: 574 (MH$^+$).

Step 2
5(S)-3-[4-[(1α,5α,6α)-6-Amino-3-azabicyclo[3.1.0]hexan-3-yl]-3-fluorophenyl]-5-[(isoxazolyl-3-yl)amino]methyloxazolidin-2-one.

The title compound 5(S)-3-[4-[(1α,5α,6α)-6-amino-3-azabicyclo[3.1.0]hexan-3-yl]-3-fluorophenyl]-5-[(isoxazolyl-3-yl)amino]methyloxazolidin-2-one (124 mg) was prepared from 5(S)-3-[4-[(1α,5α,6α)-6-(t-butoxycarbonyl)amino-3-azabicyclo[3.1.0]hexan-3-yl]-3-fluorophenyl]-5-[N-(t-butoxycarbonyl)-N-(isoxazolyl-3-yl)]aminomethyloxazolidin-2-one (272 mg) in the same manner as described for EXAMPLE 64.

MS (FAB$^+$) m/z: 374 (MH$^+$).

HRMS (FAB$^+$) for $C_{18}H_{21}FN_5O_3$ (MH$^+$): calcd, 374.1628; found, 374.1605.

EXAMPLE 125

5(S)-3-[4-[(1α,5α,6α)-6-Amino-3-azabicyclo[3.1.0]hexan-3-yl]-3-fluorophenyl]-5-[(1,2,4-oxadiazolyl-3-yl)amino]methyloxazolidin-2-one.
Step 1
5(S)-3-[4-[(1α,5α,6α)-6-(t-Butoxycarbonyl)amino-3-azabicyclo[3.1.0]hexan-3-yl]-3-fluorophenyl]-5-[N-(t-butoxycarbonyl)-N-(1,2,4-oxadiazolyl-3-yl)]aminomethyloxazolidin-2-one.

The title compound 5(S)-3-[4-[(1α,5α,6α)-6-(t-butoxycarbonyl)amino-3-azabicyclo[3.1.0]hexan-3-yl]-3-fluorophenyl]-5-[N-(t-butoxycarbonyl)-N-(1,2,4-oxadiazolyl-3-yl)]aminomethyloxazolidin-2-one (234 mg) was prepared from 5(R)-3-[4-[(1α,5α,6α)-6-(t- butoxycarbonyl)amino-3-azabicyclo[3.1.0]hexan-3-yl]-3-fluorophenyl]-5-hydroxymethyl oxazolidin-2-one (280 mg) and 3-N-(t-butoxycarbonyl)amino-1,2,4-oxadiazole (191 mg) in the same manner as described for EXAMPLE 122.

MS (FAB$^+$) m/z: 575 (MH$^+$).

Step 2

5(S)-3-[4-[(1α,5α,6α)-6-Amino-3-azabicyclo[3.1.0]hexan-3-yl]-3-fluorophenyl]-5-[(1,2,4-oxadiazolyl-3-yl)amino]methyloxazolidin-2-one.

The title compound 5(S)-3-[4-[(1α,5α,6α)-6-amino-3-azabicyclo[3.1.0]hexan-3-yl]-3-fluorophenyl)-5-[(1,2,4-oxadiazolyl-3-yl)amino]methyloxazolidin-2-one (87 mg) was prepared from 5(S)-3-[4-[(1α,5α,6α)-6-(t-butoxycarbonyl)amino-3-azabicyclo[3.1.0]hexan-3-yl]-3-fluorophenyl]-5-[N-(t-butoxycarbonyl)-N-(1,2,4-oxadiazolyl-3-yl)]aminomethyl oxazolidin-2-one (234 mg) in the same manner as described for EXAMPLE 64

MS (FAB$^+$) m/z: 375 (MH$^+$).

HRMS (FAB$^+$) for $C_{17}H_{20}FN_6O_3$ (MH$^+$): calcd, 375.1581; found, 375.1583.

EXAMPLE 126

5(S)-3-[4-[(1α,5α,6α)-6-Amino-3-azabicyclo[3.1.0]hexan-3-yl]-3,5-difluorophenyl]-5-[(1,2,4-oxadiazolyl-3-yl)amino]methyloxazolidin-2-one.

Step 1

5(R)-3-[4-[(1α,5α,6α)-6-(N-Benzyl)amino-3-azabicyclo[3.1.0]hexan-3-yl]-3,5-difluorophenyl]-5-hydroxymethyloxazolidin-2-one.

The title compound 5(R)-3-[4-[(1α,5α,6α)-6-(N-benzyl)amino-3-azabicyclo[3.1.0]hexan-3-yl]-3,5-difluorophenyl]-5-hydroxymethyloxazolidin-2-one was prepared from 5(R)-3-[4-[(1α,5α,6α)-6-(N-benzyl-N-t-butylcarbonyl)amino-3-azabicyclo[3.1.0]hexan-3-yl]-3,5-difluorophenyl]-5-hydroxymethyloxazolidin-2-one in the same manner as described for EXAMPLE 1.

MS (FAB$^+$) m/z: 416 (MH$^+$).

HRMS (FAB$^+$) for $C_{22}H_{24}F_2N_3O_3$ (MH$^+$): calcd, 416.1786; found, 416.1820.

Step 2

5(R)-3-[4-[(1α,5α,6α)-6-(N-t-Butoxycarbonyl)amino-3-azabicyclo[3.1.0]hexan-3-yl]-3,5-difluorophenyl]-5-hydroxymethyloxazolidin-2-one.

The title compound 5(R)-3-[4-[(1α,5α,6α)-6-(N-t-butoxycarbonyl)amino-3-azabicyclo[3.1.0]hexan-3-yl]-3,5-difluorophenyl]-5-hydroxymethyloxazolidin-2-one (2.44 g) was prepared from 5(R)-3-[4-[(1α,5α,6α)-6-(N-benzyl)amino-3-azabicyclo[3.1.0]hexan-3-yl]-3,5-difluorophenyl]-5-hydroxymethyloxazolidin-2-one (3.59 g) in the same manner as described for EXAMPLE 8 and REFFERENCE EXAMPLE 21.

MS (FAB$^+$) m/z: 426 (MH$^+$).

HRMS (FAB$^+$) for $C_{20}H_{26}F_2N_3O_5$ (MH$^+$): calcd, 426.1841; found, 426.1805.

Step 3

5(S)-3-[4-[(1α,5α,6α)-6-(N-t-Butoxycarbonyl)amino-3-azabicyclo[3.1.0]hexan-3-yl]-3,5-difluorophenyl]-5-[N-(t-butoxycarbonyl)-N-(1,2,4-oxadiazolyl-3-yl)]aminomethyloxazolidin-2-one.

The title compound 5(S)-3-[4-[(1α,5α,6α)-6-(N-t-butoxycarbonyl)amino-3-azabicyclo[3.1.0]hexan-3-yl]-3,5-difluorophenyl]-5-[N-(t-butoxycarbonyl)-N-(1,2,4-oxadiazolyl-3-yl)]aminomethyloxazolidin-2-one (320 mg) was prepared from 5(R)-3-[4-[(1α,5α,6α)-6-(N-t-butoxycarbonyl)amino-3-azabicyclo[3.1.0]hexan-3-yl]-3,5-difluorophenyl]-5-hydroxymethyloxazolidin-2-one (255 mg) and 3-N-(t-butoxycarbonyl) amino-1,2,4-oxadiazole (167 mg) in the same manner as described for EXAMPLE 122.

MS (EI$^+$) m/z: 592 (M$^+$).

HRMS (EI$^+$) for $C_{27}H_{34}F_2N_6O_7$ (M$^+$): calcd, 592.2457; found, 592.2481.

Step 4

5(S)-3-[4-[(1α,5α,6α)-6-Amino-3-azabicyclo[3.1.0]hexan-3-yl]-3,5-difluorophenyl]-5-[(1,2,4-oxadiazolyl-3-yl)amino]methyloxazolidin-2-one.

The title compound 5(S)-3-[4-[(1α,5α,6α)-6-amino-3-azabicyclo[3.1.0]hexan-3-yl]-3,5-difluorophenyl]-5-[(1,2,4-oxadiazolyl-3-yl)amino]methyloxazolidin-2-one (142 mg) was prepared from 5(S)-3-[4-[(1α,5α,6α)-6-(N-t-butoxycarbonyl)amino-3-azabicyclo[3.1.0]hexan-3-yl]-3,5-difluorophenyl]-5-[N-(t-butoxycarbonyl)-N-(1,2,4-oxadiazolyl-3-yl)]aminomethyloxazolidin-2-one (466 mg) in the same manner as described for EXAMPLE 64.

MS (FAB$^+$) m/z: 393 (MH$^+$).

HRMS (FAB$^+$) for $C_{17}H_{19}F_2N_6O_3$ (MH$^+$): calcd, 393.1487; found, 393.1491.

EXAMPLE 127

5(S)-3-[4-[(1α,5α,6α)-6-Amino-3-azabicyclo[3.1.0]hexan-3-yl]-3,5-difluorophenyl]-5-[(isoxazolyl-3-yl)amino]methyloxazolidin-2-one.

Step 1

5(S)-3-[4-[(1α,5α,6α)-6-(N-t-Butoxycarbonyl)amino-3-azabicyclo[3.1.0]hexan-3-yl]-3,5-difluorophenyl]-5-[N-(t-butoxycarbonyl)-N-(isoxazolyl-3-yl)]aminomethyloxazolidin-2-one.

The title compound 5(S)-3-[4-[(1α,5α,6α)-6-(N-t-butoxycarbonyl)amino-3-azabicyclo[3.1.0]hexan-3-yl]-3,5-difluorophenyl]-5-[N-(t-butoxycarbonyl)-N-(isoxazolyl-3-yl)]aminomethyloxazolidin-2-one (785 mg) was prepared from 5(R)-3-[4-[(1α,5α,6α)-6-(N-t-butoxycarbonyl)amino-3-azabicyclo[3.1.0]hexan-3-yl]-3,5-difluorophenyl]-5-hydroxymethyloxazolidin-2-one (596 mg) and 3-N-(t-butoxycarbonyl)aminoisoxazole (387 mg) in the same manner as described for EXAMPLE 122.

MS (EI$^+$) m/z: 591 (M$^+$).

HRMS (EI$^+$) for $C_{28}H_{35}F_2N_5O_7$ (M$^+$): calcd, 591.2505; found, 591.2482.

Step 2

5(S)-3-[4-[(1α,5α,6α)-6-Amino-3-azabicyclo[3.1.0]hexan-3-yl]-3,5-difluorophenyl]-5-[(isoxazolyl-3-yl)amino]methyloxazolidin-2-one.

The title compound 5(S)-3-[4-[(1α,5α,6α)-6-amino-3-azabicyclo[3.1.0]hexan-3-yl]-3,5-difluorophenyl]-5-[(isoxazolyl-3-yl)amino]methyloxazolidin-2-one (277 mg) was prepared from 5(S)-3-[4-[(1α,5α,6α)-6-(N-t-butoxycarbonyl)amino-3-azabicyclo[3.1.0]hexan-3-yl]-3,5-difluorophenyl]-5-[N-(t-butoxycarbonyl)-N-(isoxazolyl-3-yl)]aminomethyloxazolidin-2-one (820 mg) in the same manner as described for EXAMPLE 64.

MS (EI$^+$) m/z: 391 (M$^+$).

HRMS (EI$^+$) for $C_{18}H_{19}F_2N_5O_3$ (M$^+$): calcd, 391.1456; found, 391.1480.

EXAMPLE 128

5(S)-3-[4-[(1α,5α,6α)-6-Amino-3-azabicyclo[3.1.0]hexan-3-yl]phenyl]-5-[(isoxazolyl-3-yl)amino]methyloxazolidin-2-one.

Step 1

5(S)-3-[4-[(1α,5α,6α)-6-(N-t-Butoxycarbonyl)amino-3-azabicyclo[3.1.0]hexan-3-yl]phenyl]-5-[N-(t-butoxycarbonyl)-N-(isoxazolyl-3-yl)]aminomethyloxazolidin-2-one.

The title compound 5(S)-3-[4-[(1α,5α,6α)-6-(N-t-butoxycarbonyl)amino-3-azabicyclo[3.1.0]hexan-3-yl]phenyl]-5-[N-(t-butoxycarbonyl)-N-(isoxazolyl-3-yl)]aminomethyloxazolidin-2-one (415 mg) was prepared from 5(R)-3-[4-[(1α,5α,6α)-6-(N-t-butoxycarbonyl)amino-3-azabicyclo[3.1.0]hexan-3-yl]phenyl]-5-hydroxymethyloxazolidin-2-one (405 mg) and 3-N-(t-butoxycarbonyl)aminoisoxazole (287 mg) in the same manner as described for EXAMPLE 122.

MS (EI$^+$) m/z: 555 (M$^+$).

HRMS (EI$^+$) for $C_{28}H_{37}N_5O_7$ (M$^+$): calcd, 555.2693; found, 555.2686.

Step 2

5(S)-3-[4-[(1α,5α,6α)-6-Amino-3-azabicyclo[3.1.0]hexan-3-yl]phenyl]-5-[(isoxazolyl-3-yl)amino]methyloxazolidin-2-one.

The title compound 5(S)-3-[4-[(1α,5α,6α)-6-amino-3-azabicyclo[3.1.0]hexan-3-yl]phenyl]-5-[(isoxazolyl-3-yl)amino]methyloxazolidin-2-one (173 mg) was prepared from 5(S)-3-[4-[(1α,5α,6α)-6-(N-t-butoxycarbonyl)amino-3-azabicyclo[3.1.0]hexan-3-yl]phenyl]-5-[N-(t-butoxycarbonyl)-N-(isoxazolyl-3-yl)]aminomethyloxazolidin-2-one (415 mg) in the same manner as described for EXAMPLE 64.

MS (EI$^+$) m/z: 355 (M$^+$).

HRMS (EI$^+$) for $C_{18}H_{21}N_5O_3$ (M$^+$): calcd, 355.1644; found, 355.1618.

EXAMPLE 129

5(S)-3-[4-[(1α,5α,6α)-6-Cyanobicyclo[3.1.0]hex-2-en-3-yl]phenyl]-5[N-(1,2,4-oxadiazolyl-3-yl)]aminomethyloxazolidin-2-one.

Step 1

5(S)-5-[N-(t-Butoxycarbonyl)-N-(1,2,4-oxadiazolyl-3-yl)]aminomethyl-3-[4-[(1α,5α,6α)-6-cyanobicyclo[3.1.0]hex-2-en-3-yl]phenyl]oxazolidin-2-one.

The title compound 5(S)-5-[N-(t-butoxycarbonyl)-N-(1,2,4-oxadiazolyl-3-yl)]aminomethyl-3-[4-[(1α,5α,6α)-6-cyanobicyclo[3.1.0]hex-2-en-3-yl]phenyl]oxazolidin-2-one (238 mg) was prepared from 5(R)-3-[4-[(1α,5α,6α)-6-cyanobicyclo[3.1.0]hex-2-en-3-yl]phenyl]-5-hydroxymethyloxazolidin-2-one (180 mg) and 3-N-(t-butoxycarbonyl)amino-1,2,4-oxadiazole (135 mg) in the same manner as described for EXAMPLE 122.

MS (EI$^+$) m/z: 463 (M$^+$).

HRMS (EI$^+$) for $C_{24}H_{25}N_5O_5$ (M$^+$): calcd, 463.1856; found, 463.1840.

Step 2

5(S)-3-[4-[(1α,5α,6α)-6-Cyanobicyclo[3.1.0]hex-2-en-3-yl]phenyl]-5-[N-(1,2,4-oxadiazolyl-3-yl)]aminomethyloxazolidin-2-one.

The title compound 5(S)-3-[4-[(1α,5α,6α)-6-cyanobicyclo[3.1.0]hex-2-en-3-yl]phenyl]-5-[N-(1,2,4-oxadiazolyl-3-yl)]aminomethyloxazolidin-2-one (123 mg) was prepared from 5(S)-5-[N-(t-butoxycarbonyl)-N-(1,2,4-oxadiazolyl-3-yl)]aminomethyl-3-[4-[(1α,5α,6α)-6-cyanobicyclo[3.1.0]hex-2-en-3-yl]phenyl]oxazolidin-2-one (200 mg) in the same manner as described for EXAMPLE 64.

MS (EI$^+$) m/z: 363 (M$^+$).

HRMS (EI$^+$) for $C_{19}H_{17}N_5O_3$ (M$^+$): calcd, 363.1331; found, 363.1329.

EXAMPLE 130

5(S)-3-[4-[(1α,5α,6α)-6-Cyanobicyclo[3.1.0]hex-2-en-3-yl]phenyl]-5-[(isoxazolyl-3-yl)amino]methyloxazolidin-2-one.

Step 1

5(S)-5-[N-(t-Butoxycarbonyl)-N-(isoxazolyl-3-yl)]aminomethyl-3-[4-[(1α,5α,6α)-6-cyanobicyclo[3.1.0]hex-2-en-3-yl]phenyl]oxazolidin-2-one.

The title compound 5(S)-5-[N-(t-butoxycarbonyl)-N-(isoxazolyl-3-yl)]aminomethyl-3-[4-[(1α,5α,6α)-6-cyanobicyclo[3.1.0]hex-2-en-3-yl]phenyl]oxazolidin-2-one (280 mg) was prepared from 5(R)-3-[4-[(1α,5α,6α)-6-cyanobicyclo[3.1.0]hex-2-en-3-yl]phenyl]-5-hydroxymethyloxazolidin-2-one (180 mg) and 3-N-(t-butoxycarbonyl)aminoisoxazole (134 mg) in the same manner as described for EXAMPLE 122.

MS (EI$^+$) m/z: 462 (M$^+$).

HRMS (EI$^+$) for $C_{25}H_{26}N_4O_5$ (M$^+$): calcd, 462.1903; found, 462.1917.

Step 2

5(S)-3-[4-[(1α,5α,6α)-6-Cyanobicyclo[3.1.0]hex-2-en-3-yl]phenyl]-5-[(isoxazolyl-3-yl)amino]methyloxazolidin-2-one.

The title compound 5(S)-3-[4-[(1α,5α,6α)-6-cyanobicyclo[3.1.0]hex-2-en-3-yl]phenyl]-5-[(isoxazolyl-3-yl)amino]methyloxazolidin-2-one (147 mg) was prepared from 5(S)-5-[N-(t-butoxycarbonyl)-N-(isoxazolyl-3-yl)]aminomethyl-3-[4-[(1α,5α,6α)-6-cyanobicyclo[3.1.0]hex-2-en-3-yl]phenyl]oxazolidin-2-one (260 mg) in the same manner as described for EXAMPLE 64.

EXAMPLE 131

5(R)-3-[4-[(1α,5α,6α)-6-Cyanobicyclo[3.1.0]hex-2-en-3-yl]phenyl]-5-[(isoxazolyl-3-yloxy]methyloxazolidin-2-one.

The title compound 5(R)-3-[4-[(1α,5α,6α)-6-cyanobicyclo[3.1.0]hex-2-en-3-yl]phenyl]-5-[(isoxazolyl-3-yl)oxy]methyloxazolidin-2-one (181 mg) was prepared from 5(R)-3-[4-[(1α,5α,6α)-6-cyanobicyclo[3.1.0]hex-2-en-3-yl]phenyl]-5-hydroxymethyloxazolidin-2-one (180 mg) and 3-hydroxyisoxazole (67 mg) in the same manner as described for EXAMPLE 16.

MS (EI$^+$) m/z: 363 (M$^+$).

HRMS (EI$^+$) for $C_{20}H_{17}N_3O_4$ (M$^+$): calcd, 363.1219; found, 363.1207.

EXAMPLE 132

N-[5(S)-3-[4-[(1α,5α,6α)-6-[N-Cyano-1-iminoethyl)amino]-3-azabicyclo[3.1.0]hexan-3-yl]-3,5-difluorophenyl]-2-oxooxazolidin-5-ylmethylacetamide.

To a solution of N-[5(S)-3-[4-[(1α,5α,6α)-6-amino-3-azabicyclo[3.1.0]hexan-3-yl]-3,5-difluorophenyl]-2-oxooxazolidin-5-ylmethyl]acetamide (293 mg) in methanol (5 mL) was added N-cyano-O-methylacetimidate (118 mg), and the mixture was stirred at room temperature for 6 days. The resulting precipitates were collected by filteration, washed with cold methanol to give N-[5(S)-3-[4-[(1α,5α,6α)-6-[(N-cyano-1-iminoethyl)amino]-3-azabicyclo[3.1.0]hexan-3-yl]-3,5-difluorophenyl]-2-oxooxazolidin-5-ylmethyl]acetamide (89 mg).

MS (FAB$^+$) m/z: 433 (MH$^+$).

HRMS (FAB$^+$) for $C_{20}H_{23}F_2N_6O_3$ (MH$^+$) calcd, 433.1800; found, 433.1795.

EXAMPLE 133

N-[5(S)-3-[4-[(1α,5α,6α)-6-(5-Amino-4-cyano-1.3-oxazol-2-yl)-3-azabicyclo[3.1.0]hexan-3-yl]-3-fluorophenyl]-2-oxooxazolidin-5-ylmethyl]acetamide.

To a solution of N-[5(S)-3-[4-[(1α,5α,6α)-6-carboxyl-3-azabicyclo[3.1.0]hexan-3-yl]-3-fluorophenyl]-2-oxooxazolidin-5-ylmethyl]acetamide (180 mg) in pyridine (10 mL) was added aminomalononitrile toluenesulfonate (362 mg) and 1-[3-(dimethylamino)propyl]-3-ethylcarbodiimide hydrochloride (366 mg), and the mixture was stirred at room temperature for 5 days. After addition of water to the mixture, the resulting precipitates were collected by filtration, washed with water and dried in air. Flash chromatography (silica, ethyl acetate:methanol=9:1) of the precipitates gave N-[5(S)-3-[4-[(1α,5α,6α)-6-(5-amino-4-cyano-1,3-oxazol-2-yl)-3-azabicyclo[3.1.0]hexan-3-yl]-3-fluorophenyl]-2-oxooxazolidin-5-ylmethyl]acetamide (145 mg).

MS (FAB$^+$) m/z: 441 (MH$^+$).

HRMS (FAB$^+$) for $C_{21}H_{22}N_6O_4$ (MH$^+$): calcd, 441.1687; found, 441.1684.

EXAMPLE 134

N-[5(S)-3-[4-[(1α,5α,6α)-6-(5-Amino-4-cyano-1,3-oxazol-2-yl)bicyclo[3.1.0]hex-2-en-3-yl]-3-fluorophenyl]-2-oxooxazolidin-5-ylmethyl]acetamide.

Step 1

N-[5(S)-3-[4-[(1α,5α,6α)-6-Carboxybicyclo[3.1.0]hex-2-en-3-yl]-3-fluorophenyl]-2-oxooxazolidin-5-ylmethyl]acetamide.

The title compound N-[5(S)-3-[4-[(1α,5α,6α)-6-carboxybicyclo[3.1.0]hex-2-en-3-yl]-3-fluorophenyl]-2-oxooxazolidin-5-ylmethyl]acetamide (175 mg) was prepared from N-[5(S)-3-[4-[(1α,5α,6α)-6-formylbicyclo[3.1.0]hex-2-en-3-yl]-3-fluorophenyl]-2-oxooxazolidin-5-ylmethyl]acetamide (200 mg) in the same manner as described for EXAMPLE 23.

Step 2

N-[5(S)-3-[4-[(1α,5α,6α)-6-(5-Amino-4-cyano-1,3-oxazol-2-yl)bicyclo[3.1.0]hex-2-en-3-yl]-3-fluorophenyl]-2-oxooxazolidin-5-ylmethyl]acetamide.

The title compound N-[5(S)-3-[4-[(1α,5α,6α)-6-(5-amino-4-cyano-1,3-oxazol-2-yl)bicyclo[3.1.0]hex-2-en-3-yl]-3-fluorophenyl]-2-oxooxazolidin-5-ylmethyl]acetamide (147 mg) was prepared from N-[5(S)-3-[4-[(1α,5α,6α)-6-carboxybicyclo[3.1.0]hex-2-en-3-yl]-3-fluorophenyl]-2-oxooxazolidin-5-ylmethyl]acetamide (175 mg) and aminomalononitrile toluenesulfonate (355 mg) in the same manner as described for EXAMPLE 133.

MS (FAB$^+$) m/z: 438 (MH$^+$).

HRMS (FAB$^+$) for $C_{22}H_{21}FN_5O_4$ (MH$^+$): calcd, 438.1578; found, 438.1549.

EXAMPLE 135

N-[5(S)-3-[4-[(1α,5α,6α)-6-Amino-3-azabicyclo[3.1.0]hexan-3-yl]phenyl]-2-oxooxazolidin-5-ylmethyl]acetamide.

Step 1

5(R)-3-[4-[(1α,5α,6α)-6-(N-t-Butoxycarbonyl)amino-3-azabicyclo[3.1.0]hexan-3-yl]phenyl]-5-hydroxymethyloxazolidin-2-one.

To a solution of 4-[(1α,5α,6α)-6-(N-t-butoxycarbonyl)amino-3-azabicyclo[3.1.0]hexan-3-yl]-1-benzyloxycarbonylaminobenzene (551 mg) in dry tetrahydrofuran (20 mL) was added a solution of t-butoxylithium in tetrahydrofuran (1.0 M, 2.0 mL) at room temperature, and the mixture was stirred for 15 min. (R)-Glycidylbutyrate (0.25 mL) was added to the mixture, the mixture was stirred at room temperature for 1 hour, and then at 50° C. for 3 hours. After quenching the reaction by the addition of methanol, the mixture was extracted with ethyl acetate. The organic extracts were washed with brine, dried over anhydrous magnesium sulfate, filtered, and then concentrated in vacuo. Treatment of the residue with ethyl acetate gave 5(R)-3-[4-[(1α,5α,6α)-6-(N-t-butoxycarbonyl)amino-3-azabicyclo[3.1.0]hexan-3-yl]phenyl]-5-hydroxymethyloxazolidin-2-one (284 mg).

MS (EI$^+$) m/z: 389 (M$^+$).

HRMS (EI$^+$) for $C_{20}H_{27}N_3O_5$ (M$^+$): calcd, 389.1951; found, 389.1924.

Step 2

5(R)-5-Acetoxymethyl-3-[4-[(1α,5α,6α)-6-(N-t-butoxycarbonyl)amino-3-azabicyclo[3.1.0]hexan-3-yl]phenyl]oxazolidin-2-one.

To a solution of 5(R)-3-[4-[(1α,5α,6α)-6-(N-t-butoxycarbonyl)amino-3-azabicyclo[3.1.0]hexan-3-yl]phenyl]-5-hydroxymethyloxazolidin-2-one (3.34 g) in pyridine (20 mL) was added acetic anhydride (10 mL), the mixture was stirred at room temperature for 2 hours, and then concentrated in vacuo. Treatment of the residue with ethyl acetate gave 5(R)-5-acetoxymethyl-3-[4-[(1α,5α,6α)-6-(N-t-butoxycarbonyl)amino-3-azabicyclo[3.1.0]hexan-3-yl]phenyl]oxazolidin-2-one (3.19 g).

MS (EI$^+$) m/z: 431 (M$^+$).

HRMS (EI$^+$) for $C_{22}H_{29}N_3O_6$ (M$^+$): calcd, 431.2056; found, 431.2059.

Step 3

N-[5(S)-3-[4-[(1α,5α,6α)-6-(N-t-Butoxycarbonyl)amino-3-azabicyclo[3.1.0]hexan-3-yl]phenyl]-2-oxooxazolidin-5-ylmethyl]acetamide.

To a suspension of 5(R)-5-acetoxymethyl-3-[4-[(1α,5α,6α)-6-(N-t-butoxycarbonyl)amino-3-azabicyclo[3.1.0]hexan-3-yl]phenyl]oxazolidin-2-one (1.00 g) in methanol (100 mL) was added potassium carbonate (1.60 g), the mixture was stirred at room temperature for 1 hour, and then concentrated in vacuo. A suspension of the residue in tetrahydrofuran (100 mL) was added triethylamine (0.5 mL) and methanesulfonyl chloride (0.25 mL) at 0° C., and the mixture was stirred at the same temperature for 30 min. After dilution of the mixture with water, the mixture was extracted with ethyl acetate. The organic extracts were washed with brine, dried over anhydrous magnesium sulfate, filtered, and then concentrated in vacuo to give 5(R)-3-[4-[(1α,5α,6α)-6-(N-t-butoxycarbonyl)amino-3-azabicyclo[3.1.0]hexan-3-yl]phenyl]-5-methanesulfonyloxymethyloxazolidin-2-one (827 mg). The mixture of 5(R)-3-[4-[(1α,5α,6α)-6-(N-t-butoxycarbonyl)amino-3-azabicyclo[3.1.0]hexan-3-yl]phenyl]-5-methanesulfonyloxymethyloxazolidin-2-one (820 mg) and sodium azide (281 mg) in N,N-dimethylformamide (14 mL) was heated at 70° C. for 4 hours. After dilution of the mixture with water, the mixture was extracted with dichloromethane. The organic extracts were washed with brine, dried over anhydrous magnesium sulfate, filtered, and then concentrated in vacuo. The crude 5(R)-azidomethyl-3-[4-[(1α,5α,6α)-6-(N-t-butoxycarbonyl)amino-3-azabicyclo[3.1.0]hexan-3-yl]phenyl]oxazolidin-2-one thus obtained was converted to N-[5(S)-3-[4-[(1α,5α,6α)-6-(N-t-butoxycarbonyl)amino-3-azabicyclo[3.1.0]hexan-3-yl]phenyl]-2-oxooxazolidin-5-ylmethyl]acetamide (591 mg) according to the same manner as described for EXAMPLE 9.

MS (EI$^+$) m/z: 430 (M$^+$).

HRMS (EI$^+$) for $C_{22}H_{30}N_4O_5$ (M$^+$): calcd, 430.2216; found, 430.2219.

Step 4

N-[5(S)-3-[4-[(1α,5α,6α)-6-Amino-3-azabicyclo[3.1.0]hexan-3-yl]phenyl]-2-oxooxazolidin-5-ylmethyl]acetamide.

The title compound N-[5(S)-3-[4-[(1α,5α,6α)-6-amino-3-azabicyclo[3.1.0]hexan-3-yl]phenyl]-2-oxooxazolidin-5-ylmethyl]acetamide (192 mg) was prepared from N-[5(S)-3-[4-[(1α,5α,6α)-6-(N-t-butoxycarbonyl)amino-3-azabicyclo[3.1.0]hexan-3-yl]phenyl]-2-oxooxazolidin-5-ylmethyl]acetamide (300 mg) in the same manner as described for EXAMPLE 64.

MS (EI⁺) m/z: 330 (M⁺).

HRMS (EI⁺) for $C_{17}H_{22}N_4O_3$ (M⁺): calcd, 330.1692; found, 330.1725.

EXAMPLE 136

N-[5(S)-3-[4-[(1α,5α,6α)-6-Hydroxymethylbicyclo[3.1.0]hex-2-en-2-yl]phenyl]-2-oxooxazolidin-5-ylmethyl]acetamide.

The mixture of N-[5(S)-3-(4-iodophenyl)-2-oxooxazolidin-5-ylmethyl]acetamide (1.08 g), (1α,5α,6α)-6-[(t-butyldiphenylsilyl)oxy]methyl-2-(4,4,5,5-tetramethyl-1,3,2-dioxaborolyl)bicyclo[3.1.0]hex-2-ene (1.50 g), tetrakis(triphenylphosphine)palladium (173 mg) and 2 M sodium carbonate solution (4.5 mL) in dioxane (30 mL) was stirred at 80° C. for 2 hours. After dilution of the mixture with water, the mixture was extracted with ethyl acetate. The organic extracts were washed with brine, dried over anhydrous magnesium sulfate, filtered, and then concentrated in vacuo. Flash chromatography (silica, ethyl acetate:methanol=9:1) of the residue gave N-[5(S)-3-[4-[(1α,5α,6α)-6-[(t-butyldiphenylsilyl)oxy]methylbicyclo[3.1.0]hex-2-en-2-yl]phenyl]-2-oxooxazolidin-5-ylmethyl]acetamide. To a solution of N-[5(S)-3-[4-[(1α,5α,6α)-6-[(t-butyldiphenylsilyl)oxy]methylbicyclo[3.1.0]hex-2-en-2-yl]phenyl]-2-oxooxazolidin-5-ylmethyl]acetamide thus obtained in tetrahydrofuran (20 mL) was added acetic acid (810 μL) and a solution of tetrabutylammonium fluoride in tetrahydrofuran (1M, 9 mL) at room temperature, and the mixture was stirred at room temperature for 2 days. After dilution of the mixture with saturated sodium hydrogencarbonate solution, sodium chloride and water, the mixture was extracted with ethyl acetate-tetrahydrofuran (1:1). The organic extracts were washed with brine, dried over anhydrous magnesium sulfate, filtered, and then concentrated in vacuo. Flash chromatography (silica, ethyl acetate:methanol=8:1) of the residue gave N-[5(S)-3-[4-[(1α,5α,6α)-6-hydroxymethylbicyclo[3.1.0]hex-2-en-2-yl]phenyl]-2-oxooxazolidin-5-ylmethyl]acetamide (953 mg).

MS (EI⁺) m/z: 342 (M⁺).

HRMS (EI⁺) for $C_{19}H_{22}N_2O_4$ (M⁺): calcd, 342.1580; found, 342.1596.

EXAMPLE 137

N-[5(S)-3-[4-[(1α,5α,6α)-6-[(Hydroxyimino)methyl]bicyclo[3.1.0]hex-2-en-2-yl]phenyl]-2-oxooxazolidin-5-ylmethyl]acetamide.

The title compound N-[5(S)-3-[4-[(1α,5α,6α)-6-[(hydroxyimino)methyl]bicyclo[3.1.0]hex-2-en-2-yl]phenyl]-2-oxooxazolidin-5-ylmethyl]acetamide (390 mg) was prepared from N-[5(S)-2-[4-[(1α,5α,6α)-6-hydroxymethylbicyclo[3.1.0]hex-2-en-2-yl]phenyl]-2-oxooxazolidin-5-ylmethyl]acetamide (680 mg) in the same manner as described for EXAMPLE 49.

MS (FAB⁺) m/z: 356 (MH⁺).

HRMS (FAB⁺) for $C_{19}H_{22}N_3O_4$ (MH⁺): calcd, 356.1610; found, 356.1576.

EXAMPLE 138

N-[5(S)-3-[4-[(1α,5α,6α)-6-Cyanobicyclo[3.1.0]hex-2-en-2-yl]phenyl]-2-oxooxazolidin-5-ylmethyl]acetamide The title compound N-[5(S)-3-[4-[(1α,5α,6α)-6-cyanobicyclo[3.1.0]hex-2-en-2-yl]phenyl]-2-oxooxazolidin-5-ylmethyl]acetamide (188 mg) was prepared from N-[5(S)-3-[4-[(1α,5α,6α)-6-[(hydroxyimino)methyl]bicyclo[3.1.0]hex-2-en-2-yl]phenyl]-2-oxooxazolidin-5-ylmethyl]acetamide (250 mg) in the same manner as described for EXAMPLE 49.

MS (EI⁺) m/z: 337 (M⁺).

HRMS (EI⁺) for $C_{19}H_{19}N_3O_3$ (M⁺): calcd, 337.1426; found, 337.1451.

EXAMPLE 139

N-[5(S)-3-[3-Fluoro-4-[(1α,5α,6α)-6-Hydroxymethylbicyclo[3.1.0]hex-2-en-3-yl]phenyl]-2-oxooxazolidin-5-ylmethyl]acetamide.

Step 1

N-[5(S)-3-[4-[(1α,5α,6β)-6-[(t-Butyldiphenylsilyl)oxy]methylbicyclo[3.1.0]hex-2-en-3-yl]-3-fluorophenyl]-2-oxooxazolidin-5-ylmethyl]acetamide.

The mixture of 5(S)-3-[3-fluoro -4-(4,4,5,5-tetramethyl-1,3,2-dioxaborolyl)phenyl]-2-oxooxazolidin-5-ylmethyl]acetamide (739 mg), (1α,5α,6β)-6-[(t-butyldiphenylsilyl)oxy]methyl-3-[(trifluoromethanesulfonyl)oxy]bicyclo[3.1.0]hex-2-ene (971 mg), tetrakis(triphenylphosphine)palladium (233 mg) and 2 M potassium phosphate solution (4.89 mL) in dioxane (24 mL) was stirred at 80° C. for 1.5 hours, and concentrated in vacuo after the insoluble materials were filtered off. Flash chromatography (silica, ethyl acetate:acetone=10:1) of the residue gave N-[5(S)-3-[4-[(1α,5α,6β)-6-[(t-butyldiphenylsilyl)oxy]methylbicyclo[3.1.0]hex-2-en-3-yl]-3-fluorophenyl]-2-oxooxazolidin-5-ylmethyl]acetamide (1.29 g).

MS (FAB⁺) m/z: 598 (MH⁺).

HRMS (FAB⁺) for $C_{35}H_{39}FN_2O_4Si$ (MH⁺): calcd, 598.2663; found, 598.2627.

Step 2

N-[5(S)-3-[3-Fluoro-4-[(1α,5α,6β)-6-hydroxymethylbicyclo[3.1.0]hex-2-en-3-yl]phenyl]-2-oxooxazolidin-5-ylmethyl]acetamide.

The title compound N-[5(S)-3-[3-fluoro-4-[(1α,5α,6β)-6-hydroxymethylbicyclo[3.1.0]hex-2-en-3-yl]phenyl]-2-oxooxazolidin-5-ylmethyl]acetamide (509 mg) was prepared from N-[5(S)-3-[4-[(1α,5α,6β)-6-[(t-butyldiphenylsilyl)oxy]methylbicyclo[3.1.0]hex-2-en-3-yl]-3-fluorophenyl]-2-oxooxazolidin-5-ylmethyl]acetamide (1.29 g) in the same manner as described for EXAMPLE 48.

MS (EI⁺) m/z: 360 (M⁺).

HRMS (EI⁺) for $C_{19}H_{21}FN_2O_4$ (M⁺): calcd, 360.1485; found, 360.1464.

EXAMPLE 140

N-[5(S)-3-[4-[(1α,5α,6β)-6-Cyanobicyclo[3.1.0]hex-2-en-3-yl]-3-fluorophenyl]-2-oxooxazolidin-5-ylmethyl]acetamide.

To a suspension of N-[5(S)-3-[3-fluoro-4-[(1α,5α,6β)-6-hydroxymethylbicyclo[3.1.0]hex-2-en-3-yl]phenyl]-2-oxooxazolidin-5-ylmethyl]acetamide (360 mg), N-methylmorpholine N-oxide (181 mg) and molecular sieves 4A (powdered, 500 mg) in dichloromethane (10 mL) and acetonitrile (1 mL) was added tetrapropylammonium perruthenate (36 mg) at room temperature, the resulting mixture was stirred for 35 min. After insoluble materials were filtered off, the filtrate was concentrated in vacuo to give N-[5(S)-3-[3-fluoro-4-[(1α,5α,6β)-6-formylbicyclo[3.1.0]hex-2-en-3-yl]phenyl]-2-oxooxazolidin-5-ylmethyl]acetamide. This was used in the next step without further purification. A suspension of crude N-[5(S)-3-[3-fluoro-4-[(1α,5α,6β)-6-formylbicyclo[3.1.0]hex-2-en-3-yl]phenyl]-2-oxooxazolidin-5-ylmethyl]acetamide thus obtained in methanol (5 mL) was added N,N-dimethylhydrazine ((110 μL), and the mixture was stirred at room temperature for 20 min. To a suspension of magnesium monoperoxyphthalate hexahydrate (1.18 g) in methanol (6 μL) was added the above mixture at 0° C., and the mixture was stirred at the same temperature for 15 min. After addition of ice water to the mixture, the resulting precipitates were collected by filtration, washed with water, and then dried in air. Flash chromatography (silica, dichloromethane:methanol=5:1) of the precipitates gave N-[5(S)-3-[4-[(1α,5α,6β)-6-cyanobicyclo[3.1.0]hex-2-en-3-yl]-3-fluorophenyl]-2-oxooxazolidin-5-ylmethyl]acetamide (231 mg).

MS (FAB$^+$) m/z: 356 (MH$^+$).

HRMS (FAB$^+$) for $C_{19}H_{19}FN_3O_3$ (MH$^+$): calcd, 356.1410; found, 356.1391.

EXAMPLE 141

N-[5(S)-3-[4-[(1α,5α,6β)-6-Hydroxymethylbicyclo[3.1.0]hex-2-en-3-yl]phenyl]-2-oxooxazolidin-5-ylmethyl] acetamide.

Step 1

N-[5(S)-3-[4-[(1α,5α,6β)-6-[(t-Butyldiphenylsilyl)oxy]methylbicyclo[3.1.0]hex-2-en-3-yl]phenyl]-2-oxooxazolidin-5-ylmethyl]acetamide.

The title compound N-[5(S)-3-[4-[(1α,5α,6β)-6-[(t-butyldiphenylsilyl)oxy]methylbicyclo[3.1.0]hex-2-en-3-yl]phenyl]-2-oxooxazolidin-5-ylmethyl]acetamide (929 mg) was prepared from N-[5(S)-3-(4-iodophenyl)-2-oxooxazolidin-5-ylmethyl]acetamide (929 mg), (1α,5α,6β)-6-[(t-butyldiphenylsilyl)oxy]methyl-3-(4,4,5,5-tetramethyl-1,3,2-dioxaborolyl)bicyclo[3.1.0]hex-2-ene (1.17 g) and 2 M potassium phosphate solution (3.69 mL) instead of 2 M sodium carbonate solution in the same manner as described for EXAMPLE 136.

MS (FAB$^+$) m/z: 580 (M$^+$).

HRMS (FAB$^+$) for $C_{35}H_{40}N_2O_4Si$ (M$^+$): calcd, 580.2757; found, 580.2763.

Step 2

N-[5(S)-3-[4-[(1α,5α,6β)-6-Hydroxymethylbicyclo[3.1.0]hex-2-en-3-yl]phenyl]-2-oxooxazolidin-5-ylmethyl] acetamide.

The title compound N-[5(S)-3-[4-[(1α,5α,6β)-6-hydroxymethylbicyclo[3.1.0]hex-2-en-3-yl]phenyl]-2-oxooxazolidin-5-ylmethyl]acetamide (503 mg) was prepared from N-[5(S)-3-[4-[(1α,5α,6β)-6-[(t-butyldiphenylsilyl)oxy]methylbicyclo[3.1.0]hex-2-en-3-yl]phenyl]-2-oxooxazolidin-5-ylmethyl]acetamide (981 mg) in the same manner as described for EXAMPLE 48.

MS (EI$^+$) m/z: 342 (M$^+$).

HRMS (EI$^+$) for $C_{19}H_{22}N_2O_4$ (M$^+$): calcd, 342.1580; found, 342.1557.

EXAMPLE 142

N-[5(S)-3-[4-[(1α,5α,6β)-6-Cyanobicyclo[3.1.0]hex-2-en-3-yl]phenyl]-2-oxooxazolidin-5-ylmethyl]acetamide.

The title compound N-[5(S)-3-[4-[(1α,5α,6β)-6-cyanobicyclo[3.1.0]hex-2-en-3-yl]phenyl]-2-oxooxazolidin-5-ylmethyl]acetamide was prepared from N-[5(S)-3-[4-[(1α,5α,6β)-6-hydroxymethylbicyclo[3.1.0]hex-2-en-3-yl]phenyl]-2-oxooxazolidin-5-ylmethyl]acetamide (239 mg) in the same manner as described for EXAMPLE 140.

MS (EI$^+$) m/z: 337 (M$^+$).

HRMS (EI$^+$) for $C_{19}H_{19}N_3O_3$ (M$^+$): calcd, 337.1426; found, 337.1451.

EXAMPLE 143

N-[5 (S)-3-[4-[(1α,5α,6α)-6-Hydroxymethylbicyclo[3.1.0]hex-2-en-3-yl]phenyl]-2-oxooxazolidin-5-ylmethyl] acetamide (diastereomer A).

The title compound N-[5(S)-3-[4-[(1α,5α,6α)-6-hydroxymethylbicyclo[3.1.0]hex-2-en-3-yl]phenyl]-2-oxooxazolidin-5-ylmethyl]acetamide (diastereomer A, 270 mg) was prepared from N-[5(S)-3-(4-iodophenyl)-2-oxooxazolidin-5-ylmethyl]acetamide (902 mg) and (1α,5α,6α)-6-hydroxymethyl-3-(4,4,5,5-tetramethyl-1,3,2-dioxaborolyl)bicyclo[3.1.0]hex-2-ene (enantiomer A, >99% ee, 563 mg) in the same manner as described for EXAMPLE 136.

MS (EI$^+$) m/z: 342 (M$^+$).

HRMS (EI$^+$) for $C_{19}H_{22}N_2O_4$ (M$^+$): calcd, 342.1580; found, 342.1596.

EXAMPLE 144

N-[5(S)-3-[4-[(1α,5α,6α)-6-Cyanobicyclo[3.1.0]hex-2-en-3-yl]phenyl]-2-oxooxazolidin-5-ylmethyl]acetamide (diastereomer A).

The title compound N-[5(S)-3-[4-[(1α,5α,6α)-6-cyanobicyclo[3.1.0]hex-2-en-3-yl]phenyl]-2-oxooxazolidin-5-ylmethyl]acetamide (diastereomer A, 205 mg) was prepared from N-[5(S)-3-[4-[(1α,5α,6α)-6-hydroxymethylbicyclo[3.1.0]hex-2-en-3-yl]phenyl]-2-oxooxazolidin-5-ylmethyl]acetamide (diastereomer A, 266 mg) in the same manner as described for EXAMPLE 49.

MS (EI$^+$) m/z: 337 (M$^+$).

HRMS (EI$^+$) for $C_{19}H_{19}N_3O_3$ (M$^+$): calcd, 337.1426; found, 337.1401.

EXAMPLE 145

N-[5(S)-3-[4-[(1α,5α,6α)-6-Hydroxymethylbicyclo[3.1.0]hex-2-en-3-yl]phenyl]-2-oxooxazolidin-5-ylmethyl] acetamide (diastereomer B).

The title compound N-[5(S)-3-[4-[(1α,5α,6α)-6-hydroxymethylbicyclo[3.1.0]hex-2-en-3-yl]phenyl]-2-oxooxazolidin-5-ylmethyl]acetamide (diastereomer B, 282 mg) was prepared from N-[5(S)-3-(4-iodophenyl)-2-oxooxazolidin-5-ylmethyl]acetamide (541 mg) and (1α,5α,6α)-6-hydroxymethyl-3-(4,4,5,5-tetramethyl-1,3,2-dioxaborolyl)bicyclo[3.1.0]hex-2-ene (enantiomer B, 94.4% ee, 338 mg) in the same manner as described for EXAMPLE 136.

MS (EI$^+$) m/z: 342 (M$^+$).

HRMS (EI$^+$) for $C_{19}H_{22}N_2O_4$ (M$^+$): calcd, 342.1580; found, 342.1572.

EXAMPLE 146

N-[5(S)-3-[4-[(1α,5α,6α)-6-Cyanobicyclo[3.1.0]hex-2-en-3-yl]phenyl]-2-oxooxazolidin-5-ylmethyl]acetamide (diastereomer B).

The title compound N-[5(S)-3-[4-[(1α,5α,6α)-6-cyanobicyclo[3.1.0]hex-2-en-3-yl]phenyl]-2-oxooxazolidin-5-ylmethyl]acetamide (diastereomer B, 115 mg) was prepared from N-[5(S)-3-[4-[(1α,5α,6α)-6-hydroxymethylbicyclo[3.1.0]hex-2-en-3-yl]phenyl]-2-oxooxazolidin-5-ylmethyl]acetamide (diastereomer B, 278 mg) in the same manner as described for EXAMPLE 49.

MS (EI$^+$) m/z: 337 (M$^+$).

HRMS (EI$^+$) for $C_{19}H_{19}N_3O_3$ (M$^+$): calcd, 337.1426; found, 337.1452.

EXAMPLE 147

N-[5(S)-3-[4-[(1α,5α,6α)-6-[(1-Cyano-2-dimethylamino)ethenyl-yl]-3-azabicyclo[3.1.0]hexan-3-yl]-3-fluorophenyl]-2-oxooxazolidin-5-ylmethyl]acetamide.

A solution of N-[5(S)-3-[4-[(1α,5α,6α)-6-cyanomethyl-3-azabicyclo[3.1.0]hexan-3-yl]-3-fluorophenyl]-2-oxooxazolidin-5-ylmethyl]acetamide (242 mg) and t-butoxybis(dimethylamino)methane (210 μL) in dimethylformamide (1.3 mL) was stirred at 90° C. for 9 hours. Flash chromatography (silica, ethyl acetate:methanol=4:1) of the mixture gave N-[5(S)-3-[4-[(1α,5α,6α)-6-[(1-cyano-2-dimethylamino)ethen-1-yl]-3-azabicyclo[3.1.0]hexan-3-yl]-3-fluorophenyl]-2-oxooxazolidin-5-ylmethyl]acetamide (254 mg).

MS (EI$^+$) m/z: 427 (M$^+$).

EXAMPLE 148

N-[5(S)-3-[4-[(1α,5α,6α)-6-(3-Amino-1H-pyrazol-4-yl)-3-azabicyclo[3.1.0]hexan-3-yl]-3-fluorophenyl]-2-oxooxazolidin-5-ylmethyl]acetamide.

A solution of N-[5(S)-3-[4-[(1α,5α,6α)-6-[(1-cyano-2-dimethylamino)ethen-1-yl]-3-azabicyclo[3.1.0]hexan-3-yl]-3-fluorophenyl]-2-oxooxazolidin-5-ylmethyl]acetamide (107 mg), hydrazine hydrate (37.5 mg) and acetic acid (14 μL) in ethanol (1 mL) was stirred at 80° C. for 7 hours, and then concentrated in vacuo. Preparative thin layer chromatography (silica, dichloromethane:methanol=5:1) of the residue gave N-[5(S)-3-[4-[(1α,5α,6α)-6-(3-amino-1H-pyrazole-4-yl)-3-azabicyclo[3.1.0]hexan-3-yl]-3-fluorophenyl]-2-oxooxazolidin-5-ylmethyl]acetamide (35.0 mg).

MS (FAB$^+$) m/z: 415 (MH$^+$).

HRMS (FAB$^+$) for $C_{20}H_{24}FN_6O_3$ (MH$^+$): calcd, 415.1894; found, 415.1919.

PREPARATIVE EXAMPLE 1

4-[(1α,5α,6α)-6-(N-t-Butoxycarbonyl)amino-3-azabicyclo[3.1.0]hexan-3-yl]-3-fluoronitrobenzene.

To a suspension of (1α,5α,6α)-6-(N-t-butoxycarbonyl)amino-3-azabicyclo[3.1.0]hexane (2.97 g) and ethyldiisopropylamine (2.87 mL) in acetonitrile (17 mL) was added 3,4-difluoronitrobenzene (1.66 mL), and the mixture was stirred at 50° C. for 4.5 hours. After cooling, the resulting precipitates were collected by filtration, and then dried in vacuo to give 4-[(1α,5α,6α)-6-(N-t-butoxycarbonyl)amino-3-azabicyclo[3.1.0]hexan-3-yl]-3-fluoronitrobenzene (2.81 g). The filtrate was concentrated in vacuo, the residue was dissolved in ethyl acetate, washed with 1N hydrochloric acid, water, aqueous sodium hydrogencarbonate solution and brine, successively. The organic extracts were dried over anhydrous sodium sulfate, and then concentrated in vacuo. The residue was treated with hexane and ethyl acetate, and the resulting precipitates were collected by filtration, and then dried in vacuo to give the additional product (1.38 g). The filtrate was concentrated in vacuo. Flash chromatography (silica, hexane:ethyl acetate 10:7) of the residue gave the additional product (228 mg).

$^1$H NMR (CDCl$_3$) δ 1.46 (s, 9H), 1.90 (s, 2H), 2.41 (s, 1H), 3.63 (d, J=9.5 Hz, 2H), 3.92 (d, J=9.5 Hz, 2H), 6.52 (t, J=9.0 Hz, 1H), 7.85 (dd, J=14.2, 2.4 Hz, 1H), 7.91 (dd, J=9.0, 2.4 Hz, 1H).

MS (FAB$^+$) m/z: 338 (MH$^+$).

PREPARATIVE EXAMPLE 2

4-[(1α,5α,6α)-6-(N-Benzyl-N-t-butoxycarbonyl)amino-3-azabicyclo[3.1.0]hexan-3-yl]-3-fluoronitrobenzene.

To a solution of 4-[(1α,5α,6α)-6-(N-t-butoxycarbonyl)amino-3-azabicyclo[3.1.0]hexan-3-yl]-3-fluoronitrobenzene in N,N-dimethylformamide (89 mL) was added sodium hydride (689 mg), and the mixture was stirred at room temperature for 20 min, and then at 40° C. for 5 min. To the resulting solution were added benzyl chloride (1.75 mL) and tetrabutylammonium bromide (42.7 mg), and the mixture was stirred at 50° C. for 1 hour, and then concentrated in vacuo. The residue was dissolved in ethyl acetate, washed with water and brine, dried over anhydrous sodium sulfate, and then concentrated in vacuo. Flash chromatography (silica, hexane:ethyl acetate=5:2) of the residue gave 4-[(1α,5α,6α)-6-(N-benzyl-N-t-butoxycarbonyl)amino-3-azabicyclo[3.1.0]hexan-3-yl]-3-fluoronitrobenzene (5.19 g).

$^1$H NMR (CDCl$_3$) δ 1.49 (s, 9H), 2.01 (s, 2H), 2.27 (s, 1H), 3.62 (d, J 9.3 Hz, 2H), 3.80–3.90 (m, 2H), 4.46 (s, 2H), 6.46 (t, J=9.0 Hz, 1H), 7.20–7.40 (m, 5H), 7.83 (dd, J=14.4, 2.7 Hz, 1H), 7.89 (dd, J=9.0, 2.7 Hz, 1H).

MS (FAB$^+$) m/z: 428 (MH$^+$).

PREPARATIVE EXAMPLE 3

4-[(1α,5α,6α)-6-(N-Benzyl-N-t-butoxycarbonyl)amino-3-azabicyclo[3.1.0]hexan-3-yl]-1-benzyloxycarbonylamino-3-fluorobenzene.

A suspension of 4-[(1α,5α,6α)-6-(N-benzyl-N-t-butoxycarbonyl)amino-3-azabicyclo[3.1.0]hexan-3-yl]-3-fluoronitrobenzene (5.19 g) and palladium catalyst (10% on charcoal, 519 mg) in ethyl acetate (52 mL) was hydrogenated at 1 atm for 2 hours at room temperature. After filtration of the catalyst, the filtrate was concentrated in vacuo to give 1-amino-4-[(1α,5α,6α)-6-(N-benzyl-N-t-butoxycarbonyl)amino-3-azabicyclo[3.1.0]hexan-3-yl]-3-fluorobenzene. This was used in the next step without further purification. To a solution of crude 1-amino-4-[(1α,5α,6α)-6-(N-benzyl-N-t-butoxycarbonyl)amino-3-azabicyclo[3.1.0]hexan-3-yl]-3-fluorobenzene thus obtained in acetone (48 mL) were successively added sodium hydrogencarbonate (1.12 g), water (11 mL) and benzyl chloroformate (2.01 mL) at 0° C., and the mixture was stirred at 0° C. for 15 min. The mixture was diluted with ethyl acetate, washed with brine. The organic extracts were dried over anhydrous sodium sulfate, filtered, and then concentrated in vacuo. Flash chromatography (silica, hexane:ethyl acetate=5:2) of the residue gave 4-[(1α,5α,6α)-6-(N-benzyl-N-t-butoxycarbonyl)amino-3-azabicyclo[3.1.0]hexan-3-yl]-1-benzyloxycarbonylamino-3-fluorobenzene (6.73 g).

$^1$H NMR (CDCl$_3$) δ 1.49 (s, 9H), 1.80–1.90 (m, 2H), 2.40–2.60 (m, 1H), 3.24 (d, J=8.5 Hz, 2H), 3.50–3.80 (m, 2H), 4.45 (s, 2H), 5.17 (s, 2H), 6.40–6.60 (m, 1H), 6.80–6.90 (m, 1H), 7.10–7.50 (m, 11H).

MS (EI$^+$) m/z: 531 (M$^+$).

PREPARATIVE EXAMPLE 4

Benzyl (1α,5α,6α)-6-[(2-Tetrahydropyranyl)oxy]methyl-3-azabicyclo[3.1.0]hexan-3-ylcarboxylate.

To a solution of benzyl (1α,5α,6α)-6-hydroxymethyl-3-azabicyclo[3.1.0]hexan-3-ylcarboxylate (1.00 g) and 3,4-dihydro-2H-pyran (0.37 mL) in dichloromethane (10 mL) was added p-toluenesulfonic acid (10.0 mg), and the mixture was stirred at room temperature for 3.5 hours. The mixture was washed with saturated sodium hydrogencarbonate solution and water, dried over anhydrous sodium sulfate, filtered, and then concentrated in vacuo. Flash chromatography (silica, hexane:ethyl acetate=1:1) of the residue gave benzyl (1α,5α,6α)-6-[(2-tetrahydropyranyl)oxy]methyl-3-azabicyclo[3.1.0]hexan-3-ylcarboxylate (1.24 g).

PREPARATIVE EXAMPLE 5

Benzyl (1α,5α,6α)-6-Methoxymethyl-3-azabicyclo[3.1.0]hexan-3-ylcarboxylate.

To a suspension of sodium hydride (178 mg, 60% oil dispersion) in tetrahydrofuran (7 mL) was added a solution of benzyl(1α,5α,6α)-6-hydroxymethyl-3-azabicyclo[3.1.0]hexan-3-ylcarboxylate (1.00 g) in tetrahydrofuran (3 mL) at 0° C. After stirring the mixture at the same temperature for 10 min, the mixture was treated with methyl iodide (0.28 mL) and stirred at room temperature for 2 hours, and then concentrated in vacuo. The residue was dissolved in ethyl acetate, the resulting solution was washed with water, dried over anhydrous sodium sulfate, filtered, and then concentrated in vacuo Flash chromatography (silica, hexane:ethyl acetate=1:1) of the residue gave benzyl (1α,5α,6α)-6-methoxymethyl-3-azabicyclo[3.1.0]hexan-3-ylcarboxylate (909 mg).

$^1$H NMR (CDCl$_3$) δ 0.91–0.96 (m, 1H), 1.44–1.49 (m, 2H), 3.20–3.24 (m, 1H), 3.31–3.35 (m, 1H), 3.33 (s, 3H), 3.41–3.46 (m, 2H), 3.67 (d, J=10.7 Hz, 1H), 3.70 (d, J=10.7 Hz, $^1$H), 5.10 (s, 2H), 7.29–7.36 (m, 5H).

PREPARATIVE EXAMPLE 6

(1α,5α,6α)-6-[(2-Tetrahydropyranyl)oxy]methyl-3-azabicyclo[3.1.0]hexane.

A suspension of benzyl (1α,5α,6α)-6-[(2-tetrahydropyranyl)oxy]methyl-3-azabicyclo[3.1.0]hexan-3-ylcarboxylate (1.22 g) and palladium catalyst (10% on charcoal, 120 mg) in ethanol (12 mL) was hydrogenated at 1 atm for 2 hours at room temperature. 4F. After filtration of the catalyst, the filtrate was concentrated in vacuo to give (1α,5α,6α)-6-[(2-tetrahydropyranyl)oxy]methyl-3-azabicyclo[3.1.0]hexane (699 mg).

PREPARATIVE EXAMPLE 7

(1α,5α,6α)-6-Methoxymethyl-3-azabicyclo[3.1.0]hexane

The title compound (1α,5α,6α)-6-methoxymethyl-3-azabicyclo[3.1.0]hexane (238 mg) was prepared from benzyl (1α,5α,6α)-6-methoxymethyl-3-azabicyclo[3.1.0]hexan-3-ylcarboxylate (900 mg) in the same manner as described for PREPARATIVE EXAMPLE 6.

$^1$H NMR (CDCl$_3$) δ 0.86–0.91 (m, 1H), 1.33–1.37 (m, 2H), 2.88 (d, J=11.2 Hz, 2H), 3.01 (d, J=11.7 Hz, 2H), 3.28 (d, J=7.3 Hz, 2H), 3.34 (s, 3H).

PREPARATIVE EXAMPLE 8

3-Fluoro-4-[(1α,5α,6α)-6-[(2-tetrahydropyranyl)oxy]methyl-3-azabicyclo[3.1.0]hexan-3-yl]nitrobenzene.

The title compound 3-fluoro-4-[(1α,5α,6α)-6-[(2-tetrahydropyranyl) oxy]methyl-3-azabicyclo[3.1.0]hexan-3-yl]nitrobenzene (1.03 g) was prepared from (1α,5α,6α)-6-[(2-tetrahydropyranyl)oxy]methyl-3-azabicyclo[3.1.0]hexane (690 mg) and 3,4-difluoronitrobenzene (0.39 mL) in the same manner as described for PREPARATIVE EXAMPLE 1.

PREPARATIVE EXAMPLE 9

3-Fluoro-4-[(1α,5α,6α)-6-methoxymethyl-3-azabicyclo[3.1.0]hexan-3-yl]nitrobenzene.

The title compound 3-fluoro-4-[(1α,5α,6α)-6-methoxymethyl-3-azabicyclo[3.1.0]hexan-3-yl]nitrobenzene (421 mg) was prepared from (1α,5α,6α)-6-methoxymethyl-3-azabicyclo[3.1.0]hexane (230 mg) and 3,4-difluoronitrobenzene (0.20 mL) in the same manner as described for PREPARATIVE EXAMPLE 1.

$^1$H NMR (CDCl$_3$) δ 1.06–1.11 (m, 1H), 1.65–1.69 (m, 2H), 3.32 (d, 1J=6.8 Hz, 2H), 3.36 (s, 3H), 3.58–3.61 (m, 2H), 3.87 (dd, J=10.3, 3.4 Hz, 2H), 6.53 (t, J=8.8 Hz, 1H), 7.85 (dd, J=14.2, 2.2 Hz, 1H), 7.91 (dd, J=8.8, 2.4 Hz, 1H).

PREPARATIVE EXAMPLE 10

1-Amino-3-fluoro-4-[(1α,5α,6α)-6-[(2-tetrahydropyranyl)oxy]methyl-3-azabicyclo[3.1.0]hexan-3-yl]benzene.

The title compound 1-amino-3-fluoro-4-[(1α,5α,6α)-6-[(2-tetrahydropyranyl)oxy]methyl-3-azabicyclo[3.1.0]hexan-3-yl]benzene (926 mg) was prepared from 3-fluoro-4-[(1α,5α,6α)-6-[(2-tetrahydropyranyl)oxy]methyl-3-azabicyclo[3.1.0]hexan-3-yl]nitrobenzene (1.03 g) in the same manner as described for PREPARATIVE EXAMPLE 3.

MS (EI$^+$) m/z: 306 (M$^+$).

HRMS (EI$^+$) for C$_{17}$H$_{23}$FN$_2$O$_2$ (M$^+$): calcd, 306.1744; found, 306.1738.

PREPARATIVE EXAMPLE 11

1-Amino-3-fluoro-4-[(1α,5α,6α)-6-methoxymethyl-3-azabicyclo[3.1.0]hexan-3-yl]benzene.

The title compound 1-amino-3-fluoro-4-[(1α,5α,6α)-6-methoxymethyl-3-azabicyclo[3.1.0]hexan-3-yl]benzene (360 mg) was prepared from 3-fluoro-4-[(1α,5α,6α)-6-methoxymethyl-3-azabicyclo[3.1.0]hexan-3-yl]nitrobenzene (416 mg) in the same manner as described for PREPARATIVE EXAMPLE 3.

$^1$H NMR (CDCl$_3$) δ 1.36–1.41 (m, 1H), 1.45–1.50 (m, 2H), 3.09 (d, J=8.8 Hz, 2H), 3.29 (d, J=6.8 Hz, 2H), 3.33–3.47 (br, 2H), 3.35 (s, 3H), 3.61 (dd, J=8.8, 2.4 Hz, 2H), 6.35–6.43 (m, 2H), 6.53 (t, J=8.3 Hz, 1H).

PREPARATIVE EXAMPLE 12

1-Benzyloxycarbonylamino-3-fluoro-4-[(1α,5α,6α)-6-[(2-tetrahydropyranyl)oxy]methyl-3-azabicyclo[3.1.0]hexan-3-yl]benzene.

The title compound 1-benzyloxycarbonylamino-3-fluoro-4-[(1α,5α,6α)-6-[(2-tetrahydropyranyl)oxy]methyl-3-azabicyclo[3.1.0]hexan-3-yl]benzene (1.12 g) was prepared from 1-amino-3-fluoro-4-[(1α,5α,6α)-6-[(2-tetrahydropyranyl)oxy]methyl-3-azabicyclo[3.1.0]hexan-3-yl]benzene (915 mg) in the same manner as described for PREPARATIVE EXAMPLE 3.

MS (EI$^+$) m/z: 440 (M$^+$).

HRMS (EI$^+$) for C$_{25}$H$_{29}$FN$_2$O$_4$ (M$^+$): calcd, 440.211 1; found, 440.2097.

REPARATIVE EXAMPLE 13

1-Benzyloxycarbonylamino-3-fluoro-4-[(1α,5α,6α)-6-methoxymethyl-3-azabicyclo[3.1.0]hexan-3-yl]benzene.

The title compound 1-benzyloxycarbonylamino-3-fluoro-4-[(1α,5α,6α)-6-methoxymethyl-3-azabicyclo[3.1.0]hexan- 3-yl]benzene (539 mg) was prepared from 1-amino-3-fluoro-4-[(1α,5α,6α)-6-methoxymethyl-3-azabicyclo[3.1.0]hexan-3-yl]benzene (350 mg) in the same manner as described for PREPARATIVE EXAMPLE 3.

PREPARATIVE EXAMPLE 14

(1α,5α,6α)-6-[(t-Butyldiphenylsilyl)oxy]methylbicyclo[3.1.0]hex-2-ene.

To a solution of (1α,5α,6α)-bicyclo[3.1.0]hex-2-en-6-methanol (11.0 mg) in dichloromethane (0.4 mL) was added t-butyldiphenylsilyl chloride (32 μL), triethylamine (35 μL), and 4-(dimethylamino)pyridine (24.4 mg), and the mixture was stirred at room temperature for 3 hours. After quenching the reaction by the addition of 1 N hydrochloric acid, the mixture was extracted with ethyl acetate. The organic extracts were washed with water, sodium hydrogencarbonate solution, and brine, dried over anhydrous sodium sulfate, and then concentrated in vacuo. Flash chromatography (silica, hexane:ethyl acetate=50:1) of the residue gave (1α,5α,6α)-6-[(t-butyldiphenylsilyl)oxy]methylbicyclo[3.1.0]hex-2-ene (28.3 mg).

$^1$H NMR (CDCl$_3$) δ 0.47–0.52 (m, 1H), 1.05 (s, 9H), 1.40–1.43 (m, 1H), 1.67–1.69 (m, 1H), 2.27–2.32 (m, 1H), 2.50–2.60 (m, 1H), 3.50–3.60 (m, 2H), 5.37–5.39 (m, 1H), 5.80–5.90 (m, 1H), 7.36–7.44 (m, 6H), 7.67–7.69 (m, 4H).

MS (EI$^+$) m/z: 348 (M$^+$).

PREPARATIVE EXAMPLE 15

(1α,5α,6α)-6-[(t-Butyldiphenylsilyl)oxy]methyl-3-hydroxybicyclo[3.1.0]hexane Isomer A and B.

To a solution of (1α,5α,6α)-6-[(t-butyldiphenylsilyl)oxy]methylbicyclo[3.1.0]hex-2-ene (2.79 g) in tetrahydrofuran (28 mL) was added borane-methyl sulfide complex (927 μL) at 0° C., and the mixture was stirred at room temperature for 1.5 hours. The resulting solution was added water (22 mL), 2.5 N sodium hydroxide solution (4.8 mL), and hydrogen peroxide solution (30%, 1.36 mL) at 0° C., and the mixture was stirred at room temperature for 1 hour. After dilution the mixture with water, the resulting mixture was extracted with ethyl acetate. The organic extracts were washed with brine, dried over anhydrous sodium sulfate, and then concentrated in vacuo. Flash chromatography (silica, hexane:ethyl acetate=2:1) of the residue gave the two isomers of (1α,5α,6α)-6-[(t-butyldiphenylsilyl)oxy]methyl-3-hydroxybicyclo[3.1.0]hexane (2.38 g).

Isomer A $^1$H NMR (CDCl$_3$) δ 0.70–0.75 (m, 1H), 1.03 (s, 9H), 1.00–1.70 (m, 4H), 2.11 (dd, J=12.7, 6.8 Hz, 2H), 3.43 (d, J=6.4 Hz, 2H), 3.90–4.00 (m, 1H), 7.36–7.44 (m, 6H), 7.65–7.70 (m, 4H).

MS(CI$^+$) m/z: 367 (MH$^+$).

Isomer B $^1$H NMR (CDCl$_3$) δ 1.04 (s, 9H), 1.00–1.10 (m, 2H), 1.26–1.31 (m, 1H), 1.68 (d, J=14.2 Hz, 2H), 2.00–2.10 (m, 2H), 3.51 (d, J=6.4 Hz, 2H), 4.35 (t, J=6.4 Hz, 1H), 7.35–7.44 (m, 6H), 7.66–7.70 (m, 4H).

MS(CI$^+$) m/z: 367 (MH$^+$).

PREPARATIVE EXAMPLE 16

(1α,5α,6α)-6-[(t-Butyldiphenylsilyloxy]methyl-3-oxobicyclo[3.1.0]hexane.

To a solution of (1α,5α,6α)-6-[(t-butyldiphenylsilyl)oxy]methyl-3-hydroxybicyclo[3.1.0]hexane (2.38 g) in dimethyl sulfoxide (24 mL) was added 1-hydroxy-1,2-benziodoxol-3(1H)-one 1-oxide (2.73 g), and the mixture was stirred at room temperature for 5.5 hours. After addition of ethyl acetate and water, insoluble materials were filtered off. The organic extracts were washed with water and brine, dried over anhydrous sodium sulfate, and then concentrated in vacuo. Flash chromatography (silica, hexane:ethyl acetate= 5:1) of the mixture gave (1α,5α,6α)-6-[(t-butyldiphenylsilyl)oxy]methyl-3-oxobicyclo[3.1.0]hexane (1.82 g).

$^1$H NMR (CDCl$_3$) δ 0.60–0.65 (m, 1H), 1.04 (s, 9H), 1.38–1.40 (m, 2H), 2.14 (dd, J=18.6, 2.0 Hz, 2H), 2.50–2.60 (m, 2H), 3.62 (d, J=5.9 Hz, 2H), 7.40–7.50 (m, 6H), 7.65–7.68 (m, 4H).

MS (EI$^+$) m/z: 364 (M$^+$).

PREPARATIVE EXAMPLE 17

(1α,5α,6α)-6-[(t-butyldiphenylsilyl)oxy]methyl-3-[(trifluoromethanesulfonyl)-oxy]bicyclo[3.1.0]hex-2-ene.

To a solution of (1α,5α,6α)-6-[(t-butyldiphenylsilyl)oxy]methyl-3-oxobicyclo[3.1.0]hexane (365 mg) in tetrahydrofuran (2 mL) was added a solution of lithium diisopropylamide (2M, 650 mL) at −78° C., and the mixture was stirred at the same temperature for 30 minutes. The resulting mixture was added a solution of N-phenylbis(trifluoromethanesulfonimide) (393 mg) in tetrahydrofuran (2 mL) at −78° C., the mixture was stirred at room temperature for 17 hours, and then concentrated in vacuo. Flash chromatography (silica, hexane:ethyl acetate=25:1) of the residue gave (1α,5α,6α)-6-[(t-butyldiphenylsilyl)oxy]methyl-3-[(trifluoromethanesulfonyl)oxy]bicyclo[3.1.0]hex-2-ene (313 mg).

$^1$H NMR (CDCl$_3$) δ 0.77–0.82 (m, 1H), 1.04 (s, 9H), 1.30–1.50 (m, 1H), 1.60–1.70 (m, $^1$H), 2.48–2.53 (m, 1H), 2.79–2.85 (m, 1H), 3.50–3.60 (m, 2H), 5.78–5.79 (m, 1H), 7.40–7.50 (m, 6H), 7.60–7.70 (m, 4H).

PREPARATIVE EXAMPLE 18

(1α,5α,6α)-6-[(t-Butoxycarbonyl)amino]bicyclo[3.1.0]hex-2-ene.

To a solution of (1α,5α,6α)-bicyclo[3.1.0]hex-2-en-6-carboxylic acid (1.52 g) in dichloromethane (30 mL) were added triethylamine (1.87 mL) and ethyl chloroformate (1.32 mL) at 0° C., the mixture was stirred at the same temperature for 10 minutes, and then concentrated in vacuo. After dilution the resulting residue with acetone (15 mL), a solution of sodium azide (1.59 g) in water (8 mL) was added at 0° C., and the mixture was stirred at the same temperature for 10 minutes. After dilution the mixture with ice water, the mixture was extracted with ethyl acetate. The organic extracts were washed with brine, dried over anhydrous sodium sulfate, and then concentrated in vacuo. The resulting residue was diluted with toluene (30 mL) and t-butanol (4.5 mL), the mixture was heated at reflux for 28 hours, and then concentrated in vacuo. Flash chromatography (silica, hexane:ethyl acetate=10:3) of the residue gave (1α,5α,6α)-6-[(t-butoxycarbonyl)amino]bicyclo[3.1.0]hex-2-ene (1.61 g).

$^1$H NMR (CDCl$_3$) δ 1.45 (s, 9H), 1.66 (t, J=6.9 Hz, 1H), 1.86 (brs, 1H), 2.01–2.04 (m, 1H), 2.42 (d, J=17.6 Hz, 1H), 2.59 (dd, J=17.6, 6.9 Hz, 1H), 5.46–5.49 (m, 1H), 5.80–5.90 (m, 1H).

MS (EI$^+$) m/z: 195 (M$^+$).

PREPARATIVE EXAMPLE 19

(1α,5α,6α)-6-[(t-Butoxycarbonyl)amino]-3-hydroxybicyclo[3.1.0]hex-2-ene.

To a solution of (1α,5α,6α)-6-[(t-butoxycarbonyl)amino]bicyclo[3.1.0]hex-2-ene (335 mg) in tetrahydrofuran (5 mL) was added borane-methyl sulfide complex (199 μL) at 0° C., and the mixture was stirred at room temperature for 1.5 hours. The resulting solution was added water (3 mL), 2.5 N sodium hydroxide solution (1.03 mL), and hydrogen peroxide solution (30%, 292 μL) at 0° C., and the mixture was stirred at room temperature for 1.5 hours. After dilution the mixture with ice water, the resulting mixture was extracted with ethyl acetate. The organic extracts were washed with brine, dried over anhydrous sodium sulfate, and then concentrated in vacuo. Recrystallization with acetonitrile of the residue gave (1α,5α,6α)-6-[(t-butoxycarbonyl)amino]-3-hydroxybicyclo[3.1.0]hex-2-ene (146 mg). Flash chromatography (silica, hexane:ethyl acetate=2:1) of the residue gave further amount of (1α,5α,6α)-6-[(t-butyldiphenylsilyl)oxy]methyl-3-hydroxybicyclo[3.1.0]hexane (128 mg).

$^1$H NMR (CDCl$_3$) δ 1.43 (s, 9H), 1.30–1.80 (m, 4H), 2.10–2.20 (m, 3H), 3.90–4.00 (m, 1H)

MS(CI$^+$) m/z: 214 (MH$^+$).

PREPARATIVE EXAMPLE 20

(1α,5α,6α)-6-[(t-Butoxycarbonyl)amino]-3-oxobicyclo[3.1.0]hexane.

To a solution of (1α,5α,6α)-6-[(t-butoxycarbonyl)amino]-3-hydroxybicyclo[3.1.0]hex-2-ene (265 mg) in dimethyl sulfoxide (3 mL) was added 1-hydroxy-1,2-benziodoxol-3 (1H)-one 1-oxide (521 mg), and the mixture was stirred at room temperature for 9 hours. After addition of ethyl acetate and water, insoluble materials were filtered off. The organic extracts were washed with water and brine, dried over anhydrous sodium sulfate, and then concentrated in vacuo. Flash chromatography (silica, hexane:ethyl acetate=5:1) of the residue gave (1α,5α,6α)-6-[(t-butoxycarbonyl)amino]-3-oxobicyclo[3.1.0]hexane (209 mg).

$^1$H NMR (CDCl$_3$) δ 1.45 (s, 9H), 1.72 (m, 2H), 2.09 (brs, 1H), 2.29 (d, J=20.1 Hz, 2H), 2.58–2.65 (m, 2H).

MS (FAB$^+$) m/z: 212 (MH$^+$).

PREPARATIVE EXAMPLE 21

(1α,5α,6α)-6-[Bis(t-butoxycarbonyl)amino]-3-oxobicyclo[3.1.0]hexane.

To a solution of (1α,5α,6α)-6-[(t-butoxycarbonyl)amino]-3-oxobicyclo[3.1.0]hexane (917 mg) and di-t-butyl dicarbonate (1.89 g) in dichloromethane (4 mL) and acetonitrile (4 mL) was added 4-(dimethylamino)pyridine (212 mg), the mixture was stirred at room temperature for overnight, and then concentrated in vacuo. Flash chromatography (silica, hexane:ethyl acetate=2:1) of the residue gave (1α,5α,6α)-6-[bis(t-butoxycarbonyl)amino]-3-oxobicyclo[3.1.0]hexane (1.10 g).

$^1$H NMR (CDCl$_3$) δ 1.51 (s, 18H), 1.82–1.84 (m, 2H), 2.09–2.10 (m, 1H), 2.29–2.34 (m, 2H), 2.60–2.70 (m, 2H).

MS (FAB$^+$) m/z: 312 (MH$^+$).

PREPARATIVE EXAMPLE 22

(1α,5α,6α)-6-[Bis(t-butoxycarbonyl)amino]-3-[(trifluoromethanesulfonyl)-oxy]bicyclo[3.1.0]hex-2-ene.

To a solution of (1α,5α,6α)-6-[bis(t-butoxycarbonyl)amino]-3-oxobicyclo[3.1.0]hexane (1.10 g) in tetrahydrofuran (6 mL) was added a solution of lithium diisopropylamide (2M, 2.30 mL) at −78° C., and the mixture was stirred at the same temperature for 30 minutes. The resulting mixture was added a solution of N-phenylbis(trifluoromethanesulfonimide) (1.33 g) in tetrahydrofuran (7 mL) at −78° C., the mixture was stirred at room temperature for 17 hours, and then concentrated in vacuo. Flash chromatography (silica, hexane:acetone=5:1) of the residue gave (1α,5α,6α)-6-[bis(t-butoxycarbonyl)amino]-3-[(trifluoromethane sulfonyl)oxy]-bicyclo[3.1.0]hex-2-ene (1.30 g).

$^1$H NMR (CDCl$_3$) δ 1.52 (s, 18H), 1.76–1.80 (m, 1H), 2.00–2.20 (m, 1H), 2.19–2.20 (m, 1H), 2.68–2.72 (m, 1H), 2.90–3.00 (m, 1H), 5.04 (m, 1H).

MS (FAB$^+$) m/z: 444 (MH$^+$).

PREPARATIVE EXAMPLE 23

Benzyl (1α,5α,6α)-6-Formyl-3-azabicyclo[3.1.0]hexan-3-ylcarboxylate.

The title compound benzyl (1α,5α,6α)-6-formyl-3-azabicyclo[3.1.0]hexan-3-ylcarboxylate (168 mg) was prepared from benzyl (1α,5α,6α)-6-hydroxymethyl-3-azabicyclo[3.1.0]hexan-3-ylcarboxylate (196 mg) in the same manner as described for EXAMPLE 22.

MS (EI$^+$) m/z: 245 (M$^+$).

HRMS (EI$^+$) for C$_{14}$H$_{15}$NO$_3$ (M$^+$): calcd, 245.1052; found, 245.1034.

PREPARATIVE EXAMPLE 24

Benzyl (1α,5α,6α)-6-Acetyl-3-azabicyclo[3.1.0]hexan-3-ylcarboxylate.

Step 1

Benzyl (1α,5α,6α)-6-(1-hydroxy)ethyl-3-azabicyclo[3.1.0]hexan-3-ylcarboxylate.

To a solution of benzyl (1α,5α,6α)-6-formyl-3-azabicyclo[3.1.0]hexan-3-ylcarboxylate (45 mg) in tetrahydrofuran (2 mL) was added methyl magnesiumbromide (3 M solution in diethylether, 122 μL) at 0° C., and the mixture was stirred at room temperature for 2 hours. After quenching the reaction by the addition of saturated ammonium chloride solution, the mixture was exrtacted with ethyl acetate. The organic extracts were washed with brine, dried over anhydrous magnesium sulfate, and then concentrated in vacuo to give benzyl (1α,5α,6α)-6-(1-hydroxy)ethyl-3-azabicyclo[3.1.0]hexan-3-ylcarboxylate.

Step 2

Benzyl (1α,5α,6α)-6-acetyl-3-azabicyclo[3.1.0]hexan-3-ylcarboxylate

The title compound benzyl (1α,5α,6α)-6-acetyl-3-azabicyclo[3.1.0]hexan-3-ylcarboxylate (34.0 mg) was prepared from the above crude benzyl (1α,5α,6α)-6-(1-hydroxy)ethyl-3-azabicyclo[3.1.0]hexan-3-ylcarboxylate in the same manner as described for EXAMPLE 22.

MS (EI$^+$) m/z: 259 (M$^+$).

HRMS (EI$^+$) for C$_{15}$H$_{17}$NO$_3$ (M$^+$): calcd, 259.1208; found, 259.1199.

PREPARATIVE EXAMPLE 25

Benzyl (1α,5α,6α)-6-Hydroxy-3-azabicyclo[3.1.0]hexan-3-ylcarboxylate.

Step 1

Benzyl (1α,5α,6α)-6-acetoxy-3-azabicyclo[3.1.0]hexan-3-ylcarboxylate.

To a solution of benzyl (1α,5α,6α)-6-acetyl-3-azabicyclo[3.1.0]hexan-3-ylcarboxylate (23.0 mg) in dichloromethane (1 mL) was added urea-hydrogen peroxide complex (83.0 mg) and trifluoroacetic anhydride (100 mL) at 0° C., and the mixture was stirred at room temperature for 18 hours. After quenching the reaction by the addition of saturated sodium hydrogencarbonate solution and 5% sodium thiosulfate solution, the mixture was exrtacted with dichloromethane. The organic extracts were dried over anhydrous magnesium sulfate, and then concentrated in vacuo to give benzyl (1α,5α,6α)-6-acetoxy-3-azabicyclo[3.1.0]hexan-3-ylcarboxylate.

Step 2

Benzyl (1α,5α,6α)-6-hydroxy-3-azabicyclo[3.1.0]hexan-3-ylcarboxylate.

To a solution of the above crude benzyl (1α,5α,6α)-6-acetoxy-3-azabicyclo[3.1.0]hexan-3-ylcarboxylate in methanol (2 mL) was added potassium carbonate (13.8 mg), and the mixture was stirred at room temperature for 10 min, and then concentrated in vacuo. After addition of water to the residue, the mixture was extracted with ethyl acetate. The organic extracts were washed with brine, dried over anhydrous magnesium sulfate, and then concentrated in vacuo. Flash chromatography (silica, hexane:ethyl acetate=1:1) of the residue gave benzyl (1α,5α,6α)-6-hydroxy-3-azabicyclo[3.1.0]hexan-3-ylcarboxylate (6.3 mg).

MS (EI$^+$) m/z: 233 (M$^+$).

HRMS (EI$^{30}$) for $C_{13}H_{15}NO_3$ (M$^+$): calcd, 233.1052; found, 233.1067.

PREPARATIVE EXAMPLE 26

Benzyl (1α,5α,6α)-6-t-butyldimethylsilyloxy-3-azabicyclo[3.1.0]hexan-3-ylcarboxylate.

To a solution of benzyl (1α,5α,6α)-6-hydroxy-3-azabicyclo[3.1.0]hexan-3-ylcarboxylate (610 mg) in dichloromethane was added imidazole (267 mg) and t-butyldimethylsilyl chloride (434 mg) at 0° C., and the mixture was stirred at room temperature for 1 hour. The mixture was washed with water, dried over anhydrous magnesium sulfate, and then concentrated in vacuo. Flash chromatography (silica, hexane:ethyl acetate=85:15) of the residue gave benzyl (1α,5α,6α)-6-t-butyldimethylsilyloxy-3-azabicyclo[3.1.0]hexan-3-ylcarboxylate (800 mg).

MS (FAB$^+$) m/z: 348 (MH$^+$).

HRMS (FAB$^+$) for $C_{19}H_{30}NO_3Si$ (MH$^+$): calcd, 348.1995; found, 348.1989.

PREPARATIVE EXAMPLE 27

4-[(1α,5α,6α)-6-t-Butyldimethylsilyloxy-3-azabicyclo[3.1.0]hexan-3-]-3-fluoronitrobenzene.

Step 1

(1α,5α,6α)-6-t-butyldimethylsilyloxy-3-azabicyclo[3.1.0]hexane.

The title compound (1α,5α,6α)-6-t-butyldimethylsilyloxy-3-azabicyclo[3.1.0]hexane was prepared from benzyl (1α,5α,6α)-6-t-butyldimethylsilyloxy-3-azabicyclo[3.1.0]hexan-3-ylcarboxylate (780 mg) in the same manner as described for PREPARATIVE EXAMPLE 6.

MS (FAB$^+$) m/z: 214 (MH$^+$).

HRMS (FAB$^+$) for $C_{11}H_{24}NOSi$ (MH$^+$): calcd, 214.1627; found, 214.1628.

Step 2

4-[(1α,5α,6α)-6-t-Butyldimethylsilyloxy-3-azabicyclo[3.1.0]hexan-3-yl]-3-fluoronitrobenzene and 4-[(1α,5α,6α)-6-hydroxy-3-azabicyclo[3.1.0]hexan-3-yl]-3-fluoronitrobenzene.

The title compounds 4-[(1α,5α,6α)-6-t-butyldimethylsilyloxy-3-azabicyclo [3.1.0]hexan-3-yl]-3-fluoronitrobenzene (87 mg) and 4-[(1α,5α,6α)-6-hydroxy-3-azabicyclo[3.1.0]hexan-3-yl]-3-fluoronitrobenzene (270 mg) were prepared from the above crude (1α,5α,6α)-6-t-butyldimethylsilyloxy-3-azabicyclo[3.1.0]hexane and 3,4-difluoronitrobenzene (392 mg) in the same manner as described for PREPARATIVE EXAMPLE 1.

Step 3

4-[(1α,5α,6α)-6-t-Butyldimethylsilyloxy-3-azabicyclo[3.1.0]hexan-3-yl]-3-fluoronitrobenzene.

The title compound 4-[(1α,5α,6α)-6-t-butyldimethylsilyloxy-3-azabicyclo[3.1.0]hexan-3-yl]-3-fluoronitrobenzene (379 mg) was prepared from 4-[(1α,5α,6α)-6-hydroxy-3-azabicyclo[3.1.0]hexan-3-yl]-3-fluoronitrobenzene (270 mg) in the same manner as described for PREPARATIVE EXAMPLE 26.

MS (FAB$^+$) m/z: 353 (MH$^+$).

HRMS (FAB$^+$) for $C_{17}H_{26}FN_2O_3Si$ (MH$^+$): calcd, 353.1697; found, 353.1669.

PREPARATIVE EXAMPLE 28

1-Benzyloxycarbonylamino-4-[(1α,5α,6α)-6-t-butyldimethylsilyloxy-3-azabicyclo[3.1.0]hexan-3-yl]-3-fluorobenzene.

The title compound 1-benzyloxycarbonylamino-4-[(1α,5α,6α)-6-t-butyldimethylsilyloxy-3-azabicyclo[3.1.0]hexan-3-yl]-3-fluorobenzene (342 mg) was prepared from 4-[(1α,5α,6α)-6-t-butyldimethylsilyloxy-3-azabicyclo[3.1.0]hexan-3-yl]-3-fluoronitrobenzene (379 mg) in the same manner as described for PREPARATIVE EXAMPLE 3.

MS (EI$^+$) m/z: 322 (M$^+$).

HRMS (EI$^+$) for $C_7H_{27}FN_2OSi$ (M$^+$): calcd, 322.1877; found, 322.1869.

PREPARATIVE EXAMPLE 29

4-[(1α,5α,6α)-6-(N-t-Butoxycarbonyl)amino-3-azabicyclo[3.1.0]hexan-3-yl]-3,5-difluoronitrobenzene.

The title compound 4-[(1α,5α,6α)-6-(N-t-butoxycarbonyl)amino-3-azabicyclo[3.1.0]hexan-3-yl]-3,5-difluoronitrobenzene (4.59 g) was prepared from (1α,5α,6α)-6-(N-t-butoxycarbonyl)amino-3-azabicyclo[3.1.0] hexane (3.50 g) and 3,4,5-trifluoronitrobenzene (3.20 g) in the same manner as described for PREPARATIVE EXAMPLE 1.

MS (EI$^+$) m/z: 355 (M$^+$).

HRMS (EI$^+$) for $C_{16}H_{19}F_2N_3O_4$ (M$^+$): calcd, 355.1344; found, 355.1357.

PREPARATIVE EXAMPLE 30

4-[(1α,5α,6α)-6-(N-Benzyl-N-t-butoxycarbonyl)amino-3-azabicyclo[3.1.0]hexan-3-yl]-3,5-difluoronitrobenzene.

The title compound 4-[(1α,5α,6α)-6-(N-benzyl-N-t-butoxycarbonyl)amino-3-azabicyclo[3.1.0]hexan-3-yl]-3,5-difluoronitrobenzene (4.40 g) was prepared from 4-[(1α,5α,6α)-6-(N-t-butoxycarbonyl)amino-3-azabicyclo[3.1.0]hexan-3-yl]-3,5-difluoronitrobenzene (4.11 g) in the same manner as described for PREPARATIVE EXAMPLE 2.

$^1$H NMR (CDCl$_3$) δ 1.49 (s, 9H), 1.92 (s, 2H), 2.31 (s, 1H), 3.73–3.90 (m, 4H), 4.45 (s, 2H), 7.23–7.68 (m, 7H).

PREPARATIVE EXAMPLE 31

4-[(1α,5α,6α)-6-(N-Benzyl-N-t-butoxycarbonyl)amino-3-azabicyclo[3.1.0]hexan-3-yl]-1-benzyloxycarbonylamino-3,5-difluorobenzene.

The title compound 4-[(1α,5α,6α)-6-(N-benzyl-N-t-butoxycarbonyl)amino-3-azabicyclo[3.1.0]hexan-3-yl]-1-benzyloxycarbonylamino-3,5-difluorobenzene (4.72 g) was prepared from 4-[(1α,5α,6α)-6-(N-benzyl-N-t-butoxycarbonyl)amino-3-azabicyclo[3.1.0] hexan-3-yl]-3,5-difluoronitrobenzene (4.40 g) in the same manner as described for PREPARATIVE EXAMPLE 3.

MS (FAB$^+$) m/z: 550 (MH$^+$).

HRMS (FAB$^+$) for $C_{31}H_{34}F_2N_3O_4$ (MH$^+$): calcd, 550.2517; found, 550.2507.

PREPARATIVE EXAMPLE 32

3,5-Difluoro-4-[(1α,5α,6α)-6-[(2-tetrahydropyranyl)oxy]methyl-3-azabicyclo[3.1.0]hexan-3-yl]nitrobenzene.

The title compound 3,5-difluoro-4-[(1α,5α,6α)-6-[(2-tetrahydropyranyl)oxy]methyl-3-azabicyclo[3.1.0]hexan-3-yl]nitrobenzene (5.82 g) was prepared from (1α,5α,6α)-6-[(2-tetrahydropyranyl)oxy]methyl-3-azabicyclo[3.1.0] hexane (6.50 g) and 3,4,5-trifluoronitrobenzene (3.92 g) in the same manner as described for PREPARATIVE EXAMPLE 1.

MS (EI$^+$) m/z: 354 (M$^+$).

HRMS (EI$^+$) for $C_{17}H_{20}F_2N_2O_4$ (M$^+$): calcd, 354.1391; found, 354.1422.

PREPARATIVE EXAMPLE 33

1-Benzyloxycarbonylamino-3,5-difluoro-4-[(1α,5α,6α)-6-[(2-tetrahydropyranyl)oxy]methyl-3-azabicyclo[3.1.0]hexan-3-yl]benzene.

The title compound 1-benzyloxycarbonylamino-3,5-difluoro-4-[(1α,5α,6α)-6-[(2-tetrahydropyranyl)oxy]methyl-3-azabicyclo[3.1.0]hexan-3-yl]benzene (7.50 g) was prepared from 3,5-difluoro-4-[(1α,5α,6α)-6-[(2-tetrahydropyranyl)oxy]methyl-3-azabicyclo[3.1.0]hexan-3-yl]nitrobenzene (5.79 g) in the same manner as described for PREPARATIVE EXAMPLE 3.

MS (EI$^+$) m/z: 424 (M$^+$).

HRMS (EI$^+$) for $C_{17}H_{20}F_2N_2O_4$ (M$^+$): calcd, 424.1810; found, 424.1848.

PREPARATIVE EXAMPLE 34

5(R)-3-(3-Fluoro-4-iodophenyl)-5-hydroxymethyloxazolidin-2-one.
Step 1
5(R)-Acetoxymethyl-3-(3-fluorophenyl)oxazolidin-2-one.

To a solution of 5(R)-3-(3-fluorophenyl)-5-hydroxymethyloxazolidin-2-one (5.28 g) in tetrahydrofuran (53 mL) was added triethylamine (3.83 mL), acetic anhydride (2.55 mL) and (4-dimethylamino)pyridine (152 mg), and the mixture was stirred at room temperature for 1 hour. After quenching the reaction by the addition of 1 N hydrochloric acid, the mixture was extracted with ethyl acetate. The organic extracts were washed with brine, dried over anhydrous sodium sulfate, filtered, and then concentrated in vacuo to give crude 5(R)-acetoxymethyl-3-(3-fluorophenyl)oxazolidin-2-one (6.33 g).
Step 2
5(R)-Acetoxymethyl-3-(3-fluoro-4-iodophenyl)oxazolidin-2-one.

To a solution of 5(R)-acetoxymethyl-3-(3-fluorophenyl)oxazolidin-2-one (6.33 g) in acetic acid (40 mL) was added iodine monochloride (1.91 mL), the mixture was stirred at room temperature for 18 hours, and then concentrated in vacuo. The resulting residue was dissolved with ethyl acetate, the mixture was washed with aqueous sodium hydrogencarbonate solution, 20% sodium sulfite solution and brine, dried over anhydrous sodium sulfate, filtered, and then concentrated in vacuo to give crude 5(R)-acetoxymethyl-3-(3-fluoro-4-iodophenyl)oxazolidin-2-one (9.48 g).
Step 3
5(R)-3-(3-Fluoro-4-iodophenyl)-5-hydroxymethyloxazolidin-2-one.

To a solution of crude 5(R)-acetoxymethyl-3-(3-fluoro-4-iodophenyl)oxazolidin-2-one (9.48 g) in methanol (95 mL) was added potassium carbonate (6.91 g), and the mixture was stirred at room temperature for 2.5 hours. After insoluble materials were filtered off, the filtrate was concentrated in vacuo. The residue was dissolved with ethyl acetate, the mixture was washed with brine, dried over anhydrous sodium sulfate, filtered, and then concentrated in vacuo. After treating of the residue with isopropanol, the resulting precipitates were collected by filtration to give 5(R)-3-(3-fluoro-4-iodophenyl)-5-hydroxymethyloxazolidin-2-one, and the filtrate was concentrated in vacuo. Flash chromatography (silica, ethyl acetate) of the residue gave further amount of the product (total 6.24 g).

MS (EI$^+$) m/z: 337 (M$^+$).

$^1$H NMR (CDCl$_3$) δ 2.15 (t, J=6.4 Hz, 1H), 3.74–4.80 (m, 5H), 7.07 (dd, J=8.8, 2.4 Hz, 1H), 7.48 (dd, J=10.3, 2.4 Hz, 1H), 7.70 (dd, J=8.8, 6.8 Hz, 1H).

PREPARATIVE EXAMPLE 35

5M)-3-[3-Fluoro-4-(4,4,5,5-tetramethyl-1,3,2-dioxaborolyl)phenyl]-5-hydroxymethyloxazolidin-2-one.

A suspension of 5(R)-3-(3-fluoro-4-iodophenyl)-5-hydroxymethyloxazolidin-2-one (674 mg), pinacoldiboron (570 mg), potassium acetate (982 mg), and [1,1'-bis(diphenylphosphino)ferrocene]palladium(II) dichloride-dichloromethane adduct (163 mg) in dimethyl sulfoxide (13 mL) was heated at 80° C. for 2 hours. After dilution the mixture with aqueous ammonium chloride solution, the mixture was extracted ethyl acetate. The organic extracts were washed with water and brine, dried over anhydrous sodium sulfate, and then concentrated in vacuo. Flash chromatography (silica, hexane:ethyl acetate=1:5) of the residue gave 5(R)-3-[3-fluoro-4-(4,4,5,5-tetramethyl-1,3,2-dioxaborolyl)phenyl]-5-hydroxymethyloxazolidin-2-one (529 mg).

MS (EI$^+$) m/z: 337 (M$^+$).

$^1$H NMR (CDCl$_3$) δ 1.36 (s, 12H), 2.22 (br, 1H), 3.76–4.79 (m, 5H), 7.29–7.74 (m, 3H).

PREPARATIVE EXAMPLE 36

5(R)-Acetoxymethyl-3-[4-[(1α,5α,6α)-6-[(t-butyldiphenylsilyl)oxy]methylbicyclo[3.1.0]hex-2-en-3-yl]-3-fluorophenyl]oxazolidin-2-one.
Step 1
5(R)-3-[4-[(1α,5α,6α)-6-[(t-Butyldiphenylsilyl)oxy]methylbicyclo[3.1.0]hex-2-en-3-yl]-3-fluorophenyl]-5-hydroxymethyloxazolidin-2-one.

The title compound 5(R)-3-[4-[(1α,5α,6α)-6-[(t-butyldiphenylsilyl)oxy]methylbicyclo[3.1.0]hex-2-en-3-yl]-3-fluorophenyl]-5-hydroxymethyloxazolidin-2-one (523 mg) was prepared from 5(R)-3-[3-fluoro-4-(4,4,5,5-tetramethyl-1,3,2-dioxaborolyl)phenyl]-5-hydroxymethyloxazolidin-2-one (344 mg) and (1α,5α,6α)-6-[(t-butyldiphenylsilyl)oxy]methyl-3-[(trifluoromethanesulfonyl)oxy]bicyclo[3.1.0]hex-2-ene (507 mg) in the same manner as described for EXAMPLE 88.

MS (EI+) m/z: 557 (M+).

$^1$H NMR (CDCl$_3$) δ 0.74 (m, 1H), 1.05 (s, 9H), 1.52–2.09 (m, 3H), 2.69–4.78 (m, 9H), 6.46 (s, 1H), 7.15–7.70 (m, 13H).

Step 2

5(R)-Acetoxymethyl-3-[4-[(1α,5α,6α)-6-[(t-butyldiphenylsilyl)oxy]methylbicyclo[3.1.0]hex-2-en-3-yl]-3-fluorophenyl]oxazolidin-2-one.

The title compound 5(R)-acetoxymethyl-3-[4-[(1α,5α,6α)-6-[(t-butyldiphenylsilyl)oxy]methylbicyclo[3.1.0]hex-2-en-3-yl]-3-fluorophenyl]oxazolidin-2-one (939 mg) was prepared from 5(R)-3-[4-[(1α,5α,6α)-6-[(t-butyldiphenylsilyl)oxy]methylbicyclo[3.1.0]hex-2-en-3-yl]-3-fluorophenyl]-5-hydroxymethyloxazolidin-2-one (959 mg) in the same manner as described for PREPARATIVE EXAMPLE 34.

MS (FAB+) m/z: 600 (MH+).

$^1$H NMR (CDCl$_3$) δ 0.75 (m, 1H), 1.05 (s, 9H), 1.53–2.05 (m, 2H), 2.10 (s, 3H), 2.69–4.89 (m, 9H), 6.47 (d, J=2.0 Hz, 1H), 7.15–7.70 (m, 13H).

PREPARATIVE EXAMPLE 37

5(R)-Acetoxymethyl-3-[3-fluoro-4-[(1α,5α,6α)-6-hydroxymethylbicyclo[3.1.0]hex-2-en-3-yl]phenyl]oxazolidin-2-one.

The title compound 5(R)-acetoxymethyl-3-[3-fluoro-4-[(1α,5α,6α)-6-hydroxymethylbicyclo[3.1.0]hex-2-en-3-yl]phenyl]oxazolidin-2-one (444 mg) was prepared from 5(R)-acetoxymethyl-3-[4-[(1α,5α,6α)-6-[(t-butyldiphenylsilyl)oxy]methylbicyclo[3.1.0]hex-2-en-3-yl]-3-fluorophenyl]oxazolidin-2-one (878 mg) in the same manner as described for EXAMPLE 48.

MS (E+) m/z: 361 (M+).

$^1$H NMR (CDCl$_3$) δ 0.82 (m, 1H), 1.28–1.99 (m, 3H), 2.10 (s, 3H), 2.76–4.90 (m, 9H), 6.50 (t, J=2.0 Hz, 1H), 7.16–7.41 (m, 3H).

PREPARATIVE EXAMPLE 38

5(R)-Acetoxymethyl 1-3-[4-[(1α,5α,6α)-6-cyanobicyclo[3.1.0]hex-2-en-3-yl]-3-fluorophenyl]oxazolidin-2-one.

The title compound 5(R)-acetoxymethyl-3-[4-[(1α,5α,6α)-6-cyanobicyclo[3.1.0]hex-2-en-3-yl]-3-fluorophenyl]oxazolidin-2-one (436 mg) was prepared from 5(R)-acetoxymethyl-3-[3-fluoro-4-[(1α,5α,6α)-6-hydroxymethylbicyclo[3.1.0]hex-2-en-3-yl]phenyl]oxazolidin-2-one (442 mg) in the same manner as described for EXAMPLE 49.

MS (EI+) m/z: 356 (M+).

$^1$H NMR (CDCl$_3$) δ 1.29 (t, J=3.4 Hz, 1H), 2.02 (s, 3H), 2.39–3.12 (m, 4H), 3.80–4.96 (m, 5H), 6.14 (s, 1H), 7.27–7.52 (m, 3H).

PREPARATIVE EXAMPLE 39

5(R)-3-[4-[(1α,5α,6α)-6-Cyanobicyclo[3.1.0]hex-2-en-3-yl]-3-fluorophenyl]-5-hydroxymethyloxazolidin-2-one.

The title compound 5(R)-3-[4-[(1α,5α,6α)-6-cyanobicyclo[3.1.0]hex-2-en-3-yl]-3-fluorophenyl]-5-hydroxymethyloxazolidin-2-one (178 mg) was prepared from 5(R)-acetoxymethyl-3-[4-[(1α,5α,6α)-6-cyanobicyclo[3.1.0]hex-2-en-3-yl]-3-fluorophenyl]oxazolidin-2-one (436 mg) in the same manner as described for PREPARATIVE EXAMPLE 34.

MS (E) m/z: 314 (M+).

$^1$H NMR (DMSO-d6) δ 1.30 (t, J=3.4 Hz, 1H), 2.38–3.13 (m, 4H), 3.51–5.23 (m, 6H), 6.41 (s, 1H), 7.28–7.54 (m, 3H).

PREPARATIVE EXAMPLE 40

4-[(1α,5α,6α)-6-(N-t-Butoxycarbonyl)amino-3-azabicyclo[3.1.0]hexan-3-yl]nitrobenzene.

The title compound 4-[(1α,5α,6α)-6-(N-t-butoxycarbonyl)amino-3-azabicyclo[3.1.0]hexan-3-yl]nitrobenzene (10.04 g) was prepared from (1α,5α,6α)-6-(N-t-butoxycarbonyl)amino-3-azabicyclo[3.1.0]hexane (9.76 g) and 4-fluoronitrobenzene (5.7 mL) in the same manner as described for PREPARATIVE EXAMPLE 1.

MS (EI+) m/z: 319 (M+).

HRMS (EI+) for C$_{16}$H$_{21}$N$_3$O$_4$ (M+): calcd, 319.1532; found, 319.1501.

PREPARATIVE EXAMPLE 41

4-[(1α,5α,6α)-6-(N-t-Butoxycarbonyl)amino-3-azabicyclo[3.1.0]hexan-3-yl]-1-benzyloxycarbonylaminobenzene.

The title compound 4-[(1α,5α,6α)-6-(N-t-butoxycarbonyl)amino-3-azabicyclo[3.1.0]hexan-3-yl]-1-benzyloxycarbonylaminobenzene (10.60 g) was prepared from 4-[(1α,5α,6α)-6-(N-t-butoxycarbonyl)amino-3-azabicyclo[3.1.0]hexan-3-yl]nitrobenzene (8.88 g) in the same manner as described for PREPARATIVE EXAMPLE 3

MS (EI+) m/z: 423 (M+).

HRMS (EI+) for C$_{24}$H$_{29}$N$_3$O$_4$ ((M+)): calcd, 423.2158; found, 423.2139.

PREPARATIVE EXAMPLE 42

5(R)-5-Acetoxymethyl-3-[4-[(1α,5α,6α)-6-hydroxymethylbicyclo[3.1.0]hex-2-en-3-yl]phenyl]oxazolidin-2-one.

The title compound 5(R)-5-acetoxymethyl-3-[4-[(1α,5α,6α)-6-hydroxymethylbicyclo[3.1.0]hex-2-en-3-yl]phenyl]oxazolidin-2-one (2.81 g) was prepared from 5(R)-5-acetoxymethyl-3-[4-[(1α,5α,6α)-6-(t-butyldiphenylsilyl)oxymethylbicyclo[3.1.0]hex-2-en-3-yl]phenyl]oxazolidin-2-one (5.10 g) in the same manner as described for EXAMPLE 48.

MS (EI+) m/z: 343 (M+).

HRMS (EI+) for C$_{19}$H$_{21}$NO$_5$ (M+): calcd, 343.1420; found, 343.1404.

PREPARATIVE EXAMPLE 43

5(R)-5-Acetoxymethyl-3-[4-[(1α,5α,6α)-6-cyanobicyclo[3.1.0]hex-2-en-3-yl]phenyl]oxazolidin-2-one.

The title compound 5(R)-5-acetoxymethyl-3-[4-[(1α,5α,6α)-6-cyanobicyclo[3.1.0]hex-2-en-3-yl]phenyl]oxazolidin-2one (2.20 g) was prepared from 5(R)-5-acetoxymethyl-3-[4-[(1α,5α,6α)-6-hydroxymethylbicyclo[3.1.0]hex-2-en-3-yl]phenyl]-5-oxazolidin-2-one (2.60 g) in the same manner as described for EXAMPLE 49.

MS (EI+) m/z: 338 (M+).

HRMS (EI+) for C$_{19}$H$_{19}$N$_2$O$_4$ (M+): calcd, 338.1267; found, 338.1260.

PREPARATIVE EXAMPLE 44

5(R)-3-[4-[(1α,5α,6α)-6-Cyanobicyclo[3.1.0]hex-2-en-3-yl]phenyl]-5-hydroxymethyloxazolidin-2-one.

To a suspension of 5(R)-5-acetoxymethyl-3-[4-[(1α,5α,6α)-6-cyanobicyclo[3.1.0]hex-2-en-3-yl]phenyl]oxazolidin-2-one (1.93 g) in methanol was added potassium carbonate (788 mg), the mixture was stirred at room temperature for 10 min, and then concentrated in vacuo. After addition of water and 5% hydrochloric acid to the residue, the resulting mixture extracted with dichloromethane. The organic extracts were washed with brine, dried over anhydrous magnesium sulfate, filtered, and then concentrated in vacuo. Treatment of the residue with ethyl acetate gave 5(R)-3-[4-[(1α,5α,6α)-6-cyanobicyclo[3.1.0]hex-2-en-3-yl]phenyl]-5-hydroxymethyloxazolidin-2-one (1.60 g).

MS (EI$^+$) m/z: 296 (M$^+$).

HRMS (EI$^+$) for $C_{17}H_{16}N_2O_3$ (M$^+$): calcd, 296.1161; found, 296.1148.

PREPARATIVE EXAMPLE 45

(1α,5α,6α)-6-[(t-Butyldiphenylsilyl)oxy]methyl-2-oxobicyclo[3.1.0]hexane.

To a solution of (1α,5α,6α)-6-[(t-butyldiphenylsilyl)oxy]methylbicyclo [3.1.0]hex-2-ene (10.00 g) in tetrahydrofuran (80 mL) was added borane-methyl sulfide complex (3.33 mL) under ice water cooling, and the mixture was stirred at room temperature for 1.5 hours. The resulting solution was added water (58 mL), 2.5 N sodium hydroxide solution (17.2 mL), and hydrogen peroxide solution (30%, 4.88 mL) at 0° C., and the mixture was stirred at room temperature for 2 hours. After dilution the mixture with ice water, the resulting mixture was extracted with ether. The organic extracts were washed with brine, dried over anhydrous sodium sulfate, and then concentrated in vacuo. To a solution of chromium oxide (5.74 g) in pyridine (57 mL) was added a solution of the above residue in pyridine (10 mL) at 0° C., and the mixture was stirred at room temperature for 12 hours. After addition of ethyl acetate to the mixture, insoluble materials were filtered off, and then concentrated in vacuo. The ethereal solution of the residue was washed with 1 N hydrochloric acid, water, aqueous sodium hydrogencarbonate and brine, dried over anhydrous magnesium sulfate, filtered, and then concentrated in vacuo. Flash chromatography (silica, hexane:ethyl acetate=4:1) of the precipitates gave (1α,5α,6α)-6-[(t-butyldiphenylsilyl)oxy]methyl-2-oxobicyclo[3.1.0]hexane (935 mg).

MS (CI) m/z: 365 (MH$^+$).

HRMS (CI) for $C_{23}H_{29}O_2Si$ (MH$^+$): calcd, 365.1937; found, 365.1947.

PREPARATIVE EXAMPLE 46

(1α,5α,6α)-6-[(t-Butyldiphenylsilyl)oxy]methyl-2-[(trifluoromethanesulfonyl) oxy]bicyclo[3.1.0]hex-2-ene.

The title compound (1α,5α,6α)-6-[(t-butyldiphenylsilyl)oxy]methyl-2-[(trifluoromethanesulfonyl)oxy]bicyclo[3.1.0]hex-2-ene (5.20 g) was prepared from (1α,5α,6α)-6-[(t-butyldiphenylsilyl)oxy]methyl-2-oxobicyclo[3.1.0]hexane (4.65 g) in the same manner as described for PREPARATIVE EXAMPLE 17.

MS (CI) m/z: 497 (MH$^+$).

HRMS (CI) for $C_{24}H_{28}F_3O_4SSi$ (MH$^+$): calcd, 497.1430; found, 497.1441.

PREPARATIVE EXAMPLE 47

(1α,5α,6α)-6-[(t-Butyldiphenylsilyl)oxy]methyl-2-(4,4,5,5-tetramethyl-1,3,2-dioxaborolyl)bicyclo[3.1.0]hex-2-ene.

The mixture of (1α,5α,6α)-6-[(t-butyldiphenylsilyl)oxy]methyl-2-[(trifluoromethanesulfonyl)oxy]bicyclo[3.1.0]hex-2-ene (5.20 g), pinacoldiboron (2.93 g), potassium phenoxide (2.08 g), bis(triphenylphosphine) dichloropalladium (367 mg) and triphenylphosphine (275 mg) in toluene (100 mL) was stirred at 50° C. for 12 hours, and then concentrated in vacuo after insoluble materials were filtered off. Flash chromatography (silica, hexane: ether=9:1) of the precipitates gave (1α,5α,6α)-6-[(t-butyldiphenylsilyl)oxy]methyl-2-(4,4,5,5-tetramethyl-1,3,2-dioxaborolyl)bicyclo[3.1.0]hex-2-ene (3.15 g).

MS (CI) m/z: 475 (MH$^+$).

HRMS (CI) for $C_{29}H_{40}BO_3Si$ (MH$^+$): calcd, 475.2840; found, 475.2842.

PREPARATIVE EXAMPLE 48

N-[5(S)-3-[3-Fluoro-4-(4,4,5,5-tetramethyl-1,3,2-dioxaborolyl)phenyl]-2-oxooxazolidin-5-ylmethyl]acetamide.

The title compound N-[5(S)-3-[3-fluoro-4-(4,4,5,5-tetramethyl-1,3,2-dioxaborolyl)phenyl]-2-oxooxazolidin-5-ylmethyl]acetamide (758 mg) was prepared from N-[5(S)-3-(3-fluoro-4-iodophenyl)-2-oxooxazolidin-5-ylmethyl] acetamide (1.13 g) and pinacoldiboron (855 mg) in the same manner as described for PREPARATIVE EXAMPLE 35.

MS (EI$^+$) m/z: 378 (M$^+$).

HRMS (EI$^+$) for $C_{18}C_{24}BFN_2O_5$ (M$^+$): calcd, 378.1762; found, 378.1786.

PREPARATIVE EXAMPLE 49

(1α,5α,6α)-6-[(t-Butyldiphenylsilyl)oxy]methyl-2-(4,4,5,5-tetramethyl-1,3,2-ioxaborolyl)bicyclo[3.1.0]hex-2-ene.

The title compound (1α,5α,6α)-6-[(t-butyldiphenylsilyl)oxy]methyl-2-(4,4,5,5-tetramethyl-1,3,2-dioxaborolyl)bicyclo[3.1.0]hex-2-ene was prepared from (1α,5α,6α)-6-[(t-butyldiphenylsilyl)oxy]methyl-2-[(trifluoromethanesulfonyl)oxy]bicyclo [3.1.0]hex-2-ene (124 mg) in the same manner as described for PREPARATIVE EXAMPLE 47.

MS (EI$^+$) m/z: 474 (M$^+$).

HRMS (EI$^+$) for $C_{29}H_{39}BO_3Si$ ((M$^+$)): calcd, 474.2762; found, 474.2799.

PREPARATIVE EXAMPLE 50

(1α,5α,6α)-6-hydroxymethyl-2-(4,4,5,5-tetramethyl-1,3,2-dioxaborolyl)bicyclo[3.1.0]hex-2-ene.

To a solution of (1α,5α,6α)-6-[(t-butyldiphenylsilyl)oxy]methyl-2-(4,4,5,5-tetramethyl-1,3,2-dioxaborolyl)bicyclo [3.1.0]hex-2-ene (4.00 g) in methanol (50 mL) was added a solution of 2 M HCl in ether, the mixture was stirred at 60° C. for 20 min, and then concentrated in vacuo. The mixture of the above residue, anhydrous magnesium sulfate (10.10 g) and pinacol (1.99 g) in toluene (50 mL) was stirred at 80° C. for 30 min. After the insoluble materials were filtered off, the mixture was washed with water, dried over anhydrous magnesium sulfate, filtered, and then concentrated in vacuo. Flash chromatography (silica, hexane:ethyl acetate=2:1) of the residue gave (1α,5α,6α)-6-hydroxymethyl-2-(4,4,5,5-tetramethyl-1,3,2-dioxaborolyl)bicyclo[3.1.0]hex-2-ene (1.40 g). Optical resolution of this compound was performed by HPLC using CHIRALPAK AS (hexane:2-propanol=50:1, RT=24.2 min and 26.7 min).

MS (CI) m/z: 237 (MH$^+$).

HRMS (CI) for $C_{13}H_{22}BO_3$ (MH$^+$): calcd, 237.1662; found, 237.1682.

The invention has been described herein with reference to certain preferred embodiments. However, as obvious variations thereon will become apparent to those of skill in the art, the invention is not to be considered as limited thereto.

What is claimed is:

1. A compound of the following formula I:

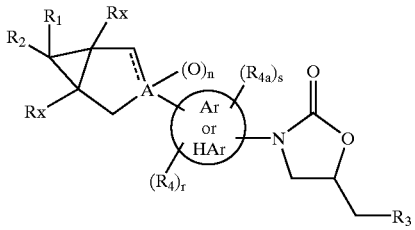

its enantiomer, diastereomer, or pharmaceutically acceptable salt thereof wherein:

A represents C (when - - - is present), CH, or N (when - - - is not present);

- - - represents a bond;

R represents hydrogen, or $C_{1-6}$ alkyl;

$R_1$ and $R_2$ independently represent i) hydrogen, ii) $NR_5R_6$, iii) $CR_7R_8R_9$, $C(R)_2OR_{14}$, $CH_2NHR_{14}$, iv) $C(=O)R_{13}$, $C(=NOH)H$, $C(=NOR_{13})H$, $C(=NOR_{13})R_{13}$, $C(=NOH)R_{13}$, $C(=O)N(R_{13})_2$, $C(=NOH)N(R_{13})_2$, $NHC(=X_1)N(R_{13})_2$, $(C=NH)R_7$, $N(R_{13})C(=X_1)N(R_{13})_2$, $COOR_{13}$, $SO_2R_{14}$, $N(R_{13})SO_2R_{14}$, $N(R_{13})COR_{14}$, or $(C_{1-6}alkyl)CN$, CN, $CH=C(R)_2$, OH, $C(=O)CHR_{13}$, $C(=NR_{13})R_{13}$, $NHC(=X_1)R_{13}$;

v)

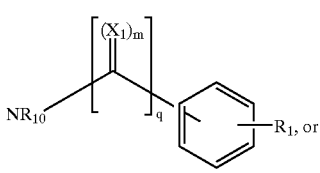

vi) $C_{5-10}$ heterocycle optionally substituted with 1–3 groups of $R_7$, which may be attached through either a carbon or a heteroatom;

represents aryl, $R_x$ represents hydrogen or $C_{1-6}$ alkyl;

$R_3$ represent i) $NH(C=X_2)R_{12}$, ii) $NHSO_2R_{14}$, iii) $NH(CH_2)_{0-4}aryl$, iv) $NH(CH_2)_{0-4}heteroaryl$, v) $S(CH_2)_{0-4}aryl$, vi) $S(CH_2)_{0-4}heteroaryl$, vii) $O(CH_2)_{0-4}aryl$, or viii) $O(CH_2)_{0-4}heteroaryl$;

$R_4$ and $R_{4a}$ independently represent i) hydrogen, ii) halogen, iii) $C_{1-6}$ alkoxy, or iv) $C_{1-6}$ alkyl r and s independently are 1–3, with the provision that when $(R_{4a})_s$ and $(R_4)_r$ are attached to an Ar or HAr ring the sum of r and s is less than or equal to 4;

$R_5$ and $R_6$ independently represent i) hydrogen, ii) $C_{1-6}$ alkyl optionally substituted with 1–3 groups of halogen, CN, OH, $C_{1-6}$ alkoxy, amino, imino, hydroxyamino, alkoxyamino, $C_{1-6}$ acyloxy, $C_{1-6}$ alkylsulfenyl, $C_{1-6}$ alkylsulfinyl, $C_{1-6}$ alkylsulfonyl, aminosulfonyl, $C_{1-6}$ alkylaminosulfonyl, $C_{1-6}$ dialkylaminosulfonyl, 4-morpholinylsulfonyl, phenyl, pyridine, 5-isoxazolyl, ethylenyloxy, or ethynyl, said phenyl and pyridine optionally substituted with 1–3 halogen, CN, OH, $CF_3$, $C_{1-6}$ alkyl or $C_{1-6}$ alkoxy;

iii) $C_{1-6}$ acyl optionally substituted with 1–3 groups of halogen, OH, SH, $C_{1-6}$ alkoxy, naphthalenoxy, phenoxy, amino, $C_{1-6}$ acylamino, hydroxylamino, alkoxylamino, $C_{1-6}$ acyloxy, aralkyloxy, phenyl, pyridine, $C_{1-6}$ alkylcarbonyl, $C_{1-6}$ alkylamino, $C_{1-6}$ dialkylamino, $C_{1-6}$ hydroxyacyloxy, $C_{1-6}$ alkylsulfenyl, phthalimido, maleimido, succinimido, said phenoxy, phenyl and pyridine optionally substituted with 1–3-groups of halo, OH, CN, $C_{1-6}$ alkoxy, amino, $C_{1-6}$ acylamino, $CF_3$ or $C_{1-6}$ alkyl;

iv) $C_{1-6}$ alkylsulfonyl optionally substituted with 1–3 groups of halogen, OH, $C_{1-6}$ alkoxy, amino, hydroxylamino, alkoxylamino, $C_{1-6}$ acyloxy, or phenyl; said phenyl optionally substituted with 1–3 groups of halo, OH, $C_{1-6}$ alkoxy, amino, $C_{1-6}$ acylamino, $CF_3$ or $C_{1-6}$ alkyl;

v) arylsulfonyl optionally substituted with 1–3 of halogen, $C_{1-6}$ alkoxy, OH or $C_{1-6}$ alkyl;

vi) $C_{1-6}$ alkoxycarbonyl optionally substituted with 1–3 of halogen, OH, $C_{1-6}$ alkoxy, $C_{1-6}$ acyloxy, or phenyl, said phenyl optionally substituted with 1–3 groups of halo, OH, $C_{1-6}$ alkoxy, amino, $C_{1-6}$ acylamino, $CF_3$ or $C_{1-6}$ alkyl;

vii) aminocarbonyl, $C_{1-6}$ alkylaminocarbonyl or $C_{1-6}$ dialkylaminocarbonyl, said alkyl groups optionally substituted with 1–3 groups of halogen, OH, $C_{1-6}$ alkoxy or phenyl;

viii) five to six membered heterocycles optionally substituted with 1–3 groups of halogen, OH, CN, amino, $C_{1-6}$ acylamino, $C_{1-6}$ alkylsulfonylamino, $C_{1-6}$ alkoxycarbonylamino, $C_{1-6}$ alkoxy, $C_{1-6}$ acyloxy or $C_{1-6}$ alkyl, said alkyl optionally substituted with 1–3 groups of halogen, or $C_{1-6}$ alkoxy;

ix) $C_{3-6}$ cycloalkylcarbonyl optionally substituted with 1–3 groups of halogen, OH, $C_{1-6}$ alkoxy or CN;

x) benzoyl optionally substituted with 1–3 groups of halogen, OH, $C_{1-6}$ alkoxy, $C_{1-6}$ alkyl, $CF_3$, $C_{1-6}$ alkanoyl, amino or $C_{1-6}$ acylamino;

xi) pyrrolylcarbonyl optionally substituted with 1–3 of $C_{1-6}$ alkyl;

xii) $C_{1-2}$ acyloxyacetyl where the acyl is optionally substituted with amino, $C_{1-6}$ alkylamino, $C_{1-6}$ dialkylamino, 4-morpholino, 4-aminophenyl, 4-(dialkylamino)phenyl, 4-(glycylamino)phenyl; or $R_5$ and $R_6$ taken together with any intervening atoms can form a 3 to 7 membered heterocyclic ring containing 1-2 heteroatoms independently chosen from O, S, SO, SO$_2$, N, or NR$_8$;

R$_7$ represent i) hydrogen, halogen, OH, C$_{1-6}$ alkoxy, C$_{1-6}$ alkyl, alkenyl, ii) amino, C$_{1-6}$ alkylamino, C$_{1-6}$ dialkylamino, hydroxylamino or C$_{1-2}$ alkoxyamino all of which can be optionally substituted on the nitrogen with C$_{1-6}$ acyl, C$_{1-6}$ alkylsulfonyl or C$_{1-6}$ alkoxycarbonyl, said acyl and alkylsulfonyl optionally substituted with 1–2 of halogen or OH;

R$_8$ and R$_9$ independently represents i) H, CN, ii) C$_{1-6}$ alkyl optionally substituted with 1–3 halogen, CN, OH, C$_{1-6}$ alkoxy, C$_{1-6}$ acyloxy, or amino, iii) phenyl optionally substituted with 1–3 groups of halogen, OH, C$_{1-6}$ alkoxy; or R$_7$ and R$_8$ taken together can form a 3–7 membered ring optionally interrupted with 1–2 heteroatoms chosen from O, S, SO, SO$_2$, NH, and NR$_8$;

X$_1$ represents O, S or NR$_{13}$, NCN, or NSO$_2$R$_{14}$;

X$_2$ represents O, S, NH or NSO$_2$R$_{14}$;

R$_{10}$ represents hydrogen, C$_{1-6}$ alkyl or CO$_2$R$_{15}$;

R$_{11}$ represents hydrogen, C$_{1-6}$ alkyl, C$_{1-6}$ alkanoyl, halogen, amino, C$_{1-6}$ acylamino, C$_{1-6}$ alkoxy, OH or CF$_3$, NHC$_{1-6}$ alkyl, or N(C$_{1-6}$ alkyl)$_2$, where said alkyl may be substituted with 1–3 groups of halo, OH or C$_{1-6}$ alkoxy;

R$_{12}$ represents hydrogen, C$_{1-6}$ alkyl, NH$_2$, C$_{1-6}$ alkylamino, C$_{1-6}$ alkoxy or C$_{1-6}$ dialkylamino, where said alkyl may be substituted with 1–3 groups of halo, OH or C$_{1-6}$ alkoxy;

Each R$_{13}$ represents independently hydrogen, C$_{1-6}$ alkyl, NR$_5$R$_6$, SR$_8$, S(O)R$_8$, S(O)$_2$R$_8$, CN, C$_{1-6}$ alkylS(O)R, C$_{1-6}$ alkoxycarbonyl, hydroxycarbonyl, C$_{1-6}$ acyl, C$_{3-7}$ membered carbon ring optionally interrupted with 1–4 heteroatoms chosen from O, S, SO, SO$_2$, NH and NR$_8$ where said C$_{1-6}$ alkyl or C$_{1-6}$ acyl groups may be independently substituted with 0–3 halogens, hydroxy, N(R)$_2$, CO$_2$R, C$_{6-10}$aryl, C$_{5-10}$heteroaryl, or C$_{1-6}$alkoxy groups;

When two R$_{13}$ groups are attached to the same atom or two adjacent atoms they may be taken together to form a 3–7 membered ring optionally interrupted with 1–2 heteroatoms chosen from O, S, SO, SO$_2$, NH, and NR$_8$;

R$_{14}$ represents amino, C$_{1-6}$ alkyl, C$_{1-6}$ haloalkyl, five to six membered heterocycles or phenyl, said phenyl and heterocycles optionally substituted with 1–3 group of halo, C$_{1-6}$ alkoxy, C$_{1-6}$ acylamino, or C$_{1-6}$ alkyl, hydroxy and/or amino, said amino and hydroxy optionally protected with an amino or hydroxy protecting group;

R$_{15}$ is C$_{1-6}$ alkyl or benzyl said benzyl optionally substituted with 1–3 groups of halo, OH, C$_{1-6}$ alkoxy, amino, C$_{1-6}$ acylamino, or C$_{1-6}$ alkyl; and m, n, and q represents 0–1.

2. A compound according to claim 1 wherein A is CH.

3. A compound according to claim 1 wherein A is C and - - - is present.

4. A compound according to claim 1 wherein A is N.

5. A compound according to claim 1 wherein R$_1$ and R$_2$ independently represent H, NR$_5$R$_6$, CN, OH, C(R)$_2$OR$_{14}$, NHC(=X$_1$)N(R$_{13}$)$_2$, C(=NOH)N(R$_{13}$)$_2$, or CR$_7$R$_8$R$_9$.

6. A compound according to claim 1 wherein

is phenyl.

7. A compound according to claim 5 wherein one of R$_1$ and R$_2$ is H and the other is NR$_5$R$_6$.

8. A compound according to claim 5 wherein one of R$_1$ and R$_2$ is H and the other is CN.

9. A compound according to claim 1 wherein R$_5$ and R$_6$ independently are:

i) hydrogen, ii) C$_{1-6}$ alkyl optionally substituted with 1–3 groups of halogen, CN, OH, C$_{1-6}$ alkoxy, amino, imino, hydroxyamino, alkoxyamino, C$_{1-6}$ acyloxy, C$_{1-6}$ alkylsulfenyl, C$_{1-6}$ alkylsulfinyl, C$_{1-6}$ alkylsulfonyl, aminosulfonyl, C$_{1-6}$ alkylaminosulfonyl, C$_{1-6}$ dialkylaminosulfonyl, 4-morpholinylsulfonyl, phenyl, pyridine, 5-isoxazolyl, ethyenyloxy, or ethynyl, said phenyl and pyridine optionally substituted with 1–3 halogen, CN, OH, CF$_3$, C$_{1-6}$ alkyl or C$_{1-6}$ alkoxy;

iii) C$_{1-6}$ acyl optionally substituted with 1–3 groups of halogen, OH, SH, C$_{1-6}$ alkoxy, naphthalenoxy, phenoxy, amino, C$_{1-6}$ acylamino, hydroxylamino, alkoxylamino, C$_{1-6}$ acyloxy, aralkyloxy, phenyl, pyridine, C$_{1-6}$ alkylcarbonyl, C$_{1-6}$ alkylamino, C$_{1-6}$ dialkylamino, C$_{1-6}$ hydroxyacyloxy, C$_{1-6}$ alkylsulfenyl, phthalimido, maleimido, succinimido, said phenoxy, phenyl and pyridine optionally substituted with 1–3 groups of halo, OH, CN, C$_{1-6}$ alkoxy, amino, C$_{1-6}$ acylamino, CF$_3$ or C$_{1-6}$ alkyl;

iv) benzoyl optionally substituted with 1–3 groups of halogen, OH, C$_{1-6}$ alkoxy, C$_{1-6}$ alkyl, CF$_3$, C$_{1-6}$ alkanoyl, amino or C$_{1-6}$ acylamino.

10. A compound according to claim 1 wherein X$_1$ represents O.

11. A compound according to claim 1 wherein one of R$_1$ or R$_2$ is hydrogen and the other is:

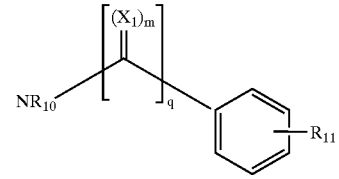

wherein R$_{10}$, X$_1$, m, q, and R$_{11}$ are as described in claim 1.

12. A compound according to claim 1, of the structural formula II:

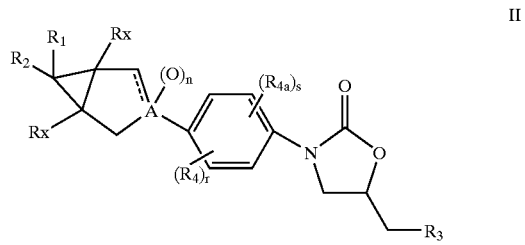

wherein R$_1$, R$_2$, R$_3$, R$_4$, R$_{4a}$, and Rx are as described in claim 1 and A is N.

13. A compound according to claim 12 wherein $R_1$ and $R_2$ independently represent H, $NR_5R_6$, CN, OH, $C(R)_2OR_{14}$, $NHC(=X1)N(R_{13})_2$, $C(=NOH)N(R_{13})_2$, or $CR_7R_8R_9$.

14. A compound according to claim 13 wherein one of $R_1$ and $R_2$ is H and the other is $NR_5R_6$.

15. A compound according to claim 13 wherein one of $R_1$ and $R_2$ is H and the other is CN.

16. A compound according to claim 1 of the structural formula II:

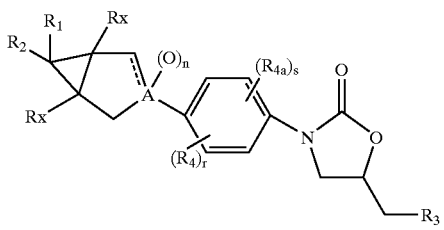

wherein $R_1$, $R_2$, $R_3$, $R_4$, $R_{4a}$, and Rx are as described in claim 1 and A is C wherein - - - is present.

17. A compound according to claim 16 wherein $R_1$ and $R_2$ independently represent H, $NR_5R_6$, CN, OH, $C(R)_2OR_{14}$, $NHC(=X1)N(R_{13})_2$, $C(=NOH)N(R_{13})_2$, or $CR_7R_8R_9$.

18. A compound according to claim 17 wherein one of $R_1$ and $R_2$ is H and the other is $NR_5R_6$.

19. A compound according to claim 17 wherein one of $R_1$ and $R_2$ is H and the other is CN.

20. A compound which is:
N-[5(S)-3-[4-[(1α,5α,6α)-6-(N-Benzyl)amino-3-azabicyclo[3.1.0]hexan-3-yl]-3-fluorophenyl]-2-oxooxazolidin-5-ylmethyl]acetamide,
N-[5(S)-3-[4-[(1α,5α,6α)-6-(N-Benzyloxyacetyl)amino-3-azabicyclo[3.1.0]hexan-3-yl]-3-fluorophenyl]-2-oxooxazolidin-5-ylmethyl]acetamide,
N-[5(S)-3-[3-Fluoro-4-[(1α,5α,6α)-6-(N-hydroxyacetyl)amino-3-azabicyclo[3.1.0]hexan-3-yl]phenyl]-2-oxooxazolidin-5-ylmethyl]acetamide,
N-[5(S)-3-[4-[(1α,5α,6α)-6-(N-Benzyl-N-methyl)amino-3-azabicyclo[3.1.0]hexan-3-yl]-3-fluorophenyl]-2-oxooxazolidin-5-ylmethyl]acetamide,
N-[5(S)-3-[3-Fluoro-4-[(1α,5α,6α)-6-(N-methyl)amino-3-azabicyclo[3.1.0]hexan-3-yl]phenyl]-2-oxooxazolidin-5-ylmethyl]acetamide,
N-[5(S)-3-[4-[(1α,5α,6α)-6-(N-Benzyloxyacetyl-N-methyl)amino-3-azabicyclo[3.1.0]hexan-3-yl]-3-fluorophenyl]-2-oxooxazolidin-5-ylmethyl]acetamide,
N-[5(S)-3-[3-Fluoro-4-[(1α,5α,6α)-6-(N-hydroxyacetyl-N-methyl)amino-3-azabicyclo[3.1.0]hexan-3-yl]phenyl]-2-oxooxazolidin-5-ylmethyl]acetamide,
N-[5(S)-3-[4-[(1α,5α,6α)-6-Amino-3-azabicyclo[3.1.0]hexan-3-yl]-3-fluorophenyl]-2-oxooxazolidin-5-ylmethyl]acetamide,
N-[5(S)-3-[4-[(1α,5α,6α)-6-(N-Benzyl-N-t-butoxycarbonyl)amino-3-azabicyclo[3.1.0]hexan-3-yl]-3-fluorophenyl]-2-oxooxazolidin-5-ylmethyl]acetamide,
N-[5(S)-3-[4-[(1α,5α,6α)-6-(N-Benzyl-N-t-butoxycarbonyl)amino-3-azabicyclo[3.1.0]hexan-3-yl]-3-fluorophenyl]-2-oxooxazolidin-5-ylmethyl]thioacetamide,
N-[5(S)-3-[4-[(1α,5α,6α)-6-(N-Benzyl)amino-3-azabicyclo[3.1.0]hexan-3-yl]-3-fluorophenyl]-2-oxooxazolidin-5-ylmethyl]thioacetamide,
N-[5(S)-3-[4-[(1α,5α,6α)-6-(N-Benzyl)amino-3-azabicyclo[3.1.0]hexan-3-yl]-3-fluorophenyl]-2-oxooxazolidin-5-ylmethyl]thiourea,
N-[5(S)-3-[3-Fluoro-4-[(1α,5α,6α)-6-hydroxymethyl-3-azabicyclo[3.1.0]hexan-3-yl]phenyl]-2-oxooxazolidin-5-ylmethyl]acetamide,
N-[5(S)-3-[3-Fluoro-4-[(1α,5α,6α)-6-[(2-tetrahydropyranyl)oxy]methyl-3-azabicyclo[3.1.0]hexan-3-yl]phenyl]-2-oxooxazolidin-5-ylmethyl]acetamide,
N-[5(S)-3-[3-Fluoro-4-[(1α,5α,6α)-6-methoxymethyl-3-azabicyclo[3.1.0]hexan-3-yl]phenyl]-2-oxooxazolidin-5-ylmethyl]acetamide,
N-[5(S)-3-[3-Fluoro-4-[(1α,5α,6α)-6-(3-isoxazolyl)oxymethyl-3-azabicyclo[3.1.0]hexan-3-yl]phenyl]-2-oxooxazolidin-5-ylmethyl]acetamide,
N-[5(S)-3-[4-[(1α,5α,6α)-6-Acetylamino-3-azabicyclo[3.1.0]hexan-3-yl]-3-fluorophenyl]-2-oxooxazolidin-5-ylmethyl]acetamide,
N-[5(S)-3-[4-[(1α,5α,6α)-6-Benzoylamino-3-azabicyclo[3.1.0]hexan-3-yl]-3-fluorophenyl]-2-oxooxazolidin-5-ylmethyl]acetamide,
N-[5(S)-3-[3-Fluoro-4-[(1α,5α,6α)-6-phenylsulfonylamino-3-azabicyclo[3.1.0]hexan-3-yl]phenyl]-2-oxooxazolidin-5-ylmethyl]acetamide,
N-[5(S)-3-[3-Fluoro-4-[(1α,5α,6α)-6-methanesulfonylamino-3-azabicyclo[3.1.0]hexan-3-yl]phenyl]-2-oxooxazolidin-5-ylmethyl]acetamide,
N-[5(S)-3-[3-Fluoro-4-[(1α,5α,6α)-6-carbamoylamino-3-azabicyclo[3.1.0]hexan-3-yl]phenyl]-2-oxooxazolidin-5-ylmethyl]acetamide,
N-[5(S)-3-[3-Fluoro-4-[(1α,5α,6α)-6-formyl-3-azabicyclo[3.1.0]hexan-3-yl]phenyl]-2-oxooxazolidin-5-ylmethyl]acetamide,
N-[5(S)-3-[4-[(1α,5α,6α)-6-Carboxyl-3-azabicyclo[3.1.0]hexan-3-yl]-3-fluorophenyl]-2-oxooxazolidin-5-ylmethyl]acetamide,
N-[5(S)-3-[4-[(1α,5α,6α)-6-[(1-Iminoethyl)amino]-3-azabicyclo[3.1.0]hexan-3-fluorophenyl]-2-oxooxazolidin-5-ylmethyl]acetamide,
N-[5(S)-3-[4-[(1α,5α,6α)-6-Bromomethyl-3-azabicyclo[3.1.0]hexan-3-yl]-3-fluorophenyl]-2-oxooxazolidin-5-ylmethyl]acetamide,
N-[5(S)-3-[4-[(1α,5α,6α)-6-Cyanomethyl-3-azabicyclo[3.1.0]hexan-3-yl]-2-fluorophenyl]-2-oxooxazolidin-5-ylmethyl]acetamide,
N-[4-[1-(5(S)-Acetylaminomethyl-2-oxooxazolidin-3-yl)-3-fluoro]phenyl-(1α,5α,6α)-3-azabicyclo[3.1.0]hexan-6-yl]methylpyridinium bromide,
N-[5(S)-3-[3-Fluoro-4-[(1α,5α,6α)-6-succinimidoyloxycarbonyl-3-azabicyclo[3.1.0]hexan-3-yl]phenyl]-2-oxooxazolidin-5-ylmethyl]acetamide,
N-[5(S)-3-[4-[(1α,5α,6α)-6-Carbamoyl-3-azabicyclo[3.1.0]hexan-3-yl]phenyl]-2-oxooxazolidin-5-ylmethyl]acetamide,
N-[5(S)-3-[3-Fluoro-4-[(1α,5α,6α)-6-methoxycarbonyl-3-azabicyclo[3.1.0]hexan-3-yl]phenyl]-2-oxooxazolidin-5-ylmethyl]acetamide,
N-[5(S)-3-[4-[(1α,5α,6α)-6-[N,N"-Bis(benzyloxycarbonyl)guanigino]-3-azabicyclo[3.1.0]hexan-3-yl]-3-fluorophenyl]-2-oxooxazolidin-5-ylmethyl]acetamide,
N-[5(S)-3-[3-Fluoro-4-[(1α,5α,6α)-6-guanidino-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-methylcarbamoyl-3-azabicyclo[3.1.0]hexan-3-yl]phenyl]-2-oxooxazolidin-5-ylmethyl]acetamide, N-[5(S)-3-[4-[(1α,5α,6α)-6-Dimethylcarbamoyl-3-azabicyclo[3.1.0]hexan-3-yl]-3-fluorophenyl]-2-oxooxazolidin-5-ylmethyl]acetamide, N-[5(S)-3-[3-Fluoro-4-[(1α,5α,6α)-6-[(piperidin-1-yl)carbonyl]-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-[(morpholin-4-yl)carbonyl]-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-[N-(2-hydroxyethyl)carbamoyl]-3-azabicyclo[3.1.0]hexan-3-yl]phenyl]-2-oxooxazolidin-5-ylmethyl]acetamide, N-[5(S)-3-[4-[(1α,5α,6α)-6-(2-Aminoethyl)-3-azabicyclo[3.1.0]hexan-3-yl]-2-fluorophenyl]-2-oxooxazolidin-5-ylmethyl]acetamide, N-[5(S)-3-[3-Fluoro-4-[(1α,5α,6α)-6-(1-hydroxyethyl)-3-azabicyclo[3.1.0]hexan-3-yl]phenyl]-2-oxooxazolidin-5-ylmethyl]acetamide, N-[5(S)-3-[4-[(1α,5α,6α)-6-Acetyl-3-azabicyclo[3.1.0]hexan-3-yl]-3-fluorophenyl]-2-oxooxazolidin-5-ylmethyl]acetamide, (E)-N-[5(S)-3-[3-Fluoro-4-[(1α,5α,6α)-6-[(hydroxyimino)methyl]-3-azabicyclo[3.1.0]hexan-3-yl]phenyl]-2-oxooxazolidin-5-ylmethyl]acetamide, (Z)-N-[5(S)-3-[3-Fluoro-4-[(1α,5α,6α)-6-[(hydroxyimino)methyl]-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-[(methoxyimino)methyl]-3-azabicyclo[3.1.0]hexan-3-yl]phenyl]-2-oxooxazolidin-5-ylmethyl]acetamide, N-[5(S)-3-[4-[(1α,5α,6α)-6-[(t-Butoxycarbonylmethyloxyimino)methyl]-3-azabicyclo[3.1.0]hexan-3-yl]-3-fluorophenyl]-2-oxooxazolidin-5-ylmethyl]acetamide, N-[5(S)-3-[4-[(1α,5α,6α)-6-[(Carboxymethyloxyimino)methyl]-3-azabicyclo[3.1.0]hexan-3-yl]-3-fluorophenyl]-2-oxooxazolidin-5-ylmethyl]acetamide, N-[5(S)-3-[4-[(1α,5α,6α)-6-Cyano-3-azabicyclo[3.1.0]hexan-3-yl]-3-fluorophenyl]-2-oxooxazolidin-5-ylmethyl]acetamide, N-[((5S)-3-{4-[(1R,5R,6S)-6-cyanobicyclo[3.1.0]hex-2-en-3-yl]-3-fluorophenyl}-2-oxo-1,3-oxazolidin-5-yl)methyl]acetamide, N-[5(S)-3-[4-[(1α,5α,6α)-6-Aminobicyclo[3.1.0]hex-2-en-3-yl]-3-fluorophenyl]-2-oxooxazolidin-5-ylmethyl]acetamide hydrochloride, N-[((5S)-3-{4-[(1S,5S,6R)-6-cyanobicyclo[3.1.0]hex-2-en-3-yl]-3-fluorophenyl}-2-oxo-1,3-oxazolidin-5-yl)methyl]acetamide, N-[5(S)-3-[4-[(1R,5R,6S)-6-Cyanobicyclo[3.1.0]hex-2-en-3-yl]-3,5-difluorophenyl]-2-oxooxazolidin-5-ylmethyl]acetamide, N-[5(S)-3-[4-[(1S,5S,6R)-6-Cyanobicyclo[3.1.0]hex-2-en-3-yl]-3,5-difluorophenyl]-2-oxooxazolidin-5-ylmethyl]acetamide, N-[5(S)-3-[4-[(1R,5R,6S)-6-Aminobicyclo[3.1.0]hex-2-en-3-yl]-3-fluorophenyl]-2-oxooxazolidin-5-ylmethyl]acetamide, N-[5(S)-3-[4-[(1S,5S,6R)-6-Aminobicyclo[3.1.0]hex-2-en-3-yl]-3-fluorophenyl]-2-oxooxazolidin-5-ylmethyl]acetamide, N-[5(S)-3-[4-[(1R,5R,6S)-6-Aminobicyclo[3.1.0]hex-2-en-3-yl]-3,5-difluorophenyl]-2-oxooxazolidin-5-ylmethyl]acetamide, N-[5(S)-3-[4-[(1S,5S,6R)-6-Aminobicyclo[3.1.0]hex-2-en-3-yl]-3,5-difluorophenyl]-2-oxooxazolidin-5-ylmethyl]acetamide, N-[5(S)-3-[3-Fluoro-4-[(1R,5R,6S)-6-hydroxymethylbicyclo[3.1.0]hex-2-en-3-yl]-3,5-difluorophenyl]-2-2-oxooxazolidin-5-ylmethyl]acetamide, N-[5(S)-3-[3-Fluoro-4-[(1S,5S,6R)-6-hydroxymethylbicyclo[3.1.0]hex-2-en-3-yl]phenyl]-2-oxooxazolidin-5-ylmethyl]acetamide, N-[5(S)-3-[3,5-Difluoro-4-[(1R,5R,6S)-6-hydroxymethylbicyclo[3.1.0]hex-2-en-3-yl]phenyl]-2-oxooxazolidin-5-ylmethyl]acetamide, N-[5(S)-3-[3,5-Difluoro-4-[(1S,5S,6R)-6-hydroxymethylbicyclo[3.1.0]hex-2-en-2-yl]phenyl]-2-oxooxazolidin-5-ylmethyl]acetamide, N-[5(S)-3-[4-[(1α,4α,5α,6α)-6-Aminobicyclo[3.1.0]hexan-3-yl]-3-fluorophenyl]-2-oxooxazolidin-5-ylmethyl]acetamide, N-[5(S)-3-[4-[(1α,4β, 5α,6α)-6-Aminobicyclo[3.1.0]hexan-3-yl]-3-fluorophenyl]-2-oxooxazolidin-5-ylmethyl]acetamide, N-[5(S)-3-[4-[(1α,4α,5α,6α)-6-Aminobicyclo[3.1.0]hexan-3-yl]-3,5-difluorophenyl]-2-oxooxazolidin-5-ylmethyl]acetamide, N-[5(S)-3-[4-[(1α,4α,5α,6α)-6-Aminobicyclo[3.1.0]hexan-3-yl]-3,5-difluorophenyl]-2-oxooxazolidin-5-ylmethyl]acetamide, N-[5(S)-3-[4-[(1α,4α,5α,6α)-6-Cyanobicyclo[3.1.0]hexan-3-yl]-3-fluorophenyl]-2-oxooxazolidin-5-ylmethyl]acetamide, N-[5(S)-3-[4-[(1α,4β,5α,6α)-6-Cyanobicyclo[3.1.0]hexan-3-yl]-3-fluorophenyl]-2-oxooxazolidin-5-ylmethyl]acetamide, N-[5(S)-3-[4-[(1α,4α,5α,6α)-6-Cyanobicyclo[3.1.0]hexan-3-yl]-3,5-difluorophenyl]-2-oxooxazolidin-5-ylmethyl]acetamide, N-[5(S)-3-[4-[(1α,4β,5α,6α)-6-Cyanobicyclo[3.1.0]hexan-3-yl]-3,5difluorophenyl]-2-oxooxazolidin-5-ylmethyl]acetamide, N-[5(S)-3-[3-Fluoro-4-[(1α,4α,5α,6α)-6-hydroxymethylbicyclo[3.1.0]hexan-3-yl]phenyl]-2-oxooxazolidin-5-ylmethyl]acetamide, N-[5(S)-3-[3-Fluoro-4-[(1α,4β,5α,6α)-6-hydroxymethylbicyclo[3.1.0]hexan-3-yl]phenyl]-2-oxooxazolidin-5-ylmethyl]acetamide, N-[5(S)-3-[3,5-Difluoro-4-[(1α,4α,5α,6α)-6-hydroxymethylbicyclo[3.1.0]hexan-3-yl]phenyl]-2-oxooxazolidin-5-ylmethyl]acetamide, N-[5(S)-3-[3,5-Difluoro-4-[(1α,4β,5β,6α)-6-hydroxymethylbicyclo[3.1.0]hexan-3-yl]phenyl]-2-oxooxazolidin-5-ylmethyl]acetamide, (E)-N-[5(S)-3-[3-Fluoro-4-[(1α,5α,6α)-6-[(hydroxyimino)aminomethyl]-3-azabicyclo[3.1.0]hexan-3-yl]phenyl]-2-oxooxazolidin-5-ylmethyl]acetamide, (Z)-N-[5(S)-3-[3-Fluoro-4-[(1α,5α,6α)-6-[(hydroxyimino)aminomethyl]-3-azabicyclo[3.1.0]hexan-3-yl]phenyl]-2-oxooxazolidin-5-ylmethyl]acetamide, N-[5(S)-3-[3-Fluoro-4-[(1α,5α,6α)-6-[(2-(methoxy)ethoxyimino)methyl]-3-azabicyclo[3.1.0]hexan-3-yl]phenyl]-2-oxooxazolidin-5-ylmethyl]acetamide, N-[5(S)-3-[4-[(1α,5α,6α)-6-[(2-(Dimethylamino)
ethoxyimino)methyl]-3-azabicyclo[3.1.0]hexan-3-yl]-
3-fluorophenyl]-2-oxooxazolidin-5-ylmethyl]
acetamide, N-[5(S)-3-[4-[(1α,5α,6α)-6-[(3-(Dimethylamino)
propoxyimino)methyl]-3-azabicyclo[3.1.0]hexan-3-
yl]-3-fluorophenyl]-2-oxooxazolidin-5-ylmethyl]
acetamide, N-[5(S)-3-[3-Fluoro-4-[(1α,5α,6α)-6-[(N-(4-
morpholinyl)imino)methyl]-3-azabicyclo[3.1.0]hexan-
3-yl]phenyl]-2-oxooxazolidin-5-ylmethyl]acetamide, N-[5(S)-3-[4-[(1α,5α,6α)-6-[(1-(1-t-Butoxycarboxyl-1-
methyl)ethoxy)iminomethyl]-3-azabicyclo[3.1.0]
hexan-3-yl]-3-fluorophenyl]-2-oxooxazolidin-5-
ylmethyl]acetamide, N-[5(S)-3-[4-[(1α,5α,6α)-6-[(1-(1-Carboxyl-1-methyl)
ethoxy)iminomethyl]-3-azabicyclo[3.1.0]hexan-3-yl]-
3-fluorophenyl]-2-oxooxazolidin-5-ylmethyl]
acetamide, N-[5(S)-3-[3-Fluoro-4-[(1α,5α,6α)-6-[(2-
hydroxyethoxy)iminomethyl]-3-azabicyclo[3.1.0]
hexan-3-yl]phenyl]-2-oxooxazolidin-5-ylmethyl]
acetamide, N-[5(S)-3-[3-Fluoro-4-[(1α,5α,6α)-6-[(5-
tetrazolylmethoxy)iminomethyl]-3-azabicyclo[3.1.0]
hexan-3-yl]phenyl]-2-oxooxazolidin-5-ylmethyl]
acetamide, N-[5(S)-3-[4-[(1α,5α,6α)-6-Cyano-3-azabicyclo[3.1.0]
hexan-3-yl]-3-fluorophenyl]-2-oxooxazolidin-5-
ylmethyl]acetamide, N-[5(S)-3-[4-[(1α,5α,6α)-6-Ethenyl-3-azabicyclo[3.1.0]
hexan-3-yl]-3-fluorophenyl]-2-oxooxazolidin-5-
ylmethyl]acetamide, N-[5(S)-3-[3-Fluoro-4-[(1α,5α,6α)-6-hydroxy-3-
azabicyclo[3.1.0]hexan-3-yl]phenyl]-2-oxooxazolidin-
5-ylmethyl]acetamide, N-[5(S)-3-[4-[(1α,5α,6α)-6-(t-Butyldimethylsilyl)oxy-3-
azabicyclo[3.1.0]hexan-3-yl]-3-fluorophenyl]-2-
oxooxazolidin-5-ylmethyl]acetamide, N-[5(S)-3-[3-Fluoro-4-[(1α,5α,6α)-6-(2-hydroxyethyl)-
3-azabicyclo[3.1.0]hexan-3-yl]phenyl]-2-
oxooxazolidin-5-ylmethyl]acetamide, N-[5(S)-3-[4-[(1α,5α,6α)-6-(1,2-Dihydroxyethyl)-3-
azabicyclo[3.1.0]hexan-3-yl]-3-fluorophenyl]-2-
oxooxazolidin-5-ylmethyl]acetamide, N-[5(S)-3-[4-[(1α,5α,6α)-6-(2-(t-Butyldimethylsilyl)
oxy-1-hydroxyethyl)-3-azabicyclo[3.1.0]hexan-3-yl]-
3-fluorophenyl]-2-oxooxazolidin-5-ylmethyl]
acetamide, N-[5(S)-3-[4-[(1α,5α,6α)-6-[(2-(t-Butyldimethylsilyl)
oxy)acetyl]-3-azabicyclo[3.1.0]hexan-3-yl]-3-
fluorophenyl]-2-oxooxazolidin-5-ylmethyl]acetamide, N-[5(S)-3-[3-Fluoro-4-[(1α,5α,6α)-6-hydroxyacetyl-3-
azabicyclo[3.1.0]hexan-3-yl]phenyl]-2-oxooxazolidin-
5-ylmethyl]acetamide, N-[5(S)-3-[4-[(1α,5α,6α)-6-[(1-(2,3-Dihydroxy)
propyloxy)iminomethyl]-3-azabicyclo[3.1.0]hexan-3-
yl]-3-fluorophenyl]-2-oxooxazolidin-5-ylmethyl]
acetamide, N-[5(S)-3-[4-[(1α,5α,6α)-6-[(2-(1,3-Dihydroxy)
propyloxy)iminomethyl]-3-azabicyclo[3.1.0]hexan-3-
yl]-3-fluorophenyl]-2-oxooxazolidin-5-ylmethyl]
acetamide, N-[5(S)-3-[3-Fluoro-4-[(1α,5α,6α)-6-[(1-(2-(2-
hydroxyethoxy))ethoxy)iminomethyl]-3-azabicyclo
[3.1.0]hexan-3-yl]phenyl]-2-oxooxazolidin-5-
ylmethyl]acetamide, N-[5(S)-3-[4-[(1α,5α,6α)-6-(Cyanomethyloxy)
iminomethyl]-3-azabicyclo[3.1.0]hexan-3-yl]-3-
fluorophenyl]-2-oxooxazolidin-5-ylmethyl]acetamide, N-[5(S)-3-[3-Fluoro-4-[(1α,5α,6α)-6-[(1-(2-methylthio)
ethoxy)iminomethyl]-3-azabicyclo[3.1.0]hexan-3-yl]
phenyl]-2-oxooxazolidin-5-ylmethyl]acetamide, N-[5(S)-3-[3-Fluoro-4-[(1α,5α,6α)-6-[(1-(2-
methylsulfinyl)ethoxy)iminomethyl]-3-azabicyclo
[3.1.0]hexan-3-yl]phenyl]-2-oxooxazolidin-5-
ylmethyl]acetamide, N-[5(S)-3-[3-Fluoro-4-[(1α,5α,6α)-6-[(1-(2-
methylsulfonyl)ethoxy)iminomethyl]-3-azabicyclo
[3.1.0]hexan-3-yl]phenyl]-2-oxooxazolidin-5-
ylmethyl]acetamide, N-[5(S)-3-[4-[(1α,5α,6α)-6-Aminomethyl-3-azabicyclo
[3.1.0]hexan-3-yl]-3-fluorophenyl]-2-oxooxazolidin-
5-ylmethyl]acetamide, N-[5(S)-3-[3-Fluoro-4-[(1α,5α,6α)-6-(hydroxyethyl)
amino-3-azabicyclo[3.1.0]hexan-3-yl]phenyl]-2-
oxooxazolidin-5-ylmethyl]acetamide, N-[5(S)-3-[4-[(1α,5α,6α)-6-(2-Aminoethyl)amino-3-
azabicyclo[3.1.0]hexan-3-yl]-3-fluorophenyl]-2-
oxooxazolidin-5-ylmethyl]acetamide, N-[5(S)-3-[3-Fluoro-4-[(1α,5α,6α)-6-(pyridin-2-yl)
amino-3-azabicyclo[3.1.0]hexan-3-yl]phenyl]-2-
oxooxazolidin-5-ylmethyl]acetamide, N-[5(S)-3-[4-[(1α,5α,6α)-6-(3-Cyanopyridin-2-yl)
amino-3-azabicyclo[3.1.0]hexan-3-yl]-3-
fluorophenyl]-2-oxooxazolidin-5-ylmethyl]acetamide, N-[5(S)-3-[4-[(1α,5α,6α)-6-(5-Cyanopyridin-2-yl)
amino-3-azabicyclo[3.1.0]hexan-3-yl]-3-
fluorophenyl]-2-oxooxazolidin-5-ylmethyl]acetamide, N-[5(S)-3-[4-[(1α,5α,6α)-6-(3-Cyanopyridin-2-yl)
amino-3-azabicyclo[3.1.0]hexan-3-yl]-3-
fluorophenyl]-2-oxooxazolidin-5-ylmethyl]acetamide, N-[5(S)-3-[3-Fluoro-4-[(1α,5α,6α)-6-(pyrimidin-2-yl)
amino-3-azabicyclo[3.1.0]hexan-3-yl]phenyl]-2-
oxooxazolidin-5-ylmethyl]acetamide, N-[5(S)-3-[4-[(1α,5α,6α)-6-(4-Aminopyrimidin-2-yl)
amino-3-azabicyclo[3.1.0]hexan-3-yl]-3-yl]-3-
fluorophenyl]-2-oxooxazolidin-5-ylmethyl]acetamide, N-[5(S)-3-[4-[(1α,5α,6α)-6-Amino-3-azabicyclo[3.1.0]
hexan-3-yl]-3,5-difluorophenyl]-2-oxooxazolidin-5-
ylmethyl]acetamide, N-[5(S)-3-[3,5-Difluoro-4-[(1α,5α,6α)-6-
hydroxymethyl-3-azabicyclo[3.1.0]hexan-3-yl]
phenyl]-2-oxooxazolidin-5-ylmethyl]acetamide, N-[5(S)-3-[3,5-Difluoro-4-[(1α,5α,6α)-6-formyl-3-
azabicyclo[3.1.0]hexan-3-yl]phenyl]-2-oxooxazolidin-
5-ylmethyl]acetamide, N-[5(S)-3-[4-[(1α,5α,6α)-6-Cyanomethyl-3-azabicyclo
[3.1.0]hexan-3-yl]-3,5-difluorophenyl]-2-
oxooxazolidin-5-ylmethyl]acetamide, N-[5(S)-3-[3,5-Difluoro-4-[(1α,5α,6α)-6-
[(hydroxyimino)methyl]-3-azabicyclo[3.1.0]hexan-3-
yl]phenyl]-2-oxooxazolidin-5-ylmethyl]acetamide, N-[5(S)-3-[4-[(1α,5α,6α)-6-Cyano-3-azabicyclo[3.1.0]
hexan-3-yl]-3,5-difluorophenyl]-2-oxooxazolidin-5-
ylmethyl]acetamide, N-[5(S)-3-[3,5-Difluoro-4-[(1α,5α,6α)-6-[(1-(2,3-
dihydroxy)propyloxy)iminomethyl]-3-azabicyclo

[3.1.0]hexan-3-yl]phenyl]-2-oxooxazolidin-5-ylmethyl]acetamide,

N-[5(S)-3-[3,5-Difluoro-4-[(1α,5α,6α)-6-[(2-(1,3-dihydroxy)propyloxy)iminomethyl]-3-azabicyclo[3.1.0]hexan-3-yl]phenyl]-2-oxooxazolidin-5-ylmethyl]acetamide, N-[5(S)-3-[3,5-Difluoro-4-[(1α,5α,6α)-6-[(1-(2-(2-hydroxyethoxy))ethoxy)iminomethyl]-3-azabicyclo[3.1.0]hexan-3-yl]phenyl]-2-oxooxazolidin-5-ylmethyl]acetamide, N-[5(S)-3-[3,5-Difluoro-4-[(1α,5α,6α)-6-[(2-hydroxyethoxy)iminomethyl]-3-azabicyclo[3.1.0]hexan-3-yl]phenyl]-2-oxooxazolidin-5-ylmethyl]acetamide, N-[5(S)-3-[4-[(1α,5α,6α)-6-Amino-3-azabicyclo[3.1.0]hexan-3-yl]-3-fluorophenyl]-2-oxooxazolidin-5-ylmethyl]difluoroacetamide, 5(S)-3-[4-[(1α,5α,6α)-6-Amino-3-azabicyclo[3.1.0]hexan-3-yl]-3-fluorophenyl]-5-(methoxythiocarbonyl)aminomethyloxazolidin-2-one, 5(R)-3-[4-[(1α,5α,6α)-6-Amino-3-azabicyclo[3.1.0]hexan-3-yl]-3-fluorophenyl]-5-(isoxazol-3-yl)oxymethyloxazolidin-2-one, 5(S)-3-[4-[(1α,5α,6α)-6-Amino-3-azabicyclo[3.1.0]hexan-3-yl]-3-fluorophenyl]-5-(isoxazol-3-yl)aminomethyloxazolidin-2-one, 5(S)-3-[4-[(1α,5α,6α)-6-Cyano-3-azabicyclo[3.1.0]hexan-3-yl]-3-fluorophenyl]-5-(isoxazol-3-yl)aminomethyloxazolidin-2-one, 5(S)-3-[4-[(1α,5α,6α)-6-Amino-3-azabicyclo[3.1.0]hexan-3-yl]-3-fluorophenyl]-5-oxadiazol-3-yl)aminomethyloxazolidin-2-one, 5(S)-3-[4-[(1α,5α,6α)-6-Cyano-3-azabicyclo[3.1.0]hexan-3-yl]-3-fluorophenyl]-5-oxadiazol-3-yl)aminomethyloxazolidin-2-one, or 5(S)-3-[4-[(1α,5α,6α)-6-Amino-3-azabicyclo[3.1.0]hexan-3-yl]-3-fluorophenyl]-5-(pyridin-2-yl)aminomethyloxazolidin-2-one.

21. A compound selected from the group consisting of:

5(S)-3-[4-[(1α,5α,6α)-6-Amino-3-azabicyclo[3.1.0]hexan-3-yl]-3,5-difluorophenyl]-5-[(1,2,4-oxadiazolyl-3-yl)amino]methyloxazolidin-2-one, 5(S)-3-[4-[(1α,5α,6α)-6-Amino-3-azabicyclo[3.1.0]hexan-3-yl]-3,5-difluorophenyl]-5-[(isoxazolyl-3-yl)amino]methyloxazolidin-2-one, 5(S)-3-[4-[(1α,5α,6α)-6-Amino-3-azabicyclo[3.1.0]hexan-3-yl]phenyl]-5-(isoxazolyl-3-yl)amino]methyloxazolidin-2-one, 5(S)-3-[4-[(1α,5α,6α)-6-Cyanobicyclo[3.1.0]hex-2-en-3-yl]phenyl]-5-[N-(1,2,3-oxadiazolyl-3-yl)]aminomethyloxazolidin-2-one, 5(S)-3-[4-[(1α,5α,6α)-6-Cyanobicyclo[3.1.0]hex-2-en-3-yl]phenyl]-5-(isoxazolyl-3-yl)amino]methyloxazolidin-2-one, 5(R)-3-[4-[(1α,5α,6α)-6-Cyanobicyclo[3.1.0]hex-2-en-3-yl]phenyl]-5-(isoxazolyl-3-yl)oxy]methyloxazolidin-2-one, N-[5(S)-3-[4-[(1α,5α,6α)-6-[(N-Cyano-1-iminoethyl)amino]-3-azabicyclo[3.1.0]hexan-3-yl]-3,5-difluorophenyl]-2-oxooxazolidin-5-ylmethyl]acetamide, N-[5(S)-3-[4-[(1α,5α,6α)-6-(5-Amino-4-cyano-1,3-oxazol-2-yl)-3-azabicyclo[3.1.0]hexan-3-yl]-3-fluorophenyl]-2-oxooxazolidin-5-ylmethyl]acetamide, N-[5(S)-3-[4-[(1α,5α,6α)-6-(5-Amino-4-cyano-1,3-oxazol-2-yl)bicyclo[3.1.0]hex-2-en-3-yl]-3-fluorophenyl]-2-oxooxazolidin-5-ylmethyl]acetamide, N-[5(S)-3-[4-[(1α,5α,6α)-6-Amino-3-azabicyclo[3.1.0]hexan-3-yl]phenyl]-2-oxooxazolidin-5-ylmethyl]acetamide, N-[5(S)-3-[4-[(1α,5α,6α)-6-Hydroxymethylbicyclo[3.1.0]hex-2-en-2-yl]phenyl]-2-oxooxazolidin-5-ylmethyl]acetamide, N-[5(S)-3-[4-[(1α,5α,6α)-6-[(Hydroxyimino)methyl]bicyclo[3.1.0]hex-2-en-2-yl]phenyl]-2-oxooxazolidin-5-ylmethyl]acetamide, N-[5(S)-3-[4-[(1α,5α,6α)-6-Cyanobicyclo[3.1.0]hex-2-en-2-yl]phenyl]-2-oxooxazolidin-5-ylmethyl]acetamide, N-[5(S)-3-[3-Fluoro-4-[(1α,5α,6β)-6-hydroxymethylbicyclo[3.1.0]hex-2-en-3-yl]phenyl]-2-oxooxazolidin-5-ylmethyl]acetamide, N-[5(S)-3-[4-[(1α,5α,6β)-6-Cyanobicyclo[3.1.0]hex-2-en-3-yl]-3-fluorophenyl]-2-oxooxazolidin-5-ylmethyl]acetamide, N-[5(S)-3-[4-[(1α,5α,6β)-6-Hydroxymethylbicyclo[3.1.0]hex-2-en-3-yl]phenyl]-2-oxooxazolidin-5-ylmethyl]acetamide, N-[5(S)-3-[4-[(1α,5α,6β)-6-Cyanobicyclo[3.1.0]hex-2-en-3-yl]phenyl]-2-oxooxazolidin-5-ylmethyl]acetamide, N-[5(S)-3-[4-[(1α,5α,6α)-6-Hydroxymethylbicyclo[3.1.0]hex-2-en-3-yl]phenyl]-2-oxooxazolidin-5-ylmethyl]acetamide (diastereomer A), N-[5(S)-3-[4-[(1α,5α,6α)-6-Cyanobicyclo[3.1.0]hex-2-en-3-yl]phenyl]-2-oxooxazolidin-5-ylmethyl]acetamide (diastereomer A), N-[5(S)-3-[4-[(1α,5α,6α)-6-Hydroxymethylbicyclo[3.1.0]hex-2-en-3-yl]phenyl]-2-oxooxazolidin-5-ylmethyl]acetamide (diastereomer B), N-[5(S)-3-[4-[(1α,5α,6α)-6-Cyanobicyclo[3.1.0]hex-2-en-3-yl]phenyl]-2-oxooxazolidin-5-ylmethyl]acetamide (diastereomer B), N-[5(S)-3-[4-[(1α,5α,6α)-6-[(Cyano-2-dimethylamino)ethen-1-yl]-3-azabicyclo[3.1.0]hexan-3-yl]-3-fluorophenyl]-2oxooxazolidin-5-ylmethyl]acetamide, or N-[5(S)-3-[4-[(1α,5α,6α)-6-(3-Amino-1H-pyrazol-4-yl)-3-azabicyclo[3.1.0]hexan-3-yl]-3-fluorophenyl]-2-oxooxazolidin-5-ylmethyl]acetamide.

22. A compound selected from the group consisting of:

(E)-N-[5(S)-3-[4-[(1α,5α,6α)-6-[Amino(hydroxyimino)methyl]-3-azabicyclo[3.1.0]hexan-3-yl]-3-fluorophenyl]-2-oxooxazolidin-5-ylmethyl]acetamide, (Z)-N-[5(S)-3-[4-[(1α,5α,6α)-6-[Amino(hydroxyimino)methyl]-3-azabicyclo[3.1.0]hexan-3-yl]-3-fluorophenyl]-2-oxooxazolidin-5-ylmethyl]acetamide, N-[5(S)-3-[4-[(1α,5α,6α)-6-[1-(2-t-Butyldiphenylsilyloxy-1-hydroxy)ethyl]-3-azabicyclo[3.1.0]hexan-3-yl]-3-fluorophenyl]-2-oxooxazolidin-5-ylmethyl]acetamide, N-[5(S)-3-[4-[(1α,5α,6α)-6-[(2-(t-Butyldiphenylsilyl)oxy)acetyl]-3-azabicyclo[3.1.0]hexan-3-yl]-3-fluorophenyl]-2-oxooxazolidin-5-ylmethyl]acetamide, N-[5(S)-3-[3,5-Difluoro-4-[(1α,5α,6α)-6-[(hydroxyimino)methyl]bicyclo[3.1.0]hex-2-en-3-yl]phenyl]-2-oxooxazolidin-5-ylmethyl]acetamide, N-[5(S)-3-[3,5-Difluoro-4-[(1α,5α,6α)-6-formylbicyclo[3.1.0]hex-2-en-3-yl]phenyl]-2-oxooxazolidin-5-ylmethyl]acetamide, N-[5(S)-3-[4-[(1R,5R,6S)-6-cyanobicyclo[3.1.0]hex-2-en-3-yl]phenyl]-2-oxooxazolidin-5-ylmethyl]acetamide, N-[5(S)-3-[4-[(1S,5S,6R)-6-cyanobicyclo[3.1.0]hex-2-en-3-yl]phenyl]-2-oxooxazolidin-5-ylmethyl]acetamide, N-[5(S)-3-[4-[(1α,5α,6α)-6-(1-Cyanoethyl)-3-azabicyclo[3.1.0]hexan-3-yl]-3-fluorophenyl]-2-oxooxazolidin-5-ylmethyl]acetamide, N-[5(S)-3-[4-[(1α,5α,6α)-6-(1-Cyano-1-methylethyl)-3-azabicyclo[3.1.0]hexan-3-yl]-3-fluorophenyl]-2-oxooxazolidin-5-ylmethyl]acetamide, 5(S)-3-[4-[(1R,5R,6S)-6-Cyanobicyclo[3.1.0]hex-2-en-3-yl]-3-fluorophenyl]-5-[(1,2,4-oxadiazolyl-3-yl)amino]methyloxazolidin-2-one, 5(S)-3-[4-[(1S,5S,6R)-6-Cyanobicyclo[3.1.0]hex-2-en-3-yl]-3-fluorophenyl]-5-[(1,2,4-oxadiazolyl-3-yl)amino]methyloxazolidin-2-one, N-[5(S)-3-[4-[(1α,5α,6α)-6-Cyano-3-azabicyclo[3.1.0]hexan-3-yl]-3-fluorophenyl]-2-oxooxazolidin-5-ylmethyl]thioacetamide, N-[5(S)-3-[4-[(1α,5α,6α)-6-Cyanobicyclo[3.1.0]hex-2-en-3-yl]phenyl]-2-oxooxazolidin-5-ylmethyl]thioacetamide, N-[5(S)-3-[4-[(1α,5α,6α)-6-(N-Benzyl-N-t-butoxycarbonyl)amino-3-azabicyclo[3.1.0]hexan-3-yl]-3,5-difluorophenyl]-2-oxooxazolidin-5-ylmethyl]acetamide, or N-[5(S)-3-[4-[(1α,3α,5α,6α)-6-Cyanobicyclo[3.1.0]hexan-3-yl]-3-fluorophenyl]-2-oxooxazolidin-5-ylmethyl]thioacetamide.

23. A compound selected from the group consisting of:

N-[5(S)-3-[3-Fluoro-4-[(1α,3α,5α,6α)-6-thiocarbamoylbicyclo[3.1.0]hexan-3-yl]phenyl]-2-oxooxazolidin-5-ylmethyl]acetamide, 5(R)-3-[3-Fluoro-4-[(1α,5α,6α)-6-[(2-tetrahydropyranyl)oxy]methyl-3-azabicyclo[3.1.0]hexan-3-yl]phenyl]-5-[(isoxazolyl-3-yl)oxy]methyloxazolidin, 5(R)-3-[3-Fluoro-4-[(1α,5α,6α)-6-hydroxymethyl-3-azabicyclo[3.1.0]hexan-3-yl]phenyl]-5-[(isoxazolyl-3-yl)oxy]methyloxazolidin-2-one, 5(R)-3-[3-Fluoro-4-[(1α,5α,6α)-6-[(isoxazolyl-3-yl)oxy]methyl-3-azabicyclo[3.1.0]hexan-3-yl]phenyl]-5-[(isoxazolyl-3-yl)oxy]methyloxazolidin-2-one, 5(R)-3-[3-Fluoro-4-[(1α,5α,6α)-6-methoxymethyl-3-azabicyclo[3.1.0]hexan-3-yl]phenyl]-5-[(isoxazolyl-3-yl)oxy]methyloxazolidin-2-one, 5(R)-3-[4-[(1α,5α,6α)-6-(t-Butoxycarbonyl)amino-3-azabicyclo[3.1.0]hexan-3-yl]-3-fluorophenyl]-5-[(isoxazolyl-3-yl)oxy]methyloxazolidin-2-one, 5(S)-3-[4-[(1R,5R,6S)-6-Cyanobicyclo[3.1.0]hex-2-en-3-yl]-3-fluorophenyl]-5-[N-(t-butoxycarbonyl)-N-(1,2,4-oxadiazolyl-3-yl)]aminomethyloxazolidin-2-one, or 5(S)-3-[4-[(1S,5S,6R)-6-Cyanobicyclo[3.1.0]hex-2-en-3-yl]-3-fluorophenyl]-5-[N-(t-butoxycarbonyl)-N-(1,2,4-oxadiazolyl-3-yl)]aminomethyloxazolidin-2-one.

24. A pharmaceutical composition comprised of a compound in accordance with claim 1 in combination with a pharmaceutically acceptable carrier.

25. A pharmaceutical composition comprised of a compound in accordance with claim 1 in combination with a pharmaceutically acceptable carrier.

26. A method of treating a bacterial infection in a mammalian patient in need thereof, comprising administering to said patient an effective amount of a compound of claim 1.

27. A method for the preparation of a compound of claim 1, wherein A is a nitrogen atom and the 3-azabicyclo[3.1.0]hexane has a 6-amino substituent, the method comprising:

1) reacting a 6-amino-3-azabicyclo[3.1.0]hexane having a protected 6-amino substituent with an aryl compound bearing a nitro group and a leaving group;

2) reducing the product from step 1) to the corresponding amino compound, and protecting the resulting amino group;

3) reacting the protected amino aryl product from step 2) with a strong base and then condensing with a glycidyl ester to form a 5-hydroxymethyloxazolidinone as a product;

4) converting the 5-hydroxymethyloxaxolidinone from step 3) to a 5-aminomethyloxazolidinone by first converting the hydroxy group to an activated leaving group, displacing the leaving group with sodium azide, and then reducing the resulting 5-azidooxazolidinone to the amine; and 5) acylating the 5-aminooxazolidinone from step 4) and converting the amino substituent to $R_3$.

28. A method according to claim 27, wherein the product from step 5) is further subjected to reductive alkylation, alkylation, or acylation.

29. A method according to claim 27, wherein the protected amino aryl product from step 2), after reaction with a strong base, is reacted with a racemic glycidyl ester to prepare a racemic oxazolidinone.

30. A method according to claim 27, wherein the protected amino aryl product from step 2), after reaction with a strong base, is reacted with a chiral glycidyl ester to prepare chiral oxazolidinone.

31. A method according to claim 30, wherein the chiral glycidylester is an R-glycidylester.

32. A method according to claim 30, wherein the chiral glycidylester is an S-glycidylester.

33. A method for the preparation of a compound of claim 1, wherein A is a nitrogen atom and the 3-azabicyclo[3.1.0]hexane has a 6-carbon substituent, the method comprising:

1) reacting a 6-amino-3-azabicyclo[3.1.0]hexane having a protected 6-hydroxyl or 6-alkyl substituent with an aryl compound bearing a nitro group and a leaving group;

2) reducing the product from step 1) to the corresponding amino compound, and protecting the resulting amino group;

3) reacting the protected amino aryl product from step 2) with a strong base and then condensing with a glycidyl ester to form a 5-hydroxymethyloxazolidinone as a product;

4) converting the 5-hydroxymethyloxazolidinone from step 3) to a 5-aminomethyloxazolidinone by first converting the hydroxy group to an activated leaving group, displacing the leaving group with sodium azide, and then reducing the resulting 5-azidooxazolidinone to the amine; and 5) acylating the 5-aminooxazolidinone from step 4) and converting the amino substituent to $R_3$.

34. A method according to claim 33, wherein the protected aminoaryl product from step 2), after reaction with a strong base, is reacted with a racemic glycidyl ester to prepare a racemic oxazolidinone.

35. A method according to claim 33, wherein the protected aminoaryl product from step 2), after reaction with strong base, is reacted with a chiral glycidyl ester to prepare a chiral oxazolidinone.

36. A method according to claim 35, wherein the chiral glycidylester is an R-glycidylester.

37. A method according to claim 35, wherein the chiral glycidylester is an S-glycidylester.

38. A method for preparation of a compound of claim 1, wherein the 3-azabicyclo[3.1.0]hexane has a protected hydroxyl group in the 6-position, the method comprising:

1) removing the protecting group to provide the free hydroxyl group;
2) activating the hydroxy group displacement with a nucleophilic substituent by converting the hydroxyl group to a leaving group; and
3) reacting the product from step 2) to replace the leaving group with a nucleophilic group.

39. A method for preparation of a compound of claim 1, wherein the 3-azabicyclo-[3.1.0]hexane has a protected hydroxyl group in the 6-position, the method comprising:

1) removing the protecting group to provide the free hydroxyl group;
2) oxidizing the hydroxyl group to the aldehyde;
3) further oxidizing the aldehyde group to the carboxylic acid; and
4) converting the carboxylic acid to a leaving group and treating with a nucleophile to introduce a nucleophilic group into the 6-position.

40. A method for the preparation of a compound of claim 1, wherein A contains a carbon atom and the 3-azabicyclo [3.1.0]hexane has a 6-amino substituent, the method comprising:

1) reacting a protected 3-trifluoromethanesulfonyl-6-amino-bicyclo[3.1.0]hexene with a substituted 2-oxo-3-(4-trimethylstannylphenyl)-5-substituted oxazolidinone to produce a cross-coupled product; and
2) reducing the double bond by hydrogenation to produce the bicylo[3.1.0]hexane.

* * * * *

UNITED STATES PATENT AND TRADEMARK OFFICE
CERTIFICATE OF CORRECTION

PATENT NO. : 6,897,230 B2 Page 1 of 1
APPLICATION NO. : 10/123285
DATED : May 24, 2005
INVENTOR(S) : Yasumichi Fukuda et al.

It is certified that error appears in the above-identified patent and that said Letters Patent is hereby corrected as shown below:

On the title page

Item (73) Assignee: add -- Merck & Co., Inc. --

Signed and Sealed this

Twenty-third Day of September, 2008

JON W. DUDAS
*Director of the United States Patent and Trademark Office*